US008765909B2

(12) United States Patent
Asami et al.

(10) Patent No.: US 8,765,909 B2
(45) Date of Patent: *Jul. 1, 2014

(54) METASTIN DERIVATIVES AND USE THEREOF

(75) Inventors: Taiji Asami, Ibaraki (JP); Naoki Nishizawa, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 738 days.

This patent is subject to a terminal disclaimer.

(21) Appl. No.: 12/446,142

(22) PCT Filed: Oct. 24, 2007

(86) PCT No.: PCT/JP2007/071169
§ 371 (c)(1),
(2), (4) Date: Apr. 17, 2009

(87) PCT Pub. No.: WO2008/050897
PCT Pub. Date: May 2, 2008

(65) Prior Publication Data
US 2011/0059888 A1 Mar. 10, 2011

(30) Foreign Application Priority Data

Oct. 25, 2006 (JP) ................................. 2006-290536
Jan. 31, 2007 (JP) ................................. 2007-021387
Aug. 28, 2007 (JP) ................................. 2007-221911

(51) Int. Cl.
*C07K 7/02* (2006.01)
*A61K 38/08* (2006.01)
*A61P 35/00* (2006.01)
(52) U.S. Cl.
USPC .......... 530/332; 530/328; 514/19.2; 514/21.6
(58) Field of Classification Search
USPC ..................... 530/328, 332; 514/19.2, 21.6
See application file for complete search history.

(56) References Cited

U.S. PATENT DOCUMENTS

| 6,699,965 | B1 | 3/2004 | Watanabe et al. | |
|---|---|---|---|---|
| 6,800,611 | B2 | 10/2004 | Fujii et al. | |
| 7,625,869 | B2 * | 12/2009 | Kitada et al. | 514/1.1 |
| 7,754,220 | B2 | 7/2010 | Ohtaki et al. | |
| 2003/0096956 | A1 | 5/2003 | Suenaga et al. | |
| 2004/0142875 | A1* | 7/2004 | Fujii et al. | 514/17 |
| 2004/0185525 | A1 | 9/2004 | Nishimura et al. | |
| 2004/0236077 | A1 | 11/2004 | Matsumoto et al. | |
| 2005/0176091 | A1 | 8/2005 | Yamada et al. | |
| 2005/0240008 | A1 | 10/2005 | Ohtaki et al. | |
| 2006/0035875 | A1 | 2/2006 | Shiotsu et al. | |
| 2006/0241051 | A1 | 10/2006 | Kitada et al. | |
| 2006/0287227 | A1 | 12/2006 | Ohtaki et al. | |
| 2009/0093615 | A1 | 4/2009 | Asami et al. | |
| 2009/0099334 | A1 | 4/2009 | Asami et al. | |
| 2009/0105152 | A1 | 4/2009 | Asami et al. | |
| 2009/0215700 | A1 | 8/2009 | Asami et al. | |
| 2009/0318365 | A1 | 12/2009 | Kitada et al. | |
| 2010/0215637 | A1 | 8/2010 | Klinken et al. | |
| 2010/0286035 | A1 | 11/2010 | Ohtaki et al. | |
| 2010/0331520 | A1 | 12/2010 | Asami et al. | |
| 2011/0059888 | A1 | 3/2011 | Asami et al. | |
| 2011/0118172 | A1 | 5/2011 | Asami et al. | |
| 2012/0015868 | A1 | 1/2012 | Kitada et al. | |

FOREIGN PATENT DOCUMENTS

| EP | 0162575 | | 11/1985 |
|---|---|---|---|
| EP | 0472220 | A1 | 2/1992 |
| EP | 1126028 | | 8/2001 |
| EP | 1577323 | | 9/2005 |
| EP | 1604682 | A1 | 12/2005 |
| JP | 9-169735 | A | 6/1997 |
| JP | 2002-320496 | | 11/2002 |
| JP | 2003-26601 | | 1/2003 |
| JP | 2003-300906 | | 10/2003 |
| JP | 2004-217651 | | 8/2004 |
| RU | 2005135739 | A | 3/2006 |
| RU | 2306147 | C2 | 9/2007 |
| RU | 2311920 | C2 | 12/2007 |
| RU | 2006/145886 | A | 6/2008 |
| RU | 2344831 | C2 | 1/2009 |
| WO | 9611953 | A1 | 4/1996 |
| WO | WO97/14682 | | 4/1997 |
| WO | WO97/40071 | | 10/1997 |
| WO | WO98/39448 | | 9/1998 |
| WO | WO00/24890 | | 5/2000 |
| WO | 0100228 | | 1/2001 |

(Continued)

OTHER PUBLICATIONS

Niida et al., 2006, Bioorganic & Medicinal Chemistry Letters, 16: 134-137.*
Tomita et al., 2006, Bioorganic & Medicinal Chemistry Letters, 14: 7595-7603.*
Makri et al., 2008, The kisspeptin (Kiss-1)/GPR54 system in cancer biology, Cancer Treatment Reviews, 34: 682-692.*
Dhillo, 2008, Kisspeptin: A Novel Regulator of Reproductive Function, Journal of Neuroendocrinology, 20: 963-970.*
Mead et al., 2007, Kisspeptins: a multifunctional peptide system with a role in reproduction, cancer, and the cardiovascular system, British Journal of Pharmacology, 151: 1143-1153.*

(Continued)

*Primary Examiner* — Amber D Steele
(74) *Attorney, Agent, or Firm* — Edwards Wildman Palmer LLP; David G. Conlin

(57) ABSTRACT

The present invention provides stable metastin derivatives having excellent biological activities (a cancer metastasis suppressing activity, a cancer growth suppressing activity, a gonadotropic hormone secretion stimulating activity, sex hormone secretion stimulating activity, etc.). By substituting the constituent amino acids of metastin with specific amino acids, the metastin derivatives of the present invention achieve more improved blood stability, solubility, etc., reduced gelation tendency, improved pharmacokinetics, as well as exhibit an excellent cancer metastasis suppressing activity or a cancer growth suppressing activity. The metastin derivatives of the present invention also have a gonadotropic hormone secretion suppressing activity, sex hormone secretion suppressing activity, etc.

4 Claims, No Drawings

(56) References Cited

FOREIGN PATENT DOCUMENTS

| | | |
|---|---|---|
| WO | 0141812 A2 | 6/2001 |
| WO | WO01/44469 | 6/2001 |
| WO | 0172295 | 10/2001 |
| WO | 0179286 A2 | 10/2001 |
| WO | WO01/74377 | 10/2001 |
| WO | WO01/75104 | 10/2001 |
| WO | WO02/085399 | 10/2002 |
| WO | WO02/092829 | 11/2002 |
| WO | WO03/027149 | 4/2003 |
| WO | WO03/060125 | 7/2003 |
| WO | WO2004/038021 | 5/2004 |
| WO | 2004/060264 | 7/2004 |
| WO | WO2004/060264 | 7/2004 |
| WO | WO2004/063221 | 7/2004 |
| WO | WO 2004/063221 * 7/2004 | ............ C07K 14/47 |
| WO | 2004073730 A1 | 9/2004 |
| WO | WO2004/080479 | 9/2004 |
| WO | WO2004/087622 | 10/2004 |
| WO | 2004093894 A2 | 11/2004 |
| WO | WO2004/096855 | 11/2004 |
| WO | WO2004/101747 | 11/2004 |
| WO | WO2004/106289 | 12/2004 |
| WO | 2005042744 A1 | 5/2005 |
| WO | WO2005/095973 | 10/2005 |
| WO | 2005117939 A2 | 12/2005 |
| WO | 2006/001499 | 1/2006 |
| WO | WO 2006/001499 * 1/2006 | ............ C07K 14/47 |
| WO | WO 2006/001499 * 12/2006 | |
| WO | 2007/072997 | 6/2007 |
| WO | 2007084211 A2 | 7/2007 |
| WO | WO2007/084211 | 7/2007 |
| WO | 2007109135 A2 | 9/2007 |
| WO | 2008050897 | 5/2008 |
| WO | 2009131191 A1 | 10/2009 |
| WO | 2010/033224 A1 | 3/2010 |

OTHER PUBLICATIONS

Niida et al., avaliable online Oct. 18, 2005, Design and sysnthesis of downsized metastin (45-54) analogs with maintenance of high GPR54 agonist activity, Bioorganic & Medicinal Chemistry Letters, 16: 134-137.*

Bruehlmeier et al., "Stabilization of neurotensin analogues: effect on peptide catabolism, biodistribution and tumor binding," Nuclear Medicine and Biology (2002), 29:321-327.

Cudic et al., "Development of novel antibacterial peptides that kill resistance isolates," Peptides (2002), 23:2071-2083.

European Search Report for related application EP09075257, dated Oct. 6, 2010, see note in Office action.

Search Report and English translation for corresponding Georgian patent application (No. AP 2006 010770) issued on Nov. 30, 2009, See note in Office action.

Georgian Srch Rpt, GE, Nov. 16, 2011, Srch Rpt for Georgian patent appln AP2007011265.

International Preliminary Report on Patentability, with Notification of Transmittal, for related international application PCT/JP2007/071169, dated May 7, 2009, See Note in Office Action.

S. Hinuma et al., "A prolactin-releasing peptide in the brain", Nature, vol. 393, pp. 272-276 (1998).

J.C. Meunier et al., "Nolecular Neuroendocrinology: Working backwards to find answers", Nature, vol. 393, pp. 211-212 (1998).

H. Satake et al., "Characterization of a cDNA encoding a novel avian hypothalamic neuropeptide exerting an inhibitory effect on gonadotropin release", Biochem. J., vol. 354, pp. 379-385 (2001).

Dutta et al., "Polypeptides. Part 15. Synthesis and Biological Activity of α-Aza-analogues of Luliberin Modified in Positions 6 and 10," Journal of the Chemical Society, Perkin Transactions 1, No. 2, pp. 379-388 (1979).

Gottsch et al., "A Role for Kisspeptins in the Regulation of Gonadotropin Secretion in the Mouse," Endocrinology (2004), 145(9):4073-4077.

Han et al., "Orphan G protein-coupled receptors MrgAl and MrgC11 are distinctively activated by RF-amide-related peptides through the $G\alpha_{q/11}$ pathway," PNAS (2002), 99(23):14740-14745.

Horikoshi et al., "Dramatic Elevation of Plasma Metastin Concentrations in Human Pregnancy: Metastin as a Novel Placenta-Derived Hormone in Humans," J. Clinical Endocrinology & Metabolism (2003), 88(2):914-919.

Kotani et al., "The Metastasis Suppressor Gene KiSS-1 Encodes Kisspeptins, the Natural Ligands of the Orphan G Protein-coupled Receptor GPR54," J. Biol. Chemistry (2001), 276(37):34631-34636.

Masui et al., "Metastin and its variant forms suppress migration of pancreatic cancer cells," Biochem. and Biophys. Res. Comm. (2004), 315:85-92.

Muir et al., "AXOR12, a Novel Human G Protein-coupled Receptor, Activated by the Peptide KiSS-1," J. Biol. Chem. (2001), 276(31):28969-28975.

Niita et al., "Genome Information Convergent Type of Drug Development Research: Depolymerization of the Cancer Metastasis Suppressor Gene, KiSS-1 (Metastin)," 53rd, Nihon Yakugaku kai, Kinki Shibu Sokai • Taikai Koen Yoshi-shu (2003), Yuki 2B-13-2 (translation included), 2 pages.

Ohtaki et al., "Metastasis suppressor gene *KiSS-1* encodes peptide ligand of a G-protein-coupled receptor," Nature (2001) 441:613-617.

Ringel et al., "Metastin Receptor is Overexpressed in Papillary Thyroid Cancer and Activates MAP Kinase in Thyroid Cancer Cells," J. of Clin. Endocrinology & Metabolism (2002) 87(5):2399-2402.

Terao et al., "Expression of *KiSS-1*, a metastasis suppressor gene in trophoblast giant cells of the rat placenta," Biochimica et Biophysica Acta (2004), 1678:102-110.

Roberts et al., "Treands in the Risks and Benefits to Patients with Cancer Participating in Phase 1 Clinical Trials", JAMA, vol. 292, pp. 2130-2140 (2004).

Kola et al., "Can the pharmaceutical industry reduce attrition rates?", Nature Reviews Drug Discovery, vol. 3, pp. 711-715 (2004).

Leaf et al., "Why we are losing the war on cancer (and how to win it)", Health Administrator, 2005, XVII, pp. 172-183.

"Expert Scientific Group on Phase One Clinical Trials Final Report", Nov. 30, 2006, pp. C1, C35-C38.

Kamb et al., "What's wrong with our cancer models?", Nature Reviews Drug Discovery, vol. 4, pp. 161-165 (2005).

Navenot et al., "Kisspeptin-10-Induced Signaling of GPR54 Negatively Regulates chemotactic Responses Mediated by CXCR4: a Potential Mechanism for the Metastasis Suppressor Activity of Kisspeptins", Cancer Research, vol. 65, pp. 10450-10456 (2005).

Steeg et al., "Metastasis Suppressor Genes: Basic Biology and Potential Clinical Use", Clinical Breast Cancer, vol. 4, pp. 51-62 (2003).

Harms et al., "KISS1 metastasis suppression and emergent pathways", Clinical & Experimental Metastasis, vol. 20, pp. 11-18 (2003).

Cancer Drug Design & Discovery, Neidle, Stephen, ed. (Elsevier/Academic Press 2008), pp. 427-431.

Supplementary European Search Report for corresponding European Patent Application Serial No. EP 09803004, completed Dec. 6, 2012 (5 pages).

Roberts M.J. et al., Advanced Drug Delivery Reviews, vol. 54, No. 4, Jun. 17, 2002, pp. 459-476.

Harms et al., Clinical and Experimental Metastasis, vol. 20, pp. 11-18 (2003).

Jiang et al., Clinical and Experimental Metastasis, vol. 22, pp. 369-376 (2005).

Nash et al., Front. Biosci. vol. 11, pp. 647-659 (2006).

European Search Report for EP 03768337.2, Mar. 4, 2008.

Clements M.K. et al., Biochemical and Biophysical Research Communications 284(5), pp. 1189-1193 (2001).

Frochot C. et al., Letters in Peptide Science 4(4-6), pp. 219-225 (1997).

Stafford LJ, et al., Cancer Research, American Association for Cancer Research, 62(19), pp. 5399-5404(2002).

(56) References Cited

OTHER PUBLICATIONS

Niida et al., "Design and synthesis of downsized metastin (45-54) analogs with maintenance of high GPR54 agonistic activity," Bioorganic & Medicinal Chemistry Letters (2006) 16:134-137.

Tomita et al., "Structure-activity relationship study on small peptidic GPR54 agonists," Bioorganic & Medicinal Chemistry (2006) 14:7595-7603.

Venkatesan et al., "Synthesis and Enzyme Inhibitory Activities of Novel Peptide Isosteres," Current Medicinal Chemistry (2002) 9:2243-2270.

* cited by examiner

SEQUENCE LISTING

<160> NUMBER OF SEQ ID NOS: 218

<210> SEQ ID NO 1
<211> LENGTH: 54
<212> TYPE: PRT
<213> ORGANISM: Homo sapiens

<400> SEQUENCE: 1

Gly Thr Ser Leu Ser Pro Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 2
<211> LENGTH: 162
<212> TYPE: DNA
<213> ORGANISM: Homo sapiens

<400> SEQUENCE: 2
ggtacttctc tgtctccgcc gccggaatct tctggttctc gtcagcagcc gggtctgtct    60

-continued

```
gctccgcact ctcgtcagat cccggctccg cagggtgctg ttctggttca gcgtgaaaaa    120
gacctgccga actacaactg gaactctttc ggtctgcgtt tc                        162
```

<210> SEQ ID NO 3
<211> LENGTH: 152
<212> TYPE: PRT
<213> ORGANISM: Mus musculus

<400> SEQUENCE: 3

```
Met Tyr Leu Arg Phe Gly Val Asp Val Cys Ser Leu Ser Pro Trp Lys
1               5                   10                  15

Glu Thr Val Asp Leu Pro Leu Pro Pro Arg Met Ile Ser Met Ala Ser
            20                  25                  30

Trp Gln Leu Leu Leu Leu Cys Val Ala Thr Tyr Gly Glu Pro Leu
        35                  40                  45

Ala Lys Val Ala Pro Gly Ser Thr Gly Gln Gln Ser Gly Pro Gln Glu
    50                  55                  60

Leu Val Asn Ala Trp Glu Lys Glu Ser Arg Tyr Ala Glu Ser Lys Pro
65                  70                  75                  80

Gly Ser Ala Gly Leu Arg Ala Arg Arg Ser Ser Pro Cys Pro Val
                85                  90                  95

Glu Gly Pro Ala Gly Arg Gln Arg Pro Leu Cys Ala Ser Arg Ser Arg
            100                 105                 110

Leu Ile Pro Ala Pro Arg Gly Ala Val Leu Val Gln Arg Glu Lys Asp
        115                 120                 125

Leu Ser Thr Tyr Asn Trp Asn Ser Phe Gly Leu Arg Tyr Gly Arg Arg
    130                 135                 140

Gln Ala Ala Arg Ala Ala Arg Gly
145                 150
```

<210> SEQ ID NO 4
<211> LENGTH: 456
<212> TYPE: DNA
<213> ORGANISM: Mus musculus

<400> SEQUENCE: 4

```
atgtatctga gatttggcgt tgatgtctgc agcctgagtc cctggaagga gactgtagac    60
ctgccccttc ctcccagaat gatctcaatg gcttcttggc agctgctgct tctcctctgt   120
gtcgccacct atggggagcc gctggcaaaa gtgaagcctg gatccacagg ccagcagtcc   180
ggaccccagg aactcgttaa tgcctgggaa aaggaatcgc ggtatgcaga gagcaagcct   240
gggtctgcag gctgcgcgc tcgtaggtcg tcgccatgcc cgccggttga gggccccgcg   300
gggcgccagc ggcccctgtg tgcctcccgc agtcgcctga tccctgcgcc ccgcggagcg   360
gtgctggtgc agcgggagaa ggacctgtcc acctacaact ggaactcctt cggcctgcgc   420
tacggcagga ggcaggcggc gcgggcagca cggggc                             456
```

<210> SEQ ID NO 5
<211> LENGTH: 156
<212> TYPE: PRT
<213> ORGANISM: Mus musculus

<400> SEQUENCE: 5

```
Met Tyr Leu Arg Phe Gly Val Asp Val Cys Ser Leu Ser Pro Trp Lys
1               5                   10                  15

Glu Thr Val Asp Leu Pro Leu Pro Pro Arg Met Ile Ser Met Ala Ser
            20                  25                  30
```

```
Trp Gln Leu Leu Leu Leu Cys Val Ala Thr Tyr Gly Glu Pro Leu
        35                  40                  45

Ala Lys Val Ala Pro Leu Val Lys Pro Gly Ser Thr Gly Gln Gln Ser
 50                  55                  60

Gly Pro Gln Glu Leu Val Asn Ala Trp Glu Lys Glu Ser Arg Tyr Ala
 65                  70                  75                  80

Glu Ser Lys Pro Gly Ser Ala Gly Leu Arg Ala Arg Arg Ser Ser Pro
                 85                  90                  95

Cys Pro Pro Val Glu Gly Pro Ala Gly Arg Gln Arg Pro Leu Cys Ala
                100                 105                 110

Ser Arg Ser Arg Leu Ile Pro Ala Pro Arg Gly Ala Val Leu Val Gln
            115                 120                 125

Arg Glu Lys Asp Leu Ser Thr Tyr Asn Trp Asn Ser Phe Gly Leu Arg
    130                 135                 140

Tyr Gly Arg Arg Gln Ala Ala Arg Ala Ala Arg Gly
145                 150                 155
```

<210> SEQ ID NO 6
<211> LENGTH: 468
<212> TYPE: DNA
<213> ORGANISM: Mus musculus

<400> SEQUENCE: 6

```
atgtatctga gatttggcgt tgatgtctgc agcctgagtc cctggaagga gactgtagac      60
ctgcccctt c ctcccagaat gatctcaatg gcttcttggc agctgctgct tctcctctgt    120
gtcgccacct atggggagcc gctggcaaaa gtggcacctt tggtgaagcc tggatccaca    180
ggccagcagt ccggacccca ggaactcgtt aatgcctggg aaaaggaatc gcggtatgca    240
gagagcaagc tgggtctgc agggctgcgc gctcgtaggt cgtcgccatg cccgccggtt     300
gagggccccg cggggcgcca gcggcccctg tgtgcctccc gcagtcgcct gatccctgcg    360
ccccgcggag cggtgctggt gcagcgggag aaggacctgt ccacctacaa ctggaactcc    420
ttcggcctgc gctacggcag gaggcaggcg gcgcgggcag cacgggcc                  468
```

<210> SEQ ID NO 7
<211> LENGTH: 130
<212> TYPE: PRT
<213> ORGANISM: Rattus sp.

<400> SEQUENCE: 7

```
Met Thr Ser Leu Ala Ser Trp Gln Leu Leu Leu Leu Cys Val Ala
 1               5                  10                  15

Ser Phe Gly Glu Pro Leu Ala Lys Met Ala Pro Val Val Asn Pro Glu
                20                  25                  30

Pro Thr Gly Gln Gln Ser Gly Pro Gln Glu Leu Val Asn Ala Trp Gln
            35                  40                  45

Lys Gly Pro Arg Tyr Ala Glu Ser Lys Pro Gly Ala Ala Gly Leu Arg
 50                  55                  60

Ala Arg Arg Thr Ser Pro Cys Pro Pro Val Glu Asn Pro Thr Gly His
 65                  70                  75                  80

Gln Arg Pro Pro Cys Ala Thr Arg Ser Arg Leu Ile Pro Ala Pro Arg
                 85                  90                  95

Gly Ser Val Leu Val Gln Arg Glu Lys Asp Met Ser Ala Tyr Asn Trp
                100                 105                 110

Asn Ser Phe Gly Leu Arg Tyr Gly Arg Arg Gln Val Ala Arg Ala Ala
```

<210> SEQ ID NO 8
<211> LENGTH: 390
<212> TYPE: DNA
<213> ORGANISM: Rattus sp.

<400> SEQUENCE: 8

```
atgacctcgc tggcttcttg gcagctgctg cttctcctct gtgtggcctc ttttggggag    60
ccactggcaa aaatggcacc tgtggtgaac cctgaaccca caggccaaca gtccggaccc   120
caggaactcg ttaatgcctg gcaaaagggc ccgcggtatg cagagagcaa gcctggggct   180
gcaggactgc gcgctcgccg aacatcgcca tgcccgccgg tggagaaccc cacggggcac   240
cagcggcccc cgtgtgccac ccgcagtcgc ctgatccctg cgcccgcgg atcggtgctg    300
gtgcagcgcg agaaggacat gtcagcctac aactggaact cctttggcct gcgctacggc   360
aggaggcagg tggcgcgggc ggcacggggc                                   390
```

<210> SEQ ID NO 9
<211> LENGTH: 398
<212> TYPE: PRT
<213> ORGANISM: Homo sapiens

<400> SEQUENCE: 9

Met His Thr Val Ala Thr Ser Gly Pro Asn Ala Ser Trp Gly Ala Pro
1               5                   10                  15

Ala Asn Ala Ser Gly Cys Pro Gly Cys Gly Ala Asn Ala Ser Asp Gly
            20                  25                  30

Pro Val Pro Ser Pro Arg Ala Val Asp Ala Trp Leu Val Pro Leu Phe
        35                  40                  45

Phe Ala Ala Leu Met Leu Leu Gly Leu Val Gly Asn Ser Leu Val Ile
    50                  55                  60

Tyr Val Ile Cys Arg His Lys Pro Met Arg Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Gly Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Ala Val Ser Leu Ser Ile Trp Val Gly Ser Ala Ala Val Ser Ala Pro
                165                 170                 175

Val Leu Ala Leu His Arg Leu Ser Pro Gly Pro Arg Ala Tyr Cys Ser
            180                 185                 190

Glu Ala Phe Pro Ser Arg Ala Leu Glu Arg Ala Phe Ala Leu Tyr Asn
        195                 200                 205

Leu Leu Ala Leu Tyr Leu Leu Pro Leu Leu Ala Thr Cys Ala Cys Tyr
    210                 215                 220

Ala Ala Met Leu Arg His Leu Gly Arg Val Ala Val Arg Pro Ala Pro
225                 230                 235                 240

```
Ala Asp Ser Ala Leu Gln Gly Gln Val Leu Ala Glu Arg Ala Gly Ala
                245                 250                 255

Val Arg Ala Lys Val Ser Arg Leu Val Ala Ala Val Val Leu Leu Phe
            260                 265                 270

Ala Ala Cys Trp Gly Pro Ile Gln Leu Phe Leu Val Leu Gln Ala Leu
            275                 280                 285

Gly Pro Ala Gly Ser Trp His Pro Arg Ser Tyr Ala Ala Tyr Ala Leu
            290                 295                 300

Lys Thr Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Arg Arg
                325                 330                 335

Val Cys Pro Cys Ala Pro Arg Pro Arg Arg Pro Arg Pro Gly
            340                 345                 350

Pro Ser Asp Pro Ala Ala Pro His Ala Glu Leu His Arg Leu Gly Ser
            355                 360                 365

His Pro Ala Pro Ala Arg Ala Gln Lys Pro Gly Ser Ser Gly Leu Ala
            370                 375                 380

Ala Arg Gly Leu Cys Val Leu Gly Glu Asp Asn Ala Pro Leu
385                 390                 395

<210> SEQ ID NO 10
<211> LENGTH: 1194
<212> TYPE: DNA
<213> ORGANISM: Homo sapiens

<400> SEQUENCE: 10
atgcacaccg tggctacgtc cggacccaac gcgtcctggg gggcaccggc caacgcctcc      60
ggctgcccgg gctgtggcgc caacgcctcg acggcccag tcccttcgcc gcgggccgtg     120
gacgcctggc tcgtgccgct cttcttcgcg gcgctgatgc tgctgggcct ggtggggaac     180
tcgctggtca tctacgtcat ctgccgccac aagccgatgc ggaccgtgac caacttctac     240
atcgccaacc tggcgccac ggacgtgacc ttcctcctgt gctgcgtccc cttcacggcc     300
ctgctgtacc cgctgccgg ctgggtgctg gcgacttca tgtgcaagtt cgtcaactac     360
atccagcagg tctcggtgca ggccacgtgt gccactctga ccgccatgag tgtggaccgc     420
tggtacgtga cggtgttccc gttgcgcgcc ctgaccgcc gcacgccccg cctggcgctg     480
gctgtcagcc tcagcatctg gtaggctct gcggcggtgt ctgcgccggt gctcgccctg     540
caccgcctgt cacccgggcc gcgcgcctac tgcagtgagg ccttccccag ccgcgccctg     600
gagcgcgcct tcgcactgta caacctgctg gcgctgtacc tgctgccgct gctcgccacc     660
tgcgcctgct atgcggccat gctgcgccac ctgggccggg tcgccgtgcg cccgcgcgcc     720
gccgatagcg ccctgcaggg gcaggtgctg gcagagcgcg caggcgccgt gcgggccaag     780
gtctcgcggc tggtggcggc cgtggtcctg ctcttcgccg cctgctgggg ccccatccag     840
ctgttcctgg tgctgcaggc gctgggcccc gcgggctcct ggcacccacg cagctacgcc     900
gcctacgcgc ttaagacctg gctcactgc atgtcctaca gcaactccgc gctgaacccg     960
ctgctctacg ccttcctggg ctcgcacttc cgacaggcct tccgccgcgt ctgccctgc    1020 gcgccgcgcc gcccccgccg cccccgccgg cccggaccct cggacccgc agccccacac    1080 gcggagctgc accgcctggg gtcccacccg gccccgcca gggcgcagaa gccagggagc    1140
agtgggctgg ccgcgcgcgg gctgtgcgtc ctgggggagg acaacgcccc tctc          1194
```

```
<210> SEQ ID NO 11
<211> LENGTH: 396
<212> TYPE: PRT
<213> ORGANISM: Rattus sp.

<400> SEQUENCE: 11
```

| | | | | | | | | | | | | | | | |
|---|---|---|---|---|---|---|---|---|---|---|---|---|---|---|---|
| Met | Ala | Ala | Glu | Ala | Thr | Leu | Gly | Pro | Asn | Val | Ser | Trp | Trp | Ala | Pro |
| 1 | | | | 5 | | | | | 10 | | | | | 15 | |
| Ser | Asn | Ala | Ser | Gly | Cys | Pro | Gly | Cys | Gly | Val | Asn | Ala | Ser | Asp | Gly |
| | | | 20 | | | | | 25 | | | | | 30 | | |
| Pro | Gly | Ser | Ala | Pro | Arg | Pro | Leu | Asp | Ala | Trp | Leu | Val | Pro | Leu | Phe |
| | | | | 35 | | | | | 40 | | | | | 45 | |
| Phe | Ala | Ala | Leu | Met | Leu | Leu | Gly | Leu | Val | Gly | Asn | Ser | Leu | Val | Ile |
| | 50 | | | | | 55 | | | | | 60 | | | | |
| Phe | Val | Ile | Cys | Arg | His | Lys | His | Met | Gln | Thr | Val | Thr | Asn | Phe | Tyr |
| 65 | | | | | 70 | | | | | 75 | | | | | 80 |
| Ile | Ala | Asn | Leu | Ala | Ala | Thr | Asp | Val | Thr | Phe | Leu | Leu | Cys | Cys | Val |
| | | | | 85 | | | | | 90 | | | | | 95 | |
| Pro | Phe | Thr | Ala | Leu | Leu | Tyr | Pro | Leu | Pro | Thr | Trp | Val | Leu | Gly | Asp |
| | | | | 100 | | | | | 105 | | | | | 110 | |
| Phe | Met | Cys | Lys | Phe | Val | Asn | Tyr | Ile | Gln | Gln | Val | Ser | Val | Gln | Ala |
| | | | 115 | | | | | 120 | | | | | 125 | | |
| Thr | Cys | Ala | Thr | Leu | Thr | Ala | Met | Ser | Val | Asp | Arg | Trp | Tyr | Val | Thr |
| | 130 | | | | | 135 | | | | | 140 | | | | |
| Val | Phe | Pro | Leu | Arg | Ala | Leu | His | Arg | Arg | Thr | Pro | Arg | Leu | Ala | Leu |
| 145 | | | | | 150 | | | | | 155 | | | | | 160 |
| Thr | Val | Ser | Leu | Ser | Ile | Trp | Val | Gly | Ser | Ala | Ala | Val | Ser | Ala | Pro |
| | | | | 165 | | | | | 170 | | | | | 175 | |
| Val | Leu | Ala | Leu | His | Arg | Leu | Ser | Pro | Gly | Pro | His | Thr | Tyr | Cys | Ser |
| | | | | 180 | | | | | 185 | | | | | 190 | |
| Glu | Ala | Phe | Pro | Ser | Arg | Ala | Leu | Glu | Arg | Ala | Phe | Ala | Leu | Tyr | Asn |
| | | | 195 | | | | | 200 | | | | | 205 | | |
| Leu | Leu | Ala | Leu | Tyr | Leu | Leu | Pro | Leu | Leu | Ala | Thr | Cys | Ala | Cys | Tyr |
| | 210 | | | | | 215 | | | | | 220 | | | | |
| Gly | Ala | Met | Leu | Arg | His | Leu | Gly | Arg | Ala | Ala | Val | Arg | Pro | Ala | Pro |
| 225 | | | | | 230 | | | | | 235 | | | | | 240 |
| Thr | Asp | Gly | Ala | Leu | Gln | Gly | Gln | Leu | Leu | Ala | Gln | Arg | Ala | Gly | Ala |
| | | | | 245 | | | | | 250 | | | | | 255 | |
| Val | Arg | Thr | Lys | Val | Ser | Arg | Leu | Val | Ala | Ala | Val | Val | Leu | Leu | Phe |
| | | | 260 | | | | | 265 | | | | | 270 | | |
| Ala | Ala | Cys | Trp | Gly | Pro | Ile | Gln | Leu | Phe | Leu | Val | Leu | Gln | Ala | Leu |
| | | | 275 | | | | | 280 | | | | | 285 | | |
| Gly | Pro | Ser | Gly | Ala | Trp | His | Pro | Arg | Ser | Tyr | Ala | Ala | Tyr | Ala | Leu |
| | | | 290 | | | | | 295 | | | | | 300 | | |
| Lys | Ile | Trp | Ala | His | Cys | Met | Ser | Tyr | Ser | Asn | Ser | Ala | Leu | Asn | Pro |
| 305 | | | | | 310 | | | | | 315 | | | | | 320 |
| Leu | Leu | Tyr | Ala | Phe | Leu | Gly | Ser | His | Phe | Arg | Gln | Ala | Phe | Cys | Arg |
| | | | | 325 | | | | | 330 | | | | | 335 | |
| Val | Cys | Pro | Cys | Gly | Pro | Gln | Arg | Gln | Arg | Arg | Pro | His | Ala | Ser | Ala |
| | | | 340 | | | | | 345 | | | | | 350 | | |
| His | Ser | Asp | Arg | Ala | Ala | Pro | His | Ser | Val | Pro | His | Ser | Arg | Ala | Ala |
| | | | | 355 | | | | | 360 | | | | | 365 | | |
| His | Pro | Val | Arg | Val | Arg | Thr | Pro | Glu | Pro | Gly | Asn | Pro | Val | Val | Arg |
| | | | 370 | | | | | 375 | | | | | 380 | | |

Ser Pro Ser Val Gln Asp Glu His Thr Ala Pro Leu
385                 390                 395

<210> SEQ ID NO 12
<211> LENGTH: 1188
<212> TYPE: DNA
<213> ORGANISM: Rattus sp.

<400> SEQUENCE: 12

| | | | | | |
|---|---|---|---|---|---|
| atggccgcag | aggcgacgtt | gggtccgaac | gtgagctggt | gggctccgtc | caacgcttcg | 60 |
| ggatgcccgg | gctgcggtgt | caatgcctcg | gatggcccag | gctccgcgcc | aaggcccctg | 120 |
| gatgcctggc | tggtgcccct | gttttcgct | gccctaatgt | tgctgggggct | agtcgggaac | 180 |
| tcactggtca | tcttcgttat | ctgccgccac | aagcacatgc | agaccgtcac | caatttctac | 240 |
| atcgctaacc | tggcggccac | agatgtcact | ttccttctgt | gctgcgtacc | cttcaccgcg | 300 |
| ctcctctatc | cgctgcccac | ctgggtgctg | ggagacttca | tgtgcaaatt | cgtcaactac | 360 |
| atccagcagg | tctcggtgca | agccacatgt | gccactttga | cagccatgag | tgtggaccgc | 420 |
| tggtacgtga | ctgtgttccc | gctgcgtgca | cttcaccgcc | gcactccgcg | cctggccctg | 480 |
| actgtcagcc | ttagcatctg | ggtgggttcc | gcagctgttt | ccgccccggt | gctggctctg | 540 |
| caccgcctgt | cgcccgggcc | tcacacctac | tgcagtgagg | cgtttcccag | ccgtgccctg | 600 |
| gagcgcgctt | cgcgctcta | caacctgctg | gccctatacc | tgctgccgct | gctcgccacc | 660 |
| tgcgcctgct | acggtgccat | gctgcgccac | ctgggccgcg | ccgctgtacg | ccccgcaccc | 720 |
| actgatggcg | ccctgcaggg | gcagctgcta | gcacagcgcg | ctggagcagt | gcgcaccaag | 780 |
| gtctcccggc | tggtggccgc | tgtcgtcctg | ctcttcgccg | cctgctgggg | cccgatccag | 840 |
| ctgttcctgg | tgcttcaagc | cctgggcccc | tcggggggcct | ggcaccctcg | aagctatgcc | 900 |
| gcctacgcgc | tcaagatctg | ggctcactgc | atgtcctaca | gcaattctgc | gctcaacccg | 960 |
| ctgctctatg | ccttcctggg | ttcccacttc | agacaggcct | tctgccgcgt | gtgccctgc | 1020 |
| ggcccgcaac | gccagcgtcg | gccccacgcg | tcagcgcact | cggaccgagc | cgcaccccat | 1080 |
| agtgtgccgc | acagccgggc | tgcgcaccct | gtccgggtca | ggaccccga | gcctgggaac | 1140 |
| cctgtggtgc | gctcgccctc | tgttcaggat | gaacacactg | ccccactc | | 1188 |

<210> SEQ ID NO 13
<211> LENGTH: 396
<212> TYPE: PRT
<213> ORGANISM: Mus musculus

<400> SEQUENCE: 13

Met Ala Thr Glu Ala Thr Leu Ala Pro Asn Val Thr Trp Trp Ala Pro
1               5                   10                  15

Ser Asn Ala Ser Gly Cys Pro Gly Cys Gly Val Asn Ala Ser Asp Asp
            20                  25                  30

Pro Gly Ser Ala Pro Arg Pro Leu Asp Ala Trp Leu Val Pro Leu Phe
        35                  40                  45

Phe Ala Thr Leu Met Leu Leu Gly Leu Val Gly Asn Ser Leu Val Ile
    50                  55                  60

Tyr Val Ile Cys Arg His Lys His Met Gln Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Ala Trp Val Leu Gly Asp

```
                100             105             110
Phe Met Cys Lys Phe Val Asn Tyr Ile Gln Gln Val Ser Val Gln Ala
            115                 120                 125
Thr Cys Ala Thr Leu Thr Ala Met Ser Val Asp Arg Trp Tyr Val Thr
            130                 135                 140
Val Phe Pro Leu Arg Ala Leu His Arg Arg Thr Pro Arg Leu Ala Leu
145                 150                 155                 160
Ala Val Ser Leu Ser Ile Trp Val Gly Ser Ala Val Ser Ala Pro
                165                 170                 175
Val Leu Ala Leu His Arg Leu Ser Pro Gly Pro Arg Thr Tyr Cys Ser
                180                 185                 190
Glu Ala Phe Pro Ser Arg Ala Leu Glu Arg Ala Phe Ala Leu Tyr Asn
            195                 200                 205
Leu Leu Ala Leu Tyr Leu Leu Pro Leu Leu Ala Thr Cys Ala Cys Tyr
            210                 215                 220
Gly Ala Met Leu Arg His Leu Gly Arg Ala Ala Val Arg Pro Ala Pro
225                 230                 235                 240
Thr Asp Gly Ala Leu Gln Gly Gln Leu Leu Ala Gln Arg Ala Gly Ala
                245                 250                 255
Val Arg Thr Lys Val Ser Arg Leu Val Ala Ala Val Leu Leu Phe
            260                 265                 270
Ala Ala Cys Trp Gly Pro Ile Gln Leu Phe Leu Val Leu Gln Ala Leu
            275                 280                 285
Gly Pro Ser Gly Ala Trp His Pro Arg Ser Tyr Ala Ala Tyr Ala Val
            290                 295                 300
Lys Ile Trp Ala His Cys Met Ser Tyr Ser Asn Ser Ala Leu Asn Pro
305                 310                 315                 320
Leu Leu Tyr Ala Phe Leu Gly Ser His Phe Arg Gln Ala Phe Cys Arg
                325                 330                 335
Val Cys Pro Cys Cys Arg Gln Arg Gln Arg Arg Pro His Thr Ser Ala
                340                 345                 350
His Ser Asp Arg Ala Ala Thr His Thr Val Pro His Ser Arg Ala Ala
            355                 360                 365
His Pro Val Arg Ile Arg Ser Pro Glu Pro Gly Asn Pro Val Val Arg
            370                 375                 380
Ser Pro Cys Ala Gln Ser Glu Arg Thr Ala Ser Leu
385                 390                 395

<210> SEQ ID NO 14
<211> LENGTH: 1188
<212> TYPE: DNA
<213> ORGANISM: Mus musculus

<400> SEQUENCE: 14
atggccaccg aggcgacatt ggctcccaat gtgacctggt gggctccgtc caacgcttca      60
ggatgcccag gctgcggtgt caacgcctcg gatgacccag gctctgcgcc aaggcccctg     120
gatgcctggc tggttcccct gttttttcgct acactcatgt tgcttgggct ggtcggaaac     180
tcattggtca tctacgttat ctgccgccac aagcacatgc agacagttac caacttctac     240
atcgctaacc tggctgccac agacgtcact ttcctactgt gctgcgtgcc cttcaccgca     300
ctcctctacc cgctgcccgc ctgggtgctg ggagacttca tgtgcaaatt cgtcaactac     360
atccagcagg tctcggtgca agccacatgt gccactctga cggccatgag tgtggaccgc     420
tggtatgtga ctgtgttccc gctgcgtgca cttcaccgcc gcactccgcg cctggcccctg     480
```

```
gctgtcagcc tcagcatctg ggtggggtca gcagctgtgt ccgccccggt gctggccctg      540
caccgcctgt cgccagggcc tcgcacctac tgcagcgagg cgtttcccag ccgcgccctg      600
gagcgcgcct tcgcgctcta caacctgctg gctctatatc tgctgccgct gctcgccacc      660
tgcgcctgct acggcgccat gctgcgccac ctgggccgtg cggctgtacg ccccgcaccc      720
actgacggcg ccctgcaggg acagctgcta gcacagcgcg ccggagcagt gcgcaccaag      780
gtctcccggc tggtggccgc tgtcgtcctg ctcttcgccg cctgctgggg cccgatccag      840
ctgttcctgg tgcttcaagc cctgggcccc tcggggcct ggcaccctcg aagctatgcc       900
gcctacgcgg tcaagatctg ggctcactgc atgtcctaca gcaactcggc gctcaatccg      960
ctgctctatg ccttcctggg ttcacacttc agacaggcct tctgccgcgt gtgcccctgc     1020
tgccggcaac gccagcgccg gccccacacg tcagcgcact cggaccgagc tgcaactcac     1080
actgtgccgc acagccgtgc tgcgcaccct gtgcggatca ggagcccgga gcctgggaac     1140
cctgtggtgc gctcgccctg cgctcagagt gaacgcactg cctcactc                  1188
```

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 15

Lys Asp Leu Pro Asn Tyr Asn Trp Asn Ser Phe Gly Leu Arg Phe
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 16

Tyr Asn Trp Asn Ser Phe Gly Leu Arg Phe
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 17

Asn Trp Asn Ser Phe Gly Leu Arg Phe
1               5

<210> SEQ ID NO 18
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: C-term amidated

<400> SEQUENCE: 18

Trp Asn Ser Phe Gly Leu Arg Phe
1               5

<210> SEQ ID NO 19
<211> LENGTH: 45
<212> TYPE: DNA
<213> ORGANISM: Homo sapiens

<400> SEQUENCE: 19
aaggacctgc cgaactacaa ctggaactcc ttcggcctgc gcttc            45

<210> SEQ ID NO 20
<211> LENGTH: 30
<212> TYPE: DNA
<213> ORGANISM: Homo sapiens

<400> SEQUENCE: 20
tacaactgga actccttcgg cctgcgcttc                             30

<210> SEQ ID NO 21
<211> LENGTH: 27
<212> TYPE: DNA
<213> ORGANISM: Homo sapiens

<400> SEQUENCE: 21
aactggaact ccttcggcct gcgcttc                                27

<210> SEQ ID NO 22
<211> LENGTH: 24
<212> TYPE: DNA
<213> ORGANISM: Homo sapiens

<400> SEQUENCE: 22
tggaactcct tcggcctgcg cttc                                   24

<210> SEQ ID NO 23
<211> LENGTH: 4
<212> TYPE: PRT
<213> ORGANISM: Homo sapiens

<400> SEQUENCE: 23

Tyr Asn Trp Asn
1

<210> SEQ ID NO 24
<211> LENGTH: 5
<212> TYPE: PRT
<213> ORGANISM: Homo sapiens

<400> SEQUENCE: 24

Asn Tyr Asn Trp Asn
1               5

<210> SEQ ID NO 25
<211> LENGTH: 6
<212> TYPE: PRT
<213> ORGANISM: Homo sapiens

<400> SEQUENCE: 25
```

```
Pro Asn Tyr Asn Trp Asn
1               5

<210> SEQ ID NO 26
<211> LENGTH: 7
<212> TYPE: PRT
<213> ORGANISM: Homo sapiens

<400> SEQUENCE: 26

Leu Pro Asn Tyr Asn Trp Asn
1               5

<210> SEQ ID NO 27
<211> LENGTH: 8
<212> TYPE: PRT
<213> ORGANISM: Homo sapiens

<400> SEQUENCE: 27

Asp Leu Pro Asn Tyr Asn Trp Asn
1               5

<210> SEQ ID NO 28
<211> LENGTH: 9
<212> TYPE: PRT
<213> ORGANISM: Homo sapiens

<400> SEQUENCE: 28

Lys Asp Leu Pro Asn Tyr Asn Trp Asn
1               5

<210> SEQ ID NO 29
<211> LENGTH: 10
<212> TYPE: PRT
<213> ORGANISM: Homo sapiens

<400> SEQUENCE: 29

Glu Lys Asp Leu Pro Asn Tyr Asn Trp Asn
1               5                   10

<210> SEQ ID NO 30
<211> LENGTH: 11
<212> TYPE: PRT
<213> ORGANISM: Homo sapiens

<400> SEQUENCE: 30

Arg Glu Lys Asp Leu Pro Asn Tyr Asn Trp Asn
1               5                   10

<210> SEQ ID NO 31
<211> LENGTH: 12
<212> TYPE: PRT
<213> ORGANISM: Homo sapiens

<400> SEQUENCE: 31

Gln Arg Glu Lys Asp Leu Pro Asn Tyr Asn Trp Asn
1               5                   10

<210> SEQ ID NO 32
<211> LENGTH: 13
<212> TYPE: PRT
<213> ORGANISM: Homo sapiens

<400> SEQUENCE: 32

Val Gln Arg Glu Lys Asp Leu Pro Asn Tyr Asn Trp Asn
```

```
1               5                   10
```

<210> SEQ ID NO 33
<211> LENGTH: 14
<212> TYPE: PRT
<213> ORGANISM: Homo sapiens

<400> SEQUENCE: 33

```
Leu Val Gln Arg Glu Lys Asp Leu Pro Asn Tyr Asn Trp Asn
1               5                   10
```

<210> SEQ ID NO 34
<211> LENGTH: 15
<212> TYPE: PRT
<213> ORGANISM: Homo sapiens

<400> SEQUENCE: 34

```
Val Leu Val Gln Arg Glu Lys Asp Leu Pro Asn Tyr Asn Trp Asn
1               5                   10                  15
```

<210> SEQ ID NO 35
<211> LENGTH: 16
<212> TYPE: PRT
<213> ORGANISM: Homo sapiens

<400> SEQUENCE: 35

```
Ala Val Leu Val Gln Arg Glu Lys Asp Leu Pro Asn Tyr Asn Trp Asn
1               5                   10                  15
```

<210> SEQ ID NO 36
<211> LENGTH: 17
<212> TYPE: PRT
<213> ORGANISM: Homo sapiens

<400> SEQUENCE: 36

```
Gly Ala Val Leu Val Gln Arg Glu Lys Asp Leu Pro Asn Tyr Asn Trp
1               5                   10                  15

Asn
```

<210> SEQ ID NO 37
<211> LENGTH: 18
<212> TYPE: PRT
<213> ORGANISM: Homo sapiens

<400> SEQUENCE: 37

```
Gln Gly Ala Val Leu Val Gln Arg Glu Lys Asp Leu Pro Asn Tyr Asn
1               5                   10                  15

Trp Asn
```

<210> SEQ ID NO 38
<211> LENGTH: 19
<212> TYPE: PRT
<213> ORGANISM: Homo sapiens

<400> SEQUENCE: 38

```
Pro Gln Gly Ala Val Leu Val Gln Arg Glu Lys Asp Leu Pro Asn Tyr
1               5                   10                  15

Asn Trp Asn
```

<210> SEQ ID NO 39
<211> LENGTH: 20
<212> TYPE: PRT
<213> ORGANISM: Homo sapiens

```
<400> SEQUENCE: 39

Ala Pro Gln Gly Ala Val Leu Val Gln Arg Glu Lys Asp Leu Pro Asn
1               5                   10                  15

Tyr Asn Trp Asn
            20

<210> SEQ ID NO 40
<211> LENGTH: 21
<212> TYPE: PRT
<213> ORGANISM: Homo sapiens

<400> SEQUENCE: 40

Pro Ala Pro Gln Gly Ala Val Leu Val Gln Arg Glu Lys Asp Leu Pro
1               5                   10                  15

Asn Tyr Asn Trp Asn
            20

<210> SEQ ID NO 41
<211> LENGTH: 22
<212> TYPE: PRT
<213> ORGANISM: Homo sapiens

<400> SEQUENCE: 41

Ile Pro Ala Pro Gln Gly Ala Val Leu Val Gln Arg Glu Lys Asp Leu
1               5                   10                  15

Pro Asn Tyr Asn Trp Asn
            20

<210> SEQ ID NO 42
<211> LENGTH: 23
<212> TYPE: PRT
<213> ORGANISM: Homo sapiens

<400> SEQUENCE: 42

Gln Ile Pro Ala Pro Gln Gly Ala Val Leu Val Gln Arg Glu Lys Asp
1               5                   10                  15

Leu Pro Asn Tyr Asn Trp Asn
            20

<210> SEQ ID NO 43
<211> LENGTH: 24
<212> TYPE: PRT
<213> ORGANISM: Homo sapiens

<400> SEQUENCE: 43

Arg Gln Ile Pro Ala Pro Gln Gly Ala Val Leu Val Gln Arg Glu Lys
1               5                   10                  15

Asp Leu Pro Asn Tyr Asn Trp Asn
            20

<210> SEQ ID NO 44
<211> LENGTH: 25
<212> TYPE: PRT
<213> ORGANISM: Homo sapiens

<400> SEQUENCE: 44

Ser Arg Gln Ile Pro Ala Pro Gln Gly Ala Val Leu Val Gln Arg Glu
1               5                   10                  15

Lys Asp Leu Pro Asn Tyr Asn Trp Asn
            20                  25
```

<210> SEQ ID NO 45
<211> LENGTH: 26
<212> TYPE: PRT
<213> ORGANISM: Homo sapiens

<400> SEQUENCE: 45

His Ser Arg Gln Ile Pro Ala Pro Gln Gly Ala Val Leu Val Gln Arg
1               5                   10                  15

Glu Lys Asp Leu Pro Asn Tyr Asn Trp Asn
            20                  25

<210> SEQ ID NO 46
<211> LENGTH: 27
<212> TYPE: PRT
<213> ORGANISM: Homo sapiens

<400> SEQUENCE: 46

Pro His Ser Arg Gln Ile Pro Ala Pro Gln Gly Ala Val Leu Val Gln
1               5                   10                  15

Arg Glu Lys Asp Leu Pro Asn Tyr Asn Trp Asn
            20                  25

<210> SEQ ID NO 47
<211> LENGTH: 28
<212> TYPE: PRT
<213> ORGANISM: Homo sapiens

<400> SEQUENCE: 47

Ala Pro His Ser Arg Gln Ile Pro Ala Pro Gln Gly Ala Val Leu Val
1               5                   10                  15

Gln Arg Glu Lys Asp Leu Pro Asn Tyr Asn Trp Asn
            20                  25

<210> SEQ ID NO 48
<211> LENGTH: 29
<212> TYPE: PRT
<213> ORGANISM: Homo sapiens

<400> SEQUENCE: 48

Ser Ala Pro His Ser Arg Gln Ile Pro Ala Pro Gln Gly Ala Val Leu
1               5                   10                  15

Val Gln Arg Glu Lys Asp Leu Pro Asn Tyr Asn Trp Asn
            20                  25

<210> SEQ ID NO 49
<211> LENGTH: 30
<212> TYPE: PRT
<213> ORGANISM: Homo sapiens

<400> SEQUENCE: 49

Leu Ser Ala Pro His Ser Arg Gln Ile Pro Ala Pro Gln Gly Ala Val
1               5                   10                  15

Leu Val Gln Arg Glu Lys Asp Leu Pro Asn Tyr Asn Trp Asn
            20                  25                  30

<210> SEQ ID NO 50
<211> LENGTH: 31
<212> TYPE: PRT
<213> ORGANISM: Homo sapiens

<400> SEQUENCE: 50

Gly Leu Ser Ala Pro His Ser Arg Gln Ile Pro Ala Pro Gln Gly Ala

```
                1               5                  10                  15
Val Leu Val Gln Arg Glu Lys Asp Leu Pro Asn Tyr Asn Trp Asn
            20                  25                  30
```

<210> SEQ ID NO 51
<211> LENGTH: 32
<212> TYPE: PRT
<213> ORGANISM: Homo sapiens

<400> SEQUENCE: 51

```
Pro Gly Leu Ser Ala Pro His Ser Arg Gln Ile Pro Ala Pro Gln Gly
1               5                   10                  15

Ala Val Leu Val Gln Arg Glu Lys Asp Leu Pro Asn Tyr Asn Trp Asn
            20                  25                  30
```

<210> SEQ ID NO 52
<211> LENGTH: 33
<212> TYPE: PRT
<213> ORGANISM: Homo sapiens

<400> SEQUENCE: 52

```
Gln Pro Gly Leu Ser Ala Pro His Ser Arg Gln Ile Pro Ala Pro Gln
1               5                   10                  15

Gly Ala Val Leu Val Gln Arg Glu Lys Asp Leu Pro Asn Tyr Asn Trp
            20                  25                  30

Asn
```

<210> SEQ ID NO 53
<211> LENGTH: 34
<212> TYPE: PRT
<213> ORGANISM: Homo sapiens

<400> SEQUENCE: 53

```
Gln Gln Pro Gly Leu Ser Ala Pro His Ser Arg Gln Ile Pro Ala Pro
1               5                   10                  15

Gln Gly Ala Val Leu Val Gln Arg Glu Lys Asp Leu Pro Asn Tyr Asn
            20                  25                  30

Trp Asn
```

<210> SEQ ID NO 54
<211> LENGTH: 35
<212> TYPE: PRT
<213> ORGANISM: Homo sapiens

<400> SEQUENCE: 54

```
Arg Gln Gln Pro Gly Leu Ser Ala Pro His Ser Arg Gln Ile Pro Ala
1               5                   10                  15

Pro Gln Gly Ala Val Leu Val Gln Arg Glu Lys Asp Leu Pro Asn Tyr
            20                  25                  30

Asn Trp Asn
        35
```

<210> SEQ ID NO 55
<211> LENGTH: 36
<212> TYPE: PRT
<213> ORGANISM: Homo sapiens

<400> SEQUENCE: 55

```
Ser Arg Gln Gln Pro Gly Leu Ser Ala Pro His Ser Arg Gln Ile Pro
1               5                   10                  15
```

Ala Pro Gln Gly Ala Val Leu Val Gln Arg Glu Lys Asp Leu Pro Asn
            20                  25                  30

Tyr Asn Trp Asn
        35

<210> SEQ ID NO 56
<211> LENGTH: 37
<212> TYPE: PRT
<213> ORGANISM: Homo sapiens

<400> SEQUENCE: 56

Gly Ser Arg Gln Gln Pro Gly Leu Ser Ala Pro His Ser Arg Gln Ile
1               5                   10                  15

Pro Ala Pro Gln Gly Ala Val Leu Val Gln Arg Glu Lys Asp Leu Pro
            20                  25                  30

Asn Tyr Asn Trp Asn
        35

<210> SEQ ID NO 57
<211> LENGTH: 38
<212> TYPE: PRT
<213> ORGANISM: Homo sapiens

<400> SEQUENCE: 57

Ser Gly Ser Arg Gln Gln Pro Gly Leu Ser Ala Pro His Ser Arg Gln
1               5                   10                  15

Ile Pro Ala Pro Gln Gly Ala Val Leu Val Gln Arg Glu Lys Asp Leu
            20                  25                  30

Pro Asn Tyr Asn Trp Asn
        35

<210> SEQ ID NO 58
<211> LENGTH: 39
<212> TYPE: PRT
<213> ORGANISM: Homo sapiens

<400> SEQUENCE: 58

Ser Ser Gly Ser Arg Gln Gln Pro Gly Leu Ser Ala Pro His Ser Arg
1               5                   10                  15

Gln Ile Pro Ala Pro Gln Gly Ala Val Leu Val Gln Arg Glu Lys Asp
            20                  25                  30

Leu Pro Asn Tyr Asn Trp Asn
        35

<210> SEQ ID NO 59
<211> LENGTH: 40
<212> TYPE: PRT
<213> ORGANISM: Homo sapiens

<400> SEQUENCE: 59

Glu Ser Ser Gly Ser Arg Gln Gln Pro Gly Leu Ser Ala Pro His Ser
1               5                   10                  15

Arg Gln Ile Pro Ala Pro Gln Gly Ala Val Leu Val Gln Arg Glu Lys
            20                  25                  30

Asp Leu Pro Asn Tyr Asn Trp Asn
        35                  40

<210> SEQ ID NO 60
<211> LENGTH: 41
<212> TYPE: PRT
<213> ORGANISM: Homo sapiens

<400> SEQUENCE: 60

Pro Glu Ser Ser Gly Ser Arg Gln Gln Pro Gly Leu Ser Ala Pro His
1               5                   10                  15

Ser Arg Gln Ile Pro Ala Pro Gln Gly Ala Val Leu Val Gln Arg Glu
            20                  25                  30

Lys Asp Leu Pro Asn Tyr Asn Trp Asn
        35                  40

<210> SEQ ID NO 61
<211> LENGTH: 42
<212> TYPE: PRT
<213> ORGANISM: Homo sapiens

<400> SEQUENCE: 61

Pro Pro Glu Ser Ser Gly Ser Arg Gln Gln Pro Gly Leu Ser Ala Pro
1               5                   10                  15

His Ser Arg Gln Ile Pro Ala Pro Gln Gly Ala Val Leu Val Gln Arg
            20                  25                  30

Glu Lys Asp Leu Pro Asn Tyr Asn Trp Asn
        35                  40

<210> SEQ ID NO 62
<211> LENGTH: 43
<212> TYPE: PRT
<213> ORGANISM: Homo sapiens

<400> SEQUENCE: 62

Pro Pro Pro Glu Ser Ser Gly Ser Arg Gln Gln Pro Gly Leu Ser Ala
1               5                   10                  15

Pro His Ser Arg Gln Ile Pro Ala Pro Gln Gly Ala Val Leu Val Gln
            20                  25                  30

Arg Glu Lys Asp Leu Pro Asn Tyr Asn Trp Asn
        35                  40

<210> SEQ ID NO 63
<211> LENGTH: 44
<212> TYPE: PRT
<213> ORGANISM: Homo sapiens

<400> SEQUENCE: 63

Ser Pro Pro Pro Glu Ser Ser Gly Ser Arg Gln Gln Pro Gly Leu Ser
1               5                   10                  15

Ala Pro His Ser Arg Gln Ile Pro Ala Pro Gln Gly Ala Val Leu Val
            20                  25                  30

Gln Arg Glu Lys Asp Leu Pro Asn Tyr Asn Trp Asn
        35                  40

<210> SEQ ID NO 64
<211> LENGTH: 45
<212> TYPE: PRT
<213> ORGANISM: Homo sapiens

<400> SEQUENCE: 64

Leu Ser Pro Pro Pro Glu Ser Ser Gly Ser Arg Gln Gln Pro Gly Leu
1               5                   10                  15

Ser Ala Pro His Ser Arg Gln Ile Pro Ala Pro Gln Gly Ala Val Leu
            20                  25                  30

Val Gln Arg Glu Lys Asp Leu Pro Asn Tyr Asn Trp Asn
        35                  40                  45

<210> SEQ ID NO 65
<211> LENGTH: 46
<212> TYPE: PRT
<213> ORGANISM: Homo sapiens

<400> SEQUENCE: 65

Ser Leu Ser Pro Pro Glu Ser Ser Gly Ser Arg Gln Gln Pro Gly
1               5                   10                  15

Leu Ser Ala Pro His Ser Arg Gln Ile Pro Ala Pro Gln Gly Ala Val
            20                  25                  30

Leu Val Gln Arg Glu Lys Asp Leu Pro Asn Tyr Asn Trp Asn
        35                  40                  45

<210> SEQ ID NO 66
<211> LENGTH: 47
<212> TYPE: PRT
<213> ORGANISM: Homo sapiens

<400> SEQUENCE: 66

Thr Ser Leu Ser Pro Pro Glu Ser Ser Gly Ser Arg Gln Gln Pro
1               5                   10                  15

Gly Leu Ser Ala Pro His Ser Arg Gln Ile Pro Ala Pro Gln Gly Ala
            20                  25                  30

Val Leu Val Gln Arg Glu Lys Asp Leu Pro Asn Tyr Asn Trp Asn
        35                  40                  45

<210> SEQ ID NO 67
<211> LENGTH: 48
<212> TYPE: PRT
<213> ORGANISM: Homo sapiens

<400> SEQUENCE: 67

Gly Thr Ser Leu Ser Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be acetylated
<220> FEATURE:
<221> NAME/KEY: MOD_RES
<222> LOCATION: (1)..(4)
<223> OTHER INFORMATION: Alanyl

<400> SEQUENCE: 68

Ala Ala Ala Ala
1

<210> SEQ ID NO 69
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 69

Tyr Asn Trp Asn
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Lys Trp Asn
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Asp Trp Asn
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Tyr Tyr Trp Asn
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Leu Trp Asn
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Asn Ala Asn
1
```

```
<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Asn Leu Asn
1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Asn Ser Asn
1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Asn Asp Asn
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Asn Lys Asn
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Asn Trp Asn
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 80

Leu Asn Trp Asn
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Asn Trp Asn
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Asn Trp Asn
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Asn Trp Asn
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp(For)

<400> SEQUENCE: 84

Tyr Asn Trp Asn
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Psi(CH2NH) bond between residues

<400> SEQUENCE: 85
```

```
Tyr Asn Trp Asn
1

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Pya(4)
<220> FEATURE:
<223> OTHER INFORMATION: C-term amidated

<400> SEQUENCE: 86

Tyr Asn Trp Asn Ser Phe Gly Leu Arg Xaa
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Tyr(Me)
<220> FEATURE:
<223> OTHER INFORMATION: C-term amidated

<400> SEQUENCE: 87

Tyr Asn Trp Asn Ser Phe Gly Leu Arg Tyr
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(2F)
<220> FEATURE:
<223> OTHER INFORMATION: C-term amidated

<400> SEQUENCE: 88

Tyr Asn Trp Asn Ser Phe Gly Leu Arg Phe
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 89

Tyr Asn Trp Asn Tyr Phe Gly Leu Arg Phe
1               5                   10
```

```
<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 90

Tyr Asn Trp Asn Leu Phe Gly Leu Arg Phe
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Tyr
<220> FEATURE:
<223> OTHER INFORMATION: C-term amidated

<400> SEQUENCE: 91

Tyr Asn Trp Asn Ser Phe Gly Leu Arg Phe
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Tyr
<220> FEATURE:
<223> OTHER INFORMATION: C-term amidated

<400> SEQUENCE: 92

Tyr Asn Trp Asn Ser Phe Gly Leu Arg Phe
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 93

Tyr Asn Trp Asn Ser Phe Gly Leu Lys Phe
1               5                   10

<210> SEQ ID NO 94
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: C-term amidated

<400> SEQUENCE: 94

Tyr Asn Trp Asn Ser Phe Gly Ala Arg Phe
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 95

Tyr Asn Trp Asn Ser Phe Ala Leu Arg Phe
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: NMePhe
<220> FEATURE:
<223> OTHER INFORMATION: C-term amidated

<400> SEQUENCE: 96

Tyr Asn Trp Asn Ser Phe Gly Leu Arg Phe
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asn
<220> FEATURE:
<223> OTHER INFORMATION: C-term amidated

<400> SEQUENCE: 97

Asn Ser Phe Gly Leu Arg Phe
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Trp
<220> FEATURE:
```

<223> OTHER INFORMATION: C-term amidated

<400> SEQUENCE: 98

Trp Asn Ser Phe Gly Leu Arg Phe
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asn
<220> FEATURE:
<223> OTHER INFORMATION: C-term amidated

<400> SEQUENCE: 99

Asn Trp Asn Ser Phe Gly Leu Arg Phe
1               5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 100

Tyr Lys Trp Asn Ser Phe Gly Leu Arg Phe
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 101

Tyr Asp Trp Asn Ser Phe Gly Leu Arg Phe
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 102

Tyr Tyr Trp Asn Ser Phe Gly Leu Arg Phe
1               5                   10

<210> SEQ ID NO 103
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 103

Tyr Leu Trp Asn Ser Phe Gly Leu Arg Phe
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Pya(3)
<220> FEATURE:
<223> OTHER INFORMATION: C-term amidated

<400> SEQUENCE: 104

Tyr Asn Trp Asn Ser Phe Gly Leu Arg Xaa
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(4F)
<220> FEATURE:
<223> OTHER INFORMATION: C-term amidated

<400> SEQUENCE: 105

Tyr Asn Trp Asn Ser Phe Gly Leu Arg Phe
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 106

Tyr Asn Ala Asn Ser Phe Gly Leu Arg Phe
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

```
<400> SEQUENCE: 107

Tyr Asn Leu Asn Ser Phe Gly Leu Arg Phe
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 108

Tyr Asn Ser Asn Ser Phe Gly Leu Arg Phe
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 109

Tyr Asn Asp Asn Ser Phe Gly Leu Arg Phe
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 110

Tyr Asn Lys Asn Ser Phe Gly Leu Arg Phe
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 111

Ala Asn Trp Asn Ser Phe Gly Leu Arg Phe
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

```
<400> SEQUENCE: 112

Leu Asn Trp Asn Ser Phe Gly Leu Arg Phe
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 113

Ser Asn Trp Asn Ser Phe Gly Leu Arg Phe
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 114

Asp Asn Trp Asn Ser Phe Gly Leu Arg Phe
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 115

Lys Asn Trp Asn Ser Phe Gly Leu Arg Phe
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(4CN)
<220> FEATURE:
<223> OTHER INFORMATION: C-term amidated

<400> SEQUENCE: 116

Tyr Asn Trp Asn Ser Phe Gly Leu Arg Phe
1               5                   10

<210> SEQ ID NO 117
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp(For)
<220> FEATURE:
<221> NAME/KEY: MOD_RES
<222> LOCATION: (10)..(10)
<223> OTHER INFORMATION: Phe(4CN)
<220> FEATURE:
<223> OTHER INFORMATION: C-term amidated

<400> SEQUENCE: 117

Tyr Asn Trp Asn Ser Phe Gly Leu Arg Phe
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Hph
<220> FEATURE:
<223> OTHER INFORMATION: C-term amidated

<400> SEQUENCE: 118

Tyr Asn Trp Asn Ser Phe Gly Leu Arg Xaa
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: NMeArg
<220> FEATURE:
<223> OTHER INFORMATION: C-term amidated

<400> SEQUENCE: 119

Tyr Asn Trp Asn Ser Phe Gly Leu Arg Phe
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(Me)
<220> FEATURE:
<223> OTHER INFORMATION: C-term amidated

<400> SEQUENCE: 120

Tyr Asn Trp Asn Ser Phe Gly Leu Arg Phe
1               5                   10
```

```
<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(asyMe2)
<220> FEATURE:
<223> OTHER INFORMATION: C-term amidated

<400> SEQUENCE: 121

Tyr Asn Trp Asn Ser Phe Gly Leu Arg Phe
1               5                   10

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr
<220> FEATURE:
<223> OTHER INFORMATION: C-term amidated

<400> SEQUENCE: 122

Tyr Asn Trp Phe Gly Leu Arg Phe
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 123

Tyr Asn Trp Phe Gly Leu Arg Phe
1               5

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(10)
<223> OTHER INFORMATION: Psi(CH2NH) bond between residues
<220> FEATURE:
<223> OTHER INFORMATION: C-term amidated

<400> SEQUENCE: 124

Tyr Asn Trp Asn Ser Phe Gly Leu Arg Phe
1               5                   10

<210> SEQ ID NO 125
<211> LENGTH: 10
```

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(9)
<223> OTHER INFORMATION: Psi(CH2NH) bond between residues
<220> FEATURE:
<223> OTHER INFORMATION: C-term amidated

<400> SEQUENCE: 125

Tyr Asn Trp Asn Ser Phe Gly Leu Arg Phe
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Har
<220> FEATURE:
<223> OTHER INFORMATION: C-term amidated

<400> SEQUENCE: 126

Tyr Asn Trp Asn Ser Phe Gly Leu Xaa Phe
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(Me2)
<220> FEATURE:
<223> OTHER INFORMATION: C-term amidated

<400> SEQUENCE: 127

Tyr Asn Trp Asn Ser Phe Gly Leu Lys Phe
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 128

Tyr Asn Trp Asn Ser Phe Ser Leu Arg Phe
1               5                   10

<210> SEQ ID NO 129
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Nle
<220> FEATURE:
<223> OTHER INFORMATION: C-term amidated

<400> SEQUENCE: 129

Tyr Asn Trp Asn Ser Phe Gly Xaa Arg Phe
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 130

Tyr Asn Trp Asn Ser Phe Gly Val Arg Phe
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 131

Tyr Asn Trp Asn Ser Phe Gly Leu Arg Tyr
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Nal(2)
<220> FEATURE:
<223> OTHER INFORMATION: C-term amidated

<400> SEQUENCE: 132

Tyr Asn Trp Asn Ser Phe Gly Leu Arg Xaa
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(F5)
<220> FEATURE:
```

```
<223> OTHER INFORMATION: C-term amidated

<400> SEQUENCE: 133

Tyr Asn Trp Asn Ser Phe Gly Leu Arg Phe
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Cha
<220> FEATURE:
<223> OTHER INFORMATION: C-term amidated

<400> SEQUENCE: 134

Tyr Asn Trp Asn Ser Phe Gly Leu Arg Xaa
1               5                   10

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(3-Indolyl)propionyl-Asn
<220> FEATURE:
<223> OTHER INFORMATION: C-term amidated

<400> SEQUENCE: 135

Asn Ser Phe Gly Leu Arg Phe
1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 136

Trp Phe Gly Leu Arg Phe
1               5

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: NMeLeu
<220> FEATURE:
<223> OTHER INFORMATION: C-term amidated

<400> SEQUENCE: 137
```

```
Tyr Asn Trp Asn Ser Phe Gly Leu Arg Phe
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeSer
<220> FEATURE:
<223> OTHER INFORMATION: C-term amidated

<400> SEQUENCE: 138

Tyr Asn Trp Asn Ser Phe Gly Leu Arg Phe
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe-Psi(CSNH)
<220> FEATURE:
<223> OTHER INFORMATION: C-term amidated

<400> SEQUENCE: 139

Tyr Asn Trp Asn Ser Phe Gly Leu Arg Phe
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(symMe2)
<220> FEATURE:
<223> OTHER INFORMATION: C-term amidated

<400> SEQUENCE: 140

Tyr Asn Trp Asn Ser Phe Gly Leu Arg Phe
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(4Cl)
<220> FEATURE:
<223> OTHER INFORMATION: C-term amidated
```

```
<400> SEQUENCE: 141

Tyr Asn Trp Asn Ser Phe Gly Leu Arg Phe
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(4NH2)
<220> FEATURE:
<223> OTHER INFORMATION: C-term amidated

<400> SEQUENCE: 142

Tyr Asn Trp Asn Ser Phe Gly Leu Arg Phe
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(4NO2)
<220> FEATURE:
<223> OTHER INFORMATION: C-term amidated

<400> SEQUENCE: 143

Tyr Asn Trp Asn Ser Phe Gly Leu Arg Phe
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Nal(1)
<220> FEATURE:
<223> OTHER INFORMATION: C-term amidated

<400> SEQUENCE: 144

Tyr Asn Trp Asn Ser Phe Gly Leu Arg Xaa
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 145

Tyr Asn Trp Asn Ser Phe Gly Leu Arg Trp
```

```
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Nle
<220> FEATURE:
<223> OTHER INFORMATION: C-term amidated

<400> SEQUENCE: 146

Tyr Asn Trp Asn Ser Phe Gly Leu Xaa Phe
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Cit
<220> FEATURE:
<223> OTHER INFORMATION: C-term amidated

<400> SEQUENCE: 147

Tyr Asn Trp Asn Ser Phe Gly Leu Xaa Phe
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(Me)
<220> FEATURE:
<221> NAME/KEY: MOD_RES
<222> LOCATION: (10)..(10)
<223> OTHER INFORMATION: NMePhe
<220> FEATURE:
<223> OTHER INFORMATION: C-term amidated

<400> SEQUENCE: 148

Tyr Asn Trp Asn Ser Phe Gly Leu Arg Phe
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asn
<220> FEATURE:
```

```
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 149

Asn Ser Phe Gly Leu Arg Phe
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Trp
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 150

Trp Asn Ser Phe Gly Leu Arg Phe
1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 151

Tyr Asn Trp Asn Ser Tyr Gly Leu Arg Phe
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Nal(1)
<220> FEATURE:
<223> OTHER INFORMATION: C-term amidated

<400> SEQUENCE: 152

Tyr Asn Trp Asn Ser Xaa Gly Leu Arg Phe
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)..(6)
<223> OTHER INFORMATION: Nal(2)
<220> FEATURE:
<223> OTHER INFORMATION: C-term amidated

<400> SEQUENCE: 153

Tyr Asn Trp Asn Ser Xaa Gly Leu Arg Phe
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe(F5)
<220> FEATURE:
<223> OTHER INFORMATION: C-term amidated

<400> SEQUENCE: 154

Tyr Asn Trp Asn Ser Phe Gly Leu Arg Phe
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe(4F)
<220> FEATURE:
<223> OTHER INFORMATION: C-term amidated

<400> SEQUENCE: 155

Tyr Asn Trp Asn Ser Phe Gly Leu Arg Phe
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cha
<220> FEATURE:
<223> OTHER INFORMATION: C-term amidated

<400> SEQUENCE: 156

Tyr Asn Trp Asn Ser Xaa Gly Leu Arg Phe
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: misc_feature
<222> LOCATION: (6)..(7)
<223> OTHER INFORMATION: Psi(CH2NH) bond between residues
<220> FEATURE:
<223> OTHER INFORMATION: C-term amidated

<400> SEQUENCE: 157

Tyr Asn Trp Asn Ser Phe Gly Leu Arg Phe
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Dap(Gly)
<220> FEATURE:
<223> OTHER INFORMATION: C-term amidated

<400> SEQUENCE: 158

Tyr Asn Trp Asn Ser Phe Gly Leu Gly Phe
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(7)
<223> OTHER INFORMATION: Psi(CSNH) bond between residues
<220> FEATURE:
<223> OTHER INFORMATION: C-term amidated

<400> SEQUENCE: 159

Tyr Asn Trp Asn Ser Phe Gly Leu Arg Phe
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: AzaGly
<220> FEATURE:
<223> OTHER INFORMATION: C-term amidated

<400> SEQUENCE: 160

Tyr Asn Trp Asn Ser Phe Gly Leu Arg Phe
1               5                   10

<210> SEQ ID NO 161
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phe(4NH2)
<220> FEATURE:
<223> OTHER INFORMATION: C-term amidated

<400> SEQUENCE: 161

Tyr Asn Trp Asn Ser Phe Gly Leu Phe Phe
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phe(4-Guanidino)
<220> FEATURE:
<223> OTHER INFORMATION: C-term amidated

<400> SEQUENCE: 162

Tyr Asn Trp Asn Ser Phe Gly Leu Phe Phe
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Dap(GnGly)
<220> FEATURE:
<223> OTHER INFORMATION: C-term amidated

<400> SEQUENCE: 163

Tyr Asn Trp Asn Ser Phe Gly Leu Gly Phe
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Trp(For)
<220> FEATURE:
<223> OTHER INFORMATION: C-term amidated

<400> SEQUENCE: 164

Tyr Asn Trp Asn Ser Phe Gly Leu Arg Trp
1               5                   10

<210> SEQ ID NO 165
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Abu
<220> FEATURE:
<223> OTHER INFORMATION: C-term amidated

<400> SEQUENCE: 165

Tyr Asn Trp Asn Ser Phe Gly Xaa Arg Phe
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ala(3-Bzt)
<220> FEATURE:
<223> OTHER INFORMATION: C-term amidated

<400> SEQUENCE: 166

Tyr Asn Trp Asn Ser Phe Gly Leu Arg Ala
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(3F)
<220> FEATURE:
<223> OTHER INFORMATION: C-term amidated

<400> SEQUENCE: 167

Tyr Asn Trp Asn Ser Phe Gly Leu Arg Phe
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(3,4F2)
<220> FEATURE:
<223> OTHER INFORMATION: C-term amidated

<400> SEQUENCE: 168

Tyr Asn Trp Asn Ser Phe Gly Leu Arg Phe
1               5                   10

<210> SEQ ID NO 169
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(3,4Cl2)
<220> FEATURE:
<223> OTHER INFORMATION: C-term amidated

<400> SEQUENCE: 169

Tyr Asn Trp Asn Ser Phe Gly Leu Arg Phe
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(3CF3)
<220> FEATURE:
<223> OTHER INFORMATION: C-term amidated

<400> SEQUENCE: 170

Tyr Asn Trp Asn Ser Phe Gly Leu Arg Phe
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ala(2-Qui)
<220> FEATURE:
<223> OTHER INFORMATION: C-term amidated

<400> SEQUENCE: 171

Tyr Asn Trp Asn Ser Phe Gly Leu Arg Ala
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: N((CH2)3Gn)Gly
<220> FEATURE:
<223> OTHER INFORMATION: C-term amidated

<400> SEQUENCE: 172

Tyr Asn Trp Asn Ser Phe Gly Leu Gly Phe
1               5                   10

<210> SEQ ID NO 173
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(Et)
<220> FEATURE:
<223> OTHER INFORMATION: C-term amidated

<400> SEQUENCE: 173

Tyr Asn Trp Asn Ser Phe Gly Leu Arg Phe
1               5                   10

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(3-Indolyl)propionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 174

Asn Ser Phe Gly Leu Arg Phe
1               5

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(8)
<223> OTHER INFORMATION: Psi(CH2NH) bond between residues
<220> FEATURE:
<223> OTHER INFORMATION: C-term amidated

<400> SEQUENCE: 175

Tyr Asn Trp Asn Ser Phe Gly Leu Arg Phe
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Indole-3-carbonyl-Asn
<220> FEATURE:
<221> NAME/KEY: MOD_RES
```

```
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 176

Asn Ser Phe Gly Leu Arg Phe
1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Indol-3-acetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 177

Asn Ser Phe Gly Leu Arg Phe
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(3-Indolyl)butyryl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 178

Asn Ser Phe Gly Leu Arg Phe
1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Diphenylacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 179

Asn Ser Phe Gly Leu Arg Phe
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Phenylpropionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 180

Asn Ser Phe Gly Leu Arg Phe
1               5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 181

Trp Asn Ser Phe Gly Leu Arg Phe
1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Acetyl-Trp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 182

Trp Asn Ser Phe Gly Leu Arg Phe
1               5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Amidino-Trp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 183

Trp Asn Ser Phe Gly Leu Arg Phe
1               5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Ala
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 184

Ala Asn Ser Phe Gly Leu Arg Phe
1               5

<210> SEQ ID NO 185
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Arg
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 185

Arg Asn Ser Phe Gly Leu Arg Phe
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Thr
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 186

Thr Asn Ser Phe Gly Leu Arg Phe
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: n-Hexanoyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 187

Asn Ser Phe Gly Leu Arg Phe
```

```
<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyclohexanecarbonyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 188

Asn Ser Phe Gly Leu Arg Phe
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-(indol-3-yl)ethylcarbamoyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 189

Asn Ser Phe Gly Leu Arg Phe
1               5

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(5)
<223> OTHER INFORMATION: Psi(CH2NH) bond between residues
<220> FEATURE:
<223> OTHER INFORMATION: C-term amidated

<400> SEQUENCE: 190

Tyr Asn Trp Asn Ser Phe Gly Leu Arg Phe
1               5                   10
```

```
<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Psi(CH2NH) bond between residues
<220> FEATURE:
<223> OTHER INFORMATION: C-term amidated

<400> SEQUENCE: 191

Tyr Asn Trp Asn Ser Phe Gly Leu Arg Phe
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(3)
<223> OTHER INFORMATION: Psi(CH2NH) bond between residues
<220> FEATURE:
<223> OTHER INFORMATION: C-term amidated

<400> SEQUENCE: 192

Tyr Asn Trp Asn Ser Phe Gly Leu Arg Phe
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Psi(CH2NH) bond between residues
<220> FEATURE:
<221> NAME/KEY: MOD_RES
<222> LOCATION: (7)..(7)
<223> OTHER INFORMATION: AzaGly
<220> FEATURE:
<221> NAME/KEY: MOD_RES
<222> LOCATION: (9)..(9)
<223> OTHER INFORMATION: Arg(Me)
<220> FEATURE:
<223> OTHER INFORMATION: C-term amidated

<400> SEQUENCE: 193

Tyr Asn Trp Asn Ser Phe Gly Leu Arg Phe
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Nar
```

```
<220> FEATURE:
<223> OTHER INFORMATION: C-term amidated

<400> SEQUENCE: 194

Tyr Asn Trp Asn Ser Phe Gly Leu Xaa Phe
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Nar(Me)
<220> FEATURE:
<223> OTHER INFORMATION: C-term amidated

<400> SEQUENCE: 195

Tyr Asn Trp Asn Ser Phe Gly Leu Xaa Phe
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Har(Me)
<220> FEATURE:
<223> OTHER INFORMATION: C-term amidated

<400> SEQUENCE: 196

Tyr Asn Trp Asn Ser Phe Gly Leu Xaa Phe
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term amidated

<400> SEQUENCE: 197

Tyr Asn Trp Asn Ser Phe Gly Leu Xaa Phe
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
```

```
<223> OTHER INFORMATION: Orn
<220> FEATURE:
<223> OTHER INFORMATION: C-term amidated

<400> SEQUENCE: 198

Tyr Asn Trp Asn Ser Phe Gly Leu Xaa Phe
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Pyridylpropionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 199

Asn Ser Phe Gly Leu Arg Phe
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-Imidazoleacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 200

Asn Ser Phe Gly Leu Arg Phe
1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Piperidinecarbonyl-Asn
<220> FEATURE:
<221> NAME/KEY: MOD_RES
```

```
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 201

Asn Ser Phe Gly Leu Arg Phe
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Piperidineacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 202

Asn Ser Phe Gly Leu Arg Phe
1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Methylpiperidino-1-acetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 203

Asn Ser Phe Gly Leu Arg Phe
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: 1-Pyridinoacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 204

Asn Ser Phe Gly Leu Arg Phe
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Pyridylpropionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 205

Asn Ser Phe Gly Leu Arg Trp
1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Benzoyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 206

Asn Ser Phe Gly Leu Arg Trp
1               5

<210> SEQ ID NO 207
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Benzoyl-Asn
<220> FEATURE:
<221> NAME/KEY: MOD_RES
<222> LOCATION: (3)..(3)
<223> OTHER INFORMATION: Phe(4F)
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 207

Asn Ser Phe Gly Leu Arg Trp
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 208

Asn Thr Phe Gly Leu Arg Trp
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Decanoyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated
```

```
<400> SEQUENCE: 209

Asn Thr Phe Gly Leu Arg Trp
1               5

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 210

Xaa Asn Thr Phe Gly Leu Arg Trp
1               5

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acetyl-Acp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 211

Xaa Asn Thr Phe Gly Leu Arg Trp
1               5

<210> SEQ ID NO 212
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[Bis-(2-Pyridylmethyl)aminomethyl]benzoyl-Phe
<220> FEATURE:
<221> NAME/KEY: MOD_RES
<222> LOCATION: (2)..(2)
<223> OTHER INFORMATION: AzaGly
<220> FEATURE:
<221> NAME/KEY: MOD_RES
```

```
<222> LOCATION: (4)..(4)
<223> OTHER INFORMATION: Arg(Me)
<220> FEATURE:
<223> OTHER INFORMATION: C-term amidated

<400> SEQUENCE: 212

Phe Gly Leu Arg Trp
1               5

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-Ureidobenzoyl-Phe
<220> FEATURE:
<221> NAME/KEY: MOD_RES
<222> LOCATION: (2)..(2)
<223> OTHER INFORMATION: AzaGly
<220> FEATURE:
<221> NAME/KEY: MOD_RES
<222> LOCATION: (4)..(4)
<223> OTHER INFORMATION: Arg(Me)
<220> FEATURE:
<223> OTHER INFORMATION: C-term amidated

<400> SEQUENCE: 213

Phe Gly Leu Arg Trp
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Hyp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 214

Xaa Asn Thr Phe Gly Leu Arg Trp
1               5

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(p-Hydroxyphenyl)propionyl-Hyp
<220> FEATURE:
```

```
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 215

Xaa Asn Thr Phe Gly Leu Arg Trp
1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 216

Glu Asn Thr Phe Gly Leu Arg Trp
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (6)..(6)
<223> OTHER INFORMATION: AzaGly
<220> FEATURE:
<221> NAME/KEY: MOD_RES
<222> LOCATION: (8)..(8)
<223> OTHER INFORMATION: Arg(Me)
<220> FEATURE:
<223> OTHER INFORMATION: C-term amidated

<400> SEQUENCE: 217

Tyr Xaa Asn Thr Phe Gly Leu Arg Trp
1               5

<210> SEQ ID NO 218
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Cha
<220> FEATURE:
<221> NAME/KEY: misc_feature
<222> LOCATION: (2)..(3)
<223> OTHER INFORMATION: Psi[(E)CH=CH] bond between residues
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: Trp(Boc)-Rink Amide MBHA resin

<400> SEQUENCE: 218

Xaa Gly Leu Arg Trp
1               5
```

METASTIN DERIVATIVES AND USE THEREOF

TECHNICAL FIELD

The present invention relates to metastin derivatives and use thereof.

BACKGROUND OF THE INVENTION

Human-derived metastin (also called KiSS-1 peptide) (WO00/24890) and mouse or rat-derived metastin (WO01/75104) are known. Sustained release preparations containing metastin are also known (WO02/85399).

Reportedly, metastin has an effect of suppressing cancer metastasis and is thus effective for preventing/treating cancers (for example, lung cancer, gastric cancer, liver cancer, pancreatic cancer, colorectal cancer, rectal cancer, colonic cancer, prostate cancer, ovarian cancer, cervical cancer, breast cancer, renal cancer, bladder cancer, brain tumor, etc.); metastin also has an effect of controlling the pancreatic function and is effective for preventing/treating pancreatic diseases (e.g., acute or chronic pancreatitis, pancreatic cancer, etc.); and metastin further has an effect of controlling placental function and is effective for preventing/treating choriocarcinoma, hydatidiform mole, invasive mole, miscarriage, fetal hypoplasia, abnormal glucose metabolism, abnormal lipid metabolism or abnormal delivery (WO00/24890, WO01/75104, WO02/85399).

DISCLOSURE OF THE INVENTION

The present invention aims at providing stable metastin derivatives having excellent biological activities (a cancer metastasis suppressing activity, a cancer growth suppressing activity, a gonadotropic hormone secretion stimulating activity, sex hormone secretion stimulating activity, a gonadotropic hormone secretion suppressing activity, sex hormone secretion suppressing activity, etc.)

The present inventors have made extensive studies to solve the foregoing problems and as a result, have found that by substituting the constituent amino acids of metastin with specific amino acids, unexpectedly blood stability, solubility, etc. are more improved, gelation tendency is reduced, pharmacokinetics are also improved, and an excellent cancer metastasis suppressing activity or a cancer growth suppressing activity is exhibited. The present inventors have further found that unexpectedly these metastin derivatives have an effect of suppressing the gonadotropic hormone secretion, an effect of suppressing the sex hormone secretion, etc., which are totally different from the effects known so far. Based on these findings, the present inventors have continued further investigations and come to accomplish the present invention.

That is, the present invention provides the following features, and so on.

[1] A metastin derivative represented by the formula below, or a salt thereof:

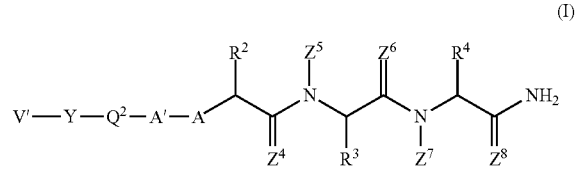

(wherein:
V' represents a group represented by formula:

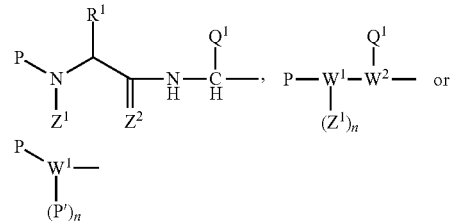

n represents 0 or 1;
$W^1$ represents N, CH or O (provided that when $W^1$ is N or CH, n represents 1 and when $W^1$ is O, n represents 0);
$W^2$ represents N or CH;
each of $Z^1$, $Z^5$ and $Z^7$ represents hydrogen atom or a $C_{1-3}$ alkyl group;
each of $Z^2$, $Z^4$, $Z^6$ and $Z^8$ represents hydrogen atom, O or S;
$R^1$ represents (1) hydrogen atom, (2) a $C_{1-8}$ alkyl group optionally substituted with a substituent selected from the group consisting of an optionally substituted carbamoyl group, an optionally substituted hydroxyl group and an optionally substituted aromatic cyclic group, (3) a cyclic or linear $C_{1-10}$ alkyl group, (4) a $C_{1-10}$ alkyl group consisting of a cyclic alkyl group and a linear alkyl group or (5) an optionally substituted aromatic cyclic group;
$R^2$ represents (1) hydrogen atom or (2) a cyclic or linear $C_{1-10}$ alkyl group, (3) a $C_{1-10}$ alkyl group consisting of a cyclic alkyl group and a linear alkyl group, or (4) a $C_{1-8}$ alkyl group optionally substituted with a substituent selected from the group consisting of an optionally substituted carbamoyl group, an optionally substituted hydroxyl group and an optionally substituted aromatic cyclic group;
$R^3$ represents (1) a $C_{1-8}$ alkyl group having an optionally substituted basic group and optionally having an additional substituent, (2) an aralkyl group having an optionally substituted basic group and optionally having an additional substituent, (3) a $C_{1-4}$ alkyl group having a non-aromatic cyclic hydrocarbon group of carbon atoms not greater than 7 having an optionally substituted basic group, and optionally having an additional substituent, or (4) a $C_{1-4}$ alkyl group having a non-aromatic heterocyclic group of carbon atoms not greater than 7 having an optionally substituted basic group and optionally having an additional substituent;
$R^4$ represents a $C_{1-4}$ alkyl group, which may optionally be substituted with a substituent selected from the group consisting of: (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and, (6) an optionally substituted non-aromatic heterocyclic group having carbon atoms not greater than 7;

$Q^1$ represents a $C_{1-4}$ alkyl group, which may optionally be substituted with a substituent selected from the group consisting of: (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and (6) an optionally substituted non-aromatic heterocyclic group having carbon atoms not greater than 7;

A represents:
(1) a nitrogen atom substituted with hydrogen atom or a $C_{1-3}$ alkyl group;
(2) a carbon atom substituted with hydrogen atom or a $C_{1-3}$ alkyl group;
(3) O; or
(4) S;

A' represents:
(1) a carbon atom, which may optionally be substituted with hydrogen atom, O, S, a halogen atom, an optionally halogenated $C_{1-3}$ alkyl group, carbamoyl group or hydroxyl group;
(2) a nitrogen atom, which may optionally be substituted with hydrogen atom or an optionally halogenated $C_{1-3}$ alkyl group;
(3) O; or
(4) S;

$Q^2$ represents:
(1) $CH_2$, CO, CS or $CH=CH_2$, which may optionally be substituted with one or two $C_{0-4}$ alkyl groups optionally substituted with a substituent selected from the group consisting of carbamoyl group, hydroxyl group, a $C_{1-3}$ alkoxy group, a halogen atom and an amino group;
(2) NH, which may optionally be substituted with a substituent selected from the group consisting of carbamoyl group and hydroxyl group; or,
(3) O;

Y represents:
(1) a group represented by formula: —CONH—, —CSNH—, —CH$_2$NH—, —NHCO—, —CH$_2$O—, —COCH$_2$—, —CH$_2$S—, —CSCH$_2$—, —CH$_2$SO—, —CH$_2$SO$_2$—, —COO—, —CSO—, —CH$_2$CH$_2$— or —CH=CH—, which may optionally be substituted with a substituent selected from the group consisting of a $C_{1-6}$ alkyl group, hydroxyl group and a halogen atom;
(2) an optionally substituted $C_{6-7}$ aromatic hydrocarbon group;
(3) an optionally substituted 4- to 7-membered aromatic heterocyclic group consisting of 1 to 5 carbon atoms and hetero atoms selected from the group consisting of nitrogen, oxygen and sulfur atoms;
(4) an optionally substituted non-aromatic cyclic hydrocarbon group having carbon atoms not greater than 5; or, (5) an optionally substituted non-aromatic heterocyclic group having carbon atoms not greater than 5 and when Y is (2), (3), (4) or (5), $Q^2$ may be a chemical bond.

P and P', which may be the same or different, each may form a ring by combining P and P' or P and $Q^1$ together and represents:
(1) hydrogen atom;
(2) an optional amino acid residue continuously or discontinuously bound from the C-terminal end of the 1st-48th amino acid sequence in the amino acid sequence represented by SEQ ID NO: 1;
(3) a group represented by formula:

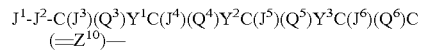

(wherein $J^1$ represents (a) hydrogen atom or (b) (i) a $C_{1-20}$ acyl group, (ii) a $C_{1-20}$ alkyl group, (iii) a $C_{6-14}$ aryl group, (iv) a carbamoyl group, (v) a carboxyl group, (vi) a sulfino group, (vii) an amidino group, (viii) a glyoxyloyl group or (ix) an amino group, which group may optionally be substituted with a substituent containing an optionally substituted cyclic group; $J^2$ represents (1) NH optionally substituted with a $C_{1-6}$ alkyl group, (2) $CH_2$ optionally substituted with a $C_{1-6}$ alkyl group, (3) O or (4) S; each of $J^3$ through $J^6$ represents hydrogen atom or a $C_{1-3}$ alkyl group;

each of $Q^3$ through $Q^6$ represents a $C_{1-4}$ alkyl group, which may optionally be substituted with a substituent selected from the group consisting of:
(1) an optionally substituted $C_{6-12}$ aromatic hydrocarbon group;
(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused-ring group;
(4) an optionally substituted 5- to 14-membered aromatic fused heterocyclic group consisting of 3 to 11 carbon atoms and hetero atoms selected from the group consisting of nitrogen, oxygen and sulfur atoms;
(5) an optionally substituted non-aromatic cyclic hydrocarbon group having carbon atoms not greater than 7;
(6) an optionally substituted non-aromatic heterocyclic group having carbon atoms not greater than 7;
(7) an optionally substituted amino group;
(8) an optionally substituted guanidino group;
(9) an optionally substituted hydroxyl group;
(10) an optionally substituted carboxyl group;
(11) an optionally substituted carbamoyl group; and,
(12) an optionally substituted sulfhydryl group;
or hydrogen atom; $J^3$ and $Q^3$, $J^4$ and $Q^4$, $J^5$ and $Q^5$ or $J^6$ and $Q^6$ may be combined together, or $Z^1$ and $R^1$, $J^2$ and $Q^3$, $Y^1$ and $Q^4$, $Y^2$ and $Q^5$, or $Y^3$ and $Q^6$ may be combined together, to form a ring; $Y^1$ through $Y^3$ each represents a group represented by formula: —CON($J^{13}$)-, —CSN($J^{13}$)-, —C($J^{14}$)N ($J^{13}$)- or —N($J^{13}$)CO— (wherein $J^{13}$ and $J^{14}$ each represents hydrogen atom or a $C_{1-3}$ alkyl group); and $Z^{10}$ represents hydrogen atom, O or S);

(4) a group represented by formula: $J^1$-$J^2$-C($J^7$)($Q^7$)$Y^2$C($J^8$) ($Q^8$)$Y^3$C($J^9$)($Q^9$)C($=Z^{10}$)—

(wherein each of $J^1$ and $J^2$ has the same significance as defined above, $J^7$ through $J^9$ have the same significance as given for $J^3$, $Q^7$ through $Q^9$ have the same significance as given for $Q^3$, $Y^2$ and $Y^3$ have the same significance as defined above, $Z^{10}$ has the same significance as defined above, $J^7$ and $Q^7$, $J^8$ and $Q^8$ or $J^9$ and $Q^9$ may be combined together, or $J^2$ and $Q^7$, $Y^2$ and $Q^8$ or $Y^3$ and $Q^9$ may be combined together, to form a ring.);

(5) a group represented by formula: $J^1$-$J^2$-C($J^{10}$)($Q^{10}$)$Y^3$C($J^{11}$)($Q^{11}$)C(=$Z^{10}$)—
(wherein $J^1$ and $J^2$ have the same significance as defined above, $J^{10}$ and $J^{11}$ have the same significance as given for $J^3$, $Q^{10}$ and $Q^{11}$ have the same significance as given for $Q^3$, $Y^3$ has the same significance as defined above, $Z^{10}$ has the same significance as defined above, $J^{10}$ and $Q^{10}$ or $J^{11}$ and $Q^{11}$ may be combined together, or $J^2$ and $Q^{10}$ or $Y^3$ and $Q^{11}$ may be combined together, to form a ring.);

(6) a group represented by formula: $J^1$-$J^2$-C($J^{12}$)($Q^{12}$)C(=$Z^{10}$)—
(wherein, $J^1$ and $J^2$ have the same significance as defined above, $J^{12}$ has the same significance as given for $J^3$, $Q^{12}$ has the same significance as given for $Q^3$, and $Z^{10}$ has the same significance as defined above; $J^{12}$ and $Q^{12}$ may be combined together, or $J^2$ and $Q^{12}$ may be combined together, to form a ring.); or, (7) a group represented by formula: $J^1$- (wherein $J^1$ has the same significance as defined above); the bonds between Y-$Q^2$, $Q^2$-A' and A'-A each independently represents a single or double bond.);

provided that Ac-D-Tyr-D-Trp-Asn-Thr-PheΨ(CH$_2$NH)Gly-Leu-Arg(Me)-Trp-NH$_2$, Ac-D-Tyr-D-Trp-Asn-Thr-Phe-Gly-Leu-Arg(Me)-Trp-NH$_2$, Ac-D-Tyr-D-Trp-Asn-Thr-D-Phe-Gly-Leu-Arg(Me)-Trp-NH2 and Ac-D-Tyr-D-Trp-Asn-Thr-Phe-Gly-Aib-Arg(Me)-Trp-NH2 are excluded.

[2] The metastin derivative according to [1] or a salt thereof wherein:

$Z^1$, $Z^5$ and $Z^7$ each represents hydrogen atom;

$Z^2$, $Z^4$, $Z^6$ and $Z^8$ each represents O;

$R^1$ represents (2) a $C_{1-8}$ alkyl group optionally substituted with an optionally substituted hydroxyl group;

$R^2$ represents a linear $C_{1-10}$ alkyl group or a $C_{1-10}$ alkyl group consisting of a cyclic alkyl group and a linear alkyl group;

$R^3$ represents (1) a $C_{1-8}$ alkyl group having an optionally substituted basic group and optionally having an additional substituent;

$R^4$ represents (4) a $C_{1-4}$ alkyl group, which may optionally be substituted with an optionally substituted 5- to 14-membered aromatic fused heterocyclic group consisting of 3 to 11 carbon atoms and hetero atoms selected from the group consisting of nitrogen, oxygen and sulfur atoms;

$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, and (5) an optionally substituted non-aromatic cyclic hydrocarbon group having carbon atoms not greater than 7;

A represents (1) a nitrogen atom substituted with hydrogen atom, (2) a carbon atom substituted with hydrogen atom, or (4) S;

A' represents (1) a carbon atom substituted with hydrogen atom or O;

$Q^2$ represents (1) an optionally substituted CH$_2$ or CH=CH$_2$ with one or two $C_{1-4}$ alkyl groups which may optionally be substituted with a substituent selected from the group consisting of carbamoyl group, hydroxyl group, a $C_{1-3}$ alkoxy group and an amino group; and, Y represents (1) a group represented by formula: —CONH—, —CSNH—, —NHCO—, —CH$_2$O—, —CH$_2$S—, —COCH$_2$—, —CH=CH— or —CH$_2$CH$_2$— $C_{1-6}$, which may optionally be substituted with a substituent selected from the group consisting of an alkyl group, hydroxyl group and a halogen group.

[3] A metastin derivative represented by the formula below, or a salt thereof:

XX0-XX2-XX3-XX4-XX5-T-XX9-XX10-NH$_2$ wherein:

XX0 represents formyl, $C_{1-20}$ alkanoyl, cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl or 6-aminocaproyl;

XX2 represents Tyr, D-Tyr, D-Ala, D-Leu, D-Phe, D-Lys, D-Trp or a chemical bond;

XX3 represents D-Asp, D-Dap, D-Ser, D-Gln, D-His, D-NMeAla, D-NMePhe, Aze(2), Pic(2), Pic(3), Hyp, Thz, NMeAla, Gly, Aib, Abz(2), Abz(3), Sar, Leu, Lys, Glu, β-alanine, Pzc(2), Orn, His(3Me), Tyr(PO$_3$H$_2$), Pro(4NH$_2$), Hyp(Bzl), Trp, Pro, 4-pyridylalanine, Tic, D-Trp, D-Ala, D-Leu, D-Phe, D-Lys, D-Glu, D-2-pyridylalanine, D-3-pyridylalanine, D-4-pyridylalanine, Aad, Pro(4F) or a chemical bond;

XX4 represents Asn, 2-amino-3-ureidopropionic acid, N$^β$-formyldiaminopropionic acid, N$^β$-acetyldiaminopropionic acid, N$^ω$-pentylasparagine, N$^ω$-cyclopropylasparagine, N$^ω$-benzylasparagine, 2,4-diaminobutanoic acid, His, Gln, Cit or D-Asn;

XX5 represents Ser, Thr, Val, NMeSer, Gly, Ala, Hyp, D-Ala, Dap or D-Thr;

T represents a group represented by formula II:

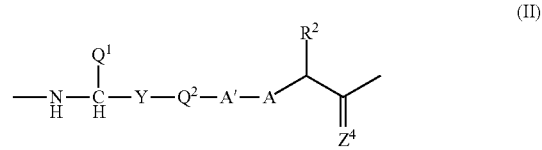

$Z^4$ represents hydrogen atom, O or S;

$R^2$ represents (1) hydrogen atom or (2) a cyclic or linear $C_{1-10}$ alkyl group, (3) a $C_{1-10}$ alkyl group consisting of a cyclic alkyl group and a linear alkyl group, or (4) a $C_{1-8}$ alkyl group optionally substituted with a substituent selected from the group consisting of an optionally substituted carbamoyl group, an optionally substituted hydroxyl group and an optionally substituted aromatic cyclic group;

$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7 and (6) an optionally substituted non-aromatic heterocyclic group having carbon atoms not greater than 7;

A represents:
(1) a nitrogen atom substituted with hydrogen atom or a $C_{1-3}$ alkyl group,
(2) a carbon atom substituted with hydrogen atom or a $C_{1-3}$ alkyl group,
(3) O, or
(4) S;

A' represents:
(1) a carbon atom, which may optionally be substituted with hydrogen atom, O, S, a halogen atom, an optionally halogenated $C_{1-3}$ alkyl group, carbamoyl group or hydroxyl group,
(2) a nitrogen atom, which may optionally be substituted with hydrogen atom or an optionally substituted $C_{1-3}$ alkyl group,
(3) O, or,
(4) S;

$Q^2$ represents:
(1) $CH_2$, CO, CS or $CH=CH_2$, which may optionally be substituted with a $C_{0-4}$ alkyl group optionally substituted with a substituent selected from the group consisting of carbamoyl group, hydroxyl group, a $C_{1-3}$ alkoxy group, a halogen atom and an amino group,
(2) NH, which may optionally be substituted with an optionally substituted $C_{1-4}$ alkyl group with a substituent selected from the group consisting of carbamoyl group and hydroxyl group, or
(3) O;

Y represents:
(1) a group represented by formula: —CONH—, —CSNH—, —CH$_2$NH—, —NHCO—, —CH$_2$O—, —COCH$_2$—, —CH$_2$S—, —CSCH$_2$—, —CH$_2$SO—, —CH$_2$SO$_2$—, —COO—, —CSO—, —CH$_2$CH$_2$— or —CH=CH—, which may optionally be substituted with a substituent selected from the group consisting of a $C_{1-6}$ alkyl group, hydroxyl group and a halogen atom,
(2) an optionally substituted $C_{6-7}$ aromatic hydrocarbon group,
(3) an optionally substituted 4- to 7-membered aromatic heterocyclic group consisting of 1 to 5 carbon atoms and hetero atoms selected from the group consisting of nitrogen, oxygen and sulfur atoms,
(4) an optionally substituted non-aromatic cyclic hydrocarbon group having carbon atoms not greater than 5, or,
(5) an optionally substituted non-aromatic cyclic hydrocarbon group having carbon atoms not greater than 5 and when Y is (2), (3), (4) or (5), $Q^2$ may be a chemical bond;
the bonds between Y-$Q^2$, $Q^2$-A' and A'-A each independently represents a single or double bond;
XX9 represents Arg, Orn, Arg(Me) or Arg(asymMe$_2$); and,
XX10 represents Phe, Trp, 2-naphthylalanine, 2-thienylalanine, tyrosine or 4-fluorophenylalanine;
provided that Ac-D-Tyr-D-Trp-Asn-Thr-PheΨ(CH$_2$NH)Gly-Leu-Arg(Me)-Trp-NH$_2$, Ac-D-Tyr-D-Trp-Asn-Thr-Phe-Gly-Leu-Arg(Me)-Trp-NH$_2$, Ac-D-Tyr-D-Trp-Asn-Thr-D-Phe-Gly-Leu-Arg(Me)-Trp-NH$_2$ and Ac-D-Tyr-D-Trp-Asn-Thr-Phe-Gly-Aib-Arg(Me)-Trp-NH$_2$ are excluded. In the formula "XX0-XX2-XX3-XX4-XX5-T-XX9-XX10-NH$_2$" described above, each of the bonds "—" between XX0, XX2, XX3, XX4, XX5, T, XX9, XX10 and NH$_2$ has different significance. For example, the bond "—" between XX0-XX1 denotes the bond between the alkanoyl group and the amino group in XX2; the bonds "—" between XX2-XX3, XX3-XX4, XX4-XX5, XX5-T, T-XX9 and XX9-XX10 normally denote the bond between C=O and NH in the amide bond to connect the adjacent amino acid residues; and the bond "—" between XX10-NH$_2$ denotes the carbonyl group and the amino group in XX10. That is, in the bond between amino acid residues, the bond denotes the bond between C=O and NH which are the residues of the carboxyl and amino groups provided for the reaction, respectively. Specific examples of the bonds include those shown by the structural formulas in TABLE 1 later described.

[4] The metastin derivative according to [3] or a salt thereof, wherein:
XX0 represents formyl, a $C_{1-6}$ alkanoyl or glycoloyl;
XX2 represents D-Tyr or a chemical bond;
XX3 represents Aze(2), Hyp, Gly, Aib, Leu, Lys, Glu, His(3Me), Tyr(PO$_3$H$_2$), Pro(4F) or Hyp(Bzl);
XX4 represents Asn or 2-amino-3-ureidopropinonic acid;
XX5 represents Ser or Thr;
$Z^4$ represents O;
$R^2$ represents a linear $C_{1-10}$ alkyl group or a $C_{1-10}$ alkyl group consisting of a cyclic alkyl group and a linear alkyl group;
$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, and (5) an optionally substituted non-aromatic cyclic hydrocarbon group having carbon atoms not greater than 7;
A represents (1) a nitrogen atom substituted with hydrogen atom, (2) a carbon atom substituted with hydrogen atom, or (4) S;
At represents (1) a carbon atom substituted with hydrogen atom or O;
$Q^2$ represents (1) an optionally substituted $CH_2$ or $CH=CH_2$ with one or two $C_{0-4}$ alkyl groups which may optionally be substituted with a substituent selected from the group consisting of carbamoyl group, hydroxyl group, a $C_{1-3}$ alkoxy group and an amino group;
Y represents (1) a group represented by formula: —CONH—, —CH$_2$O—, —CH$_2$S—, —COCH$_2$—, —CH$_2$CH$_2$—, CSNH—, —NHCO— or —CH=CH—, which may optionally be substituted with a substituent selected from the group consisting of a $C_{1-6}$ alkyl group, hydroxyl group and a halogen atom;
XX9 represents Arg or Arg(Me); and,
XX10 represents Phe or Trp.

[5] The metastin derivative according to [3], or a salt thereof, or a prodrug thereof, wherein:
XX0 represents $C_{1-12}$ alkanoyl;
XX2 represents D-Tyr;
XX3 represents Hyp, Pro(4F) or Glu;
XX4 represents Asn or 2-amino-3-ureidopropionic acid;
XX5 represents Thr;
$Z^4$ represents O,
$R^2$ represents a linear $C_{1-10}$ alkyl group or a $C_{1-10}$ alkyl group consisting of a cyclic alkyl group and a linear alkyl group;
$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, and (5) an optionally substituted non-aromatic cyclic hydrocarbon group having carbon atoms not greater than 7;

A represents (1) a nitrogen atom substituted with hydrogen atom, (2) a carbon atom substituted with hydrogen atom, or (4) S;

A' represents (1) a carbon atom substituted with hydrogen atom or O;

$Q^2$ represents (1) an optionally substituted $CH_2$ or $CH=CH_2$ with one or two $C_{1-4}$ alkyl groups which may optionally be substituted with a substituent selected from the group consisting of carbamoyl group, hydroxyl group, a $C_{1-3}$ alkoxy group and an amino group;

Y represents (1) a group represented by formula: —CONH—, —CSNH—, —NHCO—, —CH$_2$O—, —CH$_2$S—, —COCH$_2$—, —CH=CH— or —CH$_2$CH$_2$—, which may optionally be substituted with a $C_{1-6}$ alkyl group, hydroxyl group or a halogen atom;

XX9 represents Arg or Arg(Me); and,

XX10 represents Trp.

[5a] A compound below, or a salt or prodrug thereof:

Ac-D-Tyr-Hyp-Asn-Thr-Phe-Gly-Leu-Arg(Me)-Trp-NH$_2$ (Compound No. 796),

Ac-D-Tyr-Hyp-Asn-Thr-Phe-Ala-Leu-Arg(Me)-Trp-NH$_2$ (Compound No. 803),

Ac-D-Tyr-Hyp-Asn-Thr-Phe-Ser-Leu-Arg(Me)-Trp-NH$_2$ (Compound No. 804),

Ac-D-Tyr-Hyp-Asn-Thr-Phe-Aib-Leu-Arg(Me)-Trp-NH$_2$ (Compound No. 811),

Ac-D-Tyr-Hyp-Asn-Thr-Phe-Abu-Leu-Arg(Me)-Trp-NH$_2$ (Compound No. 818),

Ac-D-Tyr-Hyp-Asn-Thr-Cha-Gly-Leu-Arg(Me)-Trp-NH$_2$ (Compound No. 822),

Ac-D-Tyr-Hyp-Asn-Thr-Cha-Ala-Leu-Arg(Me)-Trp-NH$_2$ (Compound No. 823),

Ac-D-Tyr-Hyp-Asn-Thr-Phe-Dap-Leu-Arg(Me)-Trp-NH$_2$ (Compound No. 827),

Ac-D-Tyr-Hyp-Asn-Thr-Phe-Ser(Me)-Leu-Arg(Me)-Trp-NH$_2$ (Compound No. 828),

Ac-D-Tyr-Hyp-Asn-Thr-PheΨ(CH$_2$O)Gly-Leu-Arg(Me)-Trp-NH$_2$ (Compound No. 834), Ac-D-Tyr-Hyp-Asn-Thr-Pya(2)-Gly-Leu-Arg(Me)-Trp-NH$_2$ (Compound No. 839), Ac-D-Tyr-Hyp-Asn-Thr-Phe-Val-Leu-Arg(Me)-Trp-NH$_2$ (Compound No. 847), Ac-D-Tyr-Hyp-Asn-Thr-Pya(3)-Gly-Leu-Arg(Me)-Trp-NH$_2$ (Compound No. 848), Ac-D-Tyr-Hyp-Asn-Thr-Pya(4)-Gly-Leu-Arg(Me)-Trp-NH$_2$ (Compound No. 849), Ac-D-Tyr-Hyp-Asn-Thr-PheΨ(CH$_2$CH$_2$)Gly-Leu-Arg(Me)-Trp-NH$_2$ (Compound No. 850), Ac-D-Tyr-Hyp-Asn-Thr-PheΨ(COCH$_2$)Gly-Leu-Arg(Me)-Trp-NH$_2$ (Compound No. 851), Ac-D-Tyr-Glu-Asn-Thr-Phe-Gly-Leu-Arg(Me)-Trp-NH$_2$ (Compound No. 852), Ac-D-Tyr-Glu-Asn-Thr-Cha-Gly-Leu-Arg(Me)-Trp-NH$_2$ (Compound No. 853), Ac-D-Tyr-Hyp-Asn-Thr-Phe-GlyΨ(CH$_2$NH)Leu-Arg(Me)-Trp-NH$_2$ (Compound No. 854), Ac-D-Tyr-Hyp-Asn-Thr-Ala(cPr)-Gly-Leu-Arg(Me)-Trp-NH$_2$ (Compound No. 855), Ac-D-Tyr-Hyp-Asn-Thr-PheΨ((S)CHOH—CH$_2$)Gly-Leu-Arg(Me)-Trp-NH$_2$ (Compound No. 857), Ac-D-Tyr-Hyp-Asn-Thr-PheΨ((S)CHOH-(E)CH=)Gly-Leu-Arg(Me)-Trp-NH$_2$ (Compound No. 858), Ac-D-Tyr-Hyp-Asn-Thr-PheΨ((E)CH=CH)Gly-Leu-Arg(Me)-Trp-NH$_2$ (Compound No. 859), Ac-D-Tyr-Hyp-Asn-Thr-PheΨ((R)CHOH-(E)CH=)Gly-Leu-Arg(Me)-Trp-NH$_2$ (Compound No. 866), Ac-D-Tyr-Hyp-Asn-Thr-PheΨ((R)CHOH—CH$_2$)Gly-Leu-Arg(Me)-Trp-NH$_2$ (Compound No. 867), Ac-D-Tyr-Hyp-Asn-Thr-αMePhe-Gly-Leu-Arg(Me)-Trp-NH$_2$ (Compound No. 869), Ac-D-Tyr-Hyp-Asn-Thr-Phe(2Me)-Gly-Leu-Arg(Me)-Trp-NH$_2$ (Compound No. 871), Ac-D-Tyr-Hyp-Asn-Thr-Phe(3Me)-Gly-Leu-Arg(Me)-Trp-NH$_2$ (Compound No. 873), Ac-D-Tyr-Hyp-Asn-Thr-Phe(4Me)-Gly-Leu-Arg(Me)-Trp-NH$_2$ (Compound No. 875), Ac-D-Tyr-Hyp-Alb-Thr-Phe-Gly-Leu-Arg(Me)-Trp-NH$_2$ (Compound No. 885), Ac-D-Tyr-Hyp-Asn-Thr-Phe-GlyΨ((E)CH=CH)Leu-Arg(Me)-Trp-NH$_2$ (Compound No. 892), Ac-D-Tyr-Hyp-Asn-Thr-Phe-GlyΨ(CH$_2$CH$_2$)Leu-Arg(Me)-Trp-NH$_2$ (Compound No. 893), Ac-D-Tyr-Hyp-Asn-Thr-Cha-Gly-Ala(cPr)-Arg(Me)-Trp-NH$_2$ (Compound No. 894), Ac-D-Tyr-Glu-Asn-Thr-Cha-Gly-Ala(cPr)-Arg(Me)-Trp-NH$_2$ (Compound No. 895), Ac-D-Tyr-Hyp-Asn-Thr-Cha-GlyΨ((E)CH=CH)Leu-Arg(Me)-Trp-NH$_2$ (Compound No. 902), Ac-D-Tyr-Hyp-Alb-Thr-Cha-GlyΨ((E)CH=CH)Leu-Arg(Me)-Trp-NH$_2$ (Compound No. 903), Ac-D-Tyr-Glu-Asn-Thr-Cha-GlyΨ((E)CH=CH)Leu-Arg(Me)-Trp-NH$_2$ (Compound No. 904), Ac-D-Tyr-Glu-Alb-Thr-Cha-GlyΨ((E)CH=CH)Leu-Arg(Me)-Trp-NH$_2$ (Compound No. 905), Ac-D-Tyr-Hyp-Alb-Thr-Phe-GlyΨ((E)CH=CH)Leu-Arg(Me)-Trp-NH$_2$ (Compound No. 906), Ac-D-Tyr-Glu-Asn-Thr-Phe-GlyΨ((E)CH=CH)Leu-Arg(Me)-Trp-NH$_2$ (Compound No. 907), Ac-D-Tyr-Glu-Alb-Thr-Phe-GlyΨ((E)CH=CH)Leu-Arg(Me)-Trp-NH$_2$ (Compound No. 908), Ac-D-Tyr-Asp-Asn-Thr-Cha-Gly-Ala(cPr)-Arg(Me)-Trp-NH$_2$ (Compound No. 909), Ac-D-Tyr-Aad-Asn-Thr-Cha-Gly-Ala(cPr)-Arg(Me)-Trp-NH$_2$ (Compound No. 910), Ac-D-Tyr-Lys-Asn-Thr-Cha-Gly-Ala(cPr)-Arg(Me)-Trp-NH$_2$ (Compound No. 911), Ac-D-Tyr-Aib-Asn-Thr-Cha-Gly-Ala(cPr)-Arg(Me)-Trp-NH$_2$ (Compound No. 912), Ac-D-Tyr-Hyp-Gln-Thr-Cha-GlyΨ((E)CH=CH)Leu-Arg(Me)-Trp-NH$_2$ (Compound No. 913), Ac-D-Tyr-Hyp-Cit-Thr-Cha-GlyΨ((E)CH=CH)Leu-Arg(Me)-Trp-NH$_2$ (Compound No. 914), Ac-D-Tyr-Hyp-Glu-Thr-Cha-GlyΨ((E)CH=CH)Leu-Arg(Me)-Trp-NH$_2$ (Compound No. 915), Ac-D-Tyr-Hyp-Asn-Thr-Phe-Gly-Ala(cPr)-Arg(Me)-Trp-NH$_2$ (Compound No. 916), Ac-D-Tyr-Hyp-Asn-Thr-Phe-Gly-Ser(Me)-Arg(Me)-Trp-NH$_2$ (Compound No. 917), Ac-D-Tyr-Hyp-Asn-Thr-Phe-Gly-Nva-Arg(Me)-Trp-NH$_2$ (Compound No. 918), Ac-D-Tyr-Hyp-Asn-Thr-Nal(2)-Gly-Ala(cPr)-Arg(Me)-Trp-NH$_2$ (Compound No. 919), Ac-D-Tyr-Hyp-Asn-Thr-Cha-Gly-Ser(Me)-Arg(Me)-Trp-NH$_2$ (Compound No. 920), Ac-D-Tyr-Hyp-Asn-Thr-Cha-Gly-Nva-Arg(Me)-Trp-NH$_2$ (Compound No. 921), Ac-D-Tyr-Glu-Asn-Thr-Cha-Gly-Ser(Me)-Arg(Me)-Trp-NH$_2$ (Compound No. 923), Ac-D-Tyr-Glu-Asn-Thr-Cha-Gly-Nva-Arg(Me)-Trp-NH$_2$ (Compound No. 924), Ac-D-Tyr-Hyp-Asn-Thr-Phe-GlyΨ((E)CH=CH)Leu-Arg-Trp-NH$_2$ (Compound No. 925), Ac-D-Tyr-Hyp-Asn-Thr-Cha-GlyΨ((E)CH=CH)Leu-Arg-Trp-NH$_2$ (Compound No. 926),
Ac-D-Tyr-Hyp-Alb-Thr-Cha-GlyΨ((E)CH=CH)Leu-Arg-Trp-NH$_2$ (Compound No. 927),
Ac-D-Tyr-Hyp-Asn-Thr-Phe-GlyΨ(CH$_2$S)Leu-Arg(Me)-Trp-NH$_2$ (Compound No. 929),
Ac-D-Tyr-Hyp-Asn-Thr-Cha-GlyΨ(CH$_2$S)Leu-Arg(Me)-Trp-NH$_2$ (Compound No. 931),
Ac-D-Tyr-Hyp-Asn-Thr-Cha-Gly-Nle-Arg(Me)-Trp-NH$_2$ (Compound No. 932),
Ac-D-Tyr-Hyp-Asn-Thr-Cha-Gly-Leu(Me)-Arg(Me)-Trp-NH$_2$ (Compound No. 933),
Ac-D-Tyr-Hyp-Asn-Thr-Cha-Gly-Cha-Arg(Me)-Trp-NH$_2$ (Compound No. 934),
Ac-D-Tyr-Hyp-Asn-Thr-Cha-Gly-Ala(cPr)-Arg-Trp-NH$_2$ (Compound No. 940),
Ac-D-Tyr-Glu-Asn-Thr-Cha-Gly-Ala(cPr)-Arg-Trp-NH$_2$ (Compound No. 942),
Ac-D-Tyr-Hyp-Asn-Thr-PheΨ(CH$_2$S)Gly-Leu-Arg(Me)-Trp-NH$_2$ (Compound No. 944),
Ac-D-Tyr-Hyp-Asn-Thr-Ala(cBu)-Gly-Ala(cPr)-Arg(Me)-Trp-NH$_2$ (Compound No. 945),
Ac-D-Tyr-Hyp-Asn-Thr-Cha-Gly-Ala(cBu)-Arg(Me)-Trp-NH$_2$ (Compound No. 946),
Ac-D-Tyr-Hyp-Alb-Ala-Cha-Gly-Ala(cPr)-Arg(Me)-Trp-NH$_2$ (Compound No. 947),
Ac-D-Tyr-Hyp-Alb-Ser-Cha-Gly-Ala(cPr)-Arg(Me)-Trp-NH$_2$ (Compound No. 948),
Ac-D-Tyr-Hyp-Alb-Gly-Cha-Gly-Ala(cPr)-Arg(Me)-Trp-NH$_2$ (Compound No. 949),
Ac-D-Tyr-Hyp-Alb-Dap-Cha-Gly-Ala(cPr)-Arg(Me)-Trp-NH$_2$ (Compound No. 951),
Ac-D-Tyr-Hyp-Alb-Thr-Cha-GlyΨ(CH$_2$CH$_2$)Leu-Arg-Trp-NH$_2$ (Compound No. 952),
Ac-D-Tyr-Hyp-Alb-Thr-Cha-Gly-Ala(cPr)-Arg(Me)-Trp-NH$_2$ (Compound No. 953),
Ac-D-Tyr-Hyp-Asn-Thr-Cha-GlyΨ(CH$_2$CH$_2$)Leu-Arg-Trp-NH$_2$ (Compound No. 956),
Ac-D-Tyr-Hyp-Alb-Thr-Cha-GlyΨ(CH$_2$CH$_2$)Leu-Arg(Me)-Trp-NH$_2$ (Compound No. 957),
Ac-D-Tyr-Pro(4F)-Asn-Thr-Cha-Gly-Ala(cPr)-Arg(Me)-Trp-NH$_2$ (Compound No. 959), or,
Ac-D-Tyr-Hyp-Asn-Thr-PheΨ(CH$_2$CH$_2$)AzaGly-Leu-Arg(Me)-Trp-NH$_2$ (Compound No. 968).

[6] A compound selected from:
Ac-D-Tyr-Hyp-Asn-Thr-Cha-Gly-Ala(cPr)-Arg(Me)-Trp-NH$_2$ (Compound No. 894),
Ac-D-Tyr-Hyp-Asn-Thr-Cha-GlyΨ((E)CH=CH)Leu-Arg(Me)-Trp-NH$_2$ (Compound No. 902),
Ac-D-Tyr-Hyp-Alb-Thr-Cha-GlyΨ((E)CH=CH)Leu-Arg(Me)-Trp-NH$_2$ (Compound No. 903),
Ac-D-Tyr-Hyp-Asn-Thr-Cha-GlyΨ((E)CH=CH)Leu-Arg-Trp-NH$_2$ (Compound No. 926),
Ac-D-Tyr-Hyp-Alb-Thr-Cha-GlyΨ((E)CH=CH)Leu-Arg-Trp-NH$_2$ (Compound No. 927),
Ac-D-Tyr-Hyp-Alb-Thr-Cha-Gly-Ala(cPr)-Arg(Me)-Trp-NH$_2$ (Compound No. 953) and
Ac-D-Tyr-Pro(4F)-Asn-Thr-Cha-Gly-Ala(cPr)-Arg(Me)-Trp-NH$_2$ (Compound No. 959).

[7] The metastin derivative according to [1] or a salt thereof, or a prodrug thereof.

[8] The metastin derivative according to [3] or a salt thereof, or a prodrug thereof.

[9] A medicament comprising the metastin derivative according to [1] through [6] or a salt thereof, or a prodrug thereof.

[10] The medicament according to [9] above, which is an agent for suppressing cancer metastasis or an agent for suppressing cancer growth.

[11] The medicament according to [9] above, which is an agent for preventing/treating cancer.

[12] The medicament according to [9] above, which is an agent for controlling the placental function.

[13] The medicament according to [9] above, which is an agent for preventing/treating choriocarcinoma, hydatidiform mole, invasive mole, miscarriage, fetal hypoplasia, abnormal glucose metabolism, abnormal lipid metabolism or labor induction.

[14] The medicament according to [9] above, which is an agent for improving the gonadal function.

[15] The medicament according to [9] above, which is an agent for preventing/treating hormone-dependent cancer, infertility, endometriosis, early puberty or myoma of the uterus.

[16] The medicament according to [9] above, which is an agent for inducing or stimulating ovulation.

[17] The medicament according to [9] above, which is a gonadotropic hormone secretagogue agent or a sex hormone secretagogue agent.

[18] The medicament according to [9] above, which is an agent for preventing/treating Alzheimer's disease, moderate cognitive impairment or autism.

[19] The medicament according to [17] above, which is an agent for down-regulating gonadotropic hormone or sex hormone.

[20] The medicament according to [17] above, which is an agent for down-regulating human OT7T175 (metastin receptor) protein consisting of the amino acid sequence represented by SEQ ID NO: 9.

[21] The medicament according to [19] or [20] above, which is an agent for preventing/treating hormone-dependent cancer.

The present invention further provides the following features, and so on.

[22] A method for suppressing cancer metastasis or suppressing cancer growth, which comprises administering to a mammal an effective dose of the metastin derivative according to any one of [1] through [6] or a salt thereof, or a prodrug thereof.

[23] A method for preventing/treating cancer, which comprises administering to a mammal an effective dose of the metastin derivative according to any one of [1] through [6] or a salt thereof, or a prodrug thereof.

[24] A method for controlling the placental function, which comprises administering to a mammal an effective dose of the metastin derivative according to any one of [1] through [6] or a salt thereof, or a prodrug thereof.

[25] A method of preventing/treating choriocarcinoma, hydatidiform mole, invasive mole, miscarriage, fetal hypoplasia, abnormal glucose metabolism, abnormal lipid metabolism or labor induction, which comprises administering to a mammal an effective dose of the metastin derivative according to any one of [1] through [6] or a salt thereof, or a prodrug thereof.

[26] A method for improving the gonadal function, which comprises administering to a mammal an effective dose of the metastin derivative according to any one of [1] through [6] or a salt thereof, or a prodrug thereof.

[27] A method for preventing/treating hormone-dependent cancer, infertility, endometriosis, early puberty or myoma of the uterus, which comprises administering to a mammal an effective dose of the metastin derivative according to any one of [1] through [6] or a salt thereof, or a prodrug thereof.

[28] A method for inducing or stimulating ovulation, which comprises administering to a mammal an effective dose of the metastin derivative according to any one of [1] through [6] or a salt thereof, or a prodrug thereof.

[29] A method for inducing gonadotropic hormone secretion or inducing sex hormone secretion, which comprises administering to a mammal an effective dose of the metastin derivative according to any one of [1] through [6] or a salt thereof, or a prodrug thereof.

[30] A method for preventing/treating Alzheimer's disease, moderate cognitive impairment or autism, which comprises administering to a mammal an effective dose of the metastin derivative according to any one of [1] through [6] or a salt thereof, or a prodrug thereof.

[31] A method for down-regulation of gonadotropic hormone or sex hormone, which comprises administering to a mammal an effective dose of the metastin derivative according to any one of [1] through [6] or a salt thereof, or a prodrug thereof.

[32] A method for down-regulating human OT7T175 (metastin receptor) protein consisting of the amino acid sequence represented by SEQ ID NO: 9, which comprises administering to a mammal an effective dose of the metastin derivative according to any one of [1] through [6] or a salt thereof, or a prodrug thereof.

[33] A method for preventing/treating hormone-dependent cancer, which comprises administering to a mammal an effective dose of the metastin derivative according to any one of [1] through [6] or a salt thereof, or a prodrug thereof.

[34] Use of the metastin derivative according to any one of [1] through [6] or a salt thereof, or a prodrug thereof, to manufacture an agent for suppressing cancer metastasis or an agent for suppressing cancer growth.

[34a] The metastin derivative according to any one of [1] through [6] or a salt thereof, or a prodrug thereof; for use in suppressing cancer metastasis or suppressing cancer growth.

[35] Use of the metastin derivative according to any one of [1] through [6] or a salt thereof, or a prodrug thereof, to manufacture an agent for preventing/treating cancer.

[35a] The metastin derivative according to any one of [1] through [6] or a salt thereof; or a prodrug thereof, for use in preventing/treating cancer.

[36] Use of the metastin derivative according to any one of [1] through [6] or a salt thereof; or a prodrug thereof, to manufacture an agent for controlling the placental function.

[36a] The metastin derivative according to any one of [1] through [6] or a salt thereof; or a prodrug thereof, for use in controlling the placental function.

[37] Use of the metastin derivative according to any one of [1] through [6] or a salt thereof; or a prodrug thereof; to manufacture an agent for preventing/treating choriocarcinoma, hydatidiform mole, invasive mole, miscarriage, fetal hypoplasia, abnormal glucose metabolism, abnormal lipid metabolism or labor induction.

[37a] The metastin derivative according to any one of [1] through [6] or a salt thereof; or a prodrug thereof, for use in preventing/treating choriocarcinoma, hydatidiform mole, invasive mole, miscarriage, fetal hypoplasia, abnormal glucose metabolism, abnormal lipid metabolism or labor induction.

[38] Use of the metastin derivative according to any one of [1] through [6] or a salt thereof, or a prodrug thereof, to manufacture an agent for improving the gonadal function.

[38a] The metastin derivative according to any one of [1] through [6] or a salt thereof, or a prodrug thereof; for use in improving the gonadal function.

[39] Use of the metastin derivative according to any one of [1] through [6] or a salt thereof, or a prodrug thereof, to manufacture an agent for preventing/treating hormone-dependent cancer, infertility, endometriosis, early puberty or myoma of the uterus.

[39a] The metastin derivative according to any one of [1] through [6] or a salt thereof, or a prodrug thereof, for use in the prevention/treatment of hormone-dependent cancer, infertility, endometriosis, early puberty or myoma of the uterus.

[40] Use of the metastin derivative according to any one of [1] through [6] or a salt thereof, or a prodrug thereof, to manufacture an agent for inducing or stimulating ovulation.

[40a] The metastin derivative according to any one of [1] through [6] or a salt thereof, or a prodrug thereof, for use in inducing or stimulating ovulation.

[41] Use of the metastin derivative according to any one of [1] through [6] or a salt thereof, or a prodrug thereof, to manufacture a gonadotropic hormone secretagogue agent or a sex hormone secretagogue agent.

[41a] The metastin derivative according to any one of [1] through [6] or a salt thereof, or a prodrug thereof, for use in inducing gonadotropic hormone secretion or sex hormone secretion.

[42] Use of the metastin derivative according to any one of [1] through [6] or a salt thereof, or a prodrug thereof, to manufacture an agent for preventing/treating Alzheimer's disease, moderate cognitive impairment or autism.

[42a] The metastin derivative according to any one of [1] through [6] or a salt thereof, or a prodrug thereof, for use in preventing/treating Alzheimer's disease, moderate cognitive impairment or autism.

[43] Use of the metastin derivative according to any one of [1] through [6] or a salt thereof, or a prodrug thereof, to manufacture a down-regulating agent for gonadotropic hormone or sex hormone.

[43a] The metastin derivative according to any one of [1] through [6] or a salt thereof, or a prodrug thereof, for use in the down-regulation of gonadotropic hormone or sex hormone.

[44] Use of the metastin derivative according to any one of [1] through [6] or a salt thereof, or a prodrug thereof, to manufacture an agent for down-regulating human OT7T175 (metastin receptor) protein consisting of the amino acid sequence represented by SEQ ID NO: 9.

[44a] The metastin derivative according to any one of [1] through [6] or a salt thereof, or a prodrug thereof, for use in the down-regulation of human OT7T175 (metastin receptor) protein consisting of the amino acid sequence represented by SEQ ID NO: 9.

[45] Use of the metastin derivative according to any one of [1] through [6] or a salt thereof, or a prodrug thereof, to manufacture an agent for preventing/treating hormone-dependent cancer.

[45a] The metastin derivative according to any one of [1] through [6] or a salt thereof, or a prodrug thereof, for use in the prevention/treatment of hormone-dependent cancer.

The present invention further provides the following features, and so on.

[46] (1) An agent for controlling the pancreatic function, (2) an agent for preventing/treating acute or chronic pancreatitis or pancreatic cancer, (3) a hyperglycemic agent, a pancreatic glucagon secretagogue agent or an agent for promoting urine formation, (4) an agent for preventing/treating, obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, (5) an agent for suppressing gonadotropic hormone secretion or an agent for suppressing sex hormone secretion, or (6) an agent for inhibiting ovarian follicular maturation, a menstrual cycle-suspending agent or a contraceptive, which comprises the metastin derivative according to any one of [1] through [6] or a salt thereof, or a prodrug thereof.

[47] (1) A method for controlling the pancreatic function, (2) a method for preventing/treating acute or chronic pancreatitis or pancreatic cancer, (3) a hyperglycemic agent, a pancreatic glucagon secretagogue agent or an agent for promoting urine formation, (4) an agent for preventing/treating, obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, (5) an agent for suppressing gonadotropic hormone secretion or an agent for suppressing sex hormone secretion, or (6) an agent for inhibiting ovarian follicular maturation, a menstrual cycle-suspending agent or a contraceptive, which comprises administering to a mammal an effective dose of the metastin derivative according to any one of [1] through [6] or a salt thereof, or a prodrug thereof.

[48] Use of the metastin derivative according to any one of [1] through [6] or a salt thereof; or a prodrug thereof, to manufacture (1) an agent for controlling the pancreatic function, (2) an agent for preventing/treating acute or chronic pancreatitis or pancreatic cancer, (3) a hyperglycemic agent, a pancreatic glucagon secretagogue agent or an agent for promoting urine formation, (4) an agent for preventing/treating, obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, (5) an agent for suppressing gonadotropic hormone secretion or an agent for suppressing sex hormone secretion, or (6) an agent for inhibiting ovarian follicular maturation, a menstrual cycle-suspending agent or a contraceptive.

The metastin derivative of the present invention, its salts, or prodrugs thereof have excellent blood stability, in addition to excellent cancer metastasis inhibiting action or cancer growth suppressing action and are useful as agents for preventing/treating cancers (e.g., lung cancer, gastric cancer, liver cancer, pancreatic cancer, colorectal cancer, rectal cancer, colonic cancer, prostate cancer, ovarian cancer, cervical cancer, breast cancer, etc.). The metastin derivative of the present invention, its salts, or prodrugs thereof have the effects of regulating functions of the pancreas and are useful as medicaments for preventing/treating pancreatic diseases (e.g., acute or chronic pancreatitis, pancreatic cancer, etc.). The metastin derivative of the present invention, its salts, or prodrugs thereof have the effects of regulating functions of the placenta and are useful as medicaments for preventing/treating choriocarcinoma, hydatidiform mole, invasive mole, miscarriage, fetal hypoplasia, abnormal glucose metabolism, abnormal lipid metabolism or labor induction.

Also, the metastin derivative of the present invention or its salts or prodrugs have the effects of increasing sugar level, promoting pancreatic glucagon secretion and promoting urine formation, and are useful as agents for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes mellitus, fatty atrophy, insulin allergy, insulinoma, arteriosclerosis, thrombotic disorders or lipotoxicity.

In addition, the metastin derivative of the present invention or its salts or prodrugs have excellent activities of stimulating gonadotropic hormone secretion, stimulating sex hormone secretion, inducing ovulation or stimulating ovulation, and are useful as low toxic and stable agents, e.g., agents for improving gonadal function, agents for preventing/treating hormone-dependent cancer (e.g., prostate cancer, breast cancer, etc.), infertility, endometriosis, early puberty, myoma of the uterus, etc., agents for inducing or stimulating ovulation, gonadotropic hormone secretagogue agents, contraceptives, sex hormone secretagogue agents, or the like.

Furthermore, the metastin derivative of the present invention or its salts or prodrugs are useful as agents for preventing/treating Alzheimer's disease, moderate cognitive impairment, autism, etc.

The metastin derivative of the present invention or its salts or prodrugs are useful as agents for suppressing gonadotropic hormone secretion or suppressing sex hormone secretion; agents for down-regulating gonadotropic hormone or sex hormone; agents for down-regulating human OT7T175 (metastin receptor) protein consisting of the amino acid sequence represented by SEQ ID NO: 9; agents for preventing/treating hormone-dependent cancers (e.g., prostate cancer, breast cancer, etc.; particularly, hormone-sensitive prostate cancer, hormone-sensitive breast cancer, etc.); agents for preventing/treating endometriosis; agents for inhibiting ovarian follicular maturation; menstrual cycle-suspending agents; agents for treating myoma of the uterus; agents for treating early puberty; contraceptives, etc.

In addition, the metastin derivative of the present invention or its salts or prodrugs are useful as agents for potentiating immunity (e.g., prophylactic agents for infection after bone-marrow transplant, agents for potentiating immunity intended for cancer, etc); immunostimulators (e.g., regeneration of the thymus, regrowth of the thymus, enhancement of T cell development, etc); agents for preventing/treating bulbospinal muscular atrophy; agents for protecting ovary; agents for preventing/treating benign prostate hypertrophy (BPH); agents for preventing/treating gender identity disorder; or agents for in vitro fertilization (IVF). In addition, they are also useful as agents for preventing/treating infertility, hypogonadism, oligospermia, azoospermia, aspermia, asthenospermia, or necrospermia. Further, they are useful for hormone-dependent diseases (e.g., sex hormone dependent cancer such as prostate cancer, uterine cancer, breast cancer, hypophyseal tumor, etc.), prostate gland enlargement, endometriosis, uterine fibroid, early puberty, dysmenorrhea, amenorrhea, menstrual syndrome, multilocular ovary syndrome, postoperative relapse of the above-mentioned cancers, metastasis of the above-mentioned cancers, hypopituitarism, dwarfism (the case where the secretion of growth hormone was compromised with hyposecretion of pituitary hormone, etc.), menopausal disorder, indefinite complaint, sex hormone dependent disorders such as calcium phosphor bone metabolic disorders. It is also applicable for contraception (or infertility when rebound effects after cessation of the drug are utilized), etc.

Moreover, metastin per se or DNA encoding metastin, etc. are also useful as agents for suppressing gonadotropic hormone secretion or sex hormone secretion; down-regulating agents for gonadotropic hormone or suppressing sex hormone; down-regulating agents for human OT7T175 (metastin receptor) protein consisting of the amino acid sequence represented by SEQ ID NO: 9; agents for preventing/treating hormone-dependent cancers (e.g., prostate cancer, breast cancer, etc.; particularly, hormone-sensitive prostate cancer, hormone-sensitive breast cancer, etc.); agents for preventing/ treating endometriosis; agents for inhibiting ovarian follicular maturation; menstrual cycle-suspending agents; agents for treating myoma of the uterus; agents for treating early puberty; contraceptives, etc.

In the formulas described above, n represents 0 or 1; $W^1$ represents N, CH or O (provided that when $W^1$ is N or CH, n represents 1 and when $W^1$ is O, n represents 0); $W^2$ represents N or CH; each of $Z^1$, $Z^5$ and $Z^7$ represents hydrogen atom or a $C_{1-3}$ alkyl group; and each of $Z^2$, $Z^4$, $Z^6$ and $Z^8$ represents hydrogen atom, O or S.

Herein, when $Z^2$, $Z^4$, $Z^6$ or $Z^8$ represents hydrogen atom, the moiety shown by $>C=Z^2$, $>C=Z^4$, $>C=Z^6$ or $>C=Z^8$ each indicates the structure of $>CH_2$.

The $C_{1-3}$ alkyl group used includes methyl group, ethyl group, propyl group and isopropyl group.

$W^1$ is preferably N and $W^2$ is preferably CH.

$Z^1$ is preferably hydrogen atom.

$Z^2$ is preferably O.

$Z^4$ is preferably O.

$Z^5$ is preferably hydrogen atom.

$Z^6$ is preferably O.

$Z^7$ is preferably hydrogen atom.

$Z^8$ is preferably O.

Preferred combinations of $Z^1$, $Z^2$, $Z^4$, $Z^5$, $Z^6$, $Z^7$ and $Z^8$ further include the cases where $Z^1$ is hydrogen atom and each of $Z^5$ and $Z^7$ represents hydrogen atom or a $C_{1-3}$ alkyl group and each of $Z^2$, $Z^4$, $Z^6$ and $Z^8$ represents O or S.

More preferably, the combinations of $Z^1$ to $Z^8$ include:

(a) the case where $Z^1$ is hydrogen atom, $Z^5$ is hydrogen atom, $Z^7$ is hydrogen atom, $Z^2$ is O, $Z^4$ is O, $Z^6$ is O and $Z^8$ is O;

(b) the case where $Z^1$ is hydrogen atom, $Z^5$ is hydrogen atom, $Z^7$ is hydrogen atom, $Z^2$ is O, $Z^4$ is O, $Z^6$ is O and $Z^8$ is S;

(c) the case where $Z^1$ is hydrogen atom, $Z^5$ is hydrogen atom, $Z^7$ is methyl group, $Z^2$ is O, $Z^4$ is O, $Z^6$ is O and $Z^8$ is O; etc. Inter alia, (a) and (b) are preferred, more preferably (a).

$R^1$ represents (1) hydrogen atom, (2) a $C_{1-8}$ alkyl group optionally substituted with a substituent selected from the group consisting of an optionally substituted carbamoyl group, an optionally substituted hydroxyl group and an optionally substituted aromatic cyclic group, (3) a cyclic or linear $C_{1-10}$ alkyl group, (4) a $C_{1-10}$ alkyl group consisting of a cyclic alkyl group and a linear alkyl group or (5) an optionally substituted aromatic cyclic group; inter alia, (1) hydrogen atom, or (2) a $C_{1-8}$ alkyl group optionally substituted with a substituent selected from the group consisting of an optionally substituted carbamoyl group, an optionally substituted hydroxyl group and an optionally substituted aromatic cyclic group; preferably (1) hydrogen atom, or (2) a $C_{1-8}$ alkyl group substituted with a substituent selected from the group consisting of an optionally substituted carbamoyl group, an optionally substituted hydroxyl group and an optionally substituted aromatic cyclic group; and more preferably (2) a $C_{1-8}$ alkyl group substituted with an optionally substituted hydroxyl group.

The "$C_{1-8}$ alkyl group" used includes, for example, a linear $C_{1-8}$ alkyl group such as methyl, ethyl, propyl, isopropyl, butyl, isobutyl, sec-butyl, tert-butyl, pentyl, isopentyl, neopentyl, hexyl, heptyl, octyl, etc., a cyclic $C_{3-8}$ alkyl group such as cyclopropyl, cyclobutyl, cyclopentyl, cyclohexyl, etc. Inter alia, a $C_{1-3}$ alkyl group such as methyl, ethyl, etc. are particularly preferred.

The "optionally substituted carbamoyl group" used includes, for example, carbamoyl, a mono-$C_{1-6}$ alkylcarbamoyl group (e.g., methylcarbamoyl, ethylcarbamoyl, etc.), a di-$C_{1-6}$ alkylcarbamoyl group (e.g., dimethylcarbamoyl, diethylcarbamoyl, ethylmethylcarbamoyl, etc.), a mono- or di-$C_{6-14}$ arylcarbamoyl group (e.g., phenylcarbamoyl, 1-naphthylcarbamoyl, 2-naphthylcarbamoyl, etc.), a mono- or di-5- or 7-membered heterocyclic carbamoyl group containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), and the like.

The "optionally substituted hydroxyl group" used includes, for example, hydroxy group, an optionally substituted $C_{1-6}$ alkoxy group, an optionally substituted $C_{6-14}$ aryloxy group, an optionally substituted $C_{7-16}$ aralkyloxy group, etc. The "optionally substituted $C_{1-6}$ alkoxy group," "optionally substituted $C_{6-14}$ aryloxy group" and "optionally substituted $C_{7-16}$ aralkyloxy group" used are those given for the "optionally substituted $C_{1-6}$ alkoxy group," "optionally substituted $C_{6-14}$ aryloxy group" and "optionally substituted $C_{7-16}$ aralkyloxy group" in Substituent Group A, which will be later described.

The "aromatic cyclic group" in "optionally substituted aromatic cyclic group" used includes, for example, an aromatic hydrocarbon group, aromatic heterocyclic group, an aromatic fused-ring group, an aromatic fused heterocyclic group, etc.

The "aromatic hydrocarbon group" used includes, for example, a $C_{6-14}$ aryl group such as phenyl, 2-biphenylyl, 3-biphenylyl, 4-biphenylyl, cyclooctatetraenyl, etc.

The "aromatic heterocyclic group" used includes, for example, a 5- to 14-membered, preferably 5- to 10-membered, more preferably 5- or 6-membered aromatic heterocyclic group containing 1 to 4 hetero atoms of 1 or 2 species selected from nitrogen, sulfur and oxygen atoms in addition to carbon atoms. Specific examples are thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), etc.

The "aromatic fused-ring group" used includes a $C_{8-14}$ aromatic fused-ring group such as naphthyl (e.g., 1-naphthyl, 2-naphthyl), anthryl (e.g., 2-anthryl, 9-anthryl) and the like.

The "aromatic fused heterocyclic group" used includes, for example, a 5- to 14-membered (preferably 5- to 10-membered) bicyclic or tricyclic aromatic heterocyclic group containing 1 to 4 hetero atoms of 1 or 2 species selected from nitrogen, sulfur and oxygen atoms in addition to 3 to 11 carbon atoms, or a monovalent group formed by removing one optional hydrogen atom from a 7- to 10-membered aromatic bridged-hetero ring in 5- to 14-membered (preferably 5- to 10-membered) ring containing 1 to 4 hetero atoms of 1 or 2 species selected from nitrogen, sulfur and oxygen atoms in addition to carbon atoms. Specific examples of these groups used are quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl) and the like.

The "substituent" used in the "aromatic cyclic group" includes a substituent selected from Substituent Group A, which will be later described.

As R¹, there are used hydrogen atom, carbamoylmethyl, 2-carbamoylethyl, hydroxymethyl, 1-hydroxyethyl, benzyl, 4-hydroxybenzyl, 2-pyridylmethyl, 3-pyridylmethyl, 4-pyridylmethyl, 2-thienylmethyl, 3-thienylmethyl, 1-naphthylmethyl, 2-naphthylmethyl, 3-indolemethyl, methyl, ethyl, propyl, isopropyl, butyl, isobutyl, sec-butyl, tert-butyl, cyclohexylmethyl, phenyl, acetoxymethyl, methoxymethyl, etc.; among others, preferred are hydroxymethyl, 1-hydroxyethyl, benzyl, 4-hydroxybenzyl, 3-indolemethyl, methyl, isobutyl, etc., more preferably, hydroxymethyl, 1-hydroxyethyl, etc., and most preferably 1-hydroxyethyl.

R² represents (1) hydrogen atom, (2) a cyclic or linear $C_{1-10}$ alkyl group, (3) a $C_{1-10}$ alkyl group consisting of a cyclic alkyl group and a linear alkyl group, or (4) a $C_{1-8}$ alkyl group optionally substituted with a substituent selected from the group consisting of an optionally substituted carbamoyl group, an optionally substituted hydroxyl group and an optionally substituted aromatic cyclic group. Among others, preferred are (1) hydrogen atom, (2) a cyclic or linear $C_{1-10}$ alkyl group, or (3) a $C_{1-10}$ alkyl group consisting of a cyclic alkyl group and a linear alkyl group. In particular, a linear $C_{1-10}$ alkyl group or a $C_{1-10}$ alkyl group consisting of a cyclic alkyl group and a linear alkyl group is preferred.

The cyclic $C_{1-10}$ alkyl group used includes, for example, a $C_{3-8}$ cycloalkyl group such as cyclopropyl, cyclobutyl, cyclopentyl, cyclohexyl, etc.

Examples of the linear $C_{1-10}$ alkyl group include methyl, ethyl, propyl, isopropyl, butyl, isobutyl, sec-butyl, tert-butyl, pentyl, isopentyl, neopentyl, hexyl, heptyl, octyl, nonanyl, decanyl, etc.

The $C_{1-10}$ alkyl group consisting of a cyclic alkyl group and a linear alkyl group used includes, for example, a $C_{3-7}$ cycloalkyl-$C_{1-3}$ alkyl group such as cyclopentylmethyl, cyclohexylmethyl, etc.

Examples of R² include methyl, ethyl, propyl, isopropyl, butyl, isobutyl, sec-butyl, tert-butyl, cyclopropylmethyl, cyclobutylmethyl, cyclohexylmethyl, benzyl, hydroxymethyl, 2-carbamoylethyl, tert-pentyl, etc.; among others, preferred are methyl, ethyl, propyl, isopropyl, isobutyl, sec-butyl, tert-butyl, etc., more preferably, propyl, isopropyl, isobutyl, cyclopropylmethyl, etc.

R³ represents:
(1) a $C_{1-8}$ alkyl group having an optionally substituted basic group and optionally having an additional substituent,
(2) an aralkyl group having an optionally substituted basic group and optionally having an additional substituent,
(3) a $C_{1-4}$ alkyl group having a non-aromatic cyclic hydrocarbon group of carbon atoms not greater than 7 having an optionally substituted basic group, and optionally having an additional substituent, or,
(4) a $C_{1-4}$ alkyl group having a non-aromatic heterocyclic group of carbon atoms not greater than 7 having an optionally substituted basic group, and optionally having an additional substituent; particularly preferably (1) a $C_{1-8}$ alkyl group having an optionally substituted basic group and optionally having an additional substituent.

The "optionally substituted basic group" used includes, for example, (1) a guanidino group optionally having 1 or 2 substituents from $C_{1-6}$ alkyl, $C_{1-6}$ acyl (e.g., methyl, ethyl, propyl, isopropyl, butyl, acetyl, propionyl, etc.), etc., (2) an amino group optionally having 1 to 3 substituents from $C_{1-6}$ alkyl, $C_{1-6}$ acyl (e.g., methyl, ethyl, propyl, isopropyl, butyl, acetyl, propionyl, etc.), etc., (3) a $C_{1-6}$ alkylcarbonylamino group (e.g., acetamido) optionally substituted with a guanidino group optionally having 1 or 2 substituents from $C_{1-6}$ alkyl, $C_{1-6}$ acyl (e.g., methyl, ethyl, propyl, isopropyl, butyl, acetyl, propionyl, etc.), etc., (4) a $C_{1-6}$ alkylcarbonylamino group (e.g., acetamido) optionally substituted with an amino group optionally having 1 to 3 substituents from $C_{1-6}$ alkyl, $C_{1-6}$ acyl (e.g., methyl, ethyl, propyl, isopropyl, butyl, acetyl, propionyl, etc.), etc. Among others, preferred are guanidino, N-methylguanidino, N,N-dimethylguanidino, N,N'-dimethylguanidino, N-ethylguanidino, N-acetylguanidino, amino, N-methylamino, N,N-dimethylamino, aminoacetamido, guanidinoacetamido, amidino, and the like.

The "additional substituent" other than the "optionally substituted basic group" used includes a substituent selected from Substituent Group A later described.

Examples of the "$C_{1-8}$ alkyl group" used are methyl, ethyl, propyl, isopropyl, butyl, isobutyl, sec-butyl, tert-butyl, pentyl, isopentyl, neopentyl, hexyl, heptyl, octyl, etc.

The "aralkyl group" used includes, for example, a $C_{7-16}$ aralkyl group such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl, etc.

The "non-aromatic cyclic hydrocarbon group of carbon atoms not greater than 7" used includes, for example, a $C_{3-7}$ cycloalkyl group such as cyclopropyl, cyclobutyl, cyclopentyl, cyclohexyl, etc.

The "non-aromatic heterocyclic group of carbon atoms not greater than 7" used includes, for example, a 5- to 10-membered non-aromatic heterocyclic group containing 1 to 4 hetero atoms of 1 or 2 species selected from nitrogen, sulfur and oxygen atoms, in addition to 1 to 7 carbon atoms, etc. Specific examples used are pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

Examples of the "$C_{1-4}$ alkyl group" used include methyl, ethyl, propyl, isopropyl, butyl, isobutyl, sec-butyl, tert-butyl, etc.

For R³, there are used, for example, (1) 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-propylguanidino)propyl, 3-(N-acetylguanidino)propyl, 4-guanidinobutyl, 4-(N-methylguanidino)butyl, 2-guanidinoethyl, 2-(N-methylguanidino)ethyl, 4-aminobutyl, 4-(N-methylamino)butyl, 4-(N,N-dimethylamino)butyl, 3-aminopropyl, 2-aminoethyl, aminomethyl, aminoacetamidomethyl, guanidinoacetamidomethyl, 2-(guanidinocarbonyl)ethyl, (2)4-guanidinobenzyl, 4-aminobenzyl, (3)4-guanidinocyclohexylmethyl, 4-aminocyclohexylmethyl, (4)1-amidinopiperidin-4-ylmethyl, 4-pyridylmethyl, etc.; among others, preferred are 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-propylguanidino)propyl, 3-(N-acetylguanidino)propyl, 4-guanidinobutyl, 4-(N-methylguanidino)butyl, 2-guanidinoethyl, 2-(N-methylguanidino)ethyl, 4-aminobutyl, 4-(N-methylamino)butyl, 4-(N,N-dimethylamino)butyl, 3-aminopropyl, 2-aminoethyl, 4-aminobenzyl, aminoacetamidomethyl, guanidinoacetamidomethyl, etc., particularly preferably, 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-acetylguanidino)propyl, 4-guanidinobutyl, 4-(N-methylguanidino)butyl, 2-guanidinoethyl, 4-aminobutyl, etc., and most preferably, 3-guanidinopropyl and 3-(N-methylguanidino)propyl.

$R^4$ represents a $C_{1-4}$ alkyl group, which may optionally be substituted with a substituent selected from the group consisting of:

(1) an optionally substituted $C_{6-12}$ aromatic hydrocarbon group,
(2) an optionally substituted 5- to 14-membered aromatic heterocyclic group consisting of 1 to 7 carbon atoms and hetero atoms selected from the group consisting of nitrogen, oxygen and sulfur atoms,
(3) an optionally substituted $C_{8-14}$ aromatic fused-ring group,
(4) an optionally substituted 5- to 14-membered aromatic fused heterocyclic group consisting of 3 to 11 carbon atoms and hetero atoms selected from the group consisting of nitrogen, oxygen and sulfur atoms,
(5) an optionally substituted non-aromatic cyclic hydrocarbon group having carbon atoms not greater than 7, and,
(6) an optionally substituted non-aromatic heterocyclic group having carbon atoms not greater than 7; and preferably, a $C_{1-4}$ alkyl group substituted with a substituent selected from the group consisting of (1) an optionally substituted $C_{6-12}$ aromatic hydrocarbon group,
(2) an optionally substituted 5- to 14-membered aromatic heterocyclic group consisting of 1 to 7 carbon atoms and hetero atoms selected from the group consisting of nitrogen, oxygen and sulfur atoms,
(3) an optionally substituted $C_{8-14}$ aromatic fused-ring group,
(4) an optionally substituted 5- to 14-membered aromatic fused heterocyclic group consisting of 3 to 11 carbon atoms and hetero atoms selected from the group consisting of nitrogen, oxygen and sulfur atoms,
(5) an optionally substituted non-aromatic cyclic hydrocarbon group having carbon atoms not greater than 7, and,
(6) an optionally substituted non-aromatic heterocyclic group having carbon atoms not greater than 7; particularly preferred is (4) a $C_{1-4}$ alkyl group, which may optionally be substituted with an optionally substituted 5- to 14-membered aromatic fused heterocyclic group consisting of 3 to 11 carbon atoms and hetero atoms selected from the group consisting of nitrogen, oxygen and sulfur atoms.

Examples of the "$C_{1-4}$ alkyl group" used include methyl, ethyl, propyl, isopropyl, butyl, isobutyl, sec-butyl, tert-butyl, etc.

The "$C_{6-12}$ aromatic hydrocarbon group" used includes, for example, a monocyclic $C_{6-12}$ aromatic hydrocarbon group such as phenyl, cyclooctatetraenyl, etc.

The "5- to 14-membered aromatic heterocyclic group consisting of 1 to 7 carbon atoms and hetero atoms selected from the group consisting of nitrogen, oxygen and sulfur atoms" used includes, for example, a 5- to 14-membered, preferably 5- to 10-membered, more preferably 5- or 6-membered monocyclic aromatic heterocyclic group containing 1 to 4 hetero atoms of 1 or 2 species selected from nitrogen, sulfur and oxygen atoms in addition to 1 to 7 carbon atoms. Specific examples used include thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), etc.

The "$C_{8-14}$ aromatic fused-ring group" used includes, for example, naphthyl (e.g., 1-naphthyl, 2-naphthyl), anthryl (e.g., 2-anthryl, 9-anthryl), etc.

The "5- to 14-membered aromatic fused heterocyclic group consisting of 3 to 11 carbon atoms and hetero atoms selected from the group consisting of nitrogen, oxygen and sulfur atoms" used includes, for example, a 5- to 14-membered (preferably 5- to 10-membered) bicyclic or tricyclic aromatic heterocyclic group containing 1 to 4 hetero atoms of 1 or 2 species selected from nitrogen, sulfur and oxygen atoms in addition to 3 to 11 carbon atoms, or a monovalent group formed by removing one optional hydrogen atom from a 7- to 10-membered aromatic bridged-hetero ring in 5- to 14-membered (preferably 5- to 10-membered) ring containing 1 to 4 hetero atoms of 1 or 2 species selected from nitrogen, sulfur and oxygen atoms, in addition to carbon atoms. Specific examples used are quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl), etc.

The "non-aromatic cyclic hydrocarbon group of carbon atoms not greater than 7" used includes, for example, a $C_{3-7}$ cycloalkyl group such as cyclopropyl, cyclobutyl, cyclopentyl, cyclohexyl, etc.

The "non-aromatic heterocyclic group of carbon atoms not greater than 7" used includes, for example, a 5- or 10-membered non-aromatic heterocyclic group containing 1 to 4 hetero atoms of 1 or 2 species selected from nitrogen, sulfur and oxygen atoms, in addition to 1 to 7 carbon atoms, such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The substituents used for these "$C_{6-12}$ aromatic hydrocarbon group," "5- to 14-membered aromatic heterocyclic group consisting of 1 to 7 carbon atoms and hetero atoms selected from the group consisting of nitrogen, oxygen and sulfur atoms," "$C_{8-14}$ aromatic fused-ring group," "5- to 14-membered aromatic fused heterocyclic group consisting of 3 to 11 carbon atoms and hetero atoms selected from the group consisting of nitrogen, oxygen and sulfur atoms," "non-aromatic cyclic hydrocarbon group of carbon atoms not greater than 7" and "non-aromatic heterocyclic group of carbon atoms not greater than 7" include, for example, substituents selected from oxo, a halogen atom (e.g., fluorine, chlorine, bromine, iodine, etc.), $C_{1-3}$ alkylenedioxy (e.g., methylenedioxy, ethylenedioxy, etc.), nitro, cyano, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, optionally substituted $C_{6-14}$ aryl, optionally substituted $C_{7-16}$ aralkyl, optionally substituted $C_{1-6}$ alkoxy, hydroxy, optionally substituted $C_{6-14}$ aryloxy, optionally substituted $C_{7-16}$ aralkyloxy, mercapto, optionally substituted $C_{1-6}$ alkylthio, optionally substituted $C_{6-14}$ arylthio, optionally substituted $C_{7-16}$ aralkylthio, optionally substituted amino[amino, optionally substituted mono- or di-$C_{1-6}$ alkylamino (e.g., methylamino, dimethylamino, ethylamino, diethylamino, propylamino, isopropylamino, etc.), optionally substituted mono- or di-$C_{2-6}$ alkenylamino (e.g., vinylamino, propenylamino, isopropenylamino), optionally substituted $C_{2-6}$ alkynylamino (e.g., 2-butyn-1-yl-amino, 4-pentyn-1-yl-amino, 5-hexyn-1-yl-amino), optionally substituted mono- or di-$C_{3-8}$ cycloalkylamino (e.g., cyclopropylamino, cyclohexylamino), optionally substituted $C_{6-14}$ aryl-amino (e.g., phenylamino, diphenylamino, naphthylamino), optionally substituted $C_{1-6}$ alkoxy-amino (e.g., methoxyamino, ethoxyamino, propoxyamino, isopropoxyamino), formylamino, optionally substituted $C_{1-6}$ alkylcarbonylamino (e.g., acetylamino, propionylamino, pivaloylamino, etc.), optionally substituted $C_{3-8}$ cycloalkylcarbonylamino (e.g., cyclopropylcarbonylamino, cyclopentylcarbonylamino, cyclohexylcarbonylamino, etc.), optionally substituted $C_{6-14}$ aryl-carbonylamino (e.g., benzoylamino, naphthoylamino, etc.), optionally substituted $C_{1-6}$ alkoxy-carbonylamino (e.g., methoxycarbonylamino, ethoxycarbonylamino, propoxycarbonylamino, butoxycarbonylamino, etc.), optionally substituted $C_{1-6}$ alkylsulfonylamino (e.g., methylsulfonylamino, ethylsulfonylamino, etc.), optionally substituted $C_{6-14}$ arylsulfonylamino (e.g., phenylsulfonylamino, 2-naphthylsulfonylamino, 1-naphthylsulfonylamino, etc.)], formyl, carboxy, optionally substituted $C_{1-6}$ alkylcarbonyl (e.g., acetyl, propionyl, pivaloyl, etc.), optionally substituted $C_{3-8}$ cycloalkylcarbonyl (e.g., cyclopropylcarbonyl, cyclopentylcarbonyl, cyclohexylcarbonyl, 1-methyl-cyclohexyl-carbonyl, etc.), optionally substituted $C_{6-14}$ aryl-carbonyl (e.g., benzoyl, 1-naphthoyl, 2-naphthoyl, etc.), optionally substituted $C_{7-16}$ aralkyl-carbonyl (e.g., phenylacetyl, 3-phenylpropionyl, etc.), optionally substituted 5- to 7-membered heterocyclic carbonyl containing 1 to 4 hetero atoms of 1 or 2 species selected from nitrogen, sulfur and oxygen atoms in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), optionally esterified carboxyl, optionally substituted carbamoyl, optionally substituted $C_{1-6}$ alkylsulfonyl (e.g., methylsulfonyl, ethylsulfonyl, etc.), optionally substituted $C_{1-6}$ alkylsulfinyl (e.g., methylsulfinyl, ethylsulfinyl, etc.), optionally substituted $C_{6-14}$ arylsulfonyl (e.g., phenylsulfonyl, 1-naphthylsulfonyl, 2-naphthylsulfonyl, etc.), optionally substituted $C_{6-14}$ arylsulfinyl (e.g., phenylsulfinyl, 1-naphthylsulfinyl, 2-naphthylsulfinyl, etc.), optionally substituted $C_{1-6}$ alkylcarbonyloxy (e.g., acetoxy, propionyloxy, etc.), optionally substituted $C_{6-14}$ aryl-carbonyloxy (e.g., benzoyloxy, naphthylcarbonyloxy, etc.), optionally substituted $C_{1-6}$ alkoxy-carbonyloxy (e.g., methoxycarbonyloxy, ethoxycarbonyloxy, propoxycarbonyloxy, butoxycarbonyloxy, etc.), optionally substituted mono-$C_{1-6}$ alkylcarbamoyloxy (e.g., methylcarbamoyloxy, ethylcarbamoyloxy, etc.), optionally substituted di-$C_{1-6}$ alkylcarbamoyloxy (e.g., dimethylcarbamoyloxy, diethylcarbamoyloxy, etc.), optionally substituted mono- or di-$C_{6-14}$ arylcarbamoyloxy (e.g., phenylcarbamoyloxy, naphthylcarbamoyloxy, etc.), optionally substituted heterocyclic group, sulfo, sulfamoyl, sulfinamoyl, sulfenamoyl, or a group of 2 or more (e.g., 2 or 3) of these substituents combined, and the like (Substituent Group A). The number of the substituents is not particularly limited but these rings may have 1 to 5, preferably 1 to 3 substituents in substitutable positions, and when there are two or more substituents, each substituent may be the same or different.

The "optionally esterified carboxyl group" in Substituent Group A includes, for example, an optionally substituted $C_{1-6}$ alkoxy-carbonyl (e.g., methoxycarbonyl, ethoxycarbonyl, propoxycarbonyl, tert-butoxycarbonyl, etc.), an optionally substituted $C_{6-14}$ aryloxy-carbonyl (e.g., phenoxycarbonyl, etc.), an optionally substituted $C_{7-16}$ aralkyloxy-carbonyl (e.g., benzyloxycarbonyl, phenethyloxycarbonyl, etc.), and the like.

The "$C_{1-6}$ alkyl" in the "optionally substituted $C_{1-6}$ alkyl" in Substituent Group A includes, for example, methyl, ethyl, propyl, isopropyl, butyl, isobutyl, sec-butyl, tert-butyl, pentyl, isopentyl, neopentyl, hexyl, etc.

The "$C_{2-6}$ alkenyl" in the "optionally substituted $C_{2-6}$ alkenyl" in Substituent Group A includes, for example, vinyl, propenyl, isopropenyl, 2-buten-1-yl, 4-penten-1-yl, 5-hexen-1-yl, etc.

The "$C_{2-6}$ alkynyl" in the "optionally substituted $C_{2-6}$ alkynyl" in Substituent Group A includes, for example, 2-butyn-1-yl, 4-pentyn-1-yl, 5-hexyn-1-yl, etc.

The "$C_{3-8}$ cycloalkyl" in the "optionally substituted $C_{3-8}$ cycloalkyl" in Substituent Group A includes, for example, cyclopropyl, cyclobutyl, cyclopentyl, cyclohexyl, etc.

The "$C_{6-14}$ aryl" in the "optionally substituted $C_{6-14}$ aryl" in Substituent Group A includes, for example, phenyl, 1-naphthyl, 2-naphthyl, 2-biphenylyl, 3-biphenylyl, 4-biphenylyl, 2-anthryl, etc.

The "$C_{7-16}$ aralkyl" in the "optionally substituted $C_{7-16}$ aralkyl" in Substituent Group A includes, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl, etc.

The "$C_{1-6}$ alkoxy" in the "optionally substituted $C_{1-6}$ alkoxy" in Substituent Group A includes, for example, methoxy, ethoxy, propoxy, isopropoxy, butoxy, isobutoxy, sec-butoxy, pentyloxy, hexyloxy, etc.

The "$C_{6-14}$ aryloxy" in the "optionally substituted $C_{6-14}$ aryloxy" in Substituent Group A includes, for example, phenyloxy, 1-naphthyloxy, 2-naphthyloxy, etc.

The "$C_{7-16}$ aralkyloxy" in the "optionally substituted $C_{7-16}$ aralkyloxy" in Substituent Group A includes, for example, benzyloxy, phenethyloxy, etc.

The "$C_{1-6}$ alkylthio" in the "optionally substituted $C_{1-6}$ alkylthio" in Substituent Group A includes, for example, methylthio, ethylthio, propylthio, isopropylthio, butylthio, sec-butylthio, tert-butylthio, etc.

The "$C_{6-14}$ arylthio" in the "optionally substituted $C_{6-14}$ arylthio" in Substituent Group A includes, for example, phenylthio, 1-naphthylthio, 2-naphthylthio, etc.

The "$C_{7-16}$ aralkylthio" in the "optionally substituted $C_{7-16}$ aralkylthio" in Substituent Group A includes, for example, benzylthio, phenethylthio, etc.

The substituents in these "$C_{1-6}$ alkoxy-carbonyl," "$C_{1-6}$ alkyl group," "$C_{2-6}$ alkenyl," "$C_{2-6}$ alkynyl," "$C_{1-6}$ alkoxy," "$C_{1-6}$ alkylthio," "$C_{1-6}$ alkyl-amino," "$C_{2-6}$ alkenyl-amino," "$C_{2-6}$ alkynyl-amino," "$C_{1-6}$ alkoxy-amino," "$C_{1-6}$ alkyl-carbonyl," "$C_{1-6}$ alkylsulfonyl," "$C_{1-6}$ alkylsulfinyl," "$C_{1-6}$ alkyl-carbonylamino," "$C_{1-6}$ alkoxy-carbonylamino," "$C_{1-6}$ alkylsulfonylamino," "$C_{1-6}$ alkyl-carbonyloxy," "$C_{1-6}$ alkoxy-carbonyloxy," "mono-$C_{1-6}$ alkylcarbamoyloxy" and "di-$C_{1-6}$ alkylcarbamoyloxy" in Substituent Group A include, for example, 1 to 5 substituents selected from, for example, a halogen atom (e.g., fluorine atom, chlorine atom, bromine atom, iodine atom), carboxy, hydroxy, amino, mono- or di-$C_{1-6}$ alkylamino, mono- or di-$C_{6-14}$ arylamino, $C_{3-8}$ cycloalkyl, $C_1$-6 alkoxy, $C_{1-6}$ alkoxy-carbonyl, $C_{1-6}$ alkylthio, $C_{1-6}$ alkylsulfinyl, $C_{1-6}$ alkylsulfonyl, the optionally esterified carboxyl described above, carbamoyl, thiocarbamoyl, mono-$C_{1-6}$ alkylcarbamoyl (e.g., methylcarbamoyl, ethylcarbamoyl, etc.), di-$C_{1-6}$ alkylcarbamoyl (e.g., dimethylcarbamoyl, diethylcarbamoyl, ethylmethylcarbamoyl, etc.), mono- or di-$C_{6-14}$ arylcarbamoyl (e.g., phenylcarbamoyl, 1-naphthylcarbamoyl, 2-naphthylcarbamoyl, etc.), mono- or di-5- to 7-membered heterocyclic carbamoyl containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), and the like.

The substituents for the "$C_{6-14}$ aryloxy-carbonyl," "$C_{7-16}$ aralkyloxy-carbonyl," "$C_{3-8}$ cycloalkyl," "$C_{6-14}$ aryl," "$C_{7-16}$ aralkyl," "$C_{6-14}$ aryloxy," "$C_{7-16}$ aralkyloxy," "$C_{6-14}$ arylthio," "$C_{7-16}$ aralkylthio," "$C_{3-8}$ cycloalkyl-amino," "$C_{6-14}$ aryl-amino," "$C_{3-8}$ cycloalkyl-carbonyl," "$C_{6-14}$ aryl-carbonyl," "$C_{7-16}$ aralkyl-carbonyl," "5- to 7-membered heterocyclic carbonyl containing 1 to 4 hetero atoms of 1 or 2 species selected from nitrogen, sulfur and oxygen atoms in addition to carbon atoms," "$C_{6-14}$ arylsulfonyl," "$C_{6-14}$ arylsulfinyl," "$C_{3-8}$ cycloalkyl-carbonylamino," "$C_{6-14}$ aryl-carbonylamino," "$C_{6-14}$ arylsulfonylamino," "$C_{6-14}$ aryl-carbonyloxy" and "mono- or di-$C_{6-14}$ aryl-carbamoyloxy" in Substituent Group A include, for example, 1 to 5 substituents selected from, for example, a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{1-6}$ alkoxy described above, the optionally substituted $C_{1-6}$ alkylthio described above, the optionally substituted $C_{1-6}$ alkylsulfinyl described above, the optionally substituted $C_{1-6}$ alkylsulfonyl described above, the optionally esterified carboxyl described above, carbamoyl, thiocarbamoyl, mono-$C_{1-6}$ alkylcarbamoyl, di-$C_{1-6}$ alkylcarbamoyl, mono- or di-$C_{6-14}$ arylcarbamoyl, mono- or di-5- to 7-membered heterocyclic carbamoyl containing 1 to 4 hetero atoms of 1 or 2 species selected from nitrogen, sulfur and oxygen atoms in addition to carbon atoms, and the like.

The "optionally substituted heterocyclic group" in Substituent Group A includes, for example, a 5- to 14-membered (monocyclic, bicyclic or tricyclic) heterocyclic group containing 1 to 4 hetero atoms of 1 or 2 species selected from nitrogen, sulfur and oxygen atoms in addition to carbon atoms, which may optionally be substituted with a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above, the optionally substituted $C_{1-6}$ alkylthio described above, the optionally substituted $C_{6-14}$ arylthio described above, the optionally substituted $C_{7-16}$ aralkylthio described above, the optionally substituted $C_{1-6}$ alkylsulfinyl described above, the optionally substituted $C_{6-14}$ arylsulfinyl described above, the optionally substituted $C_{1-6}$ alkylsulfonyl described above, the optionally substituted $C_{6-14}$ arylsulfonyl described above, the optionally esterified carboxyl described above, carbamoyl, thiocarbamoyl, mono-$C_{1-6}$ alkylcarbamoyl, di-lower alkylcarbamoyl, mono- or di-$C_{6-14}$ arylcarbamoyl, mono- or di-5- or 7-membered heterocyclic carbamoyl containing 1 to 4 hetero atoms of 1 or 2 species selected from nitrogen, sulfur and oxygen atoms in addition to carbon atoms, or the like; preferably (i) a 5- to 14-membered (preferably, 5- to 10-membered) aromatic heterocyclic group, (ii) a 5- to 10-membered non-aromatic heterocyclic group or (iii) a monovalent group formed by removing one optional hydrogen atom from 7- to 10-membered bridged-hetero ring, and the like, are employed; among others, preferably used is a 5-membered aromatic heterocyclic group. Specifically used are an aromatic heterocyclic group such as thienyl (e.g., 2-thienyl, 3-thienyl), furyl (e.g., 2-furyl, 3-fury!), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl), etc., a non-aromatic heterocyclic group such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The "optionally substituted carbamoyl group" in Substituent Group A includes a carbamoyl group, which may optionally be substituted with the optionally substituted $C_{1-6}$ alkyl, optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted heterocyclic group described above, etc., and specific examples are carbamoyl, thiocarbamoyl, mono-$C_{1-6}$ alkylcarbamoyl (e.g., methylcarbamoyl, ethylcarbamoyl, etc.), di-$C_{1-6}$ alkylcarbamoyl (e.g., dimethylcarbamoyl, diethylcarbamoyl, ethylmethylcarbamoyl, etc.), $C_{1-6}$ alkyl ($C_{1-6}$ alkoxy)carbamoyl (e.g., methyl(methoxy)carbamoyl, ethyl(methoxy)carbamoyl), mono- or di-$C_{6-14}$ arylcarbamoyl (e.g., phenylcarbamoyl, 1-naphthylcarbamoyl, 2-naphthylcarbamoyl, etc.), mono- or di-5- to 7-membered heterocyclic carbamoyl containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), 5- to 7-membered cyclic carbamoyl (e.g., 1-pyrrolidinylcarbonyl, 1-piperidinylcarbonyl, hexamethyleneiminocarbonyl), and the like.

The "optionally substituted amino" in Substituent Group A includes an amino, which may optionally be substituted with 1 or 2 groups selected from the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above, formyl, the optionally substituted $C_{1-6}$ alkyl-carbonyl described above, the optionally substituted $C_{3-8}$ cycloalkyl-carbonyl described above, the optionally substituted $C_{6-14}$ aryl-carbonyl described above, the optionally substituted $C_{1-6}$ alkoxy-carbonyl described above, the optionally substituted $C_{1-6}$ alkylsulfonyl described above, the optionally substituted $C_{6-14}$ arylsulfonyl, and the like.

More preferably, the substituents used for these "$C_{6-12}$ aromatic hydrocarbon group," "5- to 14-membered aromatic heterocyclic group consisting of 1 to 7 carbon atoms and hetero atoms selected from the group consisting of nitrogen, oxygen and sulfur atoms," "$C_{8-14}$ aromatic fused-ring group," "5- to 14-membered aromatic fused heterocyclic group consisting of 3 to 11 carbon atoms and hetero atoms selected from the group consisting of nitrogen, oxygen and sulfur atoms," "non-aromatic cyclic hydrocarbon group of carbon atoms not greater than 7" and "non-aromatic heterocyclic group of carbon atoms not greater than 7" are a halogen atom, hydroxy, $C_{1-6}$ alkoxy, an optionally halogenated $C_{1-6}$ alkyl, an optionally halogenated $C_{1-6}$ alkoxy, amino, nitro, cyano, etc.

Examples of $R^4$ used include:
(1) "a $C_{1-4}$ alkyl group having an optionally substituted $C_{6-12}$ aromatic hydrocarbon group" such as benzyl, 2-fluorobenzyl, 3-fluorobenzyl, 4-fluorobenzyl, 4-chlorobenzyl, 3,4-difluorobenzyl, 3,4-dichlorobenzyl, pentafluorobenzyl, 4-hydroxybenzyl, 4-methoxybenzyl, 3-trifluoromethylbenzyl, 4-aminobenzyl, 4-nitrobenzyl, 4-cyanobenzyl, phenethyl, etc.;
(2) "a $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms" such as 2-pyridylmethyl, 3-pyridylmethyl, 4-pyridylmethyl, 2-thienylmethyl, 3-thienylmethyl, 4-thiazolylmethyl, etc.;
(3) "a $C_{1-4}$ alkyl group having an optionally substituted $C_{8-14}$ aromatic fused-ring group" such as 1-naphthylmethyl, 2-naphthylmethyl, inden-2-ylmethyl, etc.;
(4) "a $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms" such as 3-indolemethyl, 1-formylindol-3-ylmethyl, 3-benzo[b]thienylmethyl, 2-quinolylmethyl, etc.;
(5) "a $C_{1-4}$ alkyl group having an optionally substituted non-aromatic cyclic hydrocarbon group of carbon atoms not greater than 7" such as cyclohexylmethyl, cyclopentylmethyl, indan-2-ylmethyl, etc.;
(6) "a $C_{1-4}$ alkyl group having an optionally substituted non-aromatic heterocyclic group of carbon atoms not greater than 7" such as 4-piperidinylmethyl, tetrahydrofurfuryl, tetrahydrofuran-2-yl, tetrahydropyran-3-yl, indolin-3-yl, etc.; among others, preferred are benzyl, 2-fluorobenzyl, 3-fluorobenzyl, 4-fluorobenzyl, 4-hydroxybenzyl, 4-aminobenzyl, 4-nitrobenzyl, 4-chlorobenzyl, 4-methoxybenzyl, 4-cyanobenzyl, 3-trifluoromethylbenzyl, 3,4-dichlorobenzyl, 3,4-difluorobenzyl, pentafluorobenzyl, 3-pyridylmethyl, 4-pyridylmethyl, 3-indolemethyl, 1-formylindol-3-ylmethyl, 3-benzo[b]thienylmethyl, 2-quinolylmethyl, 1-naphthylmethyl, 2-naphthylmethyl, cyclohexylmethyl, phenethyl, etc. are preferred, especially benzyl, 2-fluorobenzyl, 3-fluorobenzyl, 4-fluorobenzyl, 4-hydroxybenzyl, 4-aminobenzyl, 4-nitrobenzyl, 4-chlorobenzyl, 4-methoxybenzyl, 4-cyanobenzyl, 3-trifluoromethylbenzyl, 3,4-dichlorobenzyl, 3,4-difluorobenzyl, pentafluorobenzyl, 3-pyridylmethyl, 4-pyridylmethyl, 3-indolemethyl, 3-benzo[b]thienylmethyl, 1-naphthylmethyl, 2-naphthylmethyl, cyclohexylmethyl, etc., and particularly preferably 3-indolemethyl.

$Q^1$ represents a $C_{1-4}$ alkyl group, which may optionally be substituted with a substituent (preferably, a substituent selected from the group consisting of (1), (2) and (5) described below) selected from the group consisting of:
(1) an optionally substituted $C_{6-12}$ aromatic hydrocarbon group,
(2) an optionally substituted 5- to 14-membered aromatic heterocyclic group consisting of 1 to 7 carbon atoms and hetero atoms selected from the group consisting of nitrogen, oxygen and sulfur atoms,
(3) an optionally substituted $C_{8-14}$ aromatic fused-ring group,
(4) an optionally substituted 5- to 14-membered aromatic fused heterocyclic group consisting of 3 to 11 carbon atoms and hetero atoms selected from the group consisting of nitrogen, oxygen and sulfur atoms,
(5) an optionally substituted non-aromatic cyclic hydrocarbon group having carbon atoms not greater than 7, and,
(6) an optionally substituted non-aromatic heterocyclic group having carbon atoms not greater than 7; these substituents used are the same as those given for $R^4$.

Examples of $Q^1$ used include:
(1) "a $C_{1-4}$ alkyl group having an optionally substituted $C_{6-12}$ aromatic hydrocarbon group" such as benzyl, 2-fluorobenzyl, 3-fluorobenzyl, 4-fluorobenzyl, 4-chlorobenzyl, 3,4-difluorobenzyl, 3,4-dichlorobenzyl, pentafluorobenzyl, 4-hydroxybenzyl, 4-methoxybenzyl, 4-trifluoromethylbenzyl, 4-aminobenzyl, 4-nitrobenzyl, 4-cyanobenzyl, phenethyl, etc.,
(2) "a $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms" such as 2-pyridylmethyl, 3-pyridylmethyl, 4-pyridylmethyl, 2-thienylmethyl, 3-thienylmethyl, 4-thiazolylmethyl, etc.,
(3) "a $C_{1-4}$ alkyl group having an optionally substituted $C_{8-14}$ aromatic fused-ring group" such as 1-naphthylmethyl, 2-naphthylmethyl, inden-2-ylmethyl, etc.,
(4) "a $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms" such as 3-indolemethyl, 1-formylindol-3-ylmethyl, 3-benzo[b]thienylmethyl, 2-quinolylmethyl, etc.,
(5) "a $C_{1-4}$ alkyl group having an optionally substituted non-aromatic cyclic hydrocarbon group having carbon atoms not greater than 7" such as cyclohexylmethyl, cyclopentylmethyl, indan-2-ylmethyl, etc.,
(6) "a $C_{1-4}$ alkyl group having an optionally substituted non-aromatic heterocyclic group having carbon atoms not greater than 7" such as 3-piperidylmethyl, 4-piperidinylmethyl, tetrahydrofurfuryl, tetrahydrofuran-2-yl, tetrahydropyran-3-yl, indolin-3-yl, etc.; among others, preferably used are cyclohexylmethyl, benzyl, 4-fluorobenzyl, 4-hydroxybenzyl, 4-methoxybenzyl, pentafluorobenzyl, 2-pyridylmethyl, 4-pyridylmethyl, 1-naphthylmethyl, 2-naphthylmethyl, 3-indolemethyl, 3-piperidylmethyl, 2-thienylmethyl, etc.; more preferably, benzyl, 4-fluorobenzyl, 4-pyridylmethyl, cyclohexylmethyl, 3-piperidylmethyl, 2-piperidylmethyl, etc., and most preferably, benzyl and cylohexylmethyl.

$Q^2$ represents: (1) $CH_2$, CO, CS or $CH=CH_2$, which may optionally be substituted with a $C_{0-4}$ alkyl group optionally substituted with a substituent selected from the group consisting of carbamoyl group, hydroxyl group, a $C_{1-3}$ alkoxy group, a halogen atom and an amino group, (2) NH, which may optionally be substituted with a substituent selected from the group consisting of carbamoyl group and hydroxyl group, or (3) O; among others, preferred is (1) an optionally substituted $CH_2$ or $CH=CH_2$ with one or two $C_{1-4}$ alkyl groups which may optionally be substituted with a substituent selected from the group consisting of carbamoyl group, hydroxyl group, a $C_{1-3}$ alkoxy group and an amino group.

The "$C_{0-4}$ alkyl group" is used to mean a bond or a $C_{1-4}$ alkyl group. In other words, the "$C_0$ alkyl group" refers to a bond (e.g., a chemical bond "—"). Accordingly, "$CH_2$ substituted with a $C_0$ alkyl group which is substituted with a substituent selected from the group consisting of carbamoyl group, hydroxyl group, a $C_{1-3}$ alkoxy group and amino group" represents $CH_2$ substituted with a substituent selected from the group consisting of carbamoyl group, hydroxyl group, a $C_{1-3}$ alkoxy group and amino group.

The "$C_{0-4}$ alkyl group" is preferably a $C_{1-4}$ alkyl group.

The "$C_{1-4}$ alkyl group" used includes, for example, methyl, ethyl, propyl, isopropyl, butyl, isobutyl, sec-butyl, tert-butyl, etc.

The "$C_{1-3}$ alkoxy group" used includes, for example, methoxy group, ethoxy group, propoxy group, isopropoxy group, butoxy group, isobutoxy group, sec-butoxy group, tert-butoxy group, etc.

Preferred $Q^2$ are $CH_2$, $CH(CH_3)$, $CH(CH_2OH)$, $C(CH_3)_2$, $CH_2CH_3$, $CH(CH_2CH_3)$, $CH(CH_2NH_2)$, $CH(CH_2OCH_3)$, $CH(CH(CH_3)_2)$, NH, and the like, more preferably, $CH_2$, $CH(CH_3)$, $CH(CH_2OH)$, $C(CH_3)_2$, $CH_2CH_3$, $CH(CH_2CH_3)$, $CH(CH_2NH_2)$, $CH(CH_2OCH_3)$ and $CH(CH(CH_3)_2)$.

Y represents:
(1) a group represented by formula: —CONH—, —CSNH—, —CH$_2$NH—, —NHCO—, —CH$_2$O—, —COCH$_2$—, —CH$_2$S—, —CSCH$_2$—, —CH$_2$SO—, —CH$_2$SO$_2$—, —COO—, —CSO—, —CH$_2$CH$_2$— or —CH=CH—, which may optionally be substituted with a substituent selected from the group consisting of a $C_{1-6}$ alkyl group, hydroxyl group and a halogen atom;
(2) an optionally substituted $C_{6-7}$ aromatic hydrocarbon group;
(3) an optionally substituted 4- to 7-membered aromatic heterocyclic group consisting of 1 to 5 carbon atoms and hetero atoms selected from the group consisting of nitrogen, oxygen and sulfur atoms;
(4) an optionally substituted non-aromatic cyclic hydrocarbon group having carbon atoms not greater than 5; or
(5) an optionally substituted non-aromatic heterocyclic group having carbon atoms not greater than 5 and when Y is (2), (3), (4) or (5), $Q^2$ may be a chemical bond.

The "$C_{1-6}$ alkyl group" used includes, for example, methyl, ethyl, propyl, isopropyl, butyl, isobutyl, sec-butyl, tert-butyl, pentyl, isopentyl, neopentyl, hexyl, etc.

Y includes (1) a group represented by formula: —CONH—, —CSNH—, —NHCO—, —CH$_2$NH—, —CH$_2$O—, —CH$_2$S—, —COO—, —CSO—, —COCH$_2$—, —CH$_2$CH$_2$— or —CH=CH—, which may optionally be substituted with a substituent selected from the group consisting of a $C_{1-6}$ alkyl group, hydroxyl group and a halogen atom (among others, preferred are the group represented by formula: —CONH—, —CSNH—, —NHCO—, —CH$_2$NH—, —CH$_2$O—, —CH$_2$S—, —COO—, —CSO—, —COCH$_2$—, —CH$_2$CH$_2$—, —CH(OH)CH$_2$— or —CH=CH—, especially the group represented by formula: —CONH—, —CSNH—, —NHCO—, —CH$_2$NH—, —CH$_2$O—, —COCH$_2$—, —CH$_2$CH$_2$—, —CH(OH)CH$_2$— or —CH=CH—, more preferably, the group represented by formula: —CONH—, —CSNH—, —NHCO—, —CH$_2$O—, —CH$_2$S—, —COCH$_2$—, —CH=CH— or —CH$_2$CH$_2$—).

A represents:
(1) a nitrogen atom substituted with hydrogen atom or a $C_{1-3}$ alkyl group;
(2) a carbon atom substituted with hydrogen atom or a $C_{1-3}$ alkyl group;
(3) O; or
(4) S.

A preferably includes (1) a nitrogen atom substituted with hydrogen atom or a $C_{1-3}$ alkyl group (among others, a nitrogen atom substituted with hydrogen atom); (2) a carbon atom substituted with hydrogen atom or a $C_{1-3}$ alkyl group (among others, a carbon atom substituted with hydrogen atom); or (4) S.

A' represents:
(1) a carbon atom, which may optionally be substituted with hydrogen atom, O, S, a halogen atom, an optionally halogenated $C_{1-3}$ alkyl group, carbamoyl group or hydroxyl group;
(2) a nitrogen atom, which may optionally be substituted with hydrogen atom or an optionally halogenated $C_{1-3}$ alkyl group;
(3) O; or
(4) S;

Preferably A' includes (1) a carbon atom, which may optionally be substituted with hydrogen atom, O, S, a halogen atom, an optionally halogenated $C_{1-3}$ alkyl group, carbamoyl group or hydroxyl group (among others, a carbon atom substituted with hydrogen atom or O).

Preferably V' is the group represented by the formula below.

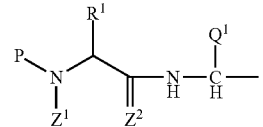

P and P', which may be the same or different, each may form a ring by combining P and P' or P and $Q^1$ together and represents:
(1) hydrogen atom,
(2) an optional amino acid residue continuously or discontinuously bound from the C-terminal end of the 1-48 amino acid sequence in the amino acid sequence represented by SEQ ID NO: 1 (54 amino acid residues of human metastin);
(3) a group represented by formula:

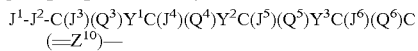

(wherein each symbol has the same significance as described above),
(4) a group represented by formula:

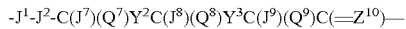

(wherein each symbol has the same significance as described above),
(5) a group represented by formula:

$J^1$-$J^2$-C($J^{10}$)($Q^{10}$)$Y^3$C($J^{11}$)($Q^{11}$)C(=$Z^{10}$)—

(wherein each symbol has the same significance as described above),
(6) a group represented by formula:

$J^1$-$J^2$-C($J^{12}$)($Q^{12}$)C(=$Z^{10}$)—

(wherein each symbol has the same significance as described above), or,
(7) a group represented by formula: $J^1$-
(wherein $J^1$ 1 has the same significance as described above).

Specific examples of the "optional amino acid residue continuously or discontinuously bound from the C-terminal end of the 1-48 amino acid sequence in the amino acid sequence represented by SEQ ID NO: 1," which are employed, include:

(1) Asn- (2) Trp Asn-, (3) Asn Trp Asn-, (4) Tyr Asn Trp Asn-, (SEQ ID NO: 23)

(5) Asn Tyr Asn Trp Asn-, (SEQ ID NO: 24)

(6) Pro Asn Tyr Asn Trp Asn-, (SEQ ID NO: 25)

(7) Leu Pro Asn Tyr Asn Trp Asn-, (SEQ ID NO: 26)

(8) Asp Leu Pro Asn Tyr Asn Trp Asn-, (SEQ ID NO: 27)

(9) Lys Asp Leu Pro Asn Tyr Asn Trp Asn-, (SEQ ID NO: 28)

(10) Glu Lys Asp Leu Pro Asn Tyr Asn Trp Asn-, (SEQ ID NO: 29)

(11) Arg Glu Lys Asp Leu Pro Asn Tyr Asn Trp Asn-, (SEQ ID NO: 30)

(12) Gln Arg Glu Lys Asp Leu Pro Asn Tyr Asn Trp Asn-, (SEQ ID NO: 31)

(13) Val Gln Arg Glu Lys Asp Leu Pro Asn Tyr Asn Trp Asn-, (SEQ ID NO: 32)

(14) Leu Val Gln Arg Glu Lys Asp Leu Pro Asn Tyr Asn Trp Asn-, (SEQ ID NO: 33)

(15) Val Leu Val Gln Arg Glu Lys Asp Leu Pro Asn Tyr Asn Trp Asn-, (SEQ ID NO: 34)

(16) Ala Val Leu Val Gln Arg Glu Lys Asp Leu Pro Asn Tyr Asn Trp Asn-, (SEQ ID NO: 35)

(17) Gly Ala Val Leu Val Gln Arg Glu Lys Asp Leu Pro Asn Tyr Asn Trp Asn-, (SEQ ID NO: 36)

(18) Gln Gly Ala Val Leu Val Gln Arg Glu Lys Asp Leu Pro Asn Tyr Asn Trp Asn-, (SEQ ID NO: 37)

(19) Pro Gln Gly Ala Val Leu Val Gln Arg Glu Lys Asp Leu Pro Asn Tyr Asn Trp Asn-, (SEQ ID NO: 38)

(20) Ala Pro Gln Gly Ala Val Leu Val Gln Arg Glu Lys Asp Leu Pro Asn Tyr Asn Trp Asn-, (SEQ ID NO: 39)

(21) Pro Ala Pro Gln Gly Ala Val Leu Val Gln Arg Glu Lys Asp Leu Pro Asn Tyr Asn Trp Asn-, (SEQ ID NO: 40)

(22) Ile Pro Ala Pro Gln Gly Ala Val Leu Val Gln Arg Glu Lys Asp Leu Pro Asn Tyr Asn Trp Asn-, (SEQ ID NO: 41)

(23) Gln Ile Pro Ala Pro Gln Gly Ala Val Leu Val Gln Arg Glu Lys Asp Leu Pro Asn Tyr Asn Trp Asn-, (SEQ ID NO: 42)

(24) Arg Gln Ile Pro Ala Pro Gln Gly Ala Val Leu Val Gln Arg Glu Lys Asp Leu Pro Asn Tyr Asn Trp Asn-, (SEQ ID NO: 43)

(25) Ser Arg Gln Ile Pro Ala Pro Gln Gly Ala Val Leu Val Gln Arg Glu Lys Asp Leu Pro Asn Tyr Asn Trp Asn-, (SEQ ID NO: 44)

(26) His Ser Arg Gln Ile Pro Ala Pro Gln Gly Ala Val Leu Val Gln Arg Glu Lys Asp Leu Pro Asn Tyr Asn Trp Asn-, (SEQ ID NO: 45)

(27) Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 46)

(28) Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 47)

(29) Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 48)

(30) Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 49)

(31) Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 50)

(32) Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 51)

(33) Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 52)

(34) Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 53)

(35) Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 54)

(36) Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 55)

(37) Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 56)

(38) Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 57)

(39) Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 58)

(40) Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 59)

(41) Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 60)

(42) Pro Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 61)

(43) Pro Pro Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-, (SEQ ID NO: 62)

(44) Ser Pro Pro Pro Glu Ser Ser Gly Ser Arg Gln Gln Pro Gly Leu Ser Ala Pro His Ser Arg Gln Ile Pro Ala Pro Gln Gly Ala Val Leu Val Gln

```
Arg Glu Lys Asp Leu Pro Asn Tyr Asn Trp Asn-,
(SEQ ID NO: 63)

(45) Leu Ser Pro Pro Pro Glu Ser Ser Gly Ser Arg
    Gln Gln Pro Gly Leu Ser Ala Pro His Ser Arg
    Gln Ile Pro Ala Pro Gln Gly Ala Val Leu Val
    Gln Arg Glu Lys Asp Leu Pro Asn Tyr Asn Trp
    Asn-, (SEQ ID NO: 64)

(46) Ser Leu Ser Pro Pro Pro Glu Ser Ser Gly Ser
    Arg Gln Gln Pro Gly Leu Ser Ala Pro His Ser
    Arg Gln Ile Pro Ala Pro Gln Gly Ala Val Leu
    Val Gln Arg Glu Lys Asp Leu Pro Asn Tyr Asn
    Trp Asn-, (SEQ ID NO: 65)

(47) Thr Ser Leu Ser Pro Pro Pro Glu Ser Ser Gly
    Ser Arg Gln Gln Pro Gly Leu Ser Ala Pro His
    Ser Arg Gln Ile Pro Ala Pro Gln Gly Ala Val
    Leu Val Gln Arg Glu Lys Asp Leu Pro Asn Tyr
    Asn Trp Asn-, (SEQ ID NO: 66)

(48) Gly Thr Ser Leu Ser Pro Pro Pro Glu Ser Ser
    Gly Ser Arg Gln Gln Pro Gly Leu Ser Ala Pro
    His Ser Arg Gln Ile Pro Ala Pro Gln Gly Ala
    Val Leu Val Gln Arg Glu Lys Asp Leu Pro Asn
    Tyr Asn Trp Asn-, and the like. (SEQ ID NO:
    67)
```

$J^1$ represents (a) hydrogen atom or (b) (i) a $C_{1-20}$ acyl group, (ii) a $C_{1-20}$ alkyl group, (iii) a $C_{6-14}$ aryl group, (iv) carbamoyl group, (v) carboxyl group, (vi) sulfino group or (vii) amidino group, (viii) glyoxyloyl group or (ix) amino group, which groups may optionally be substituted with a substituent containing an optionally substituted cyclic group;

The "cyclic group" used includes, for example, "an optionally substituted aromatic hydrocarbon group," "an optionally substituted aromatic heterocyclic group," "an optionally substituted aromatic fused-ring group," "an optionally substituted aromatic fused heterocyclic group," "an optionally substituted non-aromatic cyclic hydrocarbon group," "an optionally substituted non-aromatic heterocyclic group," etc., and examples of the "aromatic hydrocarbon group," "aromatic heterocyclic group," "aromatic fused-ring group" and "aromatic fused heterocyclic group" used are the same as those given above.

The "non-aromatic cyclic hydrocarbon group" used includes a $C_{3-8}$ cycloalkyl group such as cyclopropyl, cyclobutyl, cyclopentyl, cyclohexyl, etc.

The "non-aromatic heterocyclic group" used includes a 5- to 10-membered non-aromatic heterocyclic group containing 1 to 4 hetero atoms of 1 or 2 species selected from nitrogen, sulfur and oxygen atoms in addition to 1 to 7 carbon atoms such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The substituent optionally present on the "cyclic group" includes the same substituents as Substituent Group A described above.

The "$C_{1-20}$ acyl group" used includes, for example, formyl, $C_{1-18}$ alkyl-carbonyl (e.g., $C_{1-18}$ alkyl-carbonyl such as acetyl, propionyl, pivaloyl, octanoyl, decanoyl, palmitoyl, etc.) and the like.

The "$C_{1-20}$ alkyl group" used include, for example, methyl, ethyl, propyl, isopropyl, butyl, isobutyl, sec-butyl, tert-butyl, pentyl, isopentyl, neopentyl, hexyl, heptyl, octyl, nonanyl, decanyl, tridecyl, pentadecyl, etc.

The "$C_{6-14}$ aryl group" used includes, for example, phenyl, 1-naphthyl, 2-naphthyl, biphenyl, etc.

(1) The $C_{1-15}$ acyl group, which may optionally be substituted with a substituent containing a cyclic group, includes (i) formyl, (ii) $C_{1-14}$ alkyl-carbonyl (e.g., $C_{1-6}$ alkyl-carbonyl such as acetyl, propionyl, pivaloyl, etc.), (iii) $C_{3-8}$ cycloalkyl-carbonyl (e.g., cyclopropylcarbonyl, cyclopentylcarbonyl, cyclohexylcarbonyl, 1-methylcyclohexylcarbonyl, etc.), (iv) $C_{3-8}$ cycloalkyl-$C_{1-6}$ alkyl-carbonyl (e.g., cyclopropylacetyl, cyclopentylacetyl, cyclohexylacetyl, etc.), (v) $C_{6-14}$ aryl-carbonyl (e.g., benzoyl, 1-naphthoyl, 2-naphthoyl, etc.), $C_{6-14}$ aralkyl-carbonyl (e.g., phenylacetyl, 3-phenylpropionyl, etc.), (vi) 5- to 7-membered monocyclic heterocyclic carbonyl containing 1 to 4 hetero atoms of 1 or 2 species selected from nitrogen, sulfur and oxygen atoms in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), (vii) 5- to 7-membered monocyclic heterocycle, which contains 1 to 4 hetero atoms of 1 or 2 species selected from nitrogen, sulfur and oxygen atoms in addition to carbon atoms, —$C_{1-6}$ alkylcarbonyl (e.g., 3-pyridylacetyl, 4-pyridylacetyl, 2-thienylacetyl, 2-furylacetyl, morpholinoacetyl, thiomorpholinoacetyl, piperidin-2-acetyl, pyrrolidine-2-ylacetyl, etc.), (viii) 5- to 14-membered (preferably, 5- to 10-membered) bicyclic or tricyclic aromatic heterocyclic carbonyl containing 1 to 4 hetero atoms of 1 or 2 species selected from nitrogen, sulfur and oxygen atoms in addition to 3 to 11 carbon atoms (e.g., 2-indolecarbonyl, 3-indolecarbonyl, 2-quinolylcarbonyl, 1-isoquinolylcarbonyl, 2-benzo[b]thienylcarbonyl, 2-benzo[b]furanylcarbonyl, etc.), (ix) 5- to 14-membered (preferably 5- to 10-membered) bicyclic or tricyclic aromatic heterocycle, which contains 1 to 4 hetero atoms of 1 or 2 species selected from nitrogen, sulfur and oxygen atoms in addition to 3 to 11 carbon atoms, —$C_{1-6}$ alkylcarbonyl (e.g., 2-indoleacetyl, 3-indoleacetyl, 2-quinolylacetyl, 1-isoquinolylacetyl, 2-benzo[b]thienylacetyl, 2-benzo[b]furanylacetyl, etc.), etc., among others, preferably used are acetyl, 2-indolecarbonyl, 3-indolecarbonyl, 3-indoleacetyl, 3-indolepropionyl, 2-indolinecarbonyl, 3-phenylpropionyl, diphenylacetyl, 2-pyridinecarbonyl, 3-pyridinecarbonyl, 4-pyridinecarbonyl, 1-pyridinioacetyl, 2-pyridineacetyl, 3-pyridineacetyl, 4-pyridineacetyl, 3-(1-pyridinio)propionyl, 3-(pyridin-2-yl)propionyl, 3-(pyridin-3-yl)propionyl, 3-(pyridin-4-yl)propionyl, 4-imidazoleacetyl, cyclohexanecarbonyl, 1-piperidineacetyl, 1-methyl-1-piperidinioacetyl, 4-piperidinecarbonyl, 2-pyrimidinecarbonyl, 4-pyrimidinecarbonyl, 5-pyrimidinecarbonyl, 2-pyrimidineacetyl, 4-pyrimidineacetyl, 5-pyrimidineacetyl, 3-(pyrimidin-2-yl)propionyl, 3-(pyrimidin-4-yl)propionyl, 3-(pyrimidin-5-yl)propionyl, butanoyl, hexanoyl, octanoyl, D-glucuronyl, amino-(4-hydroxyphenyl)acetyl), etc.

(2) The $C_{1-20}$ alkyl group (preferably, a $C_{1-17}$ alkyl group, more preferably, a $C_{1-15}$ alkyl group), which may optionally be substituted with a substituent containing a cyclic group, includes, for example, (i) mono- or di-$C_{1-20}$ alkyl (e.g., methyl, ethyl, propyl, isopropyl, butyl, isobutyl, sec-butyl, tert-butyl, pentyl, isopentyl, neopentyl, hexyl, heptyl, octyl, nonanyl, decanyl, tridecyl, pentadecyl), (ii) mono- or di-$C_{3-8}$ cycloalkyl (e.g., cyclopropyl, cyclopentyl, etc.), (iii) mono- or di-$C_{3-8}$ cycloalkyl-$C_{1-12}$ (preferably, $C_{1-9}$, more preferably, $C_{1-7}$) alkyl (e.g., cyclopropylmethyl, cyclopentylmethyl, cyclohexylethyl, etc.), (iv) mono- or di-$C_{7-20}$ (preferably, $C_{7-17}$, more preferably $C_{7-15}$) aralkyl (e.g., benzyl, phenethyl, etc.), (v) mono- or di-5- to 7-membered monocyclic heterocycle, which contains 1 to 4 hetero atoms of 1 or 2 species selected from nitrogen, sulfur and oxygen atoms in addition to carbon atoms, —$C_{1-6}$ alkyl group (e.g., 3-pyridylmethyl, 4-pyridylmethyl, 2-thienylmethyl, furfuryl, etc.), (vi) monoor di-5- to 14-membered (preferably, 5- to 10-membered) bicyclic or tricyclic aromatic heterocycle, which contains 1 to 4 hetero atoms of 1 or 2 species selected from nitrogen, sulfur and oxygen atoms in addition to 3 to 11 carbon atoms, —$C_{1-6}$ alkyl (e.g., 2-indolemethyl, 3-indolemethyl, 3-(indol-3-yl) propyl, 2-quinolylmethyl, 1-isoquinolylmethyl, 2-benzo [b]thienylmethyl, 2-benzo[b]furanylmethyl, etc.), etc.; among others, methyl, ethyl, benzyl, 3-(indol-3-yl)propyl, etc. are preferably used.

(3) The $C_{6-14}$ aryl group, which may optionally be substituted with a substituent containing a cyclic group, includes, for example, a $C_{6-14}$ aryl group (e.g., phenyl, naphthyl, biphenyl), which may optionally be substituted with (i) a $C_{6-14}$ carbocyclic group (e.g., cycloalkyl, phenyl, 1-naphthyl, 2-naphthyl, etc.), (ii) a 5- to 7-membered monocyclic heterocyclic group containing 1 to 4 hetero atoms of 1 or 2 species selected from nitrogen, sulfur and oxygen atoms in addition to carbon atoms (e.g., 3-pyridyl, 2-thienyl, etc.), (iii) a 5- to 14-membered (preferably, 5- to 10-membered) bicyclic or tricyclic aromatic heterocyclic group containing 1 to 4 hetero atoms of 1 or 2 species selected from nitrogen, sulfur and oxygen atoms in addition to 3 to 11 carbon atoms (e.g., 2-indolyl, 3-indolyl, 2-quinolyl, 1-isoquinolyl, 2-benzo[b] thienyl, 2-benzo[b]furanyl, etc.), etc.

(4) The optionally substituted carbamoyl group, which may optionally be substituted with a substituent containing a cyclic group, includes (i) carbamoyl, (ii) mono- or di-$C_{1-15}$ alkylcarbamoyl (e.g., methylcarbamoyl, ethylcarbamoyl), (iii) mono- or di-$C_{3-8}$ cycloalkylcarbamoyl (e.g., cyclopropylcarbamoyl, cyclopentylcarbamoyl, cyclohexylcarbamoyl, etc.), (iv) mono- or di-$C_{3-8}$ cycloalkyl-$C_{1-6}$ alkyl-carbamoyl (e.g., cyclopropylmethylcarbamoyl, cyclopentylmethylcarbamoyl, 2-cyclohexylethylcarbamoyl, etc.) (v) mono- or di-$C_{6-14}$ aryl-carbamoyl (e.g., phenylcarbamoyl, etc.), a mono- or di-$C_{6-14}$ aralkyl-carbamoyl (e.g., benzylcarbamoyl, phenethylcarbamoyl, etc.), (vi) mono- or di-5- to 7-membered monocyclic heterocyclic carbamoyl containing 1 to 4 hetero atoms of 1 or 2 species selected from nitrogen, sulfur and oxygen atoms in addition to carbon atoms (e.g., 3-pyridinecarbamoyl, 2-thiophenecarbamoyl, piperidin-3-ylcarbamoyl, etc.), (vii) mono- or di-5- to 7-membered monocyclic heterocycle, which contains 1 to 4 hetero atoms of 1 or 2 species selected from nitrogen, sulfur and oxygen atoms in addition to carbon atoms, —$C_{1-6}$ alkylcarbamoyl (e.g., 3-pyridylmethylcarbamoyl, 2-(pyridin-2-yl)ethylcarbamoyl, 2-(piperidin-1-yl)ethylcarbamoyl, etc.), (viii) mono- or di-5- to 14-membered (preferably, 5- to 10-membered) bicyclic or tricyclic aromatic heterocyclic carbamoyl containing 1 to 4 hetero atoms of 1 or 2 species selected from nitrogen, sulfur and oxygen atoms in addition to 3 to 11 carbon atoms (e.g., 4-indolecarbamoyl, 5-indolecarbamoyl, 3-quinolylcarbamoyl, 5-quinolylcarbamoyl, etc.), (ix) mono- or di-5- to 14-membered (preferably, 5- to 10-membered) bicyclic or tricyclic aromatic heterocyclic-$C_{1-6}$ alkylcarbonyl containing 1 to 4 hetero atoms of 1 or 2 species selected from nitrogen, sulfur and oxygen atoms in addition to 3 to 11 carbon atoms (e.g., benzimidazol-2-ylmethylcarbamoyl, 2-(indol-3-yl)ethylcarbamoyl, etc.), (x) 5- to 7-membered cyclic carbamoyl (e.g., 1-pyrrolidinylcarbonyl, 1-piperidinylcarbonyl, hexamethyleneiminocarbonyl, etc.), (xi) $C_{1-15}$ acylcarbamoyl ($C_{1-15}$ acyl as used herein has the same significance as the "$C_{1-15}$ acyl group" in the "$C_{1-15}$ acyl group, which may optionally be substituted with a substituent containing a cyclic group"), (xii) $C_{1-15}$ alkylaminocarbamoyl ($C_{1-15}$ alkyl as used herein has the same significance as the "$C_{1-15}$ alkyl group" in the "$C_{1-15}$ alkyl group, which may optionally be substituted with a substituent containing a cyclic group"), (xiii) $C_{6-14}$ arylaminocarbamoyl ($C_{6-14}$ aryl as used herein has the same significance as "$C_{6-14}$ aryl group, which may optionally be substituted with a substituent containing a cyclic group"), etc.; among others, 2-(indol-3-yl)ethylcarbamoyl, etc. are preferably used.

(5) The carboxyl group, which may optionally be substituted with a substituent containing a cyclic group, includes (i) $C_{1-15}$ alkyloxycarbonyl ($C_{1-15}$ alkyl herein has the same significance as the "$C_{1-15}$ alkyl group" in the "$C_{1-15}$ alkyl group, which may optionally be substituted with a substituent containing a cyclic group," e.g., tert-butyloxycarbonyl, benzyloxycarbonyl, 9-fluorenylmethoxycarbonyl), (ii) $C_{6-14}$ aryloxycarbonyl ($C_{6-14}$ aryl herein has the same significance as the "$C_{6-14}$ aryl group" in the "$C_{6-14}$ aryl group, which may optionally be substituted with a substituent containing a cyclic group," e.g., phenoxycarbonyl), etc.

(6) The sulfino group, which may optionally be substituted with a substituent containing a cyclic group, includes (i) $C_{1-15}$ alkylsulfonyl ($C_{1-15}$ alkyl as used herein has the same significance as the "$C_{1-15}$ alkyl group" in the "$C_{1-15}$ alkyl group, which may optionally be substituted with a substituent containing a cyclic group," e.g., benzylsulfonyl), (ii) $C_{6-14}$ arylsulfonyl ($C_{6-14}$ aryl as used herein has the same significance as the "$C_{6-14}$ aryl group" in the "$C_{6-14}$ aryl group, which may optionally be substituted with a substituent containing a cyclic group," e.g., tosyl), etc.

(7) The amidino group, which may optionally be substituted with a substituent containing a cyclic group, includes (i) amidino, (ii) $C_{1-15}$ alkylamidino ($C_{1-15}$ alkyl as used herein has the same significance as the "$C_{1-15}$ alkyl group" in the "$C_{1-15}$ alkyl group, which may optionally be substituted with a substituent containing a cyclic group," e.g., N-methylamidino), (iii) $C_{1-15}$ acylamidino ($C_{1-15}$ acyl as used herein has the same significance as the "$C_{1-15}$ acyl group" in the "$C_{1-15}$ acyl group, which may optionally be substituted with a substituent containing a cyclic group," e.g., N-acetylamidino), etc.

(8) The glyoxyloyl group, which may optionally be substituted with a substituent containing a cyclic group, includes (i) $C_{1-15}$ alkyloxalyl ($C_{1-15}$ alkyl as used herein has the same significance as the "$C_{1-15}$ alkyl group" in the "$C_{1-15}$ alkyl group, which may optionally be substituted with a substituent containing a cyclic group," e.g., ethyloxalyl), (ii) $C_{6-14}$ aryloxalyl ($C_{6-14}$ aryl as used herein has the same significance as the "$C_{6-14}$ aryl group" in the "$C_{6-14}$ aryl group, which may optionally be substituted with a substituent containing a cyclic group," e.g., phenyloxalyl), etc.

(9) The amino group, which may optionally be substituted with a substituent containing a cyclic group, includes (i) $C_{1-15}$ alkylamino ($C_{1-15}$ alkyl as used herein has the same significance as the "$C_{1-15}$ alkyl group" in the "$C_{1-15}$ alkyl group, which may optionally be substituted with a substituent containing a cyclic group").

Among those described above, preferred examples of $J^1$ used include hydrogen atom, formyl, acetyl, 3-indolecarbonyl, 3-(indol-3-yl)propionyl, 3-phenylpropionyl, diphenylacetyl, 3-(pyridin-3-yl)propionyl, 4-imidazoleacetyl, cyclohexanecarbonyl, 1-piperidineacetyl, 1-methyl-1-piperidinioacetyl, 4-piperidinecarbonyl, hexanoyl, amino-(4-hydroxyphenyl)acetyl, D-glucuronyl, 2-(indol-3-yl) ethylcarbamoyl, tert-butyloxycarbonyl, 9-fluorenylmethoxycarbonyl, amidino, 4-guanidomethylbenzoyl, benzoyl, 3-indoleacetyl, benzyloxycarbonyl, tosyl, phenyl, benzyl, phenethyl, 3-pyridinecarbonyl, 2-pyridinecarbonyl, 4-pyridinecarbonyl, propionyl, isobutyryl, phenylacetyl, 2-methylnicotinoyl, 5-methylnicotinoyl, 6-methylnicotinoyl, pyrazinecarbonyl, cyclopropanecarbonyl, trifluoroacetyl, (R)-3-hydroxy-2-methylpropionyl, 2-hydroxyisobutyryl, 3-furancarbonyl, pyrrole-2-carbonyl, 4-imidazolecarbonyl, 6-hydroxynicotinoyl, 6-chloronicotinoyl, 6-(trifluoromethyl)nicotinoyl, dimethylcarbamoyl, 1-azetidinecarbonyl, 2-azetidinecarbonyl, 4-aminobenzoyl, 4-aminomethylbenzoyl, pyrrole-3-carbonyl, pyrimidine-4-carbonyl, pyrimidine-2-carbonyl, pyridazine-4-carbonyl, 6-aminocaproyl, glycyl, glycylglycyl, glycylglycylglycyl, alanylalanylalanyl, alanylalanylalanylalanyl (SEQ ID NO: 68), acetylglycyl, acetylglycylglycyl, acetylglycylglycylglycyl, acetylalanylalanylalanyl, acetylalanylalanylalanylalanyl (SEQ ID NO: 68), D-arginylglycyl, D-arginylglycylglycyl, D-arginylglycylglycylglycyl, D-arginylalanylalanylalanyl, D-arginylalanylalanylalanylalanyl, acetyl-D-arginylglycyl, acetyl-D-arginylglycylglycyl, acetyl-D-arginylglycylglycylglycyl, acetyl-D-arginylalanylalanylalanyl, acetyl-D-arginylalanylalanylalanylalanyl, cyclopropanecarbonyl, cyclopentanecarbonyl, cyclobutanecarbonyl, cyclohexanecarbonyl, 1-naphthoyl, 2-naphthoyl, arginyl, arginylarginyl, 6-(arginylamino)caproyl, 6-(D-arginylamino)caproyl, 6-(D-arginyl-D-arginylamino)caproyl, 6-(acetyl-D-arginylamino)caproyl, 6-((R)-2, 3-diaminopropionylamino)caproyl, 6-(D-norleucylamino) caproyl, 3-(D-arginylamino)propionyl, 4-(D-arginylamino)butyryl, 4-(D-arginyl-D-arginylamino)butyryl, 4-(D-arginyl-D-arginyl-D-arginylamino)butyryl, 3-(4-hydroxyphenyl)propionyl, butyryl, methyl, adipoyl, pyroglutamyl, glycoloyl, etc.; among others, preferred are hydrogen atom, formyl, acetyl, propionyl, 3-indolecarbonyl, 3-(indo-3-yl)propionyl, 3-phenylpropionyl, 3-(pyridin-3-yl)propionyl, 4-imidazoleacetyl, cyclohexanecarbonyl, hexanoyl, amino-(4-hydroxyphenyl)acetyl, 2-(indo-3-yl)ethylcarbamoyl, 9-fluorenylmethoxycarbonyl, amidino, 4-guanidomethylbenzoyl, benzoyl, 3-indoleacetyl, benzyl, phenethyl, 3-pyridinecarbonyl, 2-pyridinecarbonyl, 4-pyridinecarbonyl, isobutyryl, phenylacetyl, 6-methylnicotinoyl, pyrazinecarbonyl, cyclopropanecarbonyl, trifluoroacetyl, (R)-3-hydroxy-2-methylpropionyl, 2-hydroxyisobutyryl, 3-furancarbonyl, pyrrole-2-carbonyl, 4-imidazolecarbonyl, 6-hydroxynicotinoyl, 6-chloronicotinoyl, 6-(trifluoromethyl)nicotinoyl, dimethylcarbamoyl, 1-azetidinecarbonyl, 4-aminobenzoyl, 4-aminomethylbenzoyl, pyrrole-3-carbonyl, pyrimidine-4-carbonyl, pyrimidine-2-carbonyl, pyridazine-4-carbonyl, 6-aminocaproyl, cyclopropanecarbonyl, 2-naphthoyl, arginyl, 6-(arginylamino)caproyl, 6-(D-arginylamino)caproyl, 6-(D-arginyl-D-arginylamino)caproyl, 6-(acetyl-D-arginylamino)caproyl, 6-((R)-2, 3-diaminopropionylamino)caproyl, 6-(D-norleucylamino)caproyl, 3-(D-arginylamino)propionyl, 4-(D-arginylamino)butyryl, 4-(D-arginyl-D-arginylamino)butyryl, 4-(D-arginyl-D-arginyl-D-arginylamino)butyryl, 3-(4-hydroxyphenyl)propionyl, butyryl, adipoyl, pyroglutamyl, etc., and acetyl is particularly preferred.

$J^2$ represents (1) NH optionally substituted with a $C_{1-6}$ alkyl group, (2) $CH_2$ optionally substituted with a $C_{1-6}$ alkyl group, (3) O or (4) S.

The "$C_{1-6}$ alkyl group" used includes methyl, ethyl, propyl, isopropyl, butyl, isobutyl, sec-butyl, tert-butyl, pentyl, isopentyl, neopentyl, hexyl, etc.

Preferably, $J^2$ is NH.

Each of $J^3$ through $J^{12}$ represents hydrogen atom or a $C_{1-3}$ alkyl group.

The "$C_{1-3}$ alkyl group" used includes methyl, ethyl, propyl, isopropyl, etc.

Preferably, $J^3$ is hydrogen atom.
Preferably, $J^4$ is hydrogen atom.
Preferably, $J^5$ is hydrogen atom.
Preferably, $J^6$ is hydrogen atom.
Preferably, $J^7$ is hydrogen atom.
Preferably, $J^8$ is hydrogen atom.
Preferably, $J^9$ is hydrogen atom.
Preferably, $J^{10}$ is hydrogen atom.
Preferably, $J^{11}$ is hydrogen atom.
Preferably, $J^{12}$ is hydrogen atom.

Each of $Q^3$ through $Q^{12}$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, (6) an optionally substituted non-aromatic heterocyclic group having carbon atoms not greater than 7, (7) an optionally substituted amino group;

(8) an optionally substituted guanidino group;

(9) an optionally substituted hydroxyl group;

(10) an optionally substituted carboxyl group;

(11) an optionally substituted carbamoyl group; and,

(12) an optionally substituted sulfhydryl group;

or hydrogen atom.

Particularly preferred $Q^3$ to $Q^9$ are a $C_{1-4}$ alkyl group having a substituent selected from the group consisting of:

(1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, (6) an optionally substituted non-aromatic heterocyclic group having carbon atoms not greater than 7, (7) an optionally substituted amino group;

(8) an optionally substituted guanidino group;

(9) an optionally substituted hydroxyl group;

(10) an optionally substituted carboxyl group;

(11) an optionally substituted carbamoyl group; and,

(12) an optionally substituted sulfhydryl group, or hydrogen atom.

The "optionally substituted $C_{6-12}$ aromatic hydrocarbon group," "optionally substituted 5- to 14-membered aromatic heterocyclic group consisting of 1 to 7 carbon atoms and hetero atoms selected from the group consisting of nitrogen, oxygen and sulfur atoms," "optionally substituted $C_{8-14}$ aromatic fused-ring group," "optionally substituted 5- to 14-membered aromatic fused heterocyclic group consisting of 3 to 11 carbon atoms and hetero atoms selected from the group consisting of nitrogen, oxygen and sulfur atoms,"

"optionally substituted non-aromatic cyclic hydrocarbon group having carbon atoms not greater than 7" and "optionally substituted non-aromatic heterocyclic group having carbon atoms not greater than 7" used are the same as those given above.

(1) As the $C_{1-4}$ alkyl group having an optionally substituted $C_{6-12}$ aromatic hydrocarbon group, there are used, for example, benzyl, 4-hydroxybenzyl, 2-chlorobenzyl, 3-chlorobenzyl, 4-chlorobenzyl, 4-aminobenzyl, etc.

(2) As the $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms, there are used, for example, 2-pyridylmethyl, 3-pyridylmethyl, 4-pyridylmethyl, 4-imidazolemethyl, etc.

(3) As the $C_{1-4}$ alkyl group having an optionally substituted $C_{8-14}$ aromatic fused-ring group, there are used, for example, 1-naphthylmethyl, 2-naphthylmethyl, etc.

(4) As the $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms, there are used, for example, 3-indolemethyl, 1-formylindol-3-ylmethyl, 2-quinolylmethyl, etc.

(5) As the $C_{1-4}$ alkyl group having an optionally substituted non-aromatic cyclic hydrocarbon group having carbon atoms not greater than 7, there are used, for example, cyclohexylmethyl, etc.

(6) As the $C_{1-4}$ alkyl group having an optionally substituted non-aromatic heterocyclic group having carbon atoms not greater than 7, there are used, for example, piperidin-1-ylmethyl, etc.

(7) As the $C_{1-4}$ alkyl group having an optionally substituted amino group, there are used, for example, 2-aminoethyl, 3-aminopropyl, 4-aminobutyl, 4-acetamidobutyl, etc.

(8) As the $C_{1-4}$ alkyl group having an optionally substituted guanidino group, there are used, for example, 3-guanidinopropyl, 3-(N-tosyl)guanidinopropyl, etc.

(9) As the $C_{1-4}$ alkyl group having an optionally substituted hydroxyl group, there are used, for example, hydroxymethyl, 1-hydroxyethyl, benzyloxymethyl, etc.

(10) As the $C_{1-4}$ alkyl group having an optionally substituted carboxyl group, there are used, for example, carboxylmethyl, 2-carboxylethyl, benzyloxycarbonylmethyl, etc.

(11) As the $C_{1-4}$ alkyl group having an optionally substituted carbamoyl group, there are used, for example, carbamoylmethyl, 2-carbamoylethyl, xanthylcarbamoyl, etc.

(12) As the $C_{1-4}$ alkyl group having an optionally substituted sulfhydryl group, there are used, for example, sulfhydrylmethyl, 2-(methylsulfhydryl)ethyl, etc.

(13) As the unsubstituted $C_{1-4}$ alkyl group, there are used, for example, methyl, ethyl, propyl, isopropyl, butyl, isobutyl, sec-butyl, tert-butyl, etc.

Preferred examples of $Q^3$ used include hydrogen atom, 4-hydroxybenzyl, 3-pyridylmethyl, 4-pyridylmethyl, methyl, isobutyl, hydroxymethyl, carboxymethyl, 4-aminobutyl, etc., particularly preferably, 4-hydroxybenzyl, 3-pyridylmethyl, 4-pyridylmethyl, etc.

Preferred examples of $Q^4$ used include carbamoylmethyl, 2-carbamoylethyl, 4-hydroxybenzyl, 4-imidazolemethyl, isobutyl, hydroxymethyl, 1-hydroxyethyl, carboxymethyl, 4-aminobutyl, etc., particularly preferably, carbamoylmethyl, 2-carbamoylethyl, 4-hydroxybenzyl, etc.

Preferred examples of $Q^5$ used include benzyl, 2-chlorobenzyl, 3-chlorobenzyl, 4-chlorobenzyl, 4-aminobenzyl, 2-pyridylmethyl, 3-pyridylmethyl, 4-pyridylmethyl, 1-naphthylmethyl, 2-naphthylmethyl, 3-indolemethyl, 1-formylindol-3-ylmethyl, 2-quinolylmethyl, cyclohexylmethyl, hydroxymethyl, 1-hydroxyethyl, methyl, isopropyl, isobutyl, sec-butyl, carboxymethyl, 4-aminobutyl, etc., particularly preferably, benzyl, 2-chlorobenzyl, 3-chlorobenzyl, 4-chlorobenzyl, 4-aminobenzyl, 2-pyridylmethyl, 3-pyridylmethyl, 4-pyridylmethyl, 1-naphthylmethyl, 2-naphthylmethyl, 3-indolemethyl, 2-quinolylmethyl, cyclohexylmethyl, 1-hydroxyethyl, isopropyl, isobutyl, sec-butyl, etc.

Preferred examples of $Q^6$ used are methyl, hydroxymethyl, 1-hydroxyethyl, carbamoylmethyl, 2-carbamoylethyl, etc., particularly preferably, carbamoylmethyl, etc.

Preferred examples of $Q^7$ used are 4-hydroxybenzyl, carbamoylmethyl, 3-pyridylmethyl, methyl, isobutyl, benzyl, 4-aminobutyl, 3-indolemethyl, etc., particularly preferably, 4-hydroxybenzyl, etc.

Preferred examples of $Q^8$ used include benzyl, 2-pyridylmethyl, 3-pyridylmethyl, 4-pyridylmethyl, 2-naphthylmethyl, 3-indolemethyl, hydroxymethyl, cyclohexylmethyl, sec-butyl, 1-hydroxyethyl, methyl, methyl, isobutyl, 4-aminobutyl, 2-carboxyethyl, 3-carboxylpropyl, etc., more preferably, 4-pyridylmethyl, 3-indolemethyl, 2-carboxyethyl, sec-butyl, and particularly preferably, 2-carboxyethyl.

Preferred examples of $Q^9$ used include hydrogen atom, methyl, ethyl, hydroxymethyl, 1-hydroxyethyl, carbamoylmethyl, 2-carbamoylethyl, ureidomethyl, acetamidomethyl, diethyl, methylcarbamoylmethyl, dimethylcarbamoylmethyl, etc., particularly preferably, carbamoylmethyl, ureidomethyl, etc.

Preferred examples of $Q^{10}$ used include 4-hydroxybenzyl, 3-indolemethyl, methyl, 1-hydroxyethyl, 3-guanidinopropyl, etc., particularly preferably, 3-indolemethyl, etc.

Preferred examples of $Q^{11}$ used include carbamoylmethyl, etc.

Preferred examples of $Q^{12}$ used include methyl, carbamoylmethyl, etc., particularly preferably, carbamoylmethyl, etc.

Each of $Y^1$ through $Y^3$ represents a group shown by formula: —CON($J^{13}$)—, —CSN($J^{13}$)—, —C($J^{14}$)N($J^{13}$)— or —N($J^{13}$)CO— (wherein each of $J^{13}$ and $J^{14}$ represents hydrogen atom or a $C_{1-3}$ alkyl group).

As the $C_{1-3}$ alkyl group shown by $J^{13}$ and $J^{14}$, methyl, ethyl, propyl or isopropyl is used.

$J^{13}$ is preferably hydrogen atom.

$J^{14}$ is preferably hydrogen atom.

$Y^1$ is preferably a group shown by formula: —CONH— or —CH$_2$NH—, etc.

$Y^2$ is preferably a group shown by formula: —CONH— or —CH$_2$NH—, etc., particularly preferably a group shown by formula: —COCN'.

$Y^3$ is preferably a group shown by formula: —CONH—, etc.

$J^3$ and $Q^3$, $J^4$ and $Q^4$, $J^5$ and $Q^5$, $J^6$ and $Q^6$, $J^7$ and $Q^7$, $J^8$ and $Q^8$, $J^9$ and $Q^9$, $J^{10}$ and $Q^{10}$, $J^{11}$ and $J^{12}$ and $Q^{12}$ may be combined together to form a ring. In this case, C($J^3$)($Q^3$), C($J^4$)($Q^4$), C($J^5$)($Q^5$), C($J^6$)($Q^6$), C($J^7$)($Q^7$), C($J^8$)($Q^8$), C($J^9$)($Q^9$), C($J^{10}$)($Q^{10}$), C($J^{11}$)($Q^{11}$) or C($J^{12}$)($Q^{12}$) may form, for example, cyclopentane, cyclohexane, piperidine, etc.

$Z^1$ and $R^1$, $J^2$ and $Q^3$, $Y^1$ and $Q^4$, $Y^2$ and $Q^5$, $Y^3$ and $Q^6$, $J^2$ and $Q^7$, $Y^2$ and $Q^8$, $Y^3$ and $Q^9$, $J^2$ and $Q^{10}$, $Y^3$ and $Q^{11}$, and $J^2$ and $Q^{12}$ (preferably, $J^2$ and $Q^3$, $Y^1$ and $Q^4$, $Y^2$ and $Q^5$, $Y^3$ and $Q^6$, $J^2$ and $Q^7$, $Y^2$ and $Q^8$, $Y^3$ and $Q^9$, $J^2$ and $Q^{10}$, $Y^3$ and $Q^{11}$, and $J^2$ and $Q^{12}$) may be combined together to form a ring. Also, the ring formed may be substituted or form a fused ring.

When $Z^1$ and $R^1$, $J^2$ and $Q^3$, $J^2$ and $Q^7$, $J^2$ and $Q^{10}$, or $J^2$ and $Q^{12}$ forms a ring, the ring is shown by $Z^1$—N—CH—$R^1$, $J^2$-C($J^3$)($Q^3$), $J^2$-C($J^7$)($Q^7$), $J^2$-C($J^{10}$)($Q^{10}$) or $J^2$-C($J^{12}$)($Q^{12}$) including, e.g., azetidine, pyrrolidine, piperidine or thiazolidine. Also, the ring formed may be substituted or may form a fused ring. As $Z^1$—N—CH—$R^1$, azetidine, pyrrolidine, 4-hydroxypyrrolidine, piperidine, etc. are preferably used.

When $Y^1$ and $Q^4$, $Y^2$ and $Q^5$, $Y^3$ and $Q^6$, $Y^2$ and $Q^8$, $Y^3$ and $Q^9$, or $Y^3$ and $Q^{11}$ forms a ring, the ring is shown by $Y^1C(J^4)(Q^4)$, $Y^2C(J^5)(Q^5)$, $Y^3C(J^6)(Q^6)$, $Y^2C(J^8)(Q^8)$, $Y^3C(J^9)(Q^9)$ or $Y^3C(J^{11})(Q^{11})$ including, e.g., pyrrolidine-2-carbonyl, piperidine-2-carbonyl or thiazolidine-4-carbonyl. Also, the ring formed may be substituted or may form a fused ring.

When $Y^2$ and Q are combined together to form a ring, it is preferred to form pyrrolidine-2-carbonyl by $Y^2C(J^8)(Q^8)$.

$Z^{10}$ represents hydrogen atom, O or S; O and S are preferred among others, and O is particularly preferred.

Preferred examples of the group represented by formula:

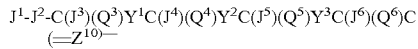

include:
Tyr Asn Trp Asn- (SEQ ID NO: 69),
Tyr Asn Trp D-Asn-,
Tyr Asn D-Trp Asn-,
Tyr D-Asn Trp Asn-,
D-Tyr Asn Trp Asn-,
Tyr Lys Trp Asn- (SEQ ID NO: 70),
Tyr Asp Trp Asn- (SEQ ID NO: 71),
Tyr Tyr Trp Asn- (SEQ ID NO: 72),
Tyr Leu Trp Asn- (SEQ ID NO: 73),
Tyr Asn Ala Asn- (SEQ ID NO: 74),
Tyr Asn Leu Asn- (SEQ ID NO: 75),
Tyr Asn Ser Asn- (SEQ ID NO: 76),
Tyr Asn Asp Asn- (SEQ ID NO: 77),
Tyr Asn Lys Asn- (SEQ ID NO: 78),
Ala Asn Trp Asn- (SEQ ID NO: 79),
Leu Asn Trp Asn- (SEQ ID NO: 80),
Ser Asn Trp Asn- (SEQ ID NO: 81),
Asp Asn Trp Asn- (SEQ ID NO: 82),
Lys Asn Trp Asn- (SEQ ID NO: 83),
Tyr Asn Trp(For) Asn- (SEQ ID NO: 84),
D-Tyr Asn D-Trp Asn-,
D-Tyr Asn Ala Asn-,
D-Tyr Asn Ser Asn-,
D-Tyr Asn Cha Asn-,
D-Tyr Asn Thr Asn-,
D-Tyr Asn Ile Asn-,
D-Tyr Gln Trp Asn-,
D-Tyr Thr Trp Asn-,
D-Tyr Asn Val Asn-,
D-Tyr D-Asn Trp Asn-,
D-Tyr D-Asn D-Trp Asn-,
D-Tyr Asn Phe Asn-,
D-Tyr Asn Nal(1) Asn-,
D-Tyr Asn Nal(2) Asn-,
D-Tyr Asn Phe(2Cl) Asn-,
D-Tyr Asn Phe(3Cl) Asn-,
D-Tyr Asn Phe(4Cl) Asn-,
D-Tyr Asn Phe(4NH$_2$) Asn-,
D-Tyr Asn Pya(3) Asn-,
D-Tyr D-Asn Phe Asn-,
D-Tyr D-Asn Cha Asn-,
D-Tyr D-Asn Thr Asn-,
D-Tyr Asn Pya(2) Asn-,
D-Tyr Asn Pya(4) Asn-,
D-Tyr D-Ser Trp Asn-,
D-Tyr D-His Trp Asn-,
D-Pya(3) D-Asn Cha Asn-,
D-Pya(3) D-Tyr Cha Asn-,
TyrΨ(CH$_2$NH)Asn Trp Asn- (SEQ ID NO: 85),
D-Tyr AsnΨ(CH$_2$NH)Trp Asn-,
TyrΨ(CH$_2$NH)Asn D-Trp Asn-,
D-Tyr Asn Ala(2-Qui) Asn-,
D-Tyr Asn D-Pya(4) Asn-,
D-Tyr Asn D-Pya(4) Asn-,
D-Tyr D-Asn Pya(4) Asn-,
Tyr D-Asn Cha Asn-,
Dap D-Tyr Asn Trp Asn-,
Arg D-Tyr D-Pya(4) Asn-,
Arg Arg D-Tyr D-Pya(4) Asn-,
Arg Acp D-Tyr D-Pya(4) Asn-,
D-Arg Acp D-Tyr D-Trp Asn-,
D-Arg D-Arg Acp D-Tyr D-Trp Asn-,
Ac D-Arg Acp D-Tyr D-Trp Asn-,
D-Dap Acp D-Tyr D-Trp Asn-,
D-Nle Acp D-Tyr D-Trp Asn-,
D-Arg β-Ala D-Tyr D-Trp Asn-,
D-Arg γ-Abu D-Tyr D-Trp Asn-,
D-Arg D-Arg γ-Abu D-Tyr D-Trp Asn-,
D-Arg D-Arg D-Arg γ-Abu D-Tyr D-Trp Asn-,
Gly D-Tyr D-Trp Asn-,
Ac Gly D-Tyr D-Trp Asn-,
D-Tyr D-Tyr D-Trp Asn-,
Ac D-Tyr D-Tyr D-Trp Asn-,
pGlu D-Tyr D-Trp Asn-,
Tyr D-Tyr D-Trp Asn-,
Ac Tyr D-Tyr D-Trp Asn-,
and the like.

Preferred examples of the group represented by formula:

$$J^1\text{-}J^2\text{-}C(J^7)(Q^7)Y^2C(J^8)(Q^8)Y^3C(J^9)(Q^9)C(=Z^{10})\text{—}$$

Include:
Fmoc Asn Trp Asn-,
D-Asn Trp Asn-,
D-Tyr Trp Asn-,
D-Tyr D-Trp Asn-,
D-Tyr Ser Asn-,
D-Tyr Thr Asn-,
D-Tyr Ile Asn-,
D-Tyr Phe Asn-,
D-Tyr Nal(2) Asn-,
D-Pya(3) Phe Asn-,
D-Pya(3) Trp Asn-,
D-Tyr D-Pya(4) Asn-,
D-Asn Cha Asn-
D-Tyr D-Pya(4) Ala-
D-Tyr D-Pya(4) Thr-
D-Tyr Pya(4) Ala-
D-Tyr D-Trp Ala-
D-Tyr D-Trp Abu-
D-Tyr D-Phe Ala-6-Aminocaproyl-
D-Tyr D-Pya(4) Asn-
Ac D-Tyr D-Pya(4) Asn-
Benzoyl D-Tyr D-Trp Asn-
Cyclopropanecarbonyl D-Tyr D-Trp Asn-
Butyryl D-Tyr D-Trp Asn-
Me D-Tyr D-Trp Asn-
Ac D-Tyr D-Trp Gln-
Ac D-Tyr D-Trp Ser-
Ac D-Tyr D-Trp Thr-
Ac D-Tyr D-Trp Alb-
Ac D-Tyr D-Trp Dap(Ac)-
Ac D-Tyr D-Trp Dap(For)-
Ac D-Tyr D-Trp Asn-
Ac D-NMeTyr D-Trp Asn-
For D-Tyr D-Trp Asn-
Propionyl D-Tyr D-Trp Asn-
Amidino D-Tyr D-Trp Asn- Ac D-Ala D-Trp Asn-
Ac D-Leu D-Trp Asn-
Ac D-Phe D-Trp Asn-
Ac D-Nal(1) D-Trp Asn-
Ac D-Nal(2) D-Trp Asn-
Ac D-Lys D-Trp Asn-
Ac D-Glu D-Trp Asn-
Ac D-Tyr D-Ala Asn-
Ac D-Tyr D-Leu Asn-
Ac D-Tyr D-Phe Asn-
Ac D-Tyr D-Thr Asn-
Ac D-Tyr D-Lys Asn-
Ac D-Tyr D-Glu Asn-
Ac D-Tyr D-Trp Asp-
Ac D-Tyr D-Trp D-Asn-
Ac D-Tyr D-Trp NMeAsn-
Ac D-Tyr Pro Asn-
Ac D-Tyr D-Pya(2) Asn-
Ac D-Tyr D-Pya(3) Asn-
Ac D-Tyr D-Pro Asn-
Ac D-Tyr Tic Asn-
Ac Tyr Trp Asn-
Ac D-Tyr NMMeTrp Asn-
Glycoloyl D-Tyr D-Trp Asn-
Ac D-Tyr D-Trp Gly-
Ac D-Tyr D-Trp Dap-
Ac D-Tyr D-Trp Asp(NHMe)-
Ac D-Tyr D-Trp Asp(NMe$_2$)-
Ac-D-Tyr-D-Trp-Asp(NHPen)-
Ac-D-Tyr-D-Trp-Asp(NHcPr)-
Ac-D-Tyr-D-Trp-Asp(NHBzl)-
Ac-D-Tyr-D-Trp-Alb-
Ac-D-Tyr-D-Pya(4)-Alb-
Ac-D-Tyr-Aze(2)-Asn-
Ac-D-Tyr-Pic(2)-Asn-
Ac-D-Tyr-Hyp-Asn-
Ac-D-Tyr-Thz-Asn-
Ac-D-Tyr-Gly-Asn-
Ac-D-Tyr-Aib-Asn-
Ac-D-Tyr-D-NMeAla-Asn-
Ac-D-Tyr-D-Gln-Asn-
Ac-D-Tyr-D-His-Asn-
Ac-D-Tyr-D-Trp-Dab-
Ac-D-Tyr-Ala-Asn-
Ac-D-Tyr-Leu-Asn-
Ac-D-Tyr-Ser-Asn-
Ac-D-Tyr-Lys-Asn-
Ac-D-Tyr-Glu-Asn-
Ac-D-Tyr-Pzc(2)-Asn-
Ac-D-Tyr-Orn-Asn-
Ac-D-Tyr-Thr-Asn-
Ac-D-Tyr-His(3Me)-Asn-
Ac-D-Tyr-Tyr(PO$_3$H$_2$)-Asn-
Glycoloyl-D-Tyr-Hyp-Asn-
Ac-D-Tyr-Pro(4NH$_2$)-Asn-
Ac-D-Tyr-Hyp(Bzl)-Asn-
Ac-D-Tyr-D-NMePhe-Asn-
Ac-D-Tyr-Hyp-Alb-
Ac-D-Tyr-Hyp-His-
Ac-D-Tyr-Hyp-Gln-
Ac-D-Tyr-Hyp-D-Asn-
Ac-D-Tyr-Hyp-Cit-
Ac-D-Tyr-Glu-Alb-
Ac-D-Tyr-Aad-Asn-
Ac-D-Tyr-Pro(4F)-Asn-
and the like; the following groups are particularly preferred.
Ac D-Tyr Hyp Asn-
Ac D-Tyr Glu Asn-
Ac-D-Tyr-Hyp-Alb-
Ac-D-Tyr-Glu-Alb-
Ac-D-Tyr-Pro(4F)-Asn- Preferred examples of the group represented by formula:

$$J^1\text{-}J^2\text{-}C(J^{10})(Q^{10})Y^3C(J^{11})(Q^{11})C(=Z^{10})-$$

include:
Fmoc Trp Asn-,
Boc Tyr Asn-,
Tyr Asn-,
D-Trp Asn-,
Ac Trp Asn-,
Amidino Trp Asn-,
Ac Ala Asn-,
Ac Arg Asn-,
Ac Thr Asn-
D-Tyr D-Pya(4)-
3-(4-Hydroxyphenyl)propionyl D-Trp Asn-
D-Trp Asn-
Ac D-Trp Asn-
Hexanoyl D-Trp Asn-
Cyclohexanecarbonyl D-Trp Asn-
Benzoyl D-Trp Asn-
3-Pyridinepropionyl D-Trp Asn-
Adipoyl D-Trp Asn-
6-Aminocaproyl D-Trp Asn-
Amidino D-Trp Asn-
Glycoloyl D-Trp Asn-
and the like.

Preferred examples of the group represented by formula:

$$J^1\text{-}J^2\text{-}C(J^{12})(Q^{12})C(=Z^{10})-$$

include:
Fmoc Asn-,
3-(Indol-3-yl)propionyl Asn-,
3-Indolecarbonyl Asn-,
3-Indoleacetyl Asn-,
4-(Indol-3-yl)butyryl Asn-,
Diphenylacetyl Asn-,
Hexanoyl Asn-,
Cyclohexanecabonyl Asn-,
2-(Indol-3-yl)ethylcabamoyl Asn-,
3-(3-Pyridyl)propionyl Asn-,
4-Imidzoleacetyl Asn-,
Piperidinecarbonyl Asn-,
1-Piperidineacetyl Asn-,
1-Methyl-1-piperidinioacetyl Asn-,
1-Pyridinioacetyl Asn-,
D-Glucronyl Asn-
3-Phenylpropionyl Asn-,
3-Phenylpropionyl Ala-
Benzoyl Asn-
Ac Asn-
Cyclopropanecarbonyl Asn-
2-Naphthoyl Asn-
and the like.

Preferred examples of the group represented by formula:
$J^{1-}$ include:
hydrogen atom
GuAmb-
3-(3-Indolyl)propionyl-
3-(3-Pyridyl)propionyl- Benzoyl-
Indole-3-carbonyl-
Indole-3-acetyl-
Ac—
Hexanoyl-
Z-
Tos-
3-Phenylpropionyl-
2-(Indol-3-yl)ethylcarbamoyl-
Benzyl-
Phenethyl-
2-Pyridinecarbonyl-
4-Pyridinecarbonyl-
Propionyl-
Isobutyryl-
Cyclohexanecarbonyl-
Phenylacetyl-
2-Methylnicotinoyl-
5-Methylnicotinoyl-
6-Methylnicotinoyl-
Pyrazinecarbonyl-
Cyclopropanecarbonyl-
Trifluoroacetyl-
(R)-3-hydroxy-2-methylpropionyl
2-Hydroxyisobutyryl-
3-Furancarbonyl-
Pyrrole-2-carbonyl-
4-Imidazolecarbonyl-
6-Hydroxynicotinoyl-
6-Chloronicotinoyl-
6-(Trifluoromethyl)nicotinoyl-
Dimethylcarbamoyl-
1-Azetidinecarbonyl-
2-Azetidinecarbonyl-
4-Aminobenzoyl-
4-Aminomethylbenzoyl-
Pyrrole-3-carbonyl-
Pyrimidine-4-carbonyl-
Pyrimidine-2-carbonyl-
Pyridazine-4-carbonyl-
4-[Bis-(2-Pyridylmethyl)aminomethyl]benzoyl-
and the like.

In the present invention, preferred P is Ac-D-Tyr-Hyp-Asn, Ac-D-Tyr-Glu-Asn or Ac-D-Tyr-Hyp-Alb-.

The metastin derivatives of the present invention or salts thereof are preferably compounds represented by formula I described above, or salts thereof, wherein:

$Z^1$, $Z^5$ and $Z^7$ each represents hydrogen atom;

$Z^2$, $Z^4$, $Z^6$ and $Z^8$ each represents O;

$R^1$ represents (2) a $C_{1-8}$ alkyl group optionally substituted with an optionally substituted hydroxyl group;

$R^2$ represents a linear $C_{1-10}$ alkyl group or a $C_{1-10}$ alkyl group consisting of a cyclic alkyl group and a linear alkyl group;

$R^3$ represents (1) a $C_{1-8}$ alkyl group having an optionally substituted basic group and optionally having an additional substituent;

$R^4$ represents (4) a $C_{1-4}$ alkyl group, which may optionally be substituted with an optionally substituted 5- to 14-membered aromatic fused heterocyclic group consisting of 3 to 11 carbon atoms and hetero atoms selected from the group consisting of nitrogen, oxygen and sulfur atoms;

$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, and (5) an optionally substituted non-aromatic cyclic hydrocarbon group having carbon atoms not greater than 7;

A represents (1) a nitrogen atom substituted with hydrogen atom, (2) a carbon atom substituted with hydrogen atom;

A' represents (1) a carbon atom substituted with hydrogen atom or O;

$Q^2$ represents (1) an optionally substituted $CH_2$ or $CH=CH_2$ with one or two $C_{1-4}$ alkyl groups which may optionally be substituted with a substituent selected from the group consisting of carbamoyl group, hydroxyl group, a $C_{1-3}$ alkoxy group and an amino group;

Y represents (1) a group represented by formula: —CONH—, —CSNH—, —NHCO—, —CH$_2$O—, —CH$_2$S—, —COCH$_2$—, —CH=CH— or —CH$_2$CH$_2$—, which may optionally be substituted with a substituent selected from the group consisting of a $C_{1-6}$ alkyl group, hydroxyl group or a halogen atom.

More preferably, the metastin derivatives of the present invention or salts thereof are compounds represented by the formula below, or salts thereof:

XX0-XX2-XX3-XX4-XX5-T-XX9-XX10-NH$_2$ wherein:

XX0 represents formyl, $C_{1-20}$ alkanoyl, cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl or 6-aminocaproyl;

XX2 represents Tyr, D-Tyr, D-Ala, D-Leu, D-Phe, D-Lys, D-Trp or a chemical bond;

XX3 represents D-Asp, D-Dap, D-Ser, D-Gln, D-His, D-NMeAla, D-NMePhe, Aze(2), Pic(2), Pic(3), Hyp, Thz, NMeAla, Gly, Aib, Abz(2), Abz(3), Sar, Leu, Lys, Glu, β-alanine, Pzc(2), Orn, His(3Me), Tyr(PO$_3$H$_2$), Pro(4NH$_2$), Hyp (Bzl), Trp, Pro, 4-pyridylalanine, Tic, D-Trp, D-Ala, D-Leu, D-Phe, D-Lys, D-Glu, D-2-pyridylalanine, D-3-pyridylalanine, D-4-pyridylalanine, Aad, Pro(4F) or a chemical bond;

XX4 represents Asn, 2-amino-3-ureidopropionic acid, N$^β$-formyldiaminopropionic acid, N$^β$-acetyldiaminopropionic acid, N$^ω$-pentylasparagine, N$^ω$-cyclopropylasparagine, N$^ω$-benzylasparagine, 2,4-diaminobutanoic acid, His, Gln, Cit or D-Asn;

XX5 represents Ser, Thr, Val, NMeSer, Gly, Ala, Hyp, D-Ala, Dap or D-Thr (more preferably, Ser, Thr, Val, NMeSer, Gly, Ala, Hyp, D-Ala or D-Thr);

T represents a group represented by formula II:

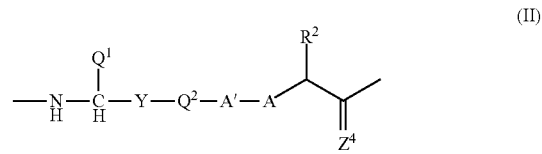

(II)

wherein:

$Z^4$ represents hydrogen atom, O or S;

$R^2$ represents (1) hydrogen atom, (2) a cyclic or linear $C_{1-10}$ alkyl group, (3) a $C_{1-10}$ alkyl group consisting of a cyclic alkyl group and a linear alkyl group, or (4) a $C_{1-8}$ alkyl group optionally substituted with a substituent selected from the group consisting of an optionally substituted carbamoyl group, an optionally substituted hydroxyl group and an optionally substituted aromatic cyclic group;

$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and (6) an optionally substituted non-aromatic heterocyclic group having carbon atoms not greater than 7;

A represents:
(1) a nitrogen atom substituted with hydrogen atom or a $C_{1-3}$ alkyl group;
(2) a carbon atom substituted with hydrogen atom or a $C_{1-3}$ alkyl group;
(3) O; or
(4) S;

A' represents:
(1) a carbon atom, which may optionally be substituted with hydrogen atom, O, S, a halogen atom, an optionally halogenated $C_{1-3}$ alkyl group, carbamoyl group or hydroxyl group;
(2) a nitrogen atom, which may optionally be substituted with hydrogen atom or an optionally halogenated $C_{1-3}$ alkyl group;
(3) O; or
(4) S;

$Q^2$ represents:
(1) $CH_2$ or $CH=CH_2$, which may optionally be substituted with a $C_{0-4}$ alkyl group optionally substituted with a substituent selected from the group consisting of carbamoyl group, hydroxyl group, a $C_{1-3}$ alkoxy group and an amino group;
(2) NH, which may optionally be substituted with an optionally substituted $C_{1-4}$ alkyl group with a substituent selected from the group consisting of carbamoyl group and hydroxyl group; or,
(3) O;

Y represents:
(1) a group represented by formula: —CONH—, —CSNH—, —$CH_2$NH—, —NHCO—, —$CH_2$O—, —COCH$_2$—, —$CH_2$S—, —CSCH$_2$—, —$CH_2$SO—, —$CH_2$SO$_2$—, —COO—, —CSO—, —$CH_2CH_2$— or —CH═CH—, which may optionally be substituted with a substituent selected from the group consisting of a $C_{1-6}$ alkyl group, hydroxyl group and a halogen atom;
(2) an optionally substituted $C_{6-7}$ aromatic hydrocarbon group;
(3) an optionally substituted 4- to 7-membered aromatic heterocyclic group consisting of 1 to 5 carbon atoms and hetero atoms selected from the group consisting of nitrogen, oxygen and sulfur atoms;
(4) an optionally substituted non-aromatic cyclic hydrocarbon group having carbon atoms not greater than 5; or
(5) an optionally substituted non-aromatic heterocyclic group having carbon atoms not greater than 5 and when Y is (2), (3), (4) or (5), $Q^2$ may be a chemical bond;

the bonds between Y-$Q^2$, $Q^2$-A' and A'-A each independently represents a single or double bond;

XX9 represents Arg, Orn, Arg(Me) or Arg(asymMe$_2$); and,
XX10 represents Phe, Trp, 2-naphthylalanine, 2-thienylalanine, tyrosine or 4-fluorophenylalanine; provided that Ac-D-Tyr-D-Trp-Asn-Thr-PheΨ(CH$_2$NH)Gly-Leu-Arg (Me)-Trp-NH$_2$, Ac-D-Tyr-D-Trp-Asn-Thr-Phe-Gly-Leu-Arg(Me)-Trp-NH$_2$, Ac-D-Tyr-D-Trp-Asn-Thr-D-Phe-Gly-Leu-Arg(Me)-Trp-NH$_2$, and, Ac-D-Tyr-D-Trp-Asn-Thr-Phe-Gly-Aib-Arg(Me)-Trp-NH$_2$ are excluded from these compounds.

More preferably, the metastin derivatives of the present invention or salts thereof are compounds represented by the following formula, or salts thereof:

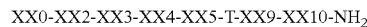

XX0-XX2-XX3-XX4-XX5-T-XX9-XX10-NH$_2$ wherein:
XX0 represents formyl, $C_{1-6}$ alkanoyl or glycoloyl;
XX2 represents D-Tyr or a chemical bond;
XX3 represents Aze(2), Hyp, Gly, Aib, Leu, Lys, Glu, His(3Me), Tyr(PO$_3$H$_2$), Pro(4F) or Hyp(Bzl);
XX4 represents Asn or 2-amino-3-ureidopropinonic acid;
XX5 represents Ser or Thr;
T represents the group represented by formula II described above;
$Z^4$ represents O;
$R^2$ represents a linear $C_{1-10}$ alkyl group or a $C_{1-10}$ alkyl group consisting of a cyclic alkyl group and a linear alkyl group;
$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, and (5) an optionally substituted non-aromatic cyclic hydrocarbon group having carbon atoms not greater than 7;
A represents (1) a nitrogen atom substituted with hydrogen atom, (2) a carbon atom substituted with hydrogen atom;
A' represents (1) a carbon atom substituted with hydrogen atom or O,
$Q^2$ represents (1) an optionally substituted $CH_2$ or $CH=CH_2$ with one or two $C_{0-4}$ alkyl groups which may optionally be substituted with a substituent selected from the group consisting of carbamoyl group, hydroxyl group, a $C_{1-3}$ alkoxy group and an amino group;
Y represents (1) a group represented by formula: —CONH—, —$CH_2$O—, —$CH_2$S—, —COCH$_2$—, —$CH_2CH_2$—, CSNH—, —NHCO— or —CH═CH—, which may optionally be substituted with a substituent selected from the group consisting of a $C_{1-6}$ alkyl group, hydroxyl group and a halogen atom;
XX9 represents Arg or Arg(Me); and,
XX10 represents Phe or Trp.

The metastin derivatives of the present invention or salts thereof, which are particularly preferred, are compounds represented by the following formula, or salts thereof:

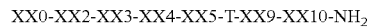

XX0-XX2-XX3-XX4-XX5-T-XX9-XX10-NH$_2$ wherein:
XX0 represents $C_{1-12}$ alkanoyl;
XX2 represents D-Tyr;
XX3 represents Hyp, Pro(4F) or Glu;
XX4 represents Asn, 2-amino-3-ureidopropionic acid;
XX5 represents Thr;

T represents the group represented by formula II described above;

$Z^4$ represents O;

$R^2$ represents a linear $C_{1-10}$ alkyl group or a $C_{1-10}$ alkyl group consisting of a cyclic alkyl group and a linear alkyl group;

$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, and, (5) an optionally substituted non-aromatic cyclic hydrocarbon group having carbon atoms not greater than 7;

A represents (1) a nitrogen atom substituted with hydrogen atom, (2) a carbon atom substituted with hydrogen atom;

A' represents (1) a carbon atom substituted with hydrogen atom or 0;

$Q^2$ represents (1) an optionally substituted $CH_2$ or $CH=CH_2$ with one or two $C_{1-4}$ alkyl groups which may optionally be substituted with a substituent selected from the group consisting of carbamoyl group, hydroxyl group, a $C_{1-3}$ alkoxy group and an amino group;

Y represents (1) a group represented by formula: —CONH—, —CSNH—, —NHCO—, —CH$_2$O—, —CH$_2$S—, —COCH$_2$—, —CH=CH— or —CH$_2$CH$_2$—, which may optionally be substituted with a $C_{1-6}$ alkyl group, hydroxyl group or a halogen atom;

XX9 represents Arg or Arg(Me); and,

XX10 represents Trp.

In the present invention, Tyr-Asn-Trp-Asn-Ser-Phe-Gly-Leu-Arg-Phe-NH$_2$ (SEQ ID NO: 16) is referred to as metastin 10 (Metastin10), i.e., MS10.

In EXAMPLES later described, the N-terminal Tyr and the C-terminal Phe in MS10 are counted as 1- and 10-positions, respectively.

```
                                          (SEQ ID NO: 16)
    Tyr-Asn-Trp-Asn-Ser-Phe-Gly-Leu-Arg-Phe-NH2
     1   2   3   4   5   6   7   8   9   10
```

For example, Compound No. 796 (EXAMPLE 1): des(1)-Ac-[D-Tyr2,Hyp3,Thr5,Arg(Me)9,Trp10]MS10 means a peptide wherein the N-terminal Tyr (1-position) is deleted, Asn at the 2-position is replaced by D-Tyr, Trp at the 3-position is replaced by Hyp, Ser at the 5-position is replaced by Thr, Arg at the 9-position is replaced by Arg(Me), the C-terminal (10-position) is replaced by Trp, and the amino group on the D-Tyr at the 2-position is modified to Ac.

The chemical bonds "—" between XX0, XX2, XX3, XX4, XX5, T, XX9, XX10 and NH$_2$ in the formula "XX0-XX2-XX3-XX4-XX5-T-XX9-XX10-NH$_2$" have the following significance, respectively.

The chemical bond "—" in the formula "XX0-XX1" means the bond between the group represented by XX0 and the amino group (α-amino group) contained in XX2. More specifically, "XX0-XX1" indicates that the hydrogen atom in the amino group (NH$_2$) contained in XX2 is substituted with a group represented by XX0.

The chemical bond "—" in the formula "XX2-XX3" means that the carboxyl group (α-carboxyl group) contained in XX2 is bound to the amino group (α-amino group) in XX3 via an amide bond. Also, the chemical bonds "—" in the formulae "XX3-XX4," "XX4-XX5" and "XX9-X10" have the same significance as described above.

The chemical bond "—" in the formula "XX5-T" represents the bond between the carboxyl group (α-carboxyl group) in XX5 and a group represented by the group represented by T. More specifically, —OH in the carboxyl group (—COOH) contained in XX5 is substituted with the group represented by T.

The chemical bond "—" in the formula "T-XX9" represents the bond between the group represented by T and the amino group (α-amino group) in XX9. More specifically, hydrogen atom in the amino group (NH$_2$) contained in XX9 is substituted with the group represented by T.

The chemical bond "—" in the formula "XX10-NH$_2$" represents the bond between the carboxyl group (α-carboxyl group) contained in XX10 and —NH$_2$. More specifically, —OH in the carboxyl group (—COOH) contained in XX10 is substituted with —NH$_2$.

Where XX2 or/and XX3 represent the chemical bonds "—," these chemical bonds "—" have the same significance as described above.

Specific examples of these chemical bonds include the bonds represented by the structural formulae shown in TABLE 1 later described, and so on.

In the metastin derivatives of the present invention, all compounds that the groups described above are optionally combined are preferably used. Among others, the following compounds are preferred.

```
                                           (SEQ ID NO: 16)
    MS10:  Tyr-Asn-Trp-Asn-Ser-Phe-Gly-Leu-Arg-Phe-NH2
            1   2   3   4   5   6   7   8   9   10
```

(Compound No. 796)
des(1)-Ac-[D-Tyr2,Hyp3,Thr5,Arg(Me)9,Trp10]MS10
Ac-D-Tyr-Hyp-Asn-Thr-Phe-Gly-Leu-Arg(Me)-Trp-NH$_2$,
(Compound No. 803)
des(1)-Ac-[D-Tyr2,Hyp3,Thr5,Ala7,Arg(Me)9,Trp10]MS10
Ac-D-Tyr-Hyp-Asn-Thr-Phe-Ala-Leu-Arg(Me)-Trp-NH$_2$
(Compound No. 804)
des(1)-Ac-[D-Tyr2,Hyp3,Thr5,Ser7,Arg(Me)9,Trp10]MS10
Ac-D-Tyr-Hyp-Asn-Thr-Phe-Ser-Leu-Arg(Me)-Trp-NH$_2$
(Compound No. 811)
des(1)-Ac-[D-Tyr2,Hyp3,Thr5,Aib7,Arg(Me)9,Trp10]MS10
Ac-D-Tyr-Hyp-Asn-Thr-Phe-Aib-Leu-Arg(Me)-Trp-NH$_2$
(Compound No. 818)
des(1)-Ac-[D-Tyr2,Hyp3,Thr5,Abu7,Arg(Me)9,Trp10]MS10
Ac-D-Tyr-Hyp-Asn-Thr-Phe-Abu-Leu-Arg(Me)-Trp-NH$_2$
(Compound No. 822)
des(1)-Ac-[D-Tyr2,Hyp3,Thr5,Cha6,Arg(Me)9,Trp10]MS10
Ac-D-Tyr-Hyp-Asn-Thr-Cha-Gly-Leu-Arg(Me)-Trp-NH$_2$
(Compound No. 823)
des(1)-Ac-[D-Tyr2,Hyp3,Thr5,Cha6,Ala7,Arg(Me)9,Trp10]MS10
Ac-D-Tyr-Hyp-Asn-Thr-Cha-Ala-Leu-Arg(Me)-Trp-NH$_2$
(Compound No. 827)
des(1)-Ac-[D-Tyr2,Hyp3,Thr5,Dap7,Arg(Me)9,Trp10]MS10
Ac-D-Tyr-Hyp-Asn-Thr-Phe-Dap-Leu-Arg(Me)-Trp-NH$_2$
(Compound No. 828)
des(1)-Ac-[D-Tyr2,Hyp3,Thr5,Ser(Me)7,Arg(Me)9,Trp10]MS10
Ac-D-Tyr-Hyp-Asn-Thr-Phe-Ser(Me)-Leu-Arg(Me)-Trp-NH$_2$ (Compound No. 834)
des(1)-Ac-[D-Tyr2,Hyp3,Thr5,Phe6Ψ(CH₂O)Gly7,Arg(Me)9,Trp10]MS10
Ac-D-Tyr-Hyp-Asn-Thr-PheΨ(CH₂O)Gly-Leu-Arg(Me)-Trp-NH₂
(Compound No. 839)
des(1)-Ac-[D-Tyr2,Hyp3,Thr5,Pya(2)6,Arg(Me)9,Trp10]MS10
Ac-D-Tyr-Hyp-Asn-Thr-Pya(2)-Gly-Leu-Arg(Me)-Trp-NH₂
(Compound No. 847)
des(1)-Ac-[D-Tyr2,Hyp3,Thr5,Val7,Arg(Me)9,Trp10]MS10
Ac-D-Tyr-Hyp-Asn-Thr-Phe-Val-Leu-Arg(Me)-Trp-NH₂
(Compound No. 848)
des(1)-Ac-[D-Tyr2,Hyp3,Thr5,Pya(3)6,Arg(Me)9,Trp10]MS10
Ac-D-Tyr-Hyp-Asn-Thr-Pya(3)-Gly-Leu-Arg(Me)-Trp-NH₂
(Compound No. 849)
des(1)-Ac-[D-Tyr2,Hyp3,Thr5,Pya(4)6,Arg(Me)9,Trp10]MS10
Ac-D-Tyr-Hyp-Asn-Thr-Pya(4)-Gly-Leu-Arg(Me)-Trp-NH₂
(Compound No. 850)
des(1)-Ac-[D-Tyr2,Hyp3,Thr5,Phe6Ψ(CH₂CH₂)Gly7,Arg(Me)9,Trp10]MS10
Ac-D-Tyr-Hyp-Asn-Thr-PheΨ(CH₂CH₂)Gly-Leu-Arg(Me)-Trp-NH₂
(Compound No. 851)
des(1)-Ac-[D-Tyr2,Hyp3,Thr5,Phe6Ψ(COCH₂)Gly7,Arg(Me)9,Trp10]MS10
Ac-D-Tyr-Hyp-Asn-Thr-PheΨ(COCH₂)Gly-Leu-Arg(Me)-Trp-NH₂
(Compound No. 852)
des(1)-Ac-[D-Tyr2,Glu3,Thr5,Arg(Me)9,Trp10]MS10
Ac-D-Tyr-Glu-Asn-Thr-Phe-Gly-Leu-Arg(Me)-Trp-NH₂
(Compound No. 853)
des(1)-Ac-[D-Tyr2,Glu3,Thr5,Cha6,Arg(Me)9,Trp10]MS10
Ac-D-Tyr-Glu-Asn-Thr-Cha-Gly-Leu-Arg(Me)-Trp-NH₂
(Compound No. 854)
des(1)-Ac-[D-Tyr2,Hyp3,Thr5,Gly7Ψ(CH₂NH)Leu8,Arg(Me)9,Trp10]MS10
Ac-D-Tyr-Hyp-Asn-Thr-Phe-GlyΨ(CH₂NH)Leu-Arg(Me)-Trp-NH₂
(Compound No. 855)
des(1)-Ac-[D-Tyr2,Hyp3,Thr5,Ala(cPr)6,Arg(Me)9,Trp10]MS10
Ac-D-Tyr-Hyp-Asn-Thr-Ala(cPr)-Gly-Leu-Arg(Me)-Trp-NH₂
(Compound No. 857)
des(1)-Ac-[D-Tyr2,Hyp3,Thr5,Phe6Ψ((S)CHOH—CH₂)Gly7,Arg(Me)9,Trp10]MS10
Ac-D-Tyr-Hyp-Asn-Thr-PheΨ((S)CHOH—CH₂)Gly-Leu-Arg(Me)-Trp-NH₂
(Compound No. 858)
des(1)-Ac-[D-Tyr2,Hyp3,Thr5,Phe6Ψ((S)CHOH-(E)CH=)Gly7,Arg(Me)9,Trp10]MS10
Ac-D-Tyr-Hyp-Asn-Thr-PheΨ((S)CHOH-(E)CH=)Gly-Leu-Arg(Me)-Trp-NH₂
(Compound No. 859)
des(1)-Ac-[D-Tyr2,Hyp3,Thr5,Phe6Ψ((E)CH═CH)Gly7,Arg(Me)9,Trp10]MS10
Ac-D-Tyr-Hyp-Asn-Thr-PheΨ((E)CH═CH)Gly-Leu-Arg(Me)-Trp-NH₂
(Compound No. 866)
des(1)-Ac-[D-Tyr2,Hyp3,Thr5,Phe6Ψ((R)CHOH-(E)CH=)Gly7,Arg(Me)9,Trp10]MS10
Ac-D-Tyr-Hyp-Asn-Thr-PheΨ((R)CHOH-(E)CH=)Gly-Leu-Arg(Me)-Trp-NH₂
(Compound No. 867)
des(1)-Ac-[D-Tyr2,Hyp3,Thr5,Phe6Ψ((R)CHOH—CH₂)Gly7,Arg(Me)9,Trp10]MS10
Ac-D-Tyr-Hyp-Asn-Thr-PheΨ((R)CHOH—CH₂)Gly-Leu-Arg(Me)-Trp-NH₂
(Compound No. 869)
des(1)-Ac-[D-Tyr2,Hyp3,Thr5, αMePhe6,Arg(Me)9,Trp10]MS10
Ac-D-Tyr-Hyp-Asn-Thr-αMePhe-Gly-Leu-Arg(Me)-Trp-NH₂
(Compound No. 871)
des(1)-Ac-[D-Tyr2,Hyp3,Thr5,Phe(2Me)6,Arg(Me)9,Trp10]MS10
Ac-D-Tyr-Hyp-Asn-Thr-Phe(2Me)-Gly-Leu-Arg(Me)-Trp-NH₂
(Compound No. 873)
des(1)-Ac-[D-Tyr2,Hyp3,Thr5,Phe(3Me)6,Arg(Me)9,Trp10]MS10
Ac-D-Tyr-Hyp-Asn-Thr-Phe(3Me)-Gly-Leu-Arg(Me)-Trp-NH₂
(Compound No. 875)
des(1)-Ac-[D-Tyr2,Hyp3,Thr5,Phe(4Me)6,Arg(Me)9,Trp10]MS10
Ac-D-Tyr-Hyp-Asn-Thr-Phe(4Me)-Gly-Leu-Arg(Me)-Trp-NH₂
(Compound No. 885)
des(1)-Ac-[D-Tyr2,Hyp3,Aib4,Thr5,Arg(Me)9,Trp10]MS10
Ac-D-Tyr-Hyp-Aib-Thr-Phe-Gly-Leu-Arg(Me)-Trp-NH₂
(Compound No. 892)
des(1)-Ac-[D-Tyr2,Hyp3,Thr5,Gly7Ψ((E)CH═CH)Leu8,Arg(Me)9,Trp10]MS10
Ac-D-Tyr-Hyp-Asn-Thr-Phe-GlyΨ((E)CH═CH)Leu-Arg(Me)-Trp-NH₂
(Compound No. 893)
des(1)-Ac-[D-Tyr2,Hyp3,Thr5,Gly7Ψ(CH₂CH₂)Leu8,Arg(Me)9,Trp10]MS10
Ac-D-Tyr-Hyp-Asn-Thr-Phe-GlyΨ(CH₂CH₂)Leu-Arg(Me)-Trp-NH₂
(Compound No. 894)
des(1)-Ac-[D-Tyr2,Hyp3,Thr5,Cha6,Ala(cPr)8,Arg(Me)9,Trp10]MS10
Ac-D-Tyr-Hyp-Asn-Thr-Cha-Gly-Ala(cPr)-Arg(Me)-Trp-NH₂
(Compound No. 895)
des(1)-Ac-[D-Tyr2,Glu3,Thr5,Cha6,Ala(cPr)8,Arg(Me)9,Trp10]MS10
Ac-D-Tyr-Glu-Asn-Thr-Cha-Gly-Ala(cPr)-Arg(Me)-Trp-NH₂
(Compound No. 902)
des(1)-Ac-[D-Tyr2,Hyp3,Thr5,Cha6,Gly7Ψ((E)CH═CH)Leu8,Arg(Me)9,Trp10]MS10
Ac-D-Tyr-Hyp-Asn-Thr-Cha-GlyΨ((E)CH═CH)Leu-Arg(Me)-Trp-NH₂
(Compound No. 903)
des(1)-Ac-[D-Tyr2,Hyp3,Aib4,Thr5,Cha6,Gly7Ψ((E)CH═CH)Leu8,Arg(Me)9, Trp10]MS10
Ac-D-Tyr-Hyp-Aib-Thr-Cha-GlyΨ((E)CH═CH)Leu-Arg(Me)-Trp-NH₂
(Compound No. 904)
des(1)-Ac-[D-Tyr2,Glu3,Thr5,Cha6,Gly7Ψ((E)CH═CH)Leu8,Arg(Me)9,Trp10]MS10

Ac-D-Tyr-Glu-Asn-Thr-Cha-GlyΨ((E)CH=CH)Leu-Arg(Me)-Trp-NH₂
(Compound No. 905)
des(1)-Ac-[D-Tyr2,Glu3,Alb4,Thr5,Cha6,Gly7Ψ((E)CH=CH)Leu8,Arg(Me)9,Trp10]MS10
Ac-D-Tyr-Glu-Alb-Thr-Cha-GlyΨ((E)CH=CH)Leu-Arg(Me)-Trp-NH₂
(Compound No. 906)
des(1)-Ac-[D-Tyr2,Hyp3,Alb4,Thr5,Gly7Ψ((E)CH=CH)Leu8,Arg(Me)9,Trp10]MS10
Ac-D-Tyr-Hyp-Alb-Thr-Phe-GlyΨ((E)CH=CH)Leu-Arg(Me)-Trp-NH₂
(Compound No. 907)
des(1)-Ac-[D-Tyr2,Glu3,Thr5,Gly7Ψ((E)CH=CH)Leu8,Arg(Me)9,Trp10]MS10
Ac-D-Tyr-Glu-Asn-Thr-Phe-GlyΨ((E)CH=CH)Leu-Arg(Me)-Trp-NH₂
(Compound No. 908)
des(1)-Ac-[D-Tyr2,Glu3,Alb4,Thr5,Gly7Ψ((E)CH=CH)Leu8,Arg(Me)9, Trp10]MS10
Ac-D-Tyr-Glu-Alb-Thr-Phe-GlyΨ((E)CH=CH)Leu-Arg(Me)-Trp-NH₂
(Compound No. 909)
des(1)-Ac-[D-Tyr2,Asp3,Thr5,Cha6,Ala(cPr)8,Arg(Me)9,Trp10]MS10
Ac-D-Tyr-Asp-Asn-Thr-Cha-Gly-Ala(cPr)-Arg(Me)-Trp-NH₂
(Compound No. 910)
des(1)-Ac-[D-Tyr2,Aad3,Thr5,Cha6,Ala(cPr)8,Arg(Me)9,Trp10]MS10
Ac-D-Tyr-Aad-Asn-Thr-Cha-Gly-Ala(cPr)-Arg(Me)-Trp-NH₂
(Compound No. 911)
des(1)-Ac-[D-Tyr2,Lys3,Thr5,Cha6,Ala(cPr)8,Arg(Me)9,Trp10]MS10
Ac-D-Tyr-Lys-Asn-Thr-Cha-Gly-Ala(cPr)-Arg(Me)-Trp-NH₂
(Compound No. 912)
des(1)-Ac-[D-Tyr2,Aib3,Thr5,Cha6,Ala(cPr)8,Arg(Me)9,Trp10]MS10
Ac-D-Tyr-Aib-Asn-Thr-Cha-Gly-Ala(cPr)-Arg(Me)-Trp-NH₂
(Compound No. 913)
des(1)-Ac-[D-Tyr2,Hyp3,Gln4,Thr5,Cha6,Gly7Ψ((E)CH=CH)Leu8,Arg(Me)9,Trp10]MS10
Ac-D-Tyr-Hyp-Gln-Thr-Cha-GlyΨ((E)CH=CH)Leu-Arg(Me)-Trp-NH₂
(Compound No. 914)
des(1)-Ac-[D-Tyr2,Hyp3,Cit4,Thr5,Cha6,GlyΨ((E)CH=CH)Leu8,Arg(Me)9,Trp10]MS10
Ac-D-Tyr-Hyp-Cit-Thr-Cha-GlyΨ((E)CH=CH)Leu-Arg(Me)-Trp-NH₂
(Compound No. 915)
des(1)-Ac-[D-Tyr2,Hyp3,Glu4,Thr5,Cha6,Gly7Ψ((E)CH=CH)Leu8,Arg(Me)9,Trp10]MS10
Ac-D-Tyr-Hyp-Glu-Thr-Cha-GlyΨ((E)CH=CH)Leu-Arg(Me)-Trp-NH₂
(Compound No. 916)
des(1)-Ac[D-Tyr2,Hyp3,Thr5,Ala(cPr)8,Arg(Me)9,Trp10]MS10
Ac-D-Tyr-Hyp-Asn-Thr-Phe-Gly-Ala(cPr)-Arg(Me)-Trp-NH₂
(Compound No. 917)
des(1)-Ac-[D-Tyr2,Hyp3,Thr5,Ser(Me)8,Arg(Me)9,Trp10]MS10
Ac-D-Tyr-Hyp-Asn-Thr-Phe-Gly-Ser(Me)-Arg(Me)-Trp-NH₂
(Compound No. 918)
des(1)-Ac-[D-Tyr2,Hyp3,Thr5,Nva8,Arg(Me)9,Trp10]MS10
Ac-D-Tyr-Hyp-Asn-Thr-Phe-Gly-Nva-Arg(Me)-Trp-NH₂
(Compound No. 919)
des(1)-Ac-[D-Tyr2,Hyp3,Thr5,Nal(2)6,Arg(Me)9,Trp10]MS10
Ac-D-Tyr-Hyp-Asn-Thr-Nal(2)-Gly-Ala(cPr)-Arg(Me)-Trp-NH₂
(Compound No. 920)
des(1)-Ac-[D-Tyr2,Hyp3,Thr5,Cha6,Ser(Me)8,Arg(Me)9,Trp10]MS10
Ac-D-Tyr-Hyp-Asn-Thr-Cha-Gly-Ser(Me)-Arg(Me)-Trp-NH₂
(Compound No. 921)
des(1)-Ac-[D-Tyr2,Hyp3,Thr5,Cha6,Nva8,Arg(Me)9,Trp10]MS10
Ac-D-Tyr-Hyp-Asn-Thr-Cha-Gly-Nva-Arg(Me)-Trp-NH₂
(Compound No. 923)
des(1)-Ac-[D-Tyr2,Glu3,Thr5,Cha6,Ser(Me)8,Arg(Me)9,Trp10]MS10
Ac-D-Tyr-Glu-Asn-Thr-Cha-Gly-Ser(Me)-Arg(Me)-Trp-NH₂
(Compound No. 924)
des(1)-Ac-[D-Tyr2,Glu3,Thr5,Cha6,Nva8,Arg(Me)9,Trp10]MS10
Ac-D-Tyr-Glu-Asn-Thr-Cha-Gly-Nva-Arg(Me)-Trp-NH₂
(Compound No. 925)
des(1)-Ac-[D-Tyr2,Hyp3,Thr5,Gly7Ψ((E)CH=CH)Leu8,Trp10]MS10
Ac-D-Tyr-Hyp-Asn-Thr-Phe-GlyΨ((E)CH=CH)Leu-Arg-Trp-NH₂
(Compound No. 926)
des(1)-Ac-[D-Tyr2,Hyp3,Thr5,Cha6,Gly7Ψ((E)CH=CH)Leu8,Trp10]MS10
Ac-D-Tyr-Hyp-Asn-Thr-Cha-GlyΨ((E)CH=CH)Leu-Arg-Trp-NH₂
(Compound No. 927)
des(1)-Ac-[D-Tyr2,Hyp3,Alb4,Thr5,Cha6,Gly7Ψ((E)CH=CH)Leu8,Trp10]MS10
Ac-D-Tyr-Hyp-Alb-Thr-Cha-GlyΨ((E)CH=CH)Leu-Arg-Trp-NH₂
(Compound No. 929)
des(1)-Ac-[D-Tyr2,Hyp3,Thr5,Gly7Ψ(CH₂S)Leu8,Arg(Me)9,Trp10]MS10
Ac-D-Tyr-Hyp-Asn-Thr-Phe-GlyΨ(CH₂S)Leu-Arg(Me)-Trp-NH₂
(Compound No. 931)
des(1)-Ac-[D-Tyr2,Hyp3,Thr5,Cha6,Gly7Ψ(CH₂S)Leu8,Arg(Me)9,Trp10]MS10
Ac-D-Tyr-Hyp-Asn-Thr-Cha-GlyΨ(CH₂S)Leu-Arg(Me)-Trp-NH₂
(Compound No. 932)
des(1)-Ac-[D-Tyr2,Hyp3,Thr5,Cha6,Nle8,Arg(Me)9,Trp10]MS10
Ac-D-Tyr-Hyp-Asn-Thr-Cha-Gly-Nle-Arg(Me)-Trp-NH₂
(Compound No. 933)
des(1)-Ac-[D-Tyr2,Hyp3,Thr5,Cha6,Leu(Me)8,Arg(Me)9,Trp10]MS10
Ac-D-Tyr-Hyp-Asn-Thr-Cha-Gly-Leu(Me)-Arg(Me)-Trp-NH₂
(Compound No. 934)
des(1)-Ac-[D-Tyr2,Hyp3,Thr5,Cha6,8,Arg(Me)9,Trp10]MS10
Ac-D-Tyr-Hyp-Asn-Thr-Cha-Gly-Cha-Arg(Me)-Trp-NH₂
(Compound No. 940)

des(1)-Ac-[D-Tyr2,Hyp3,Thr5,Cha6,Ala(cPr)8,Trp10]
MS10
Ac-D-Tyr-Hyp-Asn-Thr-Cha-Gly-Ala(cPr)-Arg-Trp-NH$_2$
(Compound No. 942)
des(1)-Ac-[D-Tyr2,Glu3, Thr5, Cha6,Ala(cPr)8,Trp10]
MS10
Ac-D-Tyr-Glu-Asn-Thr-Cha-Gly-Ala(cPr)-Arg-Trp-NH$_2$
(Compound No. 944)
des(1)-Ac-[D-Tyr2,Hyp3,Thr5,Phe6Ψ(CH$_2$S)Gly7,Arg
(Me)9,Trp10]MS10
Ac-D-Tyr-Hyp-Asn-Thr-PheΨ(CH$_2$S)Gly-Leu-Arg(Me)-
Trp-NH$_2$
(Compound No. 945)
des(1)-Ac-[D-Tyr2,Hyp3,Thr5,Ala(cBu)6,Ala(cPr)8,Arg
(Me)9,Trp10]MS10
Ac-D-Tyr-Hyp-Asn-Thr-Ala(cBu)-Gly-Ala(cPr)-Arg(Me)-
Trp-NH$_2$
(Compound No. 946)
des(1)-Ac-[D-Tyr2,Hyp3,Thr5,Cha6,Ala(cBu)8,Arg(Me)9,
Trp10]MS10
Ac-D-Tyr-Hyp-Asn-Thr-Cha-Gly-Ala(cBu)-Arg(Me)-Trp-
NH$_2$
(Compound No. 947)
des(1)-Ac-[D-Tyr2,Hyp3,Alb4,Ala5,Cha6,Ala(cPr)8,Arg
(Me)9,Trp10]MS10
Ac-D-Tyr-Hyp-Alb-Ala-Cha-Gly-Ala(cPr)-Arg(Me)-Trp-
NH$_2$
(Compound No. 948)
des(1)-Ac-[D-Tyr2,Hyp3,Alb4,Ser5,Cha6,Ala(cPr)8,Arg
(Me)9,Trp10]MS10
Ac-D-Tyr-Hyp-Alb-Ser-Cha-Gly-Ala(cPr)-Arg(Me)-Trp-
NH$_2$
(Compound No. 949)
des(1)-Ac-[D-Tyr2,Hyp3,Alb4,Gly5,Cha6,Ala(cPr)8,Arg
(Me)9,Trp10]MS10
Ac-D-Tyr-Hyp-Alb-Gly-Cha-Gly-Ala(cPr)-Arg(Me)-Trp-
NH$_2$
(Compound No. 951)
des(1)-Ac-[D-Tyr2,Hyp3,Alb4,Dap5,Cha6,Ala(cPr)8,Arg
(Me)9,Trp10]MS10
Ac-D-Tyr-Hyp-Alb-Dap-Cha-Gly-Ala(cPr)-Arg(Me)-Trp-
NH$_2$
(Compound No. 952)
des(1)-Ac-[D-Tyr2,Hyp3,Alb4,Thr5,Cha6,Gly7Ψ
(CH$_2$CH$_2$)Leu8,Trp10]MS10
Ac-D-Tyr-Hyp-Alb-Thr-Cha-GlyΨ(CH$_2$CH$_2$)Leu-Arg-Trp-
NH$_2$
(Compound No. 953)
des(1)-Ac-[D-Tyr2,Hyp3,Alb4,Thr5,Cha6,Ala(cPr)8,Arg
(Me)9,Trp10]MS10
Ac-D-Tyr-Hyp-Alb-Thr-Cha-Gly-Ala(cPr)-Arg(Me)-Trp-
NH$_2$
(Compound No. 956)
des(1)-Ac-[D-Tyr2,Hyp3,Thr5,Cha6,Gly7Ψ(CH$_2$CH$_2$)
Leu8,Trp10]MS10
Ac-D-Tyr-Hyp-Asn-Thr-Cha-GlyΨ(CH$_2$CH$_2$)Leu-Arg-Trp-
NH$_2$
(Compound No. 957)
des(1)-Ac-[D-Tyr2,Hyp3,Alb4,Thr5,Cha6,Gly7Ψ
(CH$_2$CH$_2$)Leu8,Arg(Me)9,Trp10]MS10
Ac-D-Tyr-Hyp-Alb-Thr-Cha-GlyΨ(CH$_2$CH$_2$)Leu-Arg
(Me)-Trp-NH$_2$
(Compound No. 959)
des(1)-Ac-[D-Tyr2,Pro(4F)3,Thr5,Cha6,Ala(cPr)8,Arg(Me)
9,Trp10]MS10
Ac-D-Tyr-Pro(4F)-Asn-Thr-Cha-Gly-Ala(cPr)-Arg(Me)-
Trp-NH$_2$
(Compound No. 968)
des(1)-Ac-[D-Tyr2,Hyp3,Thr5,Phe6Ψ(CH$_2$CH$_2$)AzaGly7,
Arg(Me)9,Trp10]MS10
Ac-D-Tyr-Hyp-Asn-Thr-PheΨ(CH$_2$CH$_2$)AzaGly-Leu-Arg
(Me)-Trp-NH$_2$ The structural formulae of these compounds are shown in TABLE 1.

TABLE 1

| Compound number | Structure |
|---|---|
| 796 | 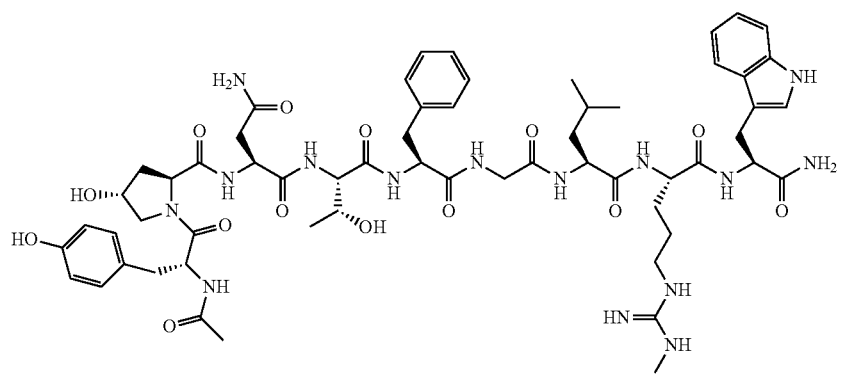 [SMILES: CNC(=N)NCCC[C@H](NC(=O)[C@H](CC(C)C)NC(=O)CNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |

TABLE 1-continued

| Compound number | Structure |
|---|---|
| 803 | 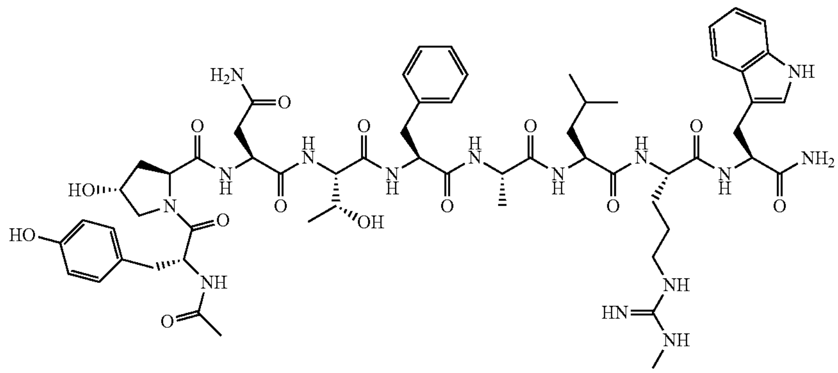 [SMILES: CNC(=N)NCCC[C@H](NC(=O)[C@H](CC(C)C)NC(=O)[C@H](C)NC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 804 | 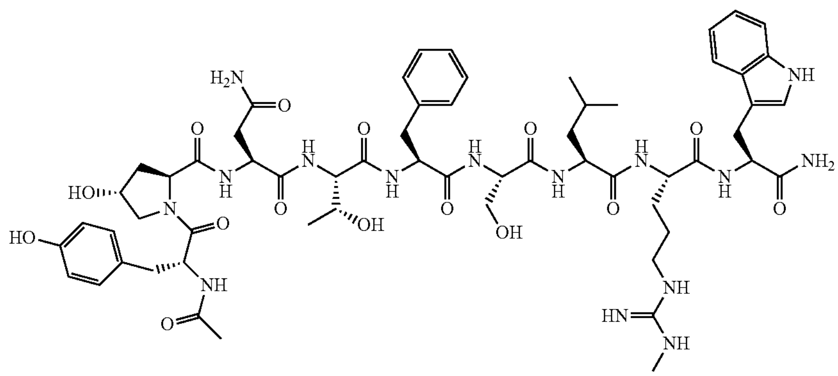 [SMILES: CNC(=N)NCCC[C@H](NC(=O)[C@H](CC(C)C)NC(=O)[C@H](CO)NC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 811 | 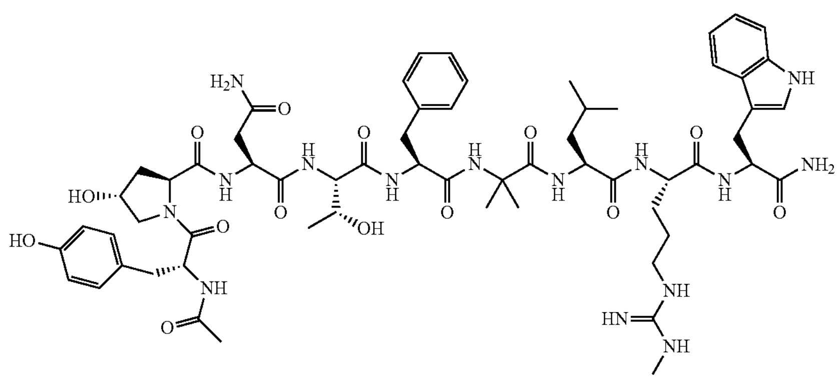 [SMILES: CNC(=N)NCCC[C@H](NC(=O)[C@H](CC(C)C)NC(=O)C(C)(C)NC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 818 | 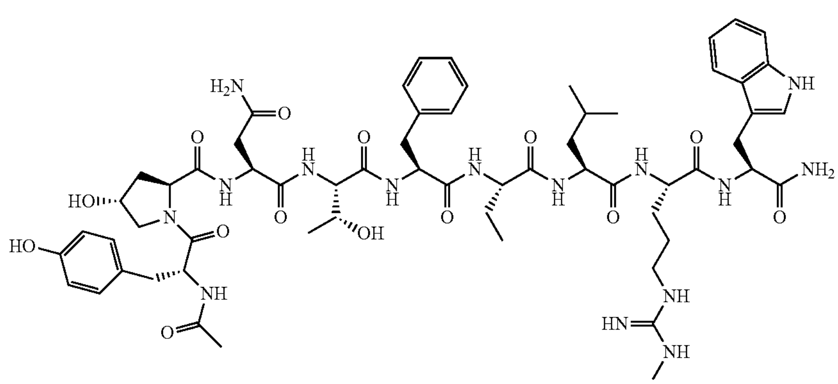 [SMILES: CC[C@H](NC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](CC(C)C)C(=O)N[C@@H](CCCNC(=N)NC)C(=O)N[C@@H](Cc1c[nH]c2ccccc12)C(N)=O] |

TABLE 1-continued
| Compound number | Structure |
|---|---|
| 822 | 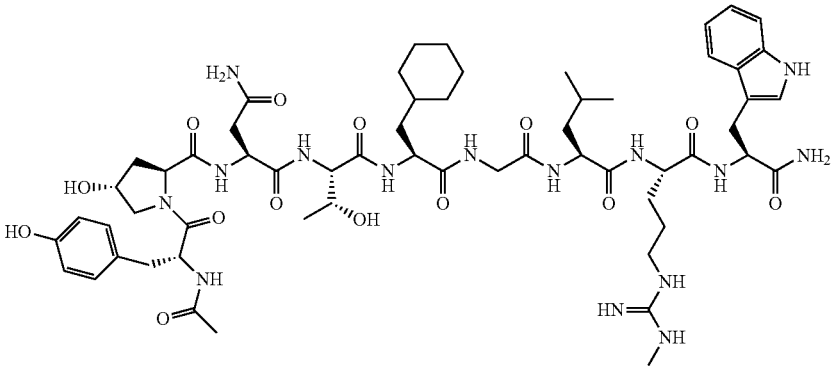 [SMILES: CNC(=N)NCCC[C@H](NC(=O)[C@H](CC(C)C)NC(=O)CNC(=O)[C@H](CC1CCCCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 823 | 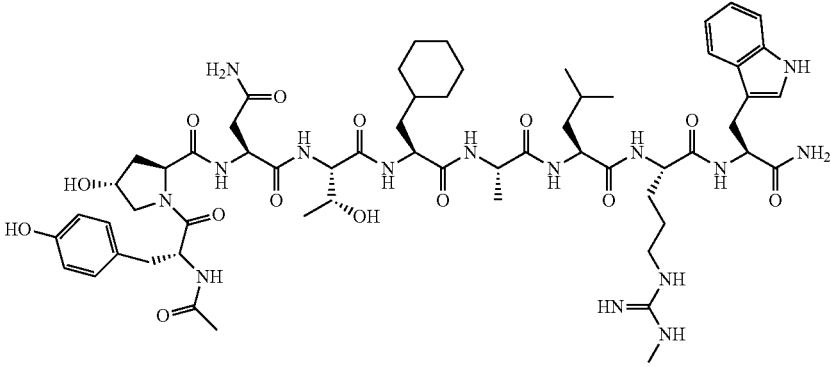 [SMILES: CNC(=N)NCCC[C@H](NC(=O)[C@H](CC(C)C)NC(=O)[C@H](C)NC(=O)[C@H](CC1CCCCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 827 | 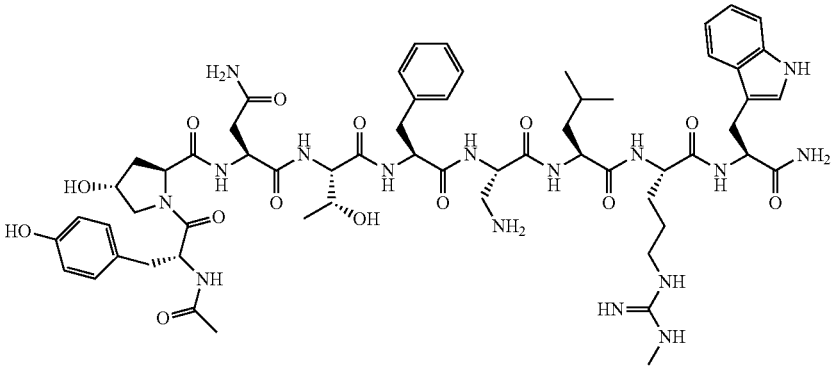 |
| 828 | 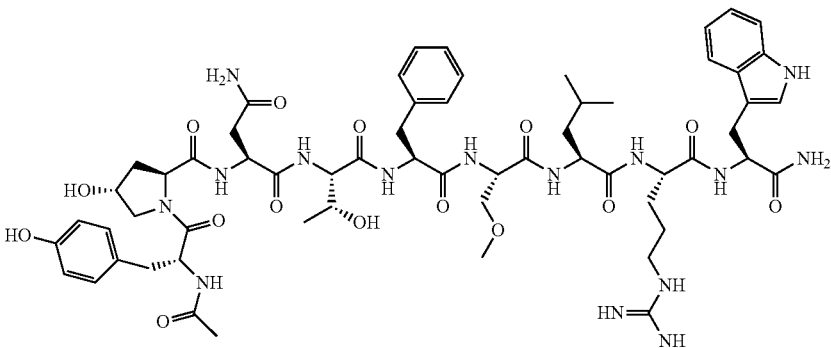 |

TABLE 1-continued
| Compound number | Structure |
|---|---|
| 834 | 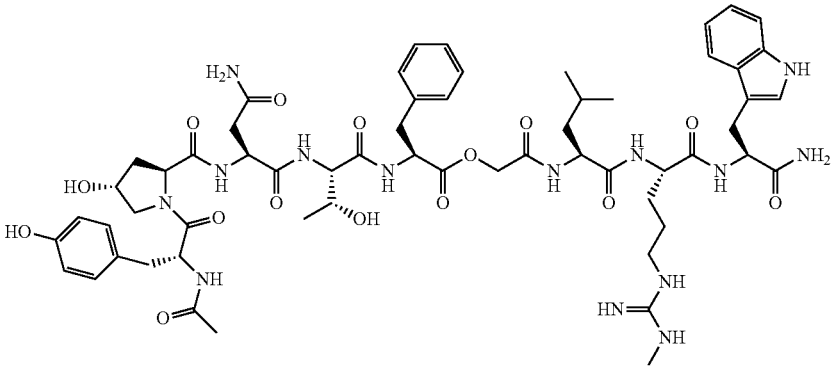 [SMILES: CNC(=N)NCCC[C@H](NC(=O)[C@H](CC(C)C)NC(=O)COC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 839 | 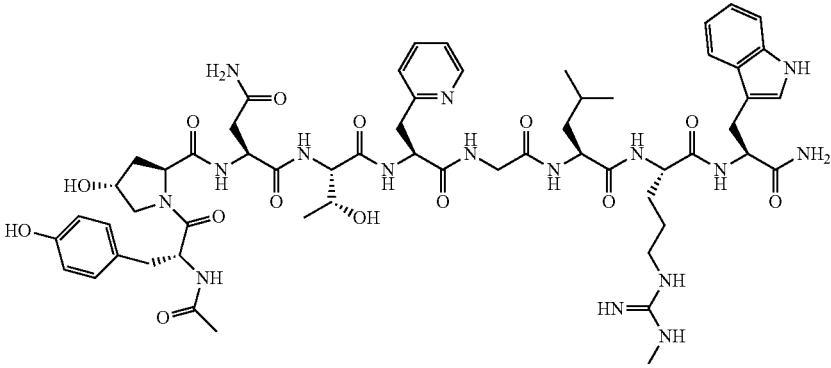 |
| 847 | 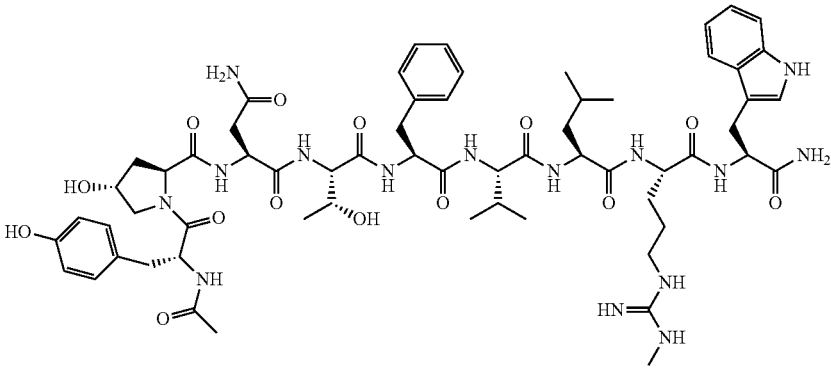 [SMILES: CNC(=N)NCCC[C@H](NC(=O)[C@H](CC(C)C)NC(=O)[C@@H](NC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(C)C)C(=O)N[C@@H](Cc1c[nH]c2ccccc12)C(N)=O] |
| 848 | 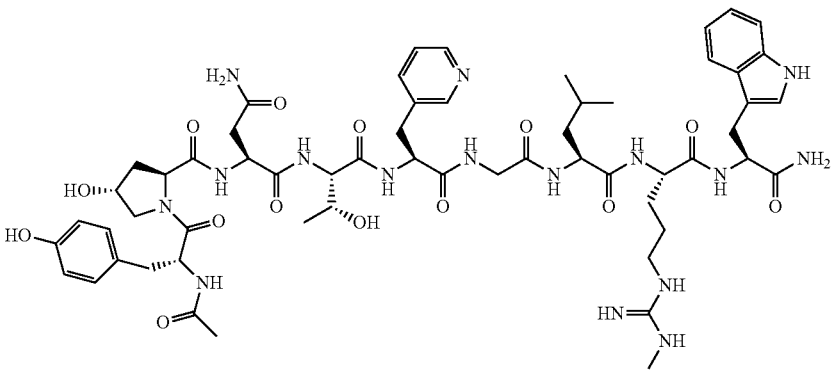 |

TABLE 1-continued

| Compound number | Structure |
| --- | --- |
| 849 | 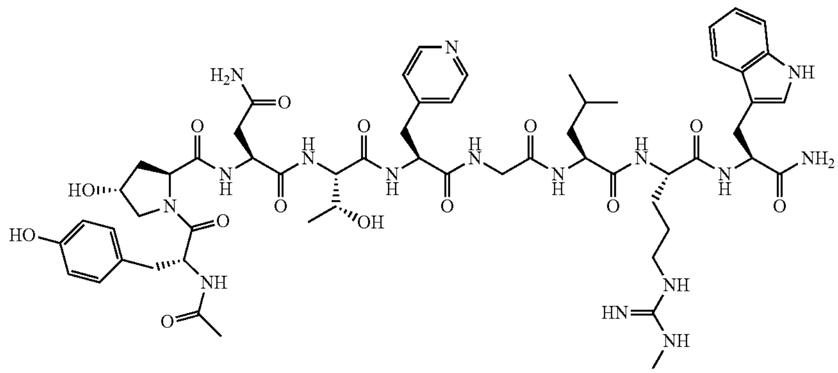 [SMILES: CNC(=N)NCCC[C@H](NC(=O)[C@H](CC(C)C)NC(=O)CNC(=O)[C@H](Cc1ccncc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 850 | 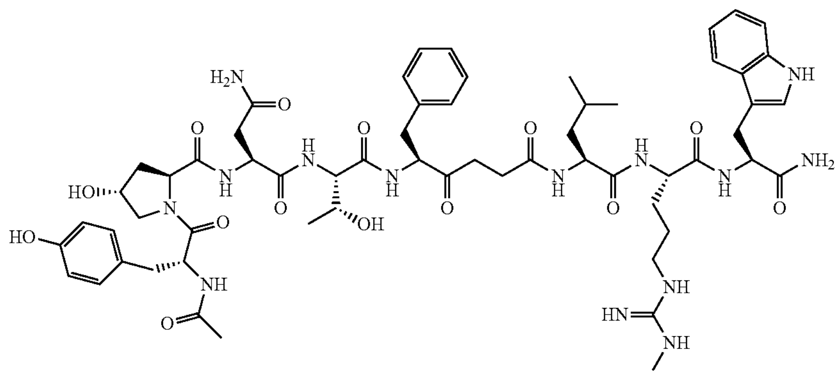 [SMILES: CNC(=N)NCCC[C@H](NC(=O)[C@H](CC(C)C)NC(=O)CCC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 851 | 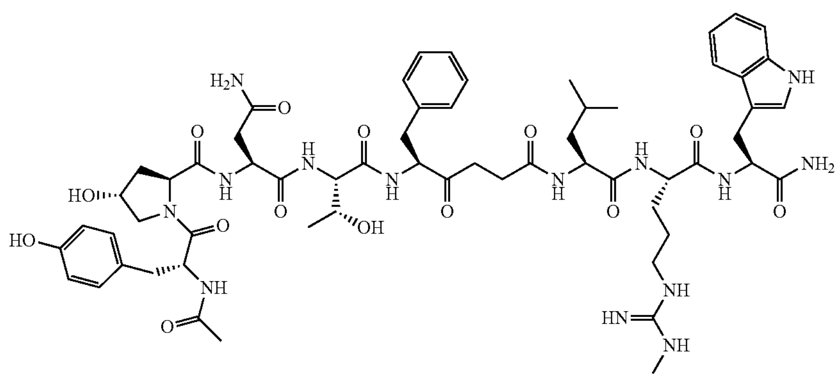 [SMILES: CNC(=N)NCCC[C@H](NC(=O)[C@H](CC(C)C)NC(=O)CCC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 852 | 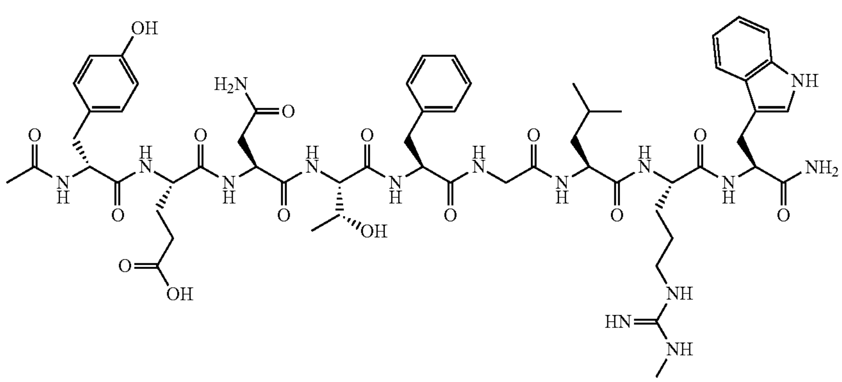 [SMILES: CNC(=N)NCCC[C@H](NC(=O)[C@H](CC(C)C)NC(=O)CNC(=O)[C@H](Cc1ccccc1)NC(=O)[C@@H](NC(=O)[C@H](CC(N)=O)NC(=O)[C@H](CCC(=O)O)NC(=O)[C@@H](Cc1ccc(O)cc1)NC(C)=O)[C@@H](C)O)C(=O)N[C@@H](Cc1c[nH]c2ccccc12)C(N)=O] |

TABLE 1-continued
| Compound number | Structure |
|---|---|
| 853 | 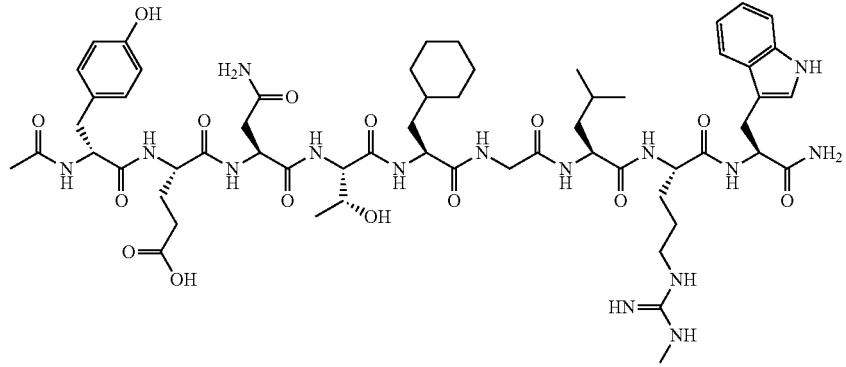 [SMILES: CNC(=N)NCCC[C@H](NC(=O)[C@H](CC(C)C)NC(=O)CNC(=O)[C@H](CC1CCCCC1)NC(=O)[C@@H](NC(=O)[C@H](CC(N)=O)NC(=O)[C@H](CCC(=O)O)NC(=O)[C@@H](Cc1ccc(O)cc1)NC(C)=O)[C@@H](C)O)C(=O)N[C@@H](Cc1c[nH]c2ccccc12)C(N)=O] |
| 854 | 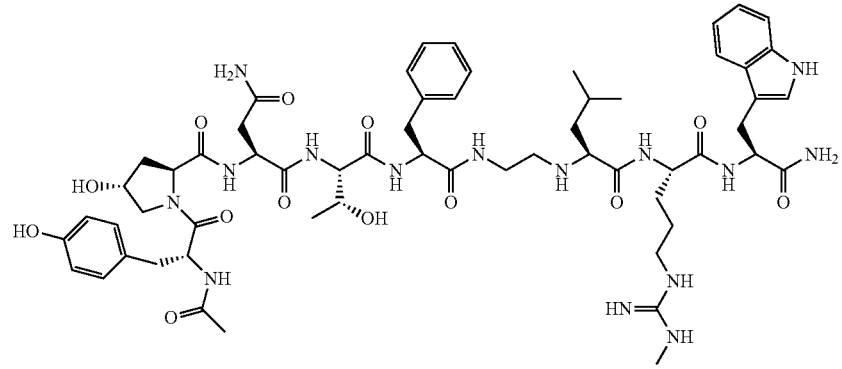 [SMILES: CNC(=N)NCCC[C@H](NC(=O)[C@H](CC(C)C)NCCNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 855 | 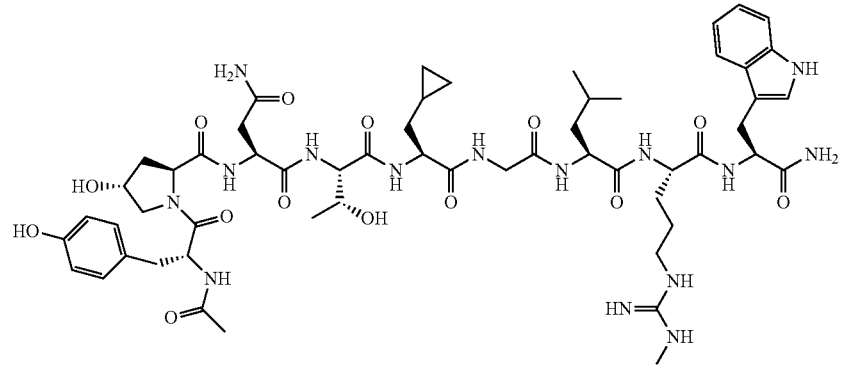 [SMILES: CNC(=N)NCCC[C@H](NC(=O)[C@H](CC(C)C)NC(=O)CNC(=O)[C@H](CC1CC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 857 | 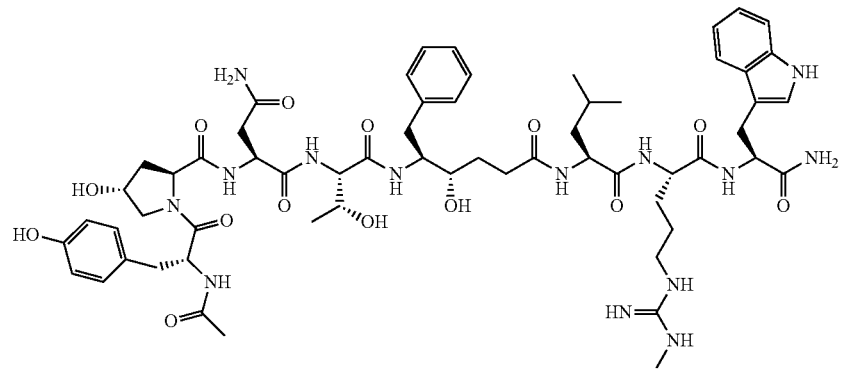 [SMILES: CNC(=N)NCCC[C@H](NC(=O)[C@H](CC(C)C)NC(=O)CC[C@H](O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |

TABLE 1-continued
| Compound number | Structure |
|---|---|
| 858 | 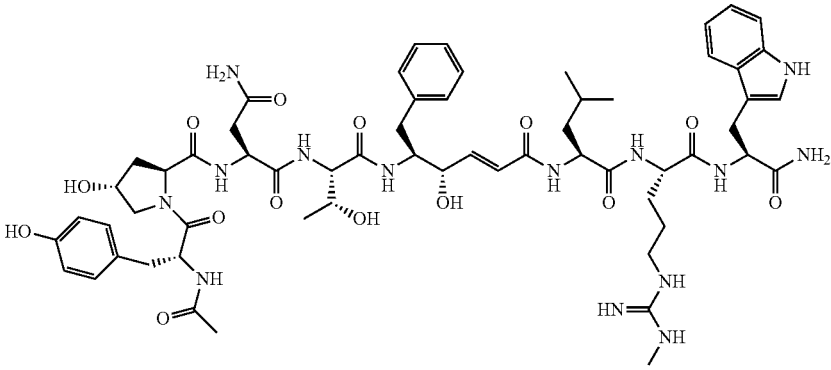 [SMILES: CNC(=N)NCCC[C@H](NC(=O)[C@H](CC(C)C)NC(=O)/C=C/[C@H](O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 859 | 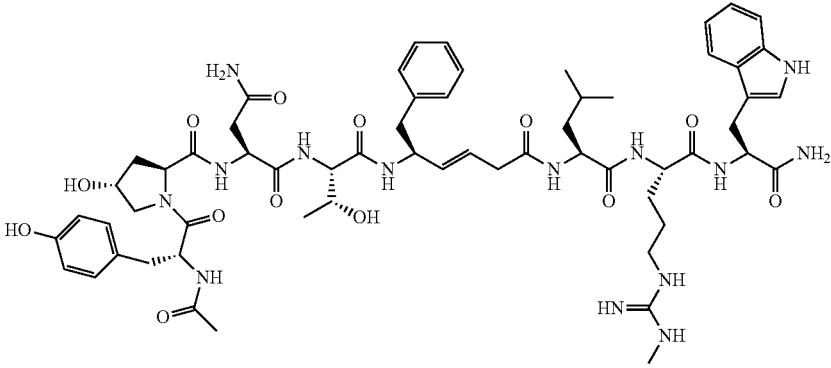 [SMILES: CNC(=N)NCCC[C@H](NC(=O)[C@H](CC(C)C)NC(=O)C/C=C/[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 866 | 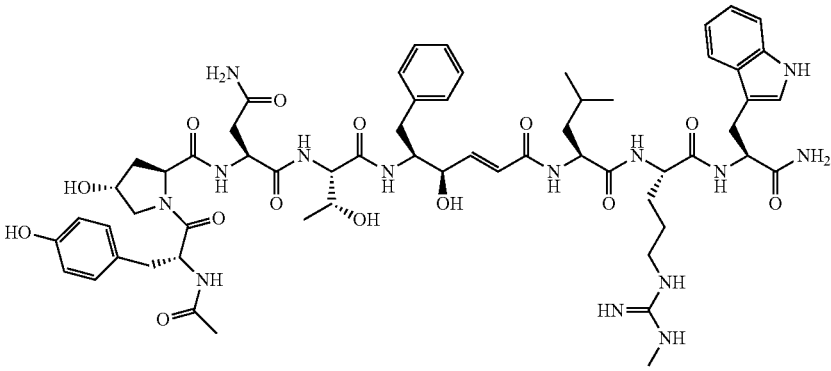 [SMILES: CNC(=N)NCCC[C@H](NC(=O)[C@H](CC(C)C)NC(=O)/C=C/[C@@H](O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 867 | 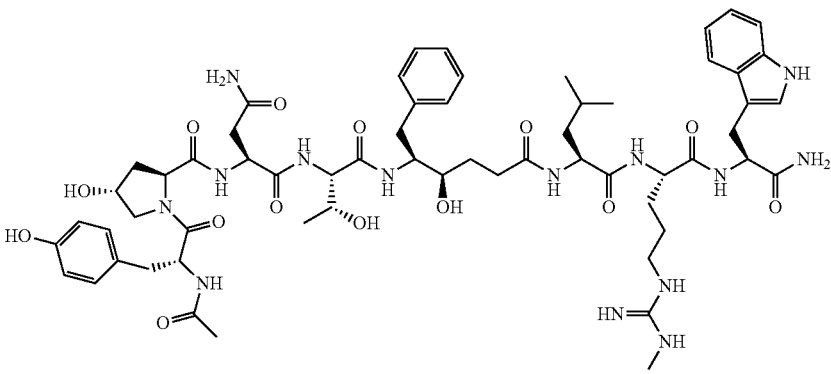 [SMILES: CNC(=N)NCCC[C@H](NC(=O)[C@H](CC(C)C)NC(=O)CC[C@@H](O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |

TABLE 1-continued

| Compound number | Structure |
|---|---|
| 869 | 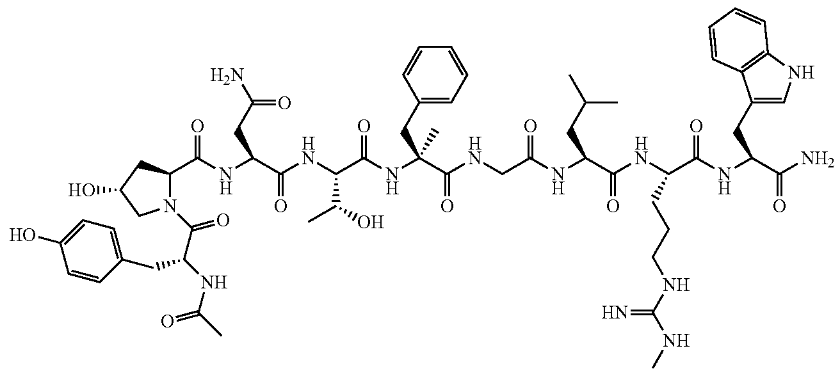 [SMILES: CNC(=N)NCCC[C@H](NC(=O)[C@H](CC(C)C)NC(=O)CNC(=O)[C@](C)(Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 871 | 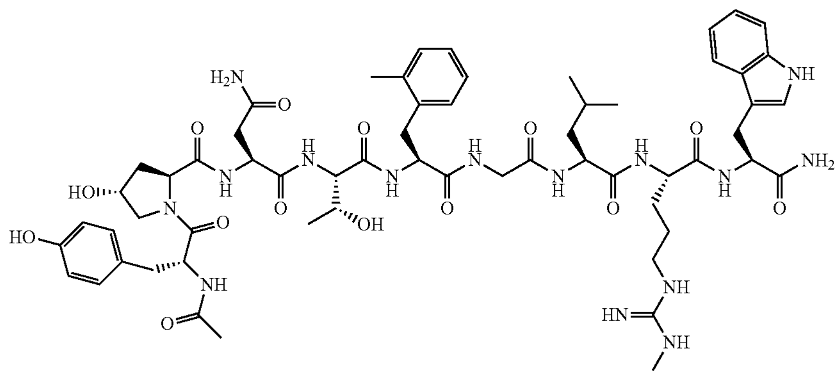 [SMILES: CNC(=N)NCCC[C@H](NC(=O)[C@H](CC(C)C)NC(=O)CNC(=O)[C@H](Cc1ccccc1C)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 873 | 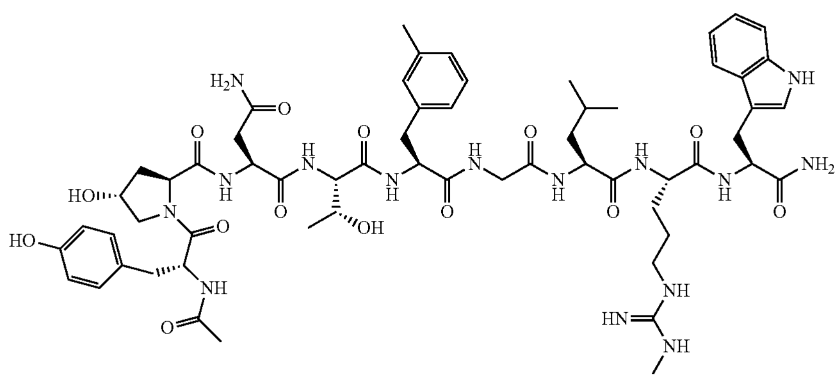 [SMILES: CNC(=N)NCCC[C@H](NC(=O)[C@H](CC(C)C)NC(=O)CNC(=O)[C@H](Cc1cccc(C)c1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 875 | 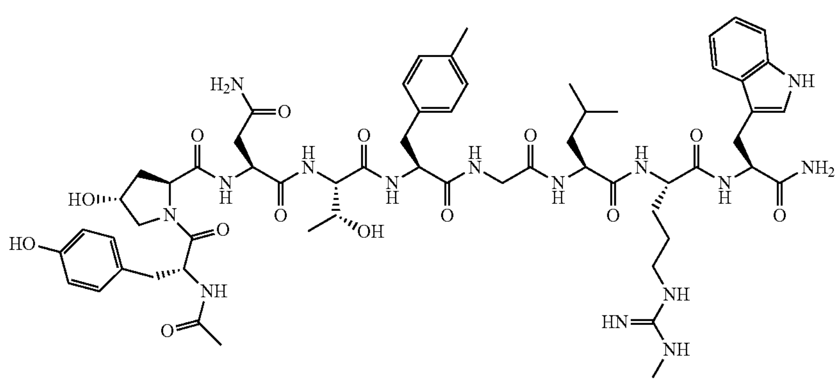 [SMILES: CNC(=N)NCCC[C@H](NC(=O)[C@H](CC(C)C)NC(=O)CNC(=O)[C@H](Cc1ccc(C)cc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |

TABLE 1-continued

| Compound number | Structure |
| --- | --- |
| 885 | 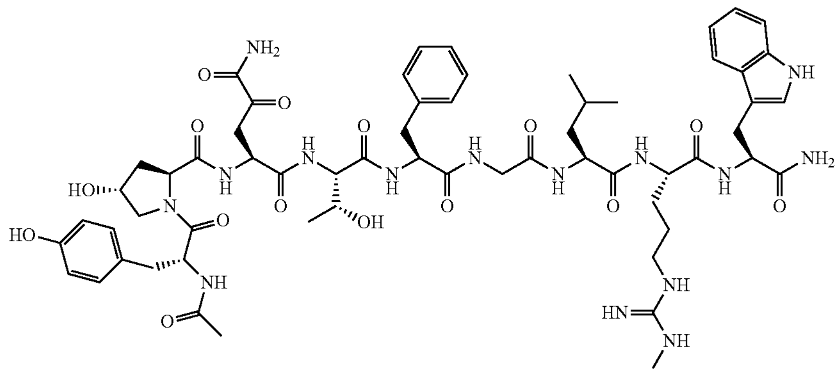 [SMILES: CNC(=N)NCCC[C@H](NC(=O)[C@H](CC(C)C)NC(=O)CNC(=O)[C@H](Cc1ccccc1)NC(=O)[C@@H](NC(=O)[C@H](CC(=O)C(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 892 | 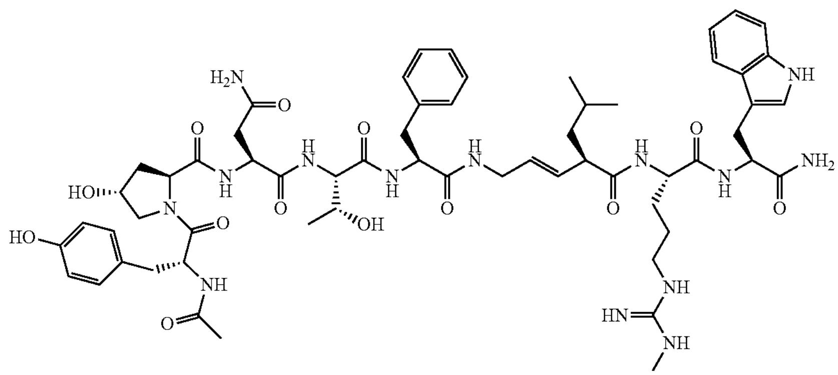 [SMILES: CNC(=N)NCCC[C@H](NC(=O)[C@@H](/C=C/CNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)CC(C)C)C(=O)N[C@@H](Cc1c[nH]c2ccccc12)C(N)=O] |
| 893 | 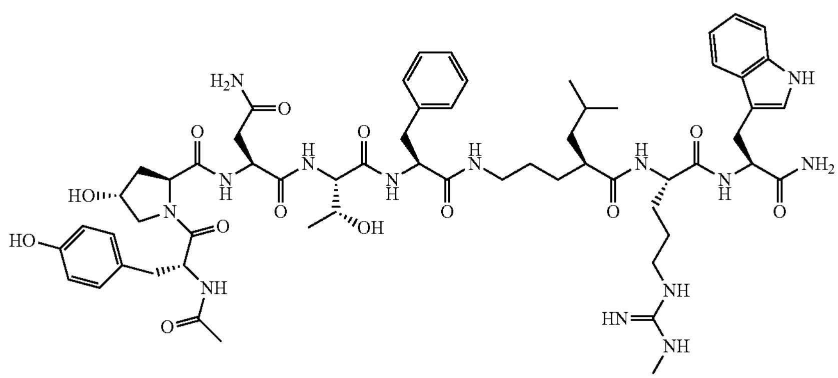 [SMILES: CNC(=N)NCCC[C@H](NC(=O)[C@@H](CCCNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)CC(C)C)C(=O)N[C@@H](Cc1c[nH]c2ccccc12)C(N)=O] |
| 894 | 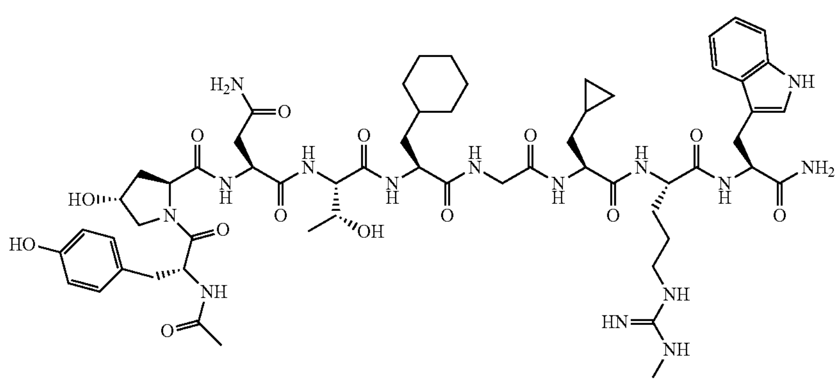 |

TABLE 1-continued

| Compound number | Structure |
|---|---|
| 895 | 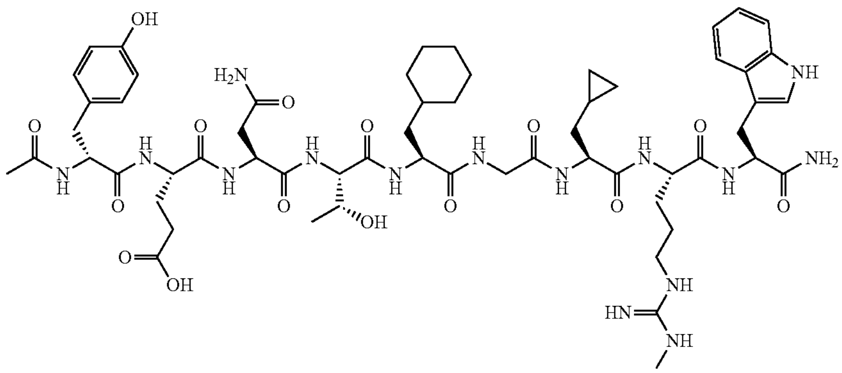 [SMILES: CNC(=N)NCCC[C@H](NC(=O)[C@H](CC1CC1)NC(=O)CNC(=O)[C@H](CC1CCCCC1)NC(=O)[C@@H](NC(=O)[C@H](CC(N)=O)NC(=O)[C@H](CCC(=O)O)NC(=O)[C@@H](Cc1ccc(O)cc1)NC(C)=O)[C@@H](C)O)C(=O)N[C@@H](Cc1c[nH]c2ccccc12)C(N)=O] |
| 902 | 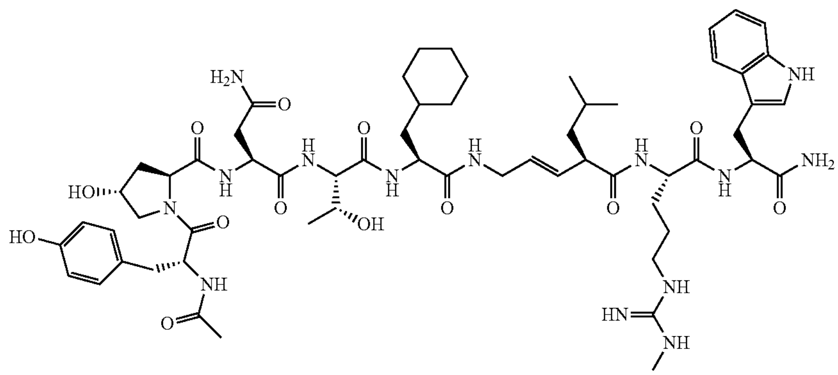 [SMILES: CNC(=N)NCCC[C@H](NC(=O)[C@@H](/C=C/CNC(=O)[C@H](CC1CCCCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)CC(C)C)C(=O)N[C@@H](Cc1c[nH]c2ccccc12)C(N)=O] |
| 903 | 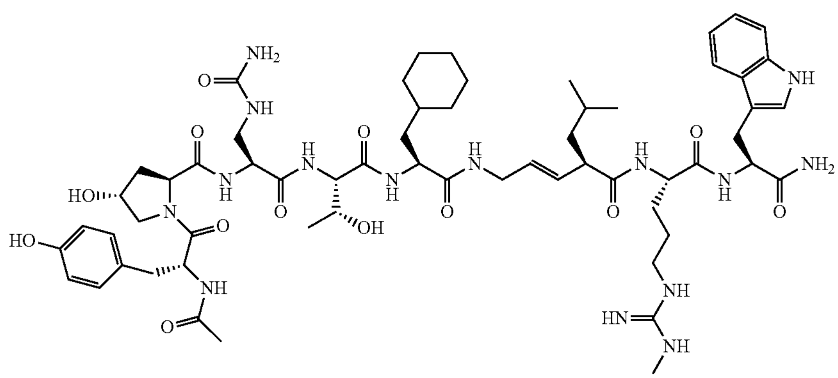 [SMILES: CNC(=N)NCCC[C@H](NC(=O)[C@@H](/C=C/CNC(=O)[C@H](CC1CCCCC1)NC(=O)[C@@H](NC(=O)[C@H](CNC(N)=O)NC(=O)[C@@H]1C[C@@H](O)CN1C(=O)[C@@H](Cc1ccc(O)cc1)NC(C)=O)[C@@H](C)O)CC(C)C)C(=O)N[C@@H](Cc1c[nH]c2ccccc12)C(N)=O] |
| 904 | 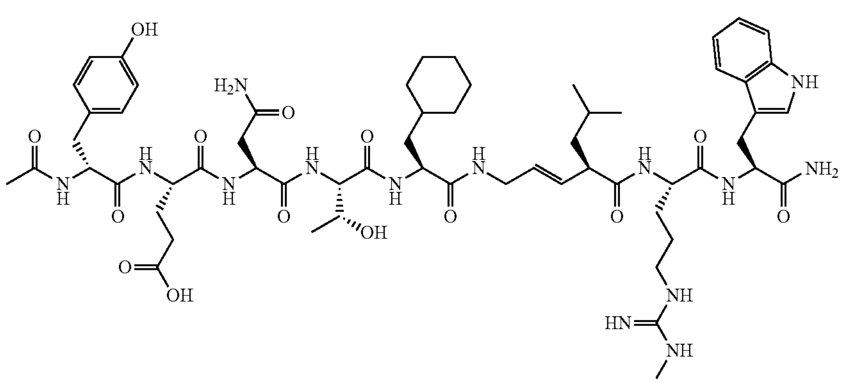 [SMILES: CNC(=N)NCCC[C@H](NC(=O)[C@@H](/C=C/CNC(=O)[C@H](CC1CCCCC1)NC(=O)[C@@H](NC(=O)[C@H](CC(N)=O)NC(=O)[C@H](CCC(=O)O)NC(=O)[C@@H](Cc1ccc(O)cc1)NC(C)=O)[C@@H](C)O)CC(C)C)C(=O)N[C@@H](Cc1c[nH]c2ccccc12)C(N)=O] |

TABLE 1-continued
| Compound number | Structure |
|---|---|
| 905 | 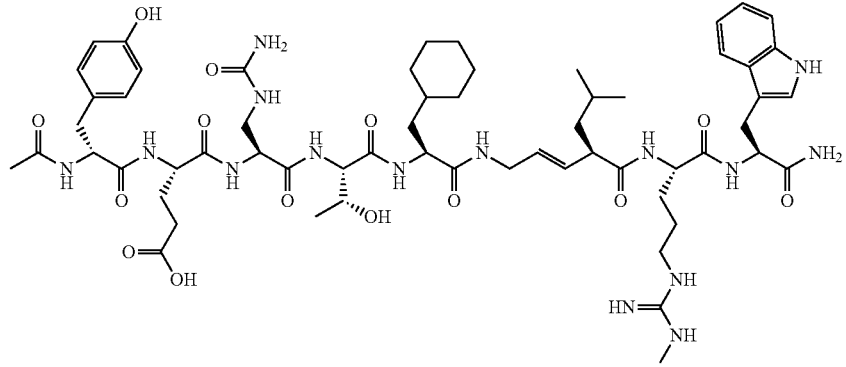 [SMILES: CNC(=N)NCCC[C@H](NC(=O)[C@@H](/C=C/CNC(=O)[C@H](CC1CCCCC1)NC(=O)[C@@H](NC(=O)[C@H](CNC(N)=O)NC(=O)[C@H](CCC(=O)O)NC(=O)[C@@H](Cc1ccc(O)cc1)NC(C)=O)[C@@H](C)O)CC(C)C)C(=O)N[C@@H](Cc1c[nH]c2ccccc12)C(N)=O] |
| 906 | 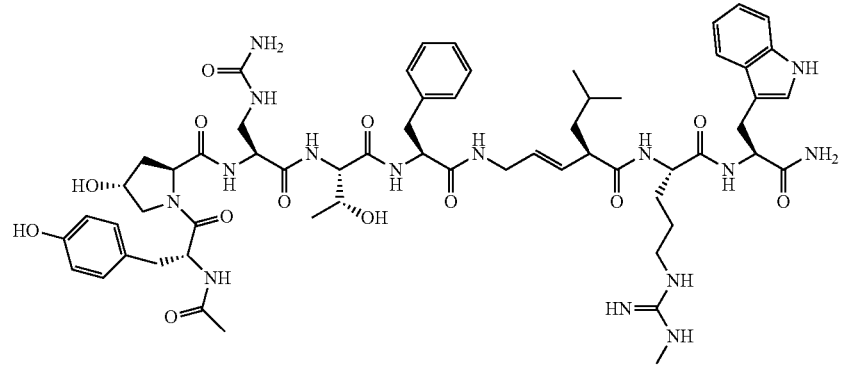 [SMILES: CNC(=N)NCCC[C@H](NC(=O)[C@@H](/C=C/CNC(=O)[C@H](Cc1ccccc1)NC(=O)[C@@H](NC(=O)[C@H](CNC(N)=O)NC(=O)[C@@H]1C[C@@H](O)CN1C(=O)[C@@H](Cc1ccc(O)cc1)NC(C)=O)[C@@H](C)O)CC(C)C)C(=O)N[C@@H](Cc1c[nH]c2ccccc12)C(N)=O] |
| 907 | 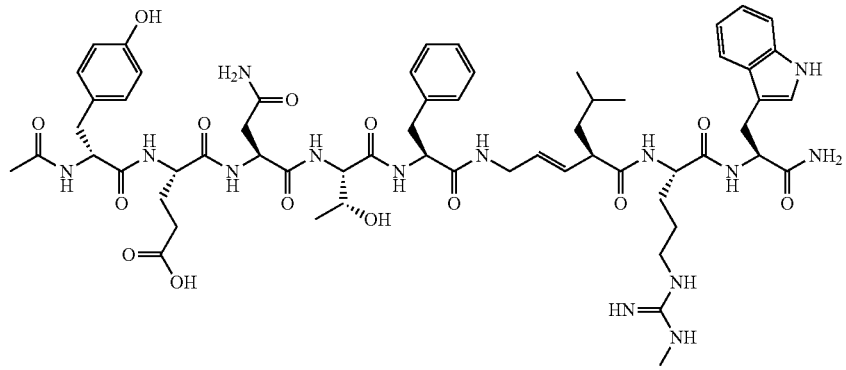 [SMILES: CNC(=N)NCCC[C@H](NC(=O)[C@@H](/C=C/CNC(=O)[C@H](Cc1ccccc1)NC(=O)[C@@H](NC(=O)[C@H](CC(N)=O)NC(=O)[C@H](CCC(=O)O)NC(=O)[C@@H](Cc1ccc(O)cc1)NC(C)=O)[C@@H](C)O)CC(C)C)C(=O)N[C@@H](Cc1c[nH]c2ccccc12)C(N)=O] |
| 908 | 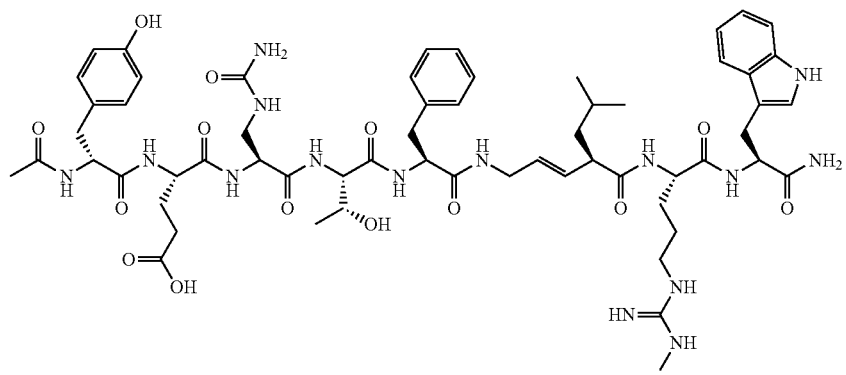 [SMILES: CNC(=N)NCCC[C@H](NC(=O)[C@@H](/C=C/CNC(=O)[C@H](Cc1ccccc1)NC(=O)[C@@H](NC(=O)[C@H](CNC(N)=O)NC(=O)[C@H](CCC(=O)O)NC(=O)[C@@H](Cc1ccc(O)cc1)NC(C)=O)[C@@H](C)O)CC(C)C)C(=O)N[C@@H](Cc1c[nH]c2ccccc12)C(N)=O] |

TABLE 1-continued

| Compound number | Structure |
| --- | --- |
| 909 | (chemical structure) |
| 910 | (chemical structure) |
| 911 | (chemical structure) |
| 912 | (chemical structure) |

TABLE 1-continued
| Compound number | Structure |
|---|---|
| 913 | 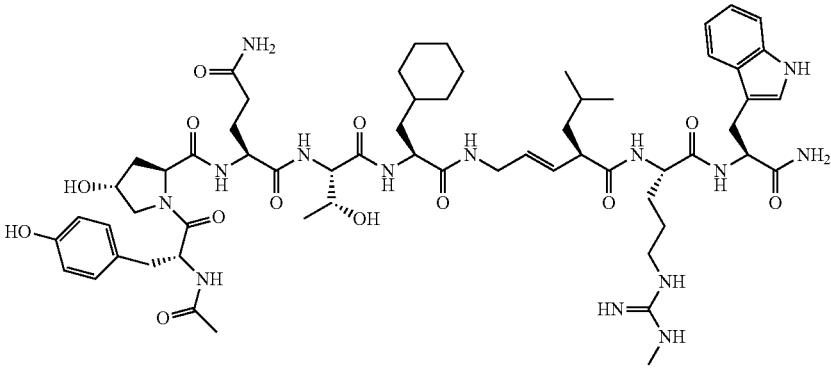 |
| 914 | 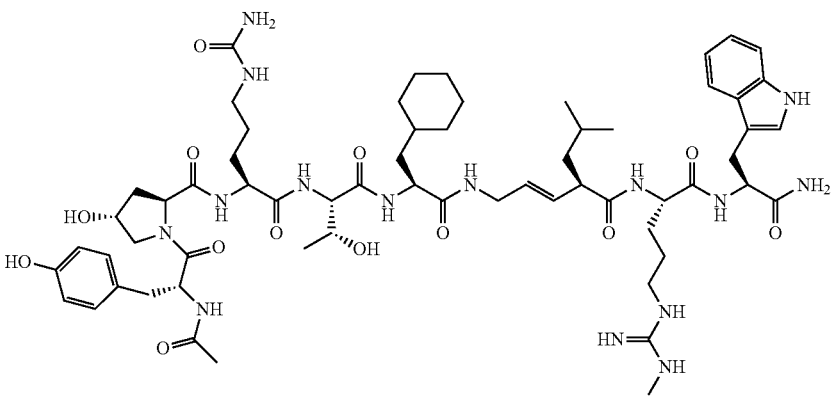 [SMILES: CNC(=N)NCCC[C@H](NC(=O)[C@@H](/C=C/CNC(=O)[C@H](CC1CCCCC1)NC(=O)[C@@H](NC(=O)[C@H](CCCNC(N)=O)NC(=O)[C@@H]1C[C@@H](O)CN1C(=O)[C@@H](Cc1ccc(O)cc1)NC(C)=O)[C@@H](C)O)CC(C)C)C(=O)N[C@@H](Cc1c[nH]c2ccccc12)C(N)=O] |
| 915 | 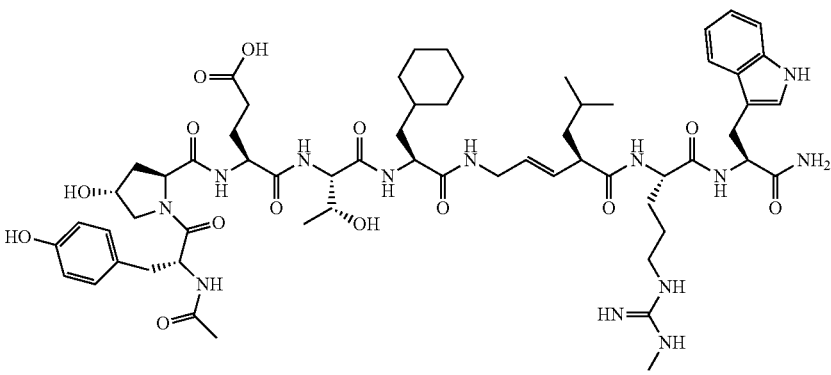 [SMILES: CNC(=N)NCCC[C@H](NC(=O)[C@@H](/C=C/CNC(=O)[C@H](CC1CCCCC1)NC(=O)[C@@H](NC(=O)[C@H](CCC(=O)O)NC(=O)[C@@H]1C[C@@H](O)CN1C(=O)[C@@H](Cc1ccc(O)cc1)NC(C)=O)[C@@H](C)O)CC(C)C)C(=O)N[C@@H](Cc1c[nH]c2ccccc12)C(N)=O] |
| 916 | 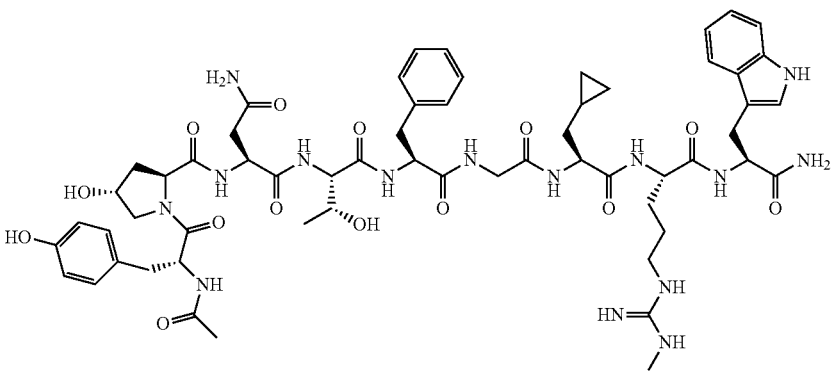 [SMILES: CNC(=N)NCCC[C@H](NC(=O)[C@H](CC1CC1)NC(=O)CNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |

| Compound number | Structure |
|---|---|
| 917 | 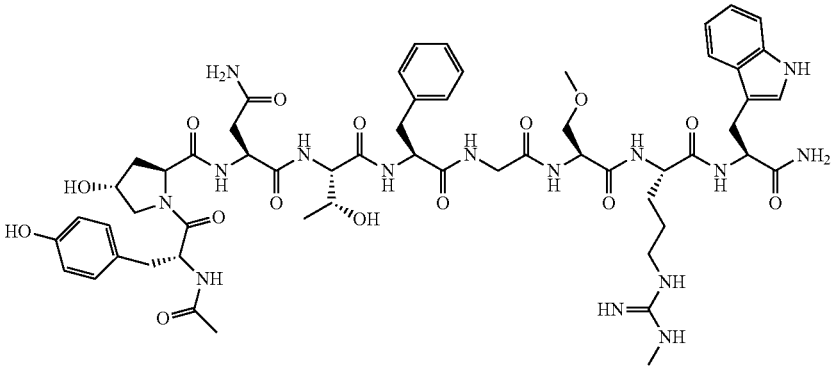 |
| 918 | 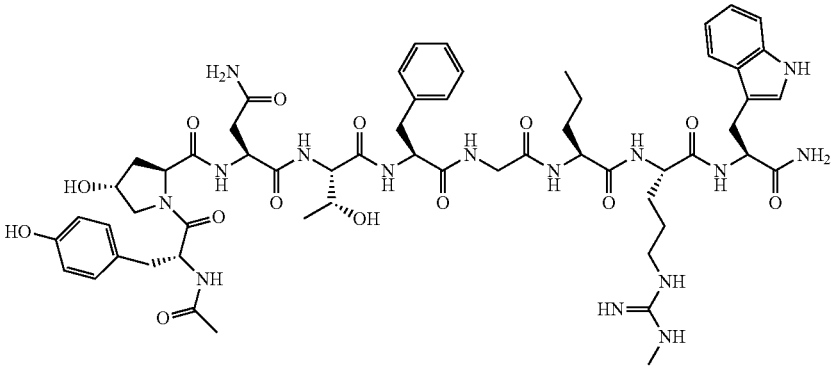 [SMILES: CNC(=N)NCCC[C@H](NC(=O)[C@H](COC)NC(=O)CNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 919 | 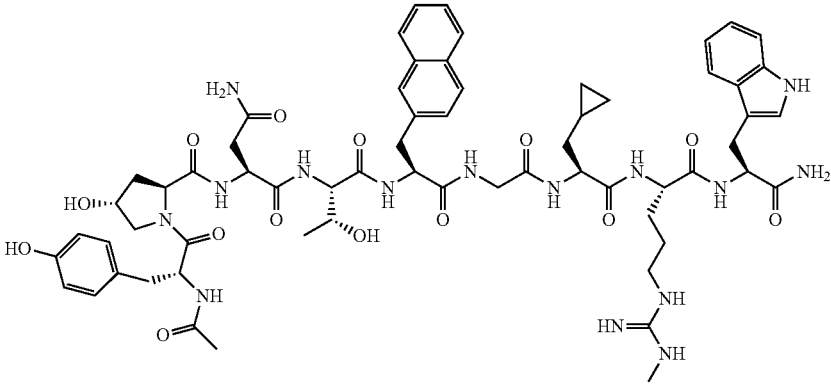 [SMILES: CNC(=N)NCCC[C@H](NC(=O)[C@H](CC1CC1)NC(=O)CNC(=O)[C@H](Cc1ccc2ccccc2c1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 920 | 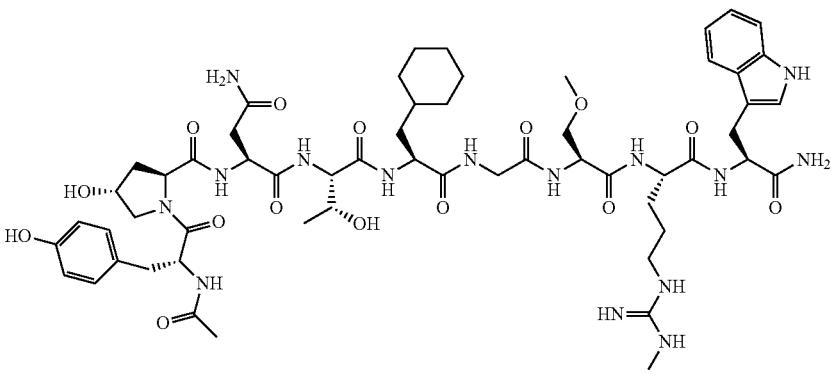 [SMILES: CNC(=N)NCCC[C@H](NC(=O)[C@H](COC)NC(=O)CNC(=O)[C@H](CC1CCCCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |

TABLE 1-continued
| Compound number | Structure |
|---|---|
| 921 | 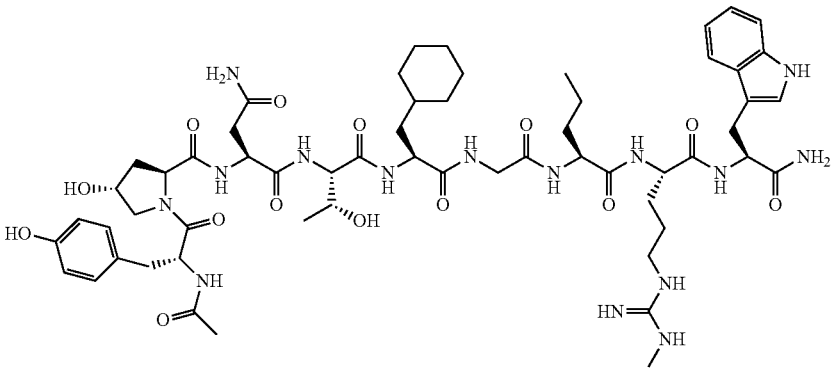 [SMILES: CCC[C@H](NC(=O)CNC(=O)[C@H](CC1CCCCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](CCCNC(=N)NC)C(=O)N[C@@H](Cc1c[nH]c2ccccc12)C(N)=O] |
| 923 | 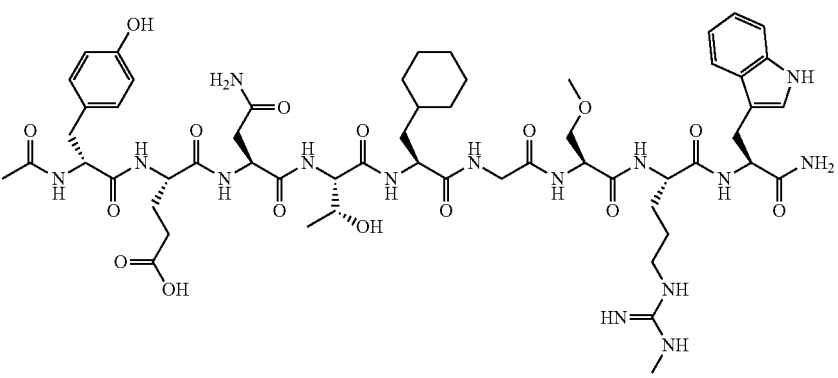 [SMILES: CNC(=N)NCCC[C@H](NC(=O)[C@H](COC)NC(=O)CNC(=O)[C@H](CC1CCCCC1)NC(=O)[C@@H](NC(=O)[C@H](CC(N)=O)NC(=O)[C@H](CCC(=O)O)NC(=O)[C@@H](Cc1ccc(O)cc1)NC(C)=O)[C@@H](C)O)C(=O)N[C@@H](Cc1c[nH]c2ccccc12)C(N)=O] |
| 924 | 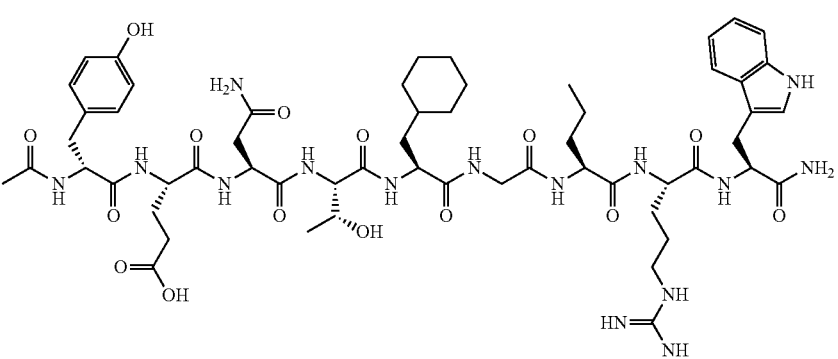 |
| 925 | 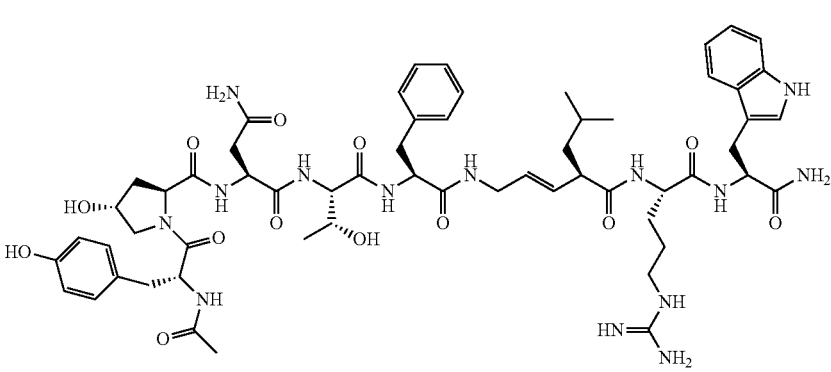 [SMILES: CC(=O)N[C@H](Cc1ccc(O)cc1)C(=O)N1C[C@H](O)C[C@H]1C(=O)N[C@@H](CC(N)=O)C(=O)N[C@H](C(=O)N[C@@H](Cc1ccccc1)C(=O)NC/C=C/[C@@H](CC(C)C)C(=O)N[C@@H](CCCNC(=N)N)C(=O)N[C@@H](Cc1c[nH]c2ccccc12)C(N)=O)[C@@H](C)O] |

TABLE 1-continued
| Compound number | Structure |
|---|---|
| 926 | 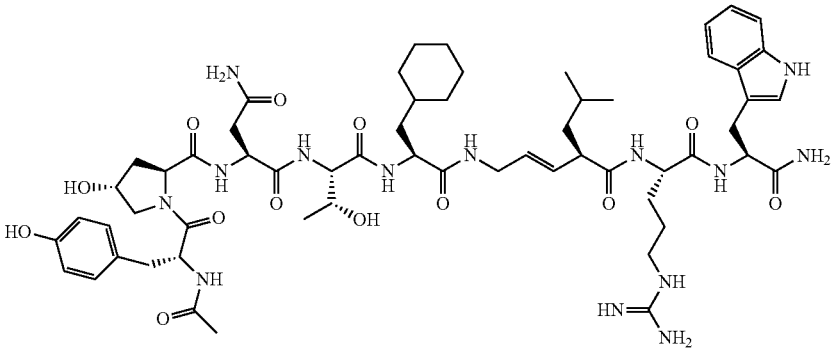 |
| 927 | 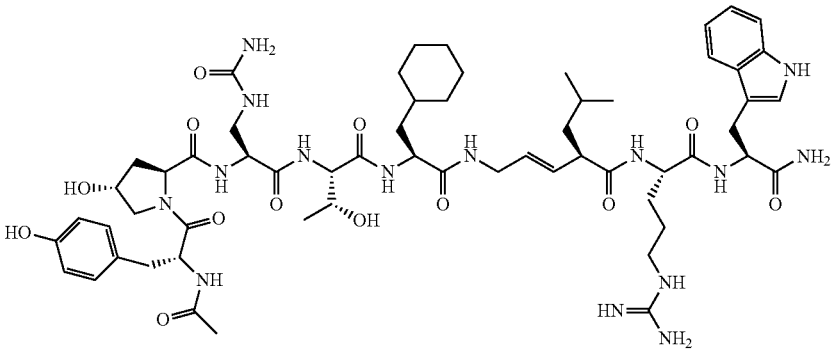 |
| 929 | 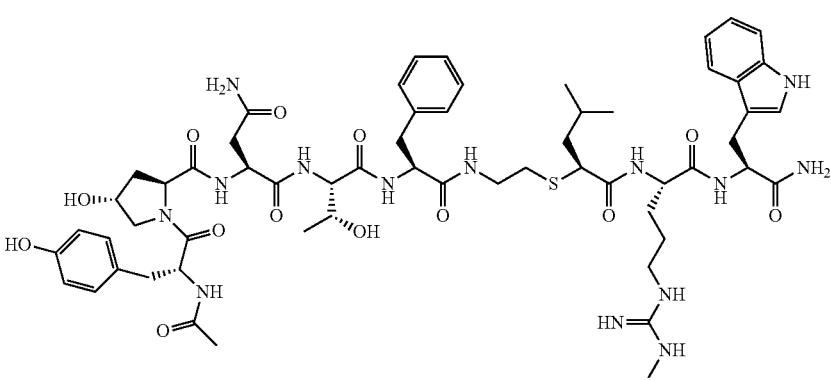 [SMILES: CNC(=N)NCCC[C@H](NC(=O)[C@H](CC(C)C)SCCNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 931 | 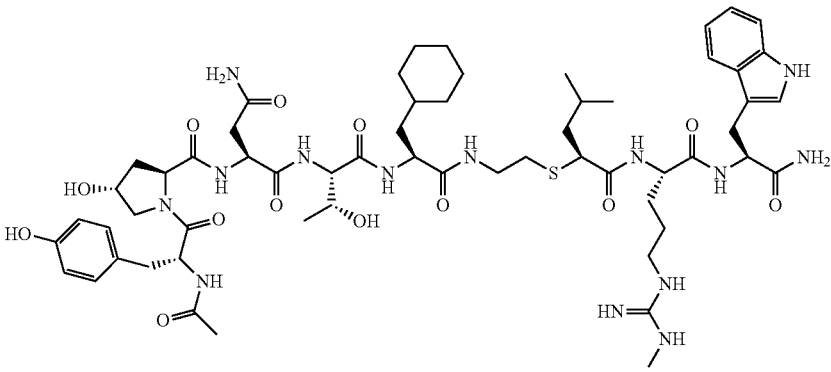 |

TABLE 1-continued

| Compound number | Structure |
|---|---|
| 932 | 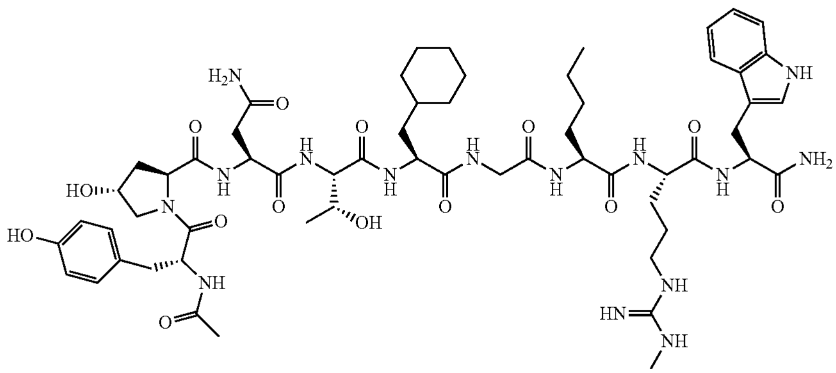 [SMILES: CCCC[C@H](NC(=O)CNC(=O)[C@H](CC1CCCCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](CCCNC(=N)NC)C(=O)N[C@@H](Cc1c[nH]c2ccccc12)C(N)=O] |
| 933 | 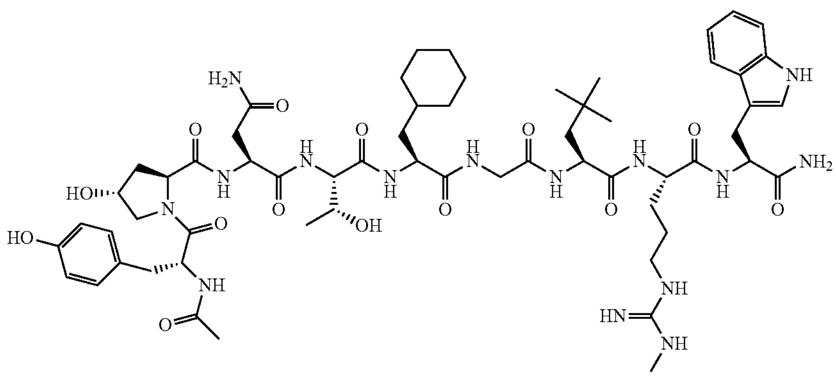 [SMILES: CNC(=N)NCCC[C@H](NC(=O)[C@H](CC(C)(C)C)NC(=O)CNC(=O)[C@H](CC1CCCCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 934 | 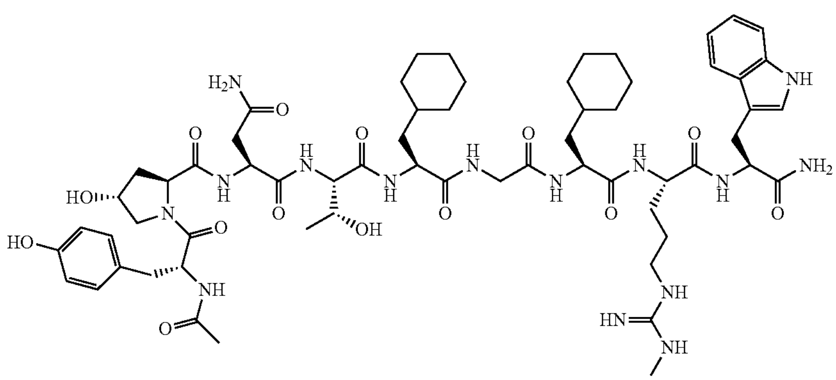 [SMILES: CNC(=N)NCCC[C@H](NC(=O)[C@H](CC1CCCCC1)NC(=O)CNC(=O)[C@H](CC1CCCCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 940 | 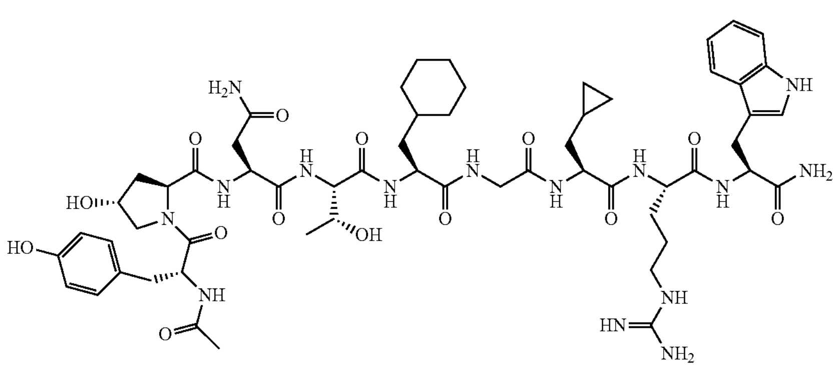 [SMILES: CC(=O)N[C@H](Cc1ccc(O)cc1)C(=O)N1C[C@H](O)C[C@H]1C(=O)N[C@@H](CC(N)=O)C(=O)N[C@H](C(=O)N[C@@H](CC1CCCCC1)C(=O)NCC(=O)N[C@@H](CC1CC1)C(=O)N[C@@H](CCCNC(=N)N)C(=O)N[C@@H](Cc1c[nH]c2ccccc12)C(N)=O)[C@@H](C)O] |

TABLE 1-continued
| Compound number | Structure |
|---|---|
| 942 | 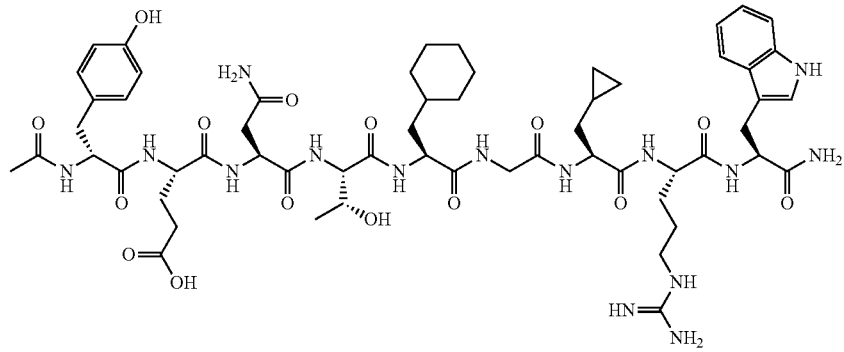 [SMILES: CC(=O)N[C@H](Cc1ccc(O)cc1)C(=O)N[C@@H](CCC(=O)O)C(=O)N[C@@H](CC(N)=O)C(=O)N[C@H](C(=O)N[C@@H](CC1CCCCC1)C(=O)NCC(=O)N[C@@H](CC1CC1)C(=O)N[C@@H](CCCNC(=N)N)C(=O)N[C@@H](Cc1c[nH]c2ccccc12)C(N)=O)[C@@H](C)O] |
| 944 | 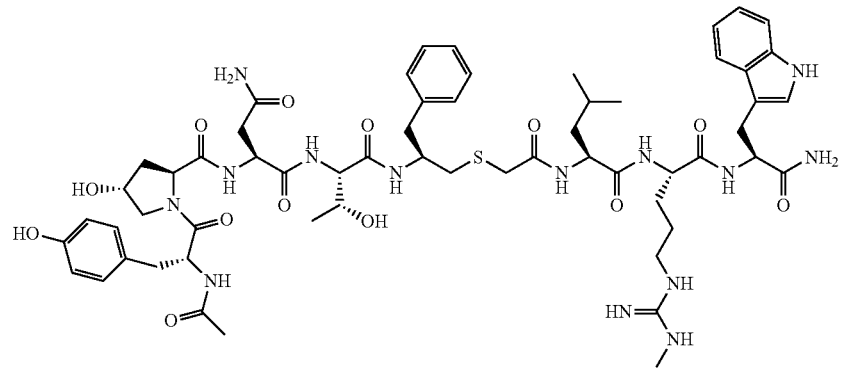 [SMILES: CNC(=N)NCCC[C@H](NC(=O)[C@H](CC(C)C)NC(=O)CSC[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 945 | 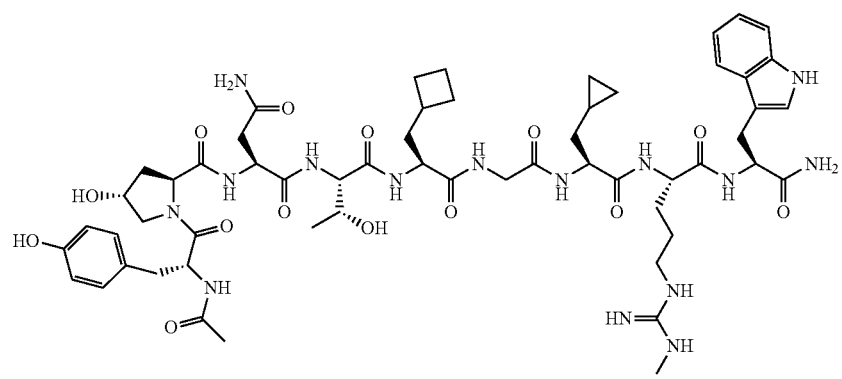 [SMILES: CNC(=N)NCCC[C@H](NC(=O)[C@H](CC1CC1)NC(=O)CNC(=O)[C@H](CC1CCC1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 946 | 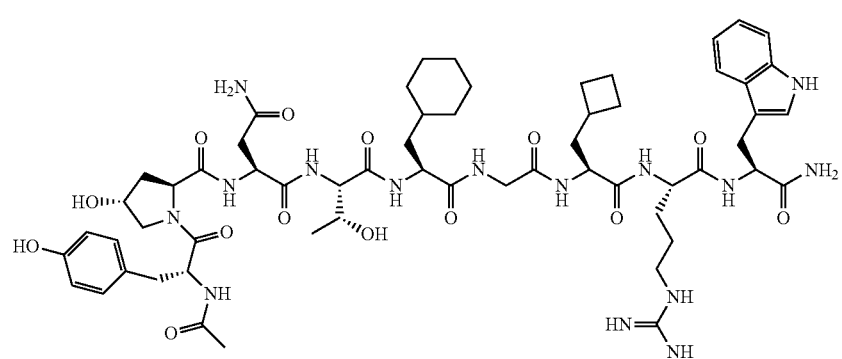 |

TABLE 1-continued
| Compound number | Structure |
|---|---|
| 947 | 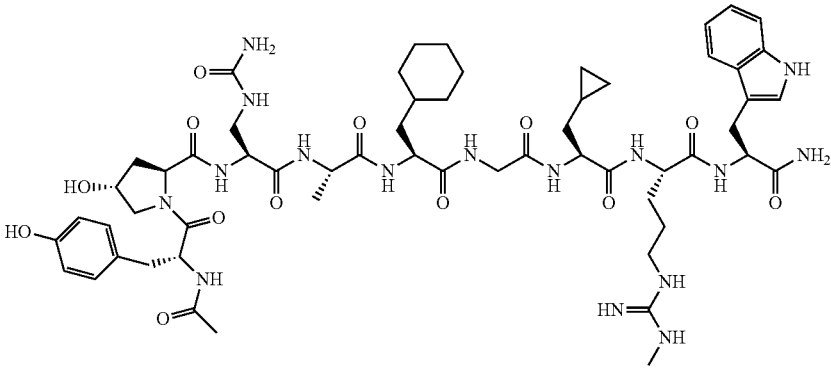 [SMILES: CNC(=N)NCCC[C@H](NC(=O)[C@H](CC1CC1)NC(=O)CNC(=O)[C@H](CC1CCCCC1)NC(=O)[C@H](C)NC(=O)[C@H](CNC(N)=O)NC(=O)[C@@H]1C[C@@H](O)CN1C(=O)[C@@H](Cc1ccc(O)cc1)NC(C)=O)C(=O)N[C@@H](Cc1c[nH]c2ccccc12)C(N)=O] |
| 948 | 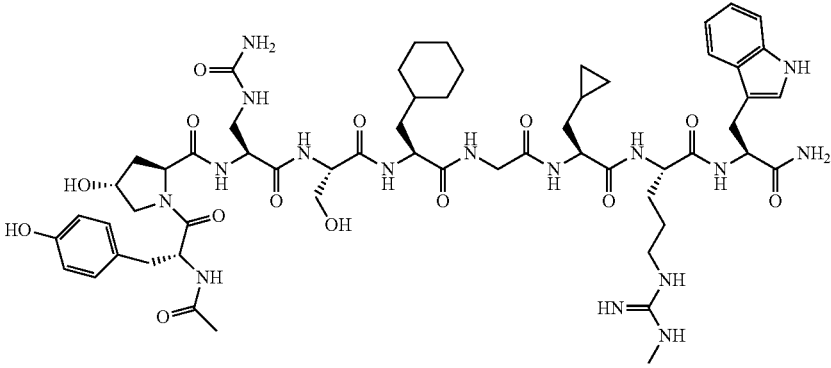 [SMILES: CNC(=N)NCCC[C@H](NC(=O)[C@H](CC1CC1)NC(=O)CNC(=O)[C@H](CC1CCCCC1)NC(=O)[C@H](CO)NC(=O)[C@H](CNC(N)=O)NC(=O)[C@@H]1C[C@@H](O)CN1C(=O)[C@@H](Cc1ccc(O)cc1)NC(C)=O)C(=O)N[C@@H](Cc1c[nH]c2ccccc12)C(N)=O] |
| 949 | 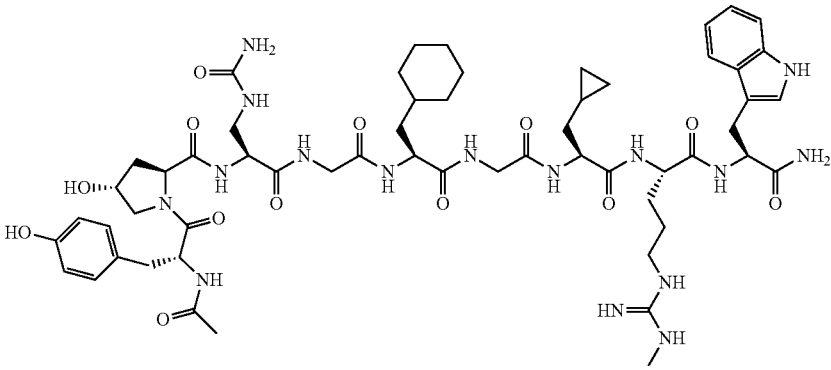 [SMILES: CNC(=N)NCCC[C@H](NC(=O)[C@H](CC1CC1)NC(=O)CNC(=O)[C@H](CC1CCCCC1)NC(=O)CNC(=O)[C@H](CNC(N)=O)NC(=O)[C@@H]1C[C@@H](O)CN1C(=O)[C@@H](Cc1ccc(O)cc1)NC(C)=O)C(=O)N[C@@H](Cc1c[nH]c2ccccc12)C(N)=O] |
| 951 | 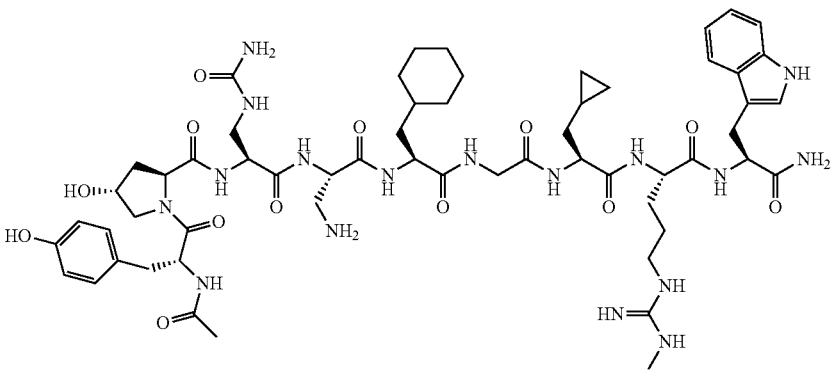 [SMILES: CNC(=N)NCCC[C@H](NC(=O)[C@H](CC1CC1)NC(=O)CNC(=O)[C@H](CC1CCCCC1)NC(=O)[C@H](CN)NC(=O)[C@H](CNC(N)=O)NC(=O)[C@@H]1C[C@@H](O)CN1C(=O)[C@@H](Cc1ccc(O)cc1)NC(C)=O)C(=O)N[C@@H](Cc1c[nH]c2ccccc12)C(N)=O] |

TABLE 1-continued

| Compound number | Structure |
|---|---|
| 952 | 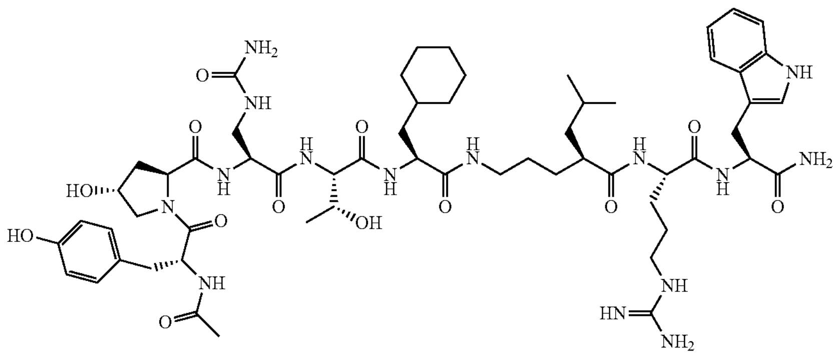 [SMILES: CC(=O)N[C@H](Cc1ccc(O)cc1)C(=O)N1C[C@H](O)C[C@H]1C(=O)N[C@@H](CNC(N)=O)C(=O)N[C@H](C(=O)N[C@@H](CC1CCCCC1)C(=O)NCCC[C@@H](CC(C)C)C(=O)N[C@@H](CCCNC(=N)N)C(=O)N[C@@H](Cc1c[nH]c2ccccc12)C(N)=O)[C@@H](C)O] |
| 953 | 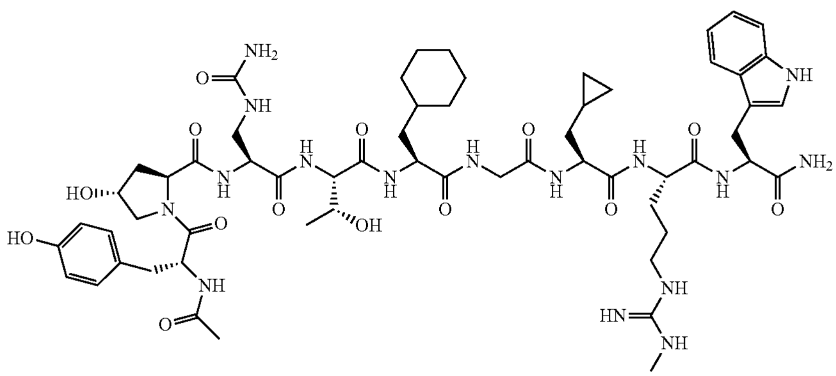 [SMILES: CNC(=N)NCCC[C@H](NC(=O)[C@H](CC1CC1)NC(=O)CNC(=O)[C@H](CC1CCCCC1)NC(=O)[C@@H](NC(=O)[C@H](CNC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |
| 956 | 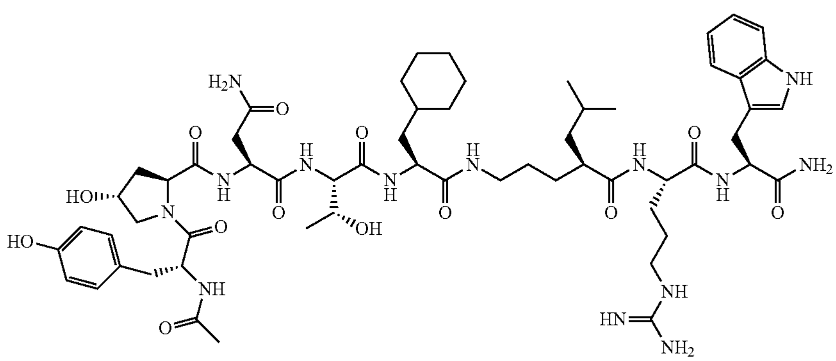 [SMILES: CC(=O)N[C@H](Cc1ccc(O)cc1)C(=O)N1C[C@H](O)C[C@H]1C(=O)N[C@@H](CC(N)=O)C(=O)N[C@H](C(=O)N[C@@H](CC1CCCCC1)C(=O)NCCC[C@@H](CC(C)C)C(=O)N[C@@H](CCCNC(=N)N)C(=O)N[C@@H](Cc1c[nH]c2ccccc12)C(N)=O)[C@@H](C)O] |
| 957 | 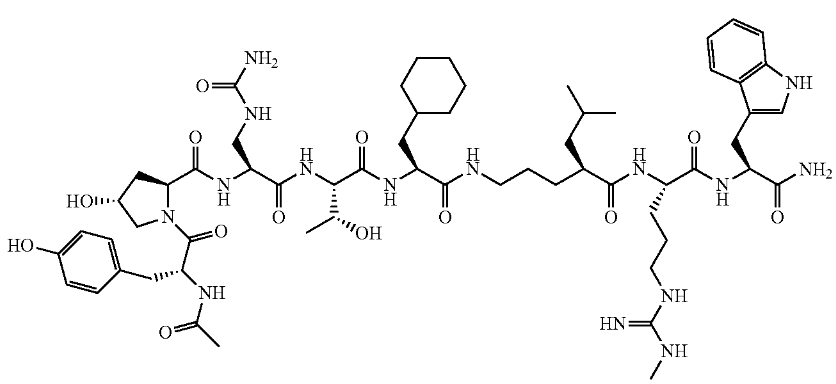 [SMILES: CNC(=N)NCCC[C@H](NC(=O)[C@@H](CCCNC(=O)[C@H](CC1CCCCC1)NC(=O)[C@@H](NC(=O)[C@H](CNC(N)=O)NC(=O)[C@@H]1C[C@@H](O)CN1C(=O)[C@@H](Cc1ccc(O)cc1)NC(C)=O)[C@@H](C)O)CC(C)C)C(=O)N[C@@H](Cc1c[nH]c2ccccc12)C(N)=O] |

TABLE 1-continued

| Compound number | Structure |
|---|---|
| 959 | 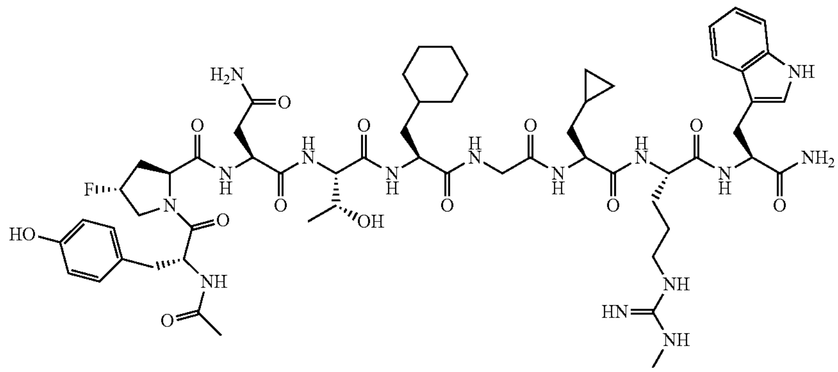 [SMILES: CNC(=N)NCCC[C@H](NC(=O)[C@H](CC1CC1)NC(=O)CNC(=O)[C@H](CC1CCCCC1)NC(=O)[C@@H](NC(=O)[C@H](CC(N)=O)NC(=O)[C@@H]1C[C@@H](F)CN1C(=O)[C@@H](Cc1ccc(O)cc1)NC(C)=O)[C@@H](C)O)C(=O)N[C@@H](Cc1c[nH]c2ccccc12)C(N)=O] |
| 968 | 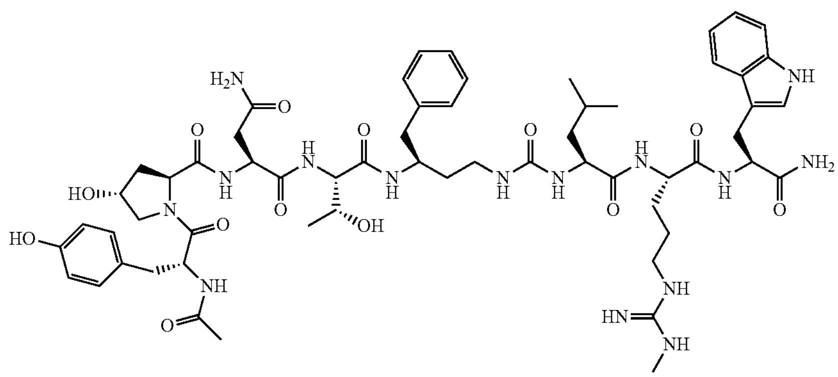 [SMILES: CNC(=N)NCCC[C@H](NC(=O)[C@H](CC(C)C)NC(=O)NCC[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O] |

The metastin derivatives of the present invention can be prepared by publicly known methods for peptide synthesis. As the methods for peptide synthesis, for example, either solid phase synthesis or liquid phase synthesis may be used. That is, the partial peptide or amino acids that can constitute the peptide of the present invention are repeatedly condensed with the remaining part to give the product having a desired sequence. Where the product has protecting groups, these protecting groups are removed to give the desired peptide. Publicly known methods for condensation and removal of the protecting groups includes those, e.g., described in (1) to (5) below.

(1) M. Bodanszky & M. A. Ondetti: Peptide Synthesis, Interscience Publishers, New York (1966)
(2) Schroeder & Luebke: The Peptide, Academic Press, New York (1965)
(3) Nobuo Izumiya, et al.: *Peptide Gosei-no-Kiso to Jikken* (Basics and experiments of peptide synthesis), published by Maruzen Co. (1975)
(4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)
(5) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the peptide of the present invention. When the peptide obtained by the above methods is in a free form, the peptide can be converted into an appropriate salt by a publicly known method; conversely when the peptide is obtained in a salt form, it can be converted into its free form by publicly known methods.

For condensation of the protected amino acids or peptides, a variety of activation reagents for peptide synthesis may be used, but trisphosphonium salts, tetramethyluronium salts, carbodiimides, etc. are particularly preferred. Examples of trisphosphonium salts include benzotriazol-1-yloxytris(pyrrolidino)phosphonium hexafluorophosphate (PyBOP), bromotris(pyrrolidino) phosphonium hexafluorophosphate (PyBroP) and 7-azabenzotriazol-1-yloxytris(pyrrolidino) phosphonium hexafluorophosphate (PyAOP), examples of tetramethyluronium salts include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluronium tetraflluoroborate (TBTU), 2-(5-norbornene-2,3-dicarboxyimido)-1,1,3,3-tetramethyluronium tetrafluoroborate (TNTU) and O—(N-succinimidyl)-1,1,3,3-tetramethyluronium tetrafluoroborate (TSTU); examples of carbodiimides include DCC, N,N'-diisopropylcarbodiimide (DIPCDI) and N-ethyl-N'-(3-dimethylaminopropyl)carbodiimide hydrochloride (EDCI.HCl); etc. For condensation using these reagents, the addition of racemization inhibitors (e.g., HONB, HOBt, HOAt, HOOBt, etc.) is preferred. Solvents used in condensation may be appropriately chosen from solvents that are known to be usable for condensation. For example, acid amides such as anhydrous or hydrous N,N-dimethylformamide, N,N-dimethylacetamide, N-methylpyrrolidone, etc., halogenated hydrocarbons such as methylene chloride, chloroform, etc., alcohols such as trifluoroethanol, phenol, etc., sulfoxides such as dimethyl sulfoxide, etc., tertiary amines such as pyridine, etc., ethers such as dioxane, tetrahydrofuran, etc., nitriles such as acetonitrile, propionitrile, etc., esters such as methyl acetate, ethyl acetate, etc., or suitable mixtures thereof, etc. are used. The reaction temperature is appropriately chosen from the range known to be applicable to peptide binding reactions and is normally suitably chosen from the range of about −20° C. to 50° C. The activated amino acid derivatives are used generally in 1.5 to 6 times excess. In the case of solid phase synthesis, the condensation is examined using the ninhydrin reaction; when the condensation is insufficient, the condensation can be completed by repeating the condensation reaction without removal of the protecting groups. When the condensation is yet insufficient even after repeating the reaction, the unreacted amino acids are acylated with acetic anhydride or acetylimidazole to cancel any adverse effect on the subsequent reaction.

Examples of the protecting groups used to protect amino groups in the starting amino acids include Z, Boc, tert-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, trityl, etc. Examples of protecting groups for a carboxyl group include, in addition to the $C_{1-6}$ alkyl group, $C_{3-8}$ cycloalkyl group and $C_{7-14}$ aralkyl group for R described above, allyl, 2-adamantyl, 4-nitrobenzyl, 4-methoxybenzyl, 4-chlorobenzyl, phenacyl group, benzyloxycarbonylhydrazide, tert-butoxycarbonylhydrazide, tritylhydrazide, etc.

The hydroxyl group of serine and threonine can be protected, for example, by esterification or etherification. Examples of groups suitable for this esterification include a group derived from organic acid such as a lower $(C_{2-4})$ alkanoyl group such as acetyl group, an aroyl group such as benzoyl group, etc. Examples of a group suitable for the etherification include benzyl group, tetrahydropyranyl group, tert-butyl group, trytyl group (Trt), etc.

Examples of groups for protecting the phenolic hydroxyl group of tyrosine include Bzl, 2,6-dichlorobenzyl ($Cl_2$-Bzl), 2-nitrobenzyl, Br—Z, tert-butyl, etc.

Examples of groups used to protect the imidazole moiety of histidine include Tos, 4-methoxy-2,3,6-trimethylbenzenesulfonyl (Mtr), DNP, Bom, Bum, Boc, Trt, Fmoc, etc. Examples of protecting groups for the guanidino group in arginine include Tos, Z, 4-methoxy-2,3,6-trimethylbenzenesulfonyl (Mtr), p-methoxybenzenesulfonyl (MBS), 2,2,5,7,8-pentamethylchroman-6-sulfonyl (Pmc), mesitylene-2-sulfonyl (Mts), 2,2,4,6,7-pentamethyldihydrobenzofuran-5-sulfonyl (Pbf), Boc, Z, $NO_2$, etc. Examples of protecting groups for side chain amino group of lysine include Z, Cl—Z, trifluoroacetyl, Boc, Fmoc, Trt, Mtr, 4,4-dimethyl-2,6-dioxocyclohexylideneyl (Dde), etc.

Examples of protecting groups for indolyl of tryptophan include formyl (For), Z, Boc, Mts, Mtr, etc.

Examples of protecting groups for asparagine and glutamine include Trt, xanthyl (Xan), 4,4'-dimethoxybenzhydryl (Mbh), 2,4,6-trimethoxybenzyl (Tmob), etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, 1-hydroxybenzotriazole (HOBt) or 1-hydroxy-7-azabenzotriazole (HOAt)], etc. Examples of activated forms of the amino groups in the starting material include the corresponding phosphorous amides.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, trimethylsilane bromide (TMSBr), trimethylsilyl trifluoromethanesulfonate, tetrafluoroboric acid, tris(trifluoro)boron, boron tribromide or a mixed solution thereof, a base treatment with diisopropylethylamine, triethylamine, piperidine, piperazine, etc., and reduction with sodium in liquid ammonia. The elimination of protecting groups by the acid treatment described above is carried out generally at a temperature of approximately −20° C. to 40° C. In the acid treatment, it is efficient to add a cation scavenger such as anisole, phenol, thioanisole, m-cresol, p-cresol, etc., dimethylsulfide, 1,4-butanedithiol, 1,2-ethanedithiol, etc. Furthermore, 2,4-dinitrophenyl group used as the protecting group for the imidazole of histidine is removed by a treatment with thiophenol. Formyl group used as the protecting group of the indole of tryptophan is removed by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, removal of the protecting groups and activation of functional groups involved in the reaction may be appropriately chosen from publicly known groups and publicly known means.

Methods for obtaining the amide of the peptide include, for example, solid phase synthesis using resins for the formation of peptide amide. In another method for obtaining the amides of the peptide, for example, the α-carboxyl group of the carboxy terminal amino acid is first protected by amidation; the peptide chain is then extended from the amino group side to a desired length. Thereafter, a peptide in which only the protecting group of the N-terminal α-amino group in the peptide chain has been removed from the peptide and a peptide (or an amino acid) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are removed by the method described above to give the desired crude peptide. This crude peptide is purified by various known purification means. Lyophilization of the major fraction gives the amide of the desired peptide.

When the metastin derivative of the present invention is present in the form of a configurational isomer, a diastereomer, a conformer, or the like, each can be isolated by the separating and purifying means described above, if desired. In addition, when the compound of the present invention is racemic, it can be separated into an S isomer and an R isomer by the conventional optical resolving means.

When steric isomers exist in the metastin derivative of the present invention, the present invention includes both of these isomers alone and the isomers present as a mixture thereof.

In addition, the metastin derivative of the present invention may also be hydrated or non-hydrated. The metastin derivative of the present invention may also be labeled with an isotope (e.g., $^3H$, $^{14}C$, $^{35}S$), etc.

Throughout the specification, the peptides are represented in accordance with the conventional way of describing peptides, that is, the N-terminus (amino terminus) at the left hand and the C-terminus (carboxyl terminus) at the right hand. In the peptides, the C-terminus is usually in the form of an amide (—$CONH_2$), a carboxyl group (—COOH), a carboxylate (—$COO^-$), an alkylamide (—CONHR) or an ester (—COOR) and the amide (—$CONH_2$) is particularly preferred. Examples of R in the ester or alkylamide include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; pivaloyloxymethyl group, which are widely used as an ester for oral use, and the like.

Examples of salts of the metastin derivative of the present invention include a metal salt, an ammonium salt, a salt with an organic base, a salt with inorganic acid, a salt with organic acid, a salt with basic or acidic amino acid, and the like. Preferred examples of the metal salts include alkali metal salts such as sodium salts, potassium salts, etc.; alkaline earth metal salts such as calcium salts, magnesium salts, barium salts, etc.; aluminum salts; and the like. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of salts with basic amino acids include salts with arginine, lysine, ornithine, etc., and preferred examples of salts with acidic amino acids include salts with aspartic acid, glutamic acid, etc.

Of these salts, pharmaceutically acceptable salts are preferable. For example, when the compound has an acidic functional group, inorganic salts such as alkali metal salts (e.g., sodium salts, potassium salts, etc.), alkaline earth metal salts (e.g., calcium salts, magnesium salts, barium salts, etc.), ammonium salts, and the like are preferable. When the compound has a basic functional group, salts with inorganic acids with hydrochloric acid, hydrobromic acid, nitric acid, sulfuric acid, phosphoric acid, etc., and salts with organic acids such as acetic acid, phthalic acid, fumaric acid, oxalic acid, tartaric acid, maleic acid, citric acid, succinic acid, methanesulfonic acid, p-toluenesulfonic acid, etc. are preferable.

The prodrug of the metastin derivative or salts thereof (hereinafter sometimes simply referred to as the metastin derivative of the present invention) is used to mean such a metastin derivative that is converted into the metastin derivative of the present invention under physiological conditions or by reactions with an enzyme, a gastric acid, etc., in vivo. In other words, the prodrug of the present invention refers to the metastin derivative that undergoes enzymatic oxidation, reduction, hydrolysis, etc. to be converted into the metastin derivative of the present invention, or the metastin derivative that undergoes hydrolysis, etc. by gastric acid, etc. to be converted into the metastin derivative of the present invention.

Examples of the prodrug of the metastin derivative of the present invention include metastin derivatives wherein the amino group in the metastin derivative of the present invention is substituted with acyl, alkyl, phosphoric acid, etc. (e.g., metastin derivatives wherein the amino group in the metastin derivative of the present invention is substituted with eicosanoyl, alanyl, pentylaminocarbonyl (5-methyl-2-oxo-1, 3-dioxolen-4-yl)methoxycarbonyl, tetrahydrofuranyl, pyrrolidylmethyl, pivaloyloxymethyl, tert-butyl, etc); metastin derivatives wherein the hydroxy group in the metastin derivative of the present invention is substituted with acyl, alkyl, phosphoric acid, boric acid, etc. (e.g., metastin derivatives wherein the hydroxy group in the metastin derivative of the present invention is substituted with acetyl, palmitoyl, propanoyl, pivaloyl, succinyl, fumaryl, alanyl, dimethylaminomethylcarbonyl, etc.); and metastin derivatives wherein the carboxy group in the metastin derivative of the present invention is substituted with ester, amide, etc. (e.g., metastin derivatives wherein the carboxy group of the metastin derivative of the present invention is converted into the ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonylethyl ester, methylamide, etc); and the like. These metastin derivatives can be produced from the metastin derivatives of the present invention by per se known methods.

The prodrugs of the metastin derivative of the present invention may be those converted into the metastin derivatives of the present invention under the physiological conditions as described in "Pharmaceutical Research and Development", Vol. 7, Drug Design, pages 163-198, published 1990 by Hirokawa Publishing Co.

The metastin derivative of the present invention or salts thereof and their Prodrugs (hereinafter sometimes briefly referred to as the compound of the present invention) have the cancer metastasis suppressing activity or cancer growth suppressing activity and are useful as medicaments including preventive/therapeutic agents for all cancers (e.g., lung cancer, gastric cancer, liver cancer, pancreatic cancer, colorectal cancer, rectal cancer, colonic cancer, prostate cancer, ovarian cancer, cervical cancer, breast cancer, etc.), as cancer metastasis inhibitors or cancer growth inhibitors.

The compound of the present invention has the effects of regulating functions of the pancreas and is useful as therapeutic/preventive agents for various pancreatic diseases (e.g., acute or chronic pancreatitis, pancreatic cancer, etc.).

The compound of the present invention has the effects of regulating the functions of placenta and is useful as medicaments such as preventive or therapeutic agents for choriocarcinoma, hydatidiform mole, invasive mole, miscarriage, fetal hypoplasia, abnormal glucose metabolism, abnormal lipid metabolism or labor induction.

Also, the compound of the present invention has the effects of increasing sugar level, promoting pancreatic glucagon secretion and promoting urine formation, and, is useful as a hyperglycemic agent, a pancreatic glucagon secretagogue agent or an agent for promoting urine formation, e.g., as medicaments including agents for preventing or treating, obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes mellitus, fatty atrophy, insulin allergy, insulinoma, arteriosclerosis, thrombotic disorders or lipotoxicity.

In addition, the compound of the present invention has the effects of stimulating gonadotropic hormone (e.g., FSH, LH, etc.) secretion, stimulating sex hormone [e.g., androgens (e.g., testosterone, androstenedione, etc.), estrogens (e.g., estradiol, estrone, etc.), progesterones, etc.] secretion, improving gonadal function and inducing or stimulating ovulation, as well as a sexual maturation effect, etc., and thus can be used as an agent for improving gonadal function, an agent for inducing or stimulating ovulation, a gonadotropic hormone secretagogue agent or a sex hormone secretagogue agent, or an agent for preventing/treating hormone-dependent cancers [e.g., prostate cancer, breast cancer, etc.], infertility

[e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular function disorder, azoospermia, hypoandrogenemia, etc.], endometriosis, early puberty, myoma of the uterus, etc.

The prodrug of the metastin derivative of the present invention or its salt is also useful as an agent for preventing/treating Alzheimer's disease, moderate cognitive impairment, autism, etc.

Furthermore, the compound of the present invention is useful as an agent for preventing/treating rheumatic diseases (e.g., rheumatoid arthritis, osteoarthritis, gout, etc.) or the like.

Test can be performed by publicly known procedures to determine that the compound is useful for rheumatic diseases. One specific example of the test procedures is described below.

Female LEW rats of 6 weeks old (weighing 150 to 200 g) are used by 8 rats per group. Bovine type II collagen is dissolved in 0.05 mol/L acetic acid solution, which is adjusted to a concentration of 3 mg/mL. An equivolume of FIA (Freund's incomplete adjuvant) is added to prepare an emulsion. The rats are inoculated with the emulsion intracutaneously in the back for sensitization (primary immunization). Seven days after the primary immunization, 0.2 mL of the same emulsion is inoculated intracutaneously at the tail base for booster immunization. On and from the day of booster immunization (Day 0), the vehicle solution and the compound solution are subcutaneously administered consecutively, respectively. On Days 0, 4, 7, 11 and 14, rat rear paw volume is measured using Plethysmometer (UGO BASILE) and the volumes for both rear paws are averaged to give a baseline size of the paws. For assessment of the action on the paw volume, the value obtained by subtracting the pre-value (Day 0) of each animal from the values on Days 4, 7, 11 and 14 is made the value of each animal and provided for statistic calculation.

The compound of the present invention is also useful as: an agent for preventing/treating autism, immunomodulation (regeneration of thymus, repopulation of thymus, enhanced T cell growth), hypertension, diabetic neuropathy, diabetic nephropathy, diabetic retinopathy, thrombotic disorders or lipotoxicity;

an agent for preventing/treating hyperlipemia, type II diabetes mellitus, hypertension, diabetic neuropathy, diabetic nephropathy or diabetic retinopathy; an antianxiety agent; an antistress agent; an anti-insomnia agent; an antimanic-depressive agent; an agent for preventing/treating hypertension (e.g., essential hypertension, renal hypertension, salt sensitive hypertension, etc.), angina pectoris (e.g., stable angina, unstable angina, etc.), myocardial infarction, cerebrovascular disorders (e.g., asymptomatic cerebrovascular disorder, transient ischemic attack, apoplexy, cerebrovascular dementia, hypertensive encephalopathy, cerebral infarction, etc.), venous insufficiency, obliterative peripheral circulatory disturbances, Raynaud's disease, arteriosclerosis including atherosclerosis (e.g., aneurysm, coronary arteriosclerosis, cerebral arteriosclerosis, peripheral arteriosclerosis, etc.), vascular thickening or occlusion and organ impairments after intervention (e.g., percutaneous coronary intervention, stent placement, coronary thrombolytic therapy, etc.), portal hypertension, respiratory disorders (e.g., asthma, pulmonary hypertension, etc.); an agent for preventing/treating impaired glucose tolerance (IGT); an insulin secretagogue, an inhibitor for transition from IGT to diabetes;

an agent for preventing/treating diabetic complications [e.g., neuropathy, nephropathy, retinopathy, cataract, macroangiopathy, osteopenia, hyperosmolar diabetic coma, infectious diseases (e.g., respiratory infection, urinary tract infection, digestive tract infection, skin soft-tissue infection, lower leg infection), diabetic gangrene, xerostomia, hypacusis, cerebrovascular disorder, peripheral circulatory disturbance], osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, polycystic ovary syndrome, renal diseases (e.g., diabetic nephropathy, glomerulonephritis, glomerulosclerosis, nephrotic syndrome, hypertensive nephrosclerosis, end stage kidney disease), muscular dystrophy, cardiac infarction, angina pectoris, cerebrovascular disorders (e.g., cerebral infarction, apoplexy), Alzheimer's disease, Parkinson's disease, dementia, insulin resistance syndrome, X Syndrome X, metabolic syndrome, hyperinsulinemia, hyperinsulinemia-induced sensory disorders, tumors (e.g., leukemia, skin cancer), irritable bowel syndrome, acute or chronic diarrhea, inflammatory diseases (e.g., deforming spondylitis, arthritis deformans, lumbago, gout, postoperative or posttraumatic inflammation, swelling, neuralgia, pharyngolaryngitis, cystitis, hepatitis (including nonalcoholic steatohepatitis), pneumonia, enteritis, inflammatory bowel disorder (including inflammatory bowel diseases), ulcerative colitis, gastric mucosa damage (including gastric mucosa damage induced by aspirin)), damages of small intestinal mucosa, malabsorption, testicular function disorder, visceral obesity syndrome, etc.; and, for reduction of visceral adiposity, inhibition of visceral fat accumulation, improvement of glucose metabolism, improvement of lipid metabolism, suppression of oxidized LDL production, improvement of lipoprotein metabolism, improvement of coronary artery metabolism, prevention or treatment of cardiovascular complication, prevention or treatment of heart failure complications, decrease in blood remnant, prevention or treatment of anovulation, prevention or treatment of hirsutism or prevention or treatment of hyperandrogenemia; as an agent for improving pancreas (β cells) function, a regenerative agent for pancreas (β cells), an agent for stimulating pancreatic (β cell) regeneration, an appetite regulator, etc.

The compounds described in WO2004/063221, the compounds described in WO2006/001499 and the compounds described in WO2007/072997, or salts thereof, are also useful as agents for preventing/treating rheumatic diseases (e.g., rheumatoid arthritis, osteoarthritis, gout, etc.) or the like.

More specifically, compounds described in WO 2004/063221 (the metastin derivatives (i) represented by, e.g., the formula below, or salts thereof:

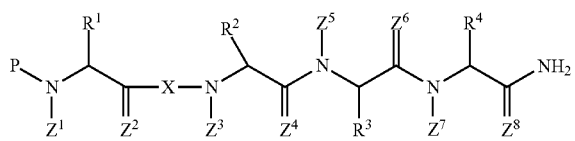

[wherein, each of $Z^1$, $Z^3$, $Z^5$ and $Z^7$ represents hydrogen atom or a $C_{1-3}$ alkyl group; each of $Z^2$, $Z^4$, $Z^6$ and $Z^8$ represents hydrogen atom, O or S;

$R^1$ represents (1) hydrogen atom, or (2) a $C_{1-8}$ alkyl group optionally substituted with a substituent selected from the group consisting of an optionally substituted carbamoyl group, an optionally substituted hydroxyl group and an optionally substituted aromatic cyclic group;

$R^2$ represents (1) hydrogen atom or (2) a cyclic or linear $C_{1-10}$ alkyl group, or (3) a $C_{1-10}$ alkyl group consisting of a cyclic alkyl group and a linear alkyl group;

$R^3$ represents:

(1) a $C_{1-8}$ alkyl group having an optionally substituted basic group and optionally having an additional substituent, (2) an aralkyl group having an optionally substituted basic group and optionally having an additional substituent, (3) a $C_{1-4}$ alkyl group having a non-aromatic cyclic hydrocarbon group of carbon atoms not greater than 7 having an optionally substituted basic group, and optionally having an additional substituent, or, (4) a $C_{1-4}$ alkyl group having a non-aromatic heterocyclic group of carbon atoms not greater than 7 having an optionally substituted basic group, and optionally having an additional substituent;

$R^4$ represents a $C_{1-4}$ alkyl group, which may optionally be substituted with a substituent selected from the group consisting of:

(1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and, (6) an optionally substituted non-aromatic heterocyclic group having carbon atoms not greater than 7;

X represents a group shown by formula:

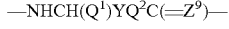
—NHCH($Q^1$)Y$Q^2$C(=$Z^9$)—

(wherein:

$Q^1$ represents a $C_{1-4}$ alkyl group, which may optionally be substituted with a substituent selected from the group consisting of:

(1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and, (6) an optionally substituted non-aromatic heterocyclic group having carbon atoms not greater than 7;

$Q^2$ represents (1) $CH_2$, which may optionally be substituted with a $C_{1-4}$ alkyl group optionally substituted with a substituent selected from the group consisting of carbamoyl group and hydroxyl group, (2) NH, which may optionally be substituted with a $C_{1-4}$ alkyl group optionally substituted with a substituent selected from the group consisting of carbamoyl group and hydroxyl group, or (3) O;

Y represents a group shown by formula: —CONH—, —CSNH—, —CH$_2$NH—, —NHCO—, —CH$_2$O—, —CH$_2$S— or —CH$_2$CH$_2$—, which may optionally be substituted with a $C_{1-6}$ alkyl group; and, $Z^9$ represents hydrogen atom, O or S); and, P represents:

(1) hydrogen atom;

(2) an optional amino acid residue continuously or discontinuously bound from the C-terminal end of the 1-48 amino acid sequence in the amino acid sequence represented by SEQ ID NO: 1;

(3) a group represented by formula:

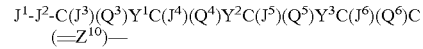
$J^1$-$J^2$-C($J^3$)($Q^3$)$Y^1$C($J^4$)($Q^4$)$Y^2$C($J^5$)($Q^5$)$Y^3$C($J^6$)($Q^6$)C(=$Z^{10}$)—

(wherein, $J^1$ represents (a) hydrogen atom or (b) (i) a $C_{1-15}$ acyl group, (ii) a $C_{1-15}$ alkyl group, (iii) a $C_{6-14}$ aryl group, (iv) a carbamoyl group, (v) a carboxyl group, (vi) a sulfino group, (vii) an amidino group or (viii) a glyoxyloyl group, which groups may optionally be substituted with a substituent containing an optionally substituted cyclic group;

$J^2$ represents (1) NH optionally substituted with a $C_{1-6}$ alkyl group, (2) $CH_2$ optionally substituted with a $C_{1-6}$ alkyl group, (3) O or (4) S;

each of $J^3$ through $J^6$ represents hydrogen atom or a $C_{1-3}$ alkyl group;

each of $Q^3$ through $Q^6$ represents a $C_{1-4}$ alkyl group, which may optionally be substituted with a substituent selected from the group consisting of:

(1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, (6) an optionally substituted non-aromatic heterocyclic group having carbon atoms not greater than 7, (7) an optionally substituted amino group, (8) an optionally substituted guanidino group, (9) an optionally substituted hydroxyl group,

(10) an optionally substituted carboxyl group,

(11) an optionally substituted carbamoyl group, and

(12) an optionally substituted sulfhydryl group, or hydrogen atom;

$J^3$ and $Q^3$, $J^4$ and $Q^4$, $J^5$ and $Q^5$ or $J^6$ and $Q^6$ may be combined together, or, $J^2$ and $Q^3$, $Y^1$ and $Q^4$, $Y^2$ and $Q^5$, or $Y^3$ and $Q^6$ may be combined together, to form a ring;

each of $Y^1$ through $Y^3$ represents a group represented by formula:
—CON($J^{13}$)—, —CSN($J^{13}$)—, —C($J^{14}$)N($J^{13}$)— or —N($J^{13}$)CO— (wherein each of $J^{13}$ and $J^{14}$ represents hydrogen atom or a $C_{1-3}$ alkyl group); and, $Z^{10}$ represents hydrogen atom, O or S);

(4) a group represented by formula:

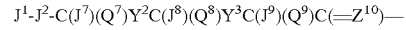
$J^1$-$J^2$-C($J^7$)($Q^7$)$Y^2$C($J^8$)($Q^8$)$Y^3$C($J^9$)($Q^9$)C(=$Z^{10}$)—

(wherein,

J¹ and J² each has the same significance as described above;
J⁷ through J⁹ have the same significance as J³;
Q⁷ through Q⁹ have the same significance as Q³;
Y² and Y³ have the same significance as described above;
Z¹⁰ has the same significance as described above;
J⁷ and Q⁷, J⁸ and Q⁸ or J⁹ and Q⁹ may be combined together, or, J² and Q⁷, Y² and Q⁸ or Y³ and Q⁹ may be combined together, to form a ring);

(5) a group represented by formula:

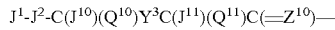

(wherein,

J¹ and J² have the same significance as described above represents;
J¹⁰ and J¹¹ have the same significance as J³;
Q¹⁰ and Q¹¹ have the same significance as Q³;
Y³ has the same significance as described above;
Z¹⁰ has the same significance as described above; and,
J¹⁰ and Q¹⁰ or J¹¹ and Q¹¹ may be combined together, or J² and Q¹⁰ or Y³ and Q¹¹ may be combined together, to form a ring);

(6) a group represented by formula:

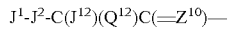

(wherein,

J¹ and J² have the same significance as described above;
J¹² has the same significance as J³;
Q¹² has the same significance as Q³;
Z¹⁰ has the same significance as described above; and,
J¹² and Q¹² may be combined together, or J² and Q¹² may be combined together, to form a ring); or, (7) a group represented by formula: J¹- (wherein, J¹ has the same significance as described above)], preferably the following compounds, or salts thereof:

```
                                      (SEQ ID NO: 16)
MS10:  Tyr-Asn-Trp-Asn-Ser-Phe-Gly-Leu-Arg-Phe-NH2
        1   2   3   4   5   6   7   8   9   10
```

Compound No. 17: [Pya(4)10]MS10
Tyr-Asn-Trp-Asn-Ser-Phe-Gly-Leu-Arg-Pya(4)-NH₂ (SEQ ID NO: 86)
Compound No. 18: [Tyr(Me)10]MS10
Tyr-Asn-Trp-Asn-Ser-Phe-Gly-Leu-Arg-Tyr(Me)-NH₂ (SEQ ID NO: 87)
Compound No. 19: [Phe(2F)10]MS10
Tyr-Asn-Trp-Asn-Ser-Phe-Gly-Leu-Arg-Phe(2F)—NH₂ (SEQ ID NO: 88)
Compound No. 23: [Tyr5]MS10
Tyr-Asn-Trp-Asn-Tyr-Phe-Gly-Leu-Arg-Phe-NH₂ (SEQ ID NO: 89)
Compound No. 24: [Leu5]MS10
Tyr-Asn-Trp-Asn-Leu-Phe-Gly-Leu-Arg-Phe-NH₂ (SEQ ID NO: 90)
Compound No. 30:Acetyl-MS10
Acetyl-Tyr-Asn-Trp-Asn-Ser-Phe-Gly-Leu-Arg-Phe-NH₂ (SEQ ID NO: 91)
Compound No. 31:Fmoc-MS10
Fmoc-Tyr-Asn-Trp-Asn-Ser-Phe-Gly-Leu-Arg-Phe-NH₂ (SEQ ID NO: 92)
Compound No. 38: [D-Ser5]MS10
Tyr-Asn-Trp-Asn-D-Ser-Phe-Gly-Leu-Arg-Phe-NH₂
Compound No. 39: [D-Asn4]MS10
Tyr-Asn-Trp-D-Asn-Ser-Phe-Gly-Leu-Arg-Phe-NH₂
Compound No. 40: [D-Trp3]MS10
Tyr-Asn-D-Trp-Asn-Ser-Phe-Gly-Leu-Arg-Phe-NH₂
Compound No. 41: [D-Asn2]MS10
Tyr-D-Asn-Trp-Asn-Ser-Phe-Gly-Leu-Arg-Phe-NH₂
Compound No. 42: [D-Tyr1]MS10
D-Tyr-Asn-Trp-Asn-Ser-Phe-Gly-Leu-Arg-Phe-NH₂
Compound No. 44: [Lys9]MS10
Tyr-Asn-Trp-Asn-Ser-Phe-Gly-Leu-Lys-Phe-NH₂ (SEQ ID NO: 93)
Compound No. 45: [Ala8]MS10
Tyr-Asn-Trp-Asn-Ser-Phe-Gly-Ala-Arg-Phe-NH₂ (SEQ ID NO: 94)
Compound No. 50: [Ala7]MS10
Tyr-Asn-Trp-Asn-Ser-Phe-Ala-Leu-Arg-Phe-NH₂ (SEQ ID NO: 95)
Compound No. 51: [NMePhe10]MS10
Tyr-Asn-Trp-Asn-Ser-Phe-Gly-Leu-Arg-NMePhe-NH₂ (SEQ ID NO: 96)
Compound No. 53: des(1-3)-Fmoc-MS10
Fmoc-Asn-Ser-Phe-Gly-Leu-Arg-Phe-NH₂ (SEQ ID NO: 97)
Compound No. 54: des(1-2)-Fmoc-MS10
Fmoc-Trp-Asn-Ser-Phe-Gly-Leu-Arg-Phe-NH₂ (SEQ ID NO: 98)
Compound No. 55: des(1)-Fmoc-MS10
Fmoc-Asn-Trp-Asn-Ser-Phe-Gly-Leu-Arg-Phe-NH₂ (SEQ ID NO: 99)
Compound No. 56: [Lys2]MS10
Tyr-Lys-Trp-Asn-Ser-Phe-Gly-Leu-Arg-Phe-NH₂ (SEQ ID NO: 100)
Compound No. 57: [Asp2]MS10
Tyr-Asp-Trp-Asn-Ser-Phe-Gly-Leu-Arg-Phe-NH₂ (SEQ ID NO: 101)
Compound No. 58: [Tyr2]MS10
Tyr-Tyr-Trp-Asn-Ser-Phe-Gly-Leu-Arg-Phe-NH₂ (SEQ ID NO: 102)
Compound No. 59: [Leu2]MS10
Tyr-Leu-Trp-Asn-Ser-Phe-Gly-Leu-Arg-Phe-NH₂ (SEQ ID NO: 103)
Compound No. 60: [Pya(3)10]MS10
Tyr-Asn-Trp-Asn-Ser-Phe-Gly-Leu-Arg-Pya(3)-NH₂ (SEQ ID NO: 104)
Compound No. 61: [Phe(4F)10]MS10
Tyr-Asn-Trp-Asn-Ser-Phe-Gly-Leu-Arg-Phe(4F)—NH₂ (SEQ ID NO: 105)
Compound No. 67: [Ala3]MS10
Tyr-Asn-Ala-Asn-Ser-Phe-Gly-Leu-Arg-Phe-NH₂ (SEQ ID NO: 106)
Compound No. 68: [Leu3]MS10
Tyr-Asn-Leu-Asn-Ser-Phe-Gly-Leu-Arg-Phe-NH₂ (SEQ ID NO: 107)
Compound No. 69: [Ser3]MS10
Tyr-Asn-Ser-Asn-Ser-Phe-Gly-Leu-Arg-Phe-NH₂ (SEQ ID NO: 108)
Compound No. 70: [Asp3]MS10
Tyr-Asn-Asp-Asn-Ser-Phe-Gly-Leu-Arg-Phe-NH₂ (SEQ ID NO: 109)
Compound No. 71: [Lys3]MS10
Tyr-Asn-Lys-Asn-Ser-Phe-Gly-Leu-Arg-Phe-NH₂ (SEQ ID NO: 110)
Compound No. 72: [Ala1]MS10
Ala-Asn-Trp-Asn-Ser-Phe-Gly-Leu-Arg-Phe-NH₂ (SEQ ID NO: 111)
Compound No. 73: [Leu1]MS10
Leu-Asn-Trp-Asn-Ser-Phe-Gly-Leu-Arg-Phe-NH₂ (SEQ ID NO: 112)
Compound No. 74: [Ser1]MS10
Ser-Asn-Trp-Asn-Ser-Phe-Gly-Leu-Arg-Phe-NH₂ (SEQ ID NO: 113)

Compound No. 75: [Asp1]MS10
Asp-Asn-Trp-Asn-Ser-Phe-Gly-Leu-Arg-Phe-NH$_2$ (SEQ ID NO: 114)
Compound No. 76: [Lys1]MS10
Lys-Asn-Trp-Asn-Ser-Phe-Gly-Leu-Arg-Phe-NH$_2$ (SEQ ID NO: 115)
Compound No. 77: [Phe(4CN)10]MS10
Tyr-Asn-Trp-Asn-Ser-Phe-Gly-Leu-Arg-Phe(4CN)—NH$_2$ (SEQ ID NO: 116)
Compound No. 78: [Trp(For)3, Phe(4CN)10]MS10
Tyr-Asn-Trp(For)-Asn-Ser-Phe-Gly-Leu-Arg-Phe(4CN)—NH$_2$ (SEQ ID NO: 117)
Compound No. 79: [Hph10]MS10
Tyr-Asn-Trp-Asn-Ser-Phe-Gly-Leu-Arg-Hph-NH$_2$ (SEQ ID NO: 118)
Compound No. 81: [NMeArg9]MS10
Tyr-Asn-Trp-Asn-Ser-Phe-Gly-Leu-NMeArg-Phe-NH$_2$ (SEQ ID NO: 119)
Compound No. 82: [Arg(Me)9]MS10
Tyr-Asn-Trp-Asn-Ser-Phe-Gly-Leu-Arg(Me)-Phe-NH$_2$ (SEQ ID NO: 120)
Compound No. 83: [Arg(asy Me$_2$)9]MS10
Tyr-Asn-Trp-Asn-Ser-Phe-Gly-Leu-Arg(asyMe$_2$)-Phe-NH$_2$ (SEQ ID NO: 121)
Compound No. 87: des(4-5)-Boc-MS10
Boc-Tyr-Asn-Trp-Phe-Gly-Leu-Arg-Phe-NH$_2$ (SEQ ID NO: 122)
Compound No. 88: des(4-5)-MS10
Tyr-Asn-Trp-Phe-Gly-Leu-Arg-Phe-NH$_2$ (SEQ ID NO: 123)
Compound No. 90: [9Ψ10,CH$_2$NH]MS10
Tyr-Asn-Trp-Asn-Ser-Phe-Gly-Leu-ArgΨ(CH$_2$NH)Phe-NH$_2$ (SEQ ID NO: 124)
Compound No. 91: [8Ψ9,CH$_2$NH]MS10
Tyr-Asn-Trp-Asn-Ser-Phe-Gly-LeuΨ(CH$_2$NH)Arg-Phe-NH$_2$ (SEQ ID NO: 125)
Compound No. 97: [Har9]MS10
Tyr-Asn-Trp-Asn-Ser-Phe-Gly-Leu-Har-Phe-NH$_2$ (SEQ ID NO: 126)
Compound No. 98: [Lys(Me$_2$)9]MS10
Tyr-Asn-Trp-Asn-Ser-Phe-Gly-Leu-Lys(Me$_2$)-Phe-NH$_2$ (SEQ ID NO: 127)
Compound No. 101: [Ser7]MS10
Tyr-Asn-Trp-Asn-Ser-Phe-Ser-Leu-Arg-Phe-NH$_2$ (SEQ ID NO: 128)
Compound No. 105: [Nle8]MS10
Tyr-Asn-Trp-Asn-Ser-Phe-Gly-Nle-Arg-Phe-NH$_2$ (SEQ ID NO: 129)
Compound No. 107: [Val8]MS10
Tyr-Asn-Trp-Asn-Ser-Phe-Gly-Val-Arg-Phe-NH$_2$ (SEQ ID NO: 130)
Compound No. 109: [Tyr10]MS10
Tyr-Asn-Trp-Asn-Ser-Phe-Gly-Leu-Arg-Tyr-NH$_2$ (SEQ ID NO: 131)
Compound No. 110: [Nal(2)10]MS10
Tyr-Asn-Trp-Asn-Ser-Phe-Gly-Leu-Arg-Nal(2)-NH$_2$ (SEQ ID NO: 132)
Compound No. 111: [Phe(F$_5$)10]MS10
Tyr-Asn-Trp-Asn-Ser-Phe-Gly-Leu-Arg-Phe(F$_5$)—NH$_2$ (SEQ ID NO: 133)
Compound No. 112: [Cha10]MS10
Tyr-Asn-Trp-Asn-Ser-Phe-Gly-Leu-Arg-Cha-NH$_2$ (SEQ ID NO: 134)
Compound No. 114: des(1-3)-3-(3-Indolyl)propionyl-MS10
3-(3-Indolyl)propionyl-Asn-Ser-Phe-Gly-Leu-Arg-Phe-NH$_2$ (SEQ ID NO: 135)
Compound No. 121: des(1-4)-[Trp5]MS10
Trp-Phe-Gly-Leu-Arg-Phe-NH$_2$ (SEQ ID NO: 136)
Compound No. 123: [NMeLeu8]MS10
Tyr-Asn-Trp-Asn-Ser-Phe-Gly-NMeLeu-Arg-Phe-NH$_2$ (SEQ ID NO: 137)
Compound No. 126: [NMeSer5]MS10
Tyr-Asn-Trp-Asn-NMeSer-Phe-Gly-Leu-Arg-Phe-NH$_2$ (SEQ ID NO: 138)
Compound No. 127: [D-Asn4,NMePhe6]MS10
Tyr-Asn-Trp-D-Asn-Ser-NMePhe-Gly-Leu-Arg-Phe-NH$_2$
Compound No. 128: [10Ψ,CSNH]MS10
Tyr-Asn-Trp-Asn-Ser-Phe-Gly-Leu-Arg-PheΨ(CSNH)NH$_2$ (SEQ ID NO: 139)
Compound No. 129: [Arg(symMe$_2$)9]MS10
Tyr-Asn-Trp-Asn-Ser-Phe-Gly-Leu-Arg(symMe$_2$)-Phe-NH$_2$ (SEQ ID NO: 140)
Compound No. 130: [Phe(4Cl)10]MS10
Tyr-Asn-Trp-Asn-Ser-Phe-Gly-Leu-Arg-Phe(4Cl)—NH$_2$ (SEQ ID NO: 141)
Compound No. 131: [Phe(4NH$_2$)10]MS10
Tyr-Asn-Trp-Asn-Ser-Phe-Gly-Leu-Arg-Phe(4NH$_2$)—NH$_2$ (SEQ ID NO: 142)
Compound No. 132: [Phe(4NO$_2$)10]MS10
Tyr-Asn-Trp-Asn-Ser-Phe-Gly-Leu-Arg-Phe(4NO$_2$)—NH$_2$ (SEQ ID NO: 143)
Compound No. 133: [Nal(1)10]MS10
Tyr-Asn-Trp-Asn-Ser-Phe-Gly-Leu-Arg-Nal(1)-NH$_2$ (SEQ ID NO: 144)
Compound No. 134: [Trp10]MS10
Tyr-Asn-Trp-Asn-Ser-Phe-Gly-Leu-Arg-Trp-NH$_2$ (SEQ ID NO: 145)
Compound No. 137: [Nle9]MS10
Tyr-Asn-Trp-Asn-Ser-Phe-Gly-Leu-Nle-Phe-NH$_2$ (SEQ ID NO: 146)
Compound No. 138: [Cit9]MS10
Tyr-Asn-Trp-Asn-Ser-Phe-Gly-Leu-Cit-Phe-NH$_2$ (SEQ ID NO: 147)
Compound No. 140: [Arg(Me)9,NMePhe10]MS10
Tyr-Asn-Trp-Asn-Ser-Phe-Gly-Leu-Arg(Me)-NMePhe-NH$_2$ (SEQ ID NO: 148)
Compound No. 141: [D-Tyr1,Arg(Me)9]MS10
D-Tyr-Asn-Trp-Asn-Ser-Phe-Gly-Leu-Arg(Me)-Phe-NH$_2$
Compound No. 142: [D-Tyr1,D-Trp3,Arg(Me)9]MS10
D-Tyr-Asn-D-Trp-Asn-Ser-Phe-Gly-Leu-Arg(Me)-Phe-NH$_2$
Compound No. 143: [D-Trp3,Arg(Me)9]MS10
Tyr-Asn-D-Trp-Asn-Ser-Phe-Gly-Leu-Arg(Me)-Phe-NH$_2$
Compound No. 144: des(1-3)-Fmoc-[Arg(Me)9]MS10
Fmoc-Asn-Ser-Phe-Gly-Leu-Arg(Me)-Phe-NH$_2$ (SEQ ID NO: 149)
Compound No. 145: des(1-2)-Fmoc-[Arg(Me)9]MS10
Fmoc-Trp-Asn-Ser-Phe-Gly-Leu-Arg(Me)-Phe-NH$_2$ (SEQ ID NO: 150)
Compound No. 146: [10Ψ,CSNH,D-Tyr1]MS10
D-Tyr-Asn-Trp-Asn-Ser-Phe-Gly-Leu-Arg-PheΨ(CSNH) NH$_2$
Compound No. 150: [Tyr6]MS10
Tyr-Asn-Trp-Asn-Ser-Tyr-Gly-Leu-Arg-Phe-NH$_2$ (SEQ ID NO: 151)
Compound No. 151: [Nal(1)6]MS10
Tyr-Asn-Trp-Asn-Ser-Nal(1)-Gly-Leu-Arg-Phe-NH$_2$ (SEQ ID NO: 152)
Compound No. 152: [Nal(2)6]MS10
Tyr-Asn-Trp-Asn-Ser-Nal(2)-Gly-Leu-Arg-Phe-NH$_2$ (SEQ ID NO: 153)
Compound No. 153: [Phe(F$_5$)6]MS10
Tyr-Asn-Trp-Asn-Ser-Phe(F$_5$)-Gly-Leu-Arg-Phe-NH$_2$ (SEQ ID NO: 154)

Compound No. 154: [Phe(4F)6]MS10
Tyr-Asn-Trp-Asn-Ser-Phe(4F)-Gly-Leu-Arg-Phe-NH$_2$ (SEQ ID NO: 155)
Compound No. 156: [Cha6]MS10
Tyr-Asn-Trp-Asn-Ser-Cha-Gly-Leu-Arg-Phe-NH$_2$ (SEQ ID NO: 156)
Compound No. 163: [6Ψ7,CH$_2$NH]MS10
Tyr-Asn-Trp-Asn-Ser-PheΨ(CH$_2$NH)Gly-Leu-Arg-Phe-NH$_2$ (SEQ ID NO: 157)
Compound No. 165: [Dap(Gly)9]-MS10
Tyr-Asn-Trp-Asn-Ser-Phe-Gly-Leu-Dap(Gly)-Phe-NH$_2$ (SEQ ID NO: 158)
Compound No. 166: [6Ψ7,CSNH]MS10
Tyr-Asn-Trp-Asn-Ser-PheΨ(CSNH)Gly-Leu-Arg-Phe-NH$_2$ (SEQ ID NO: 159)
Compound No. 169: [D-Tyr1,Ala3,Arg(Me)9]MS10
D-Tyr-Asn-Ala-Asn-Ser-Phe-Gly-Leu-Arg(Me)-Phe-NH$_2$
Compound No. 170: [D-Tyr1,Ser3,Arg(Me)9]MS10
D-Tyr-Asn-Ser-Asn-Ser-Phe-Gly-Leu-Arg(Me)-Phe-NH$_2$
Compound No. 171: [D-Tyr1,Cha3,Arg(Me)9]MS10
D-Tyr-Asn-Cha-Asn-Ser-Phe-Gly-Leu-Arg(Me)-Phe-NH$_2$
Compound No. 172: [D-Tyr1,Cha6,Arg(Me)9]MS10
D-Tyr-Asn-Trp-Asn-Ser-Cha-Gly-Leu-Arg(Me)-Phe-NH$_2$
Compound No. 173: [D-Tyr1,Ala7,Arg(Me)9]MS10
D-Tyr-Asn-Trp-Asn-Ser-Phe-Ala-Leu-Arg(Me)-Phe-NH$_2$
Compound No. 174: [D-Tyr1,Arg(Me)9,Trp10]MS10
D-Tyr-Asn-Trp-Asn-Ser-Phe-Gly-Leu-Arg(Me)-Trp-NH$_2$
Compound No. 176: [AzaGly7]MS10
Tyr-Asn-Trp-Asn-Ser-Phe-AzaGly-Leu-Arg-Phe-NH$_2$ (SEQ ID NO: 160)
Compound No. 181: [D-Tyr1,Cha3,6,Arg(Me)9]MS10
D-Tyr-Asn-Cha-Asn-Ser-Cha-Gly-Leu-Arg(Me)-Phe-NH$_2$
Compound No. 182: [D-Tyr1,Cha3,6,Arg(Me)9,Trp10]MS10
D-Tyr-Asn-Cha-Asn-Ser-Cha-Gly-Leu-Arg(Me)-Trp-NH$_2$
Compound No. 183: [Phe(4NH$_2$)9]MS10
Tyr-Asn-Trp-Asn-Ser-Phe-Gly-Leu-Phe(4NH$_2$)-Phe-NH$_2$ (SEQ ID NO: 161)
Compound No. 184: [Phe(4-Guanidino)9]MS10
Tyr-Asn-Trp-Asn-Ser-Phe-Gly-Leu-Phe(4-Guanidino)-Phe-NH$_2$ (SEQ ID NO: 162)
Compound No. 185: [Dap(GnGly)9]MS10
Tyr-Asn-Trp-Asn-Ser-Phe-Gly-Leu-Dap(GnGly)-Phe-NH$_2$ (SEQ ID NO: 163)
Compound No. 186: [Trp(For)10]MS10
Tyr-Asn-Trp-Asn-Ser-Phe-Gly-Leu-Arg-Trp(For)-NH$_2$ (SEQ ID NO: 164)
Compound No. 187: [Abu8]MS10
Tyr-Asn-Trp-Asn-Ser-Phe-Gly-Abu-Arg-Phe-NH$_2$ (SEQ ID NO: 165)
Compound No. 189: [Ala(3-Bzt)10]MS10
Tyr-Asn-Trp-Asn-Ser-Phe-Gly-Leu-Arg-Ala(3-Bzt)-NH$_2$ (SEQ ID NO: 166)
Compound No. 190: [D-Tyr1,Cha3,AzaGly7,Arg(Me)9]MS10
D-Tyr-Asn-Cha-Asn-Ser-Phe-AzaGly-Leu-Arg(Me)-Phe-NH$_2$
Compound No. 191: [D-Tyr1,Ser3,AzaGly7,Arg(Me)9]MS10
D-Tyr-Asn-Ser-Asn-Ser-Phe-AzaGly-Leu-Arg(Me)-Phe-NH$_2$
Compound No. 192: [D-Tyr1,Arg(Et)9]MS10
D-Tyr-Asn-Trp-Asn-Ser-Phe-Gly-Leu-Arg(Et)-Phe-NH$_2$
Compound No. 193: [D-Tyr1,Arg(n-Pr)9]MS10
D-Tyr-Asn-Trp-Asn-Ser-Phe-Gly-Leu-Arg(n-Pr)-Phe-NH$_2$
Compound No. 194: [D-Tyr1,Arg(Ac)9]MS10
D-Tyr-Asn-Trp-Asn-Ser-Phe-Gly-Leu-Arg(Ac)-Phe-NH$_2$
Compound No. 197: [Phe(3F)10]MS10
Tyr-Asn-Trp-Asn-Ser-Phe-Gly-Leu-Arg-Phe(3F)—NH$_2$ (SEQ ID NO: 167)
Compound No. 198: [Phe(3,4F2)10]MS10
Tyr-Asn-Trp-Asn-Ser-Phe-Gly-Leu-Arg-Phe(3,4F2)-NH$_2$ (SEQ ID NO: 168)
Compound No. 199: [Phe(3,4Cl$_2$)10]MS10
Tyr-Asn-Trp-Asn-Ser-Phe-Gly-Leu-Arg-Phe(3,4Cl$_2$)—NH$_2$ (SEQ ID NO: 169)
Compound No. 200: [Phe(3 CF$_3$)10]MS10
Tyr-Asn-Trp-Asn-Ser-Phe-Gly-Leu-Arg-Phe(3 CF$_3$)—NH$_2$ (SEQ ID NO: 170)
Compound No. 201: [Ala(2-Qui)10]MS10
Tyr-Asn-Trp-Asn-Ser-Phe-Gly-Leu-Arg-Ala(2-Qui)-NH$_2$ (SEQ ID NO: 171)
Compound No. 203: [D-Tyr1,Cha6,Arg(Me)9]MS10
D-Tyr-Asn-Trp-Asn-Ser-Cha-Gly-Leu-Arg(Me)-Phe-NH$_2$
Compound No. 204: [D-Tyr1,Ala7,Arg(Me)9]MS10
D-Tyr-Asn-Trp-Asn-Ser-Phe-Ala-Leu-Arg(Me)-Phe-NH$_2$
Compound No. 205: [D-Tyr1,Thr3,Arg(Me)9]MS10
D-Tyr-Asn-Thr-Asn-Ser-Phe-Gly-Leu-Arg(Me)-Phe-NH$_2$
Compound No. 206: [D-Tyr1,Ile3,Arg(Me)9]MS10
D-Tyr-Asn-Ile-Asn-Ser-Phe-Gly-Leu-Arg(Me)-Phe-NH$_2$
Compound No. 207: [D-Tyr1,Ser4,Arg(Me)9]MS10
D-Tyr-Asn-Trp-Ser-Ser-Phe-Gly-Leu-Arg(Me)-Phe-NH$_2$
Compound No. 208: [D-Tyr1,Thr4,Arg(Me)9]MS10
D-Tyr-Asn-Trp-Thr-Ser-Phe-Gly-Leu-Arg(Me)-Phe-NH$_2$
Compound No. 209: [D-Tyr1,Gln4,Arg(Me)9]MS10
D-Tyr-Asn-Trp-Gln-Ser-Phe-Gly-Leu-Arg(Me)-Phe-NH$_2$
Compound No. 210: [D-Tyr1,Ala4,Arg(Me)9]MS10
D-Tyr-Asn-Trp-Ala-Ser-Phe-Gly-Leu-Arg(Me)-Phe-NH$_2$
Compound No. 211: [D-Tyr1,Thr5,Arg(Me)9]MS10
D-Tyr-Asn-Trp-Asn-Thr-Phe-Gly-Leu-Arg(Me)-Phe-NH$_2$
Compound No. 212: [D-Tyr1,Ala5,Arg(Me)9]MS10
D-Tyr-Asn-Trp-Asn-Ala-Phe-Gly-Leu-Arg(Me)-Phe-NH$_2$
Compound No. 213: [D-Tyr1,Val8,Arg(Me)9]MS10
D-Tyr-Asn-Trp-Asn-Ser-Phe-Gly-Val-Arg(Me)-Phe-NH$_2$
Compound No. 214: [D-Tyr1,Gln2,Arg(Me)9]MS10
D-Tyr-Gln-Trp-Asn-Ser-Phe-Gly-Leu-Arg(Me)-Phe-NH$_2$
Compound No. 215: [D-Tyr1,Thr2,Arg(Me)9]MS10
D-Tyr-Thr-Trp-Asn-Ser-Phe-Gly-Leu-Arg(Me)-Phe-NH$_2$
Compound No. 216: des(1)-[D-Asn2,Arg(Me)9]MS10
D-Asn-Trp-Asn-Ser-Phe-Gly-Leu-Arg(Me)-Phe-NH$_2$
Compound No. 217: des(1)-[D-Tyr2,Arg(Me)9]MS10
D-Tyr-Trp-Asn-Ser-Phe-Gly-Leu-Arg(Me)-Phe-NH$_2$
Compound No. 218: [N((CH$_2$)3Gn)]Gly9MS10
Tyr-Asn-Trp-Asn-Ser-Phe-Gly-Leu-N((CH$_2$)3Gn)Gly-Phe-NH$_2$ (SEQ ID NO: 172)
Compound No. 220: [Arg(Et)9]MS10
Tyr-Asn-Trp-Asn-Ser-Phe-Gly-Leu-Arg(Et)-Phe-NH$_2$ (SEQ ID NO: 173)
Compound No. 221: [D-Tyr1,Thr3,AzaGly7,Arg(Me)9]MS10
D-Tyr-Asn-Thr-Asn-Ser-Phe-AzaGly-Leu-Arg(Me)-Phe-NH$_2$
Compound No. 222: des(1)-[D-Tyr2,AzaGly7,Arg(Me)9]MS10
D-Tyr-Trp-Asn-Ser-Phe-AzaGly-Leu-Arg(Me)-Phe-NH$_2$
Compound No. 223: des(1-2)[D-Trp3,Arg(Me)9]MS10
D-Trp-Asn-Ser-Phe-Gly-Leu-Arg(Me)-Phe-NH$_2$
Compound No. 224: des(1)-[D-Tyr2,D-Trp3,Arg(Me)9]MS10
D-Tyr-D-Trp-Asn-Ser-Phe-Gly-Leu-Arg(Me)-Phe-NH$_2$ Compound No. 225: des(1)-[D-Asn2,D-Trp3,Arg(Me)9]MS10
D-Asn-D-Trp-Asn-Ser-Phe-Gly-Leu-Arg(Me)-Phe-NH$_2$
Compound No. 226: des(1)-[D-Tyr2,Ser3,Arg(Me)9]MS10
D-Tyr-Ser-Asn-Ser-Phe-Gly-Leu-Arg(Me)-Phe-NH$_2$
Compound No. 227: des(1)-[D-Tyr2,Thr3,Arg(Me)9]MS10
D-Tyr-Thr-Asn-Ser-Phe-Gly-Leu-Arg(Me)-Phe-NH$_2$
Compound No. 228: des(1)-[D-Tyr2,Ile3,Arg(Me)9]MS10
D-Tyr-Ile-Asn-Ser-Phe-Gly-Leu-Arg(Me)-Phe-NH$_2$
Compound No. 229: [D-Tyr1,Val3,Arg(Me)9]MS10
D-Tyr-Asn-Val-Asn-Ser-Phe-Gly-Leu-Arg(Me)-Phe-NH$_2$
Compound No. 230: [D-Tyr1,D-Asn2,Arg(Me)9]MS10
D-Tyr-D-Asn-Trp-Asn-Ser-Phe-Gly-Leu-Arg(Me)-Phe-NH$_2$
Compound No. 231: [D-Tyr1,D-Asn2,D-Trp3,Arg(Me)9]MS10
D-Tyr-D-Asn-D-Trp-Asn-Ser-Phe-Gly-Leu-Arg(Me)-Phe-NH$_2$
Compound No. 232: [D-Tyr1,AzaGly7,Arg(Me)9]MS10
D-Tyr-Asn-Trp-Asn-Ser-Phe-AzaGly-Leu-Arg(Me)-Phe-NH$_2$
Compound No. 233: [D-Tyr1,Ile3,AzaGly7,Arg(Me)9]MS10
D-Tyr-Asn-Ile-Asn-Ser-Phe-AzaGly-Leu-Arg(Me)-Phe-NH$_2$
Compound No. 234: [D-Tyr1,Val3,AzaGly7,Arg(Me)9]MS10
D-Tyr-Asn-Val-Asn-Ser-Phe-AzaGly-Leu-Arg(Me)-Phe-NH$_2$
Compound No. 235: [D-Tyr1,Ala3,AzaGly7,Arg(Me)9]MS10
D-Tyr-Asn-Ala-Asn-Ser-Phe-AzaGly-Leu-Arg(Me)-Phe-NH$_2$
Compound No. 236: [D-Tyr1,D-Trp3,AzaGly7,Arg(Me)9]MS10
D-Tyr-Asn-D-Trp-Asn-Ser-Phe-AzaGly-Leu-Arg(Me)-Phe-NH$_2$
Compound No. 237: [D-Tyr1,D-Asn2,AzaGly7,Arg(Me)9]MS10
D-Tyr-D-Asn-Trp-Asn-Ser-Phe-AzaGly-Leu-Arg(Me)-Phe-NH$_2$
Compound No. 238: [D-Tyr1,D-Asn2,D-Trp3,AzaGly7,Arg(Me)9]MS10
D-Tyr-D-Asn-D-Trp-Asn-Ser-Phe-AzaGly-Leu-Arg(Me)-Phe-NH$_2$
Compound No. 239: des(1)-[D-Tyr2,Ser3,AzaGly7,Arg(Me)9]MS10
D-Tyr-Ser-Asn-Ser-Phe-AzaGly-Leu-Arg(Me)-Phe-NH$_2$
Compound No. 240: des(1)-[D-Tyr2,Ile3,AzaGly7,Arg(Me)9]MS10
D-Tyr-Ile-Asn-Ser-Phe-AzaGly-Leu-Arg(Me)-Phe-NH$_2$
Compound No. 241: des(1)-[D-Tyr2,Thr3,AzaGly7,Arg(Me)9]MS10
D-Tyr-Thr-Asn-Ser-Phe-AzaGly-Leu-Arg(Me)-Phe-NH$_2$
Compound No. 242: des(1)-[D-Tyr2,D-Trp3,AzaGly7,Arg(Me)9]MS10
D-Tyr-D-Trp-Asn-Ser-Phe-AzaGly-Leu-Arg(Me)-Phe-NH$_2$
Compound No. 244: [D-Tyr1,Phe3,AzaGly7,Arg(Me)9]MS10
D-Tyr-Asn-Phe-Asn-Ser-Phe-AzaGly-Leu-Arg(Me)-Phe-NH$_2$
Compound No. 245: [D-Tyr1,Nal(1)3,AzaGly7,Arg(Me)9]MS10
D-Tyr-Asn-Nal(1)-Asn-Ser-Phe-AzaGly-Leu-Arg(Me)-Phe-NH$_2$
Compound No. 246: [D-Tyr1,Nal(2)3,AzaGly7,Arg(Me)9]MS10
D-Tyr-Asn-Nal(2)-Asn-Ser-Phe-AzaGly-Leu-Arg(Me)-Phe-NH$_2$
Compound No. 247: [D-Tyr1,Phe(2Cl)3,AzaGly7,Arg(Me)9]MS10
D-Tyr-Asn-Phe(2Cl)-Asn-Ser-Phe-AzaGly-Leu-Arg(Me)-Phe-NH$_2$
Compound No. 248: [D-Tyr1,Phe(3Cl)3,AzaGly7,Arg(Me)9]MS10
D-Tyr-Asn-Phe(3Cl)-Asn-Ser-Phe-AzaGly-Leu-Arg(Me)-Phe-NH$_2$
Compound No. 249: [D-Tyr1,Phe(4Cl)3,AzaGly7,Arg(Me)9]MS10
D-Tyr-Asn-Phe(4Cl)-Asn-Ser-Phe-AzaGly-Leu-Arg(Me)-Phe-NH$_2$
Compound No. 250: [D-Tyr1,Phe(4NH$_2$)3,AzaGly7,Arg(Me)9]MS10
D-Tyr-Asn-Phe(4NH$_2$)-Asn-Ser-Phe-AzaGly-Leu-Arg(Me)-Phe-NH$_2$
Compound No. 251: [D-Tyr1,Pya(3)3,AzaGly7,Arg(Me)9]MS10
D-Tyr-Asn-Pya(3)-Asn-Ser-Phe-AzaGly-Leu-Arg(Me)-Phe-NH$_2$
Compound No. 252: [D-Tyr1,D-Ala3,AzaGly7,Arg(Me)9]MS10
D-Tyr-Asn-D-Ala-Asn-Ser-Phe-AzaGly-Leu-Arg(Me)-Phe-NH$_2$
Compound No. 253: [D-Tyr1,Pro3,AzaGly7,Arg(Me)9]MS10
D-Tyr-Asn-Pro-Asn-Ser-Phe-AzaGly-Leu-Arg(Me)-Phe-NH$_2$
Compound No. 254: des(1)-[D-Tyr2,Phe3,AzaGly7,Arg(Me)9]MS10
D-Tyr-Phe-Asn-Ser-Phe-AzaGly-Leu-Arg(Me)-Phe-NH$_2$
Compound No. 255: des(1)-[D-Tyr2,Nal(2)3,AzaGly7,Arg(Me)9]MS10
D-Tyr-Nal(2)-Asn-Ser-Phe-AzaGly-Leu-Arg(Me)-Phe-NH$_2$
Compound No. 256: des(1)-[D-Pya(3)2,Phe3,AzaGly7,Arg(Me)9]MS10
D-Pya(3)-Phe-Asn-Ser-Phe-AzaGly-Leu-Arg(Me)-Phe-NH$_2$
Compound No. 257: [D-Tyr1,D-Asn2,Phe3,AzaGly7,Arg(Me)9]MS10
D-Tyr-D-Asn-Phe-Asn-Ser-Phe-AzaGly-Leu-Arg(Me)-Phe-NH$_2$
Compound No. 258: [D-Pya(3)1,AzaGly7,Arg(Me)9]MS10
D-Pya(3)-Asn-Trp-Asn-Ser-Phe-AzaGly-Leu-Arg(Me)-Phe-NH$_2$
Compound No. 259: [D-Ala1,AzaGly7,Arg(Me)9]MS10
D-Ala-Asn-Trp-Asn-Ser-Phe-AzaGly-Leu-Arg(Me)-Phe-NH$_2$
Compound No. 260: des(1-3)-3-(3-Indolyl)propionyl-[AzaGly7,Arg(Me)9]MS10
3-(3-Indolyl)propionyl-Asn-Ser-Phe-AzaGly-Leu-Arg(Me)-Phe-NH$_2$ (SEQ ID NO: 174)
Compound No. 261: [7Ψ8,CH$_2$NH]MS10
Tyr-Asn-Trp-Asn-Ser-Phe-GlyΨ(CH$_2$NH)Leu-Arg-Phe-NH$_2$ (SEQ ID NO: 175)
Compound No. 265: des(1-3)-Indole-3-carbonyl-[AzaGly7,Arg(Me)9]MS10
Indole-3-carbonyl-Asn-Ser-Phe-AzaGly-Leu-Arg(Me)-Phe-NH$_2$ (SEQ ID NO: 176)
Compound No. 266: des(1-3)-Indole-3-acetyl-[AzaGly7,Arg(Me)9]MS10
Indol-3-acetyl-Asn-Ser-Phe-AzaGly-Leu-Arg(Me)-Phe-NH$_2$ (SEQ ID NO: 177)

Compound No. 267: des(1-3)-4-(3-Indolyl)butyryl-[Aza-Gly7,Arg(Me)9]MS10
4-(3-Indolyl)butyryl-Asn-Ser-Phe-AzaGly-Leu-Arg(Me)-Phe-NH$_2$ (SEQ ID NO: 178)
Compound No. 268: des(1-3)-Diphenylacetyl-[AzaGly7,Arg(Me)9]MS10
Diphenylacetyl-Asn-Ser-Phe-AzaGly-Leu-Arg(Me)-Phe-NH$_2$ (SEQ ID NO: 179)
Compound No. 269: des(1-3)-3-Phenylpropionyl-[AzaGly7,Arg(Me)9]MS10
3-Phenylpropionyl-Asn-Ser-Phe-AzaGly-Leu-Arg(Me)-Phe-NH$_2$ (SEQ ID NO: 180)
Compound No. 270: [D-Tyr1,Phe3,Ser-Phe5,AzaGly7,Arg(Me)9]MS10
D-Tyr-Asn-Phe-Asn-Ser-Phe-Phe-AzaGly-Leu-Arg(Me)-Phe-NH$_2$
Compound No. 271: des(1-2)-[AzaGly7,Arg(Me)9]MS10
Trp-Asn-Ser-Phe-AzaGly-Leu-Arg(Me)-Phe-NH$_2$ (SEQ ID NO: 181)
Compound No. 272: des(1-2)-Acetyl-[AzaGly7,Arg(Me)9]MS10
Acetyl-Trp-Asn-Ser-Phe-AzaGly-Leu-Arg(Me)-Phe-NH$_2$ (SEQ ID NO: 182)
Compound No. 273: des(1-2)-Amidino-[AzaGly7,Arg(Me)9]MS10
Amidino-Trp-Asn-Ser-Phe-AzaGly-Leu-Arg(Me)-Phe-NH$_2$ (SEQ ID NO: 183)
Compound No. 274: des(1-2)-Acetyl-[Ala3,AzaGly7,Arg(Me)9]MS10
Acetyl-Ala-Asn-Ser-Phe-AzaGly-Leu-Arg(Me)-Phe-NH$_2$ (SEQ ID NO: 184)
Compound No. 275: des(1-2)-Acetyl-[Arg3,AzaGly7,Arg(Me)9]MS10
Acetyl-Arg-Asn-Ser-Phe-AzaGly-Leu-Arg(Me)-Phe-NH$_2$ (SEQ ID NO: 185)
Compound No. 276: des(1-2)-Acetyl-[Thr3,AzaGly7,Arg(Me)9]MS10
Acetyl-Thr-Asn-Ser-Phe-AzaGly-Leu-Arg(Me)-Phe-NH$_2$ (SEQ ID NO: 186)
Compound No. 277: des(1-3)-n-Hexanoyl-[AzaGly7,Arg(Me)9]MS10
n-Hexanoyl-Asn-Ser-Phe-AzaGly-Leu-Arg(Me)-Phe-NH$_2$ (SEQ ID NO: 187)
Compound No. 278: des(1-3)-Cyclohexanecarbonyl-[AzaGly7, Arg(Me)9]MS10
Cyclohexanecarbonyl-Asn-Ser-Phe-AzaGly-Leu-Arg(Me)-Phe-NH$_2$ (SEQ ID NO: 188)
Compound No. 279: des(1-3)-2-(Indol-3-yl)ethylcarbamoyl-[AzaGly7,Arg(Me)9]MS10
2-(indol-3-yl)ethylcarbamoyl-Asn-Ser-Phe-AzaGly-Leu-Arg(Me)-Phe-NH$_2$ (SEQ ID NO: 189)
Compound No. 281: [D-Tyr1,Pya(2)6,Arg(Me)9]MS10
D-Tyr-Asn-Trp-Asn-Ser-Pya(2)-Gly-Leu-Arg(Me)-Phe-NH$_2$
Compound No. 282: [D-Tyr1,Pya(4)6,Arg(Me)9]MS10
D-Tyr-Asn-Trp-Asn-Ser-Pya(4)-Gly-Leu-Arg(Me)-Phe-NH$_2$
Compound No. 283: [D-Tyr1,D-Asn2,Cha3,AzaGly7,Arg(Me)9]MS10
D-Tyr-D-Asn-Cha-Asn-Ser-Phe-AzaGly-Leu-Arg(Me)-Phe-NH$_2$
Compound No. 284: [D-Tyr1,D-Asn2,Thr3,AzaGly7,Arg(Me)9]MS10
D-Tyr-D-Asn-Thr-Asn-Ser-Phe-AzaGly-Leu-Arg(Me)-Phe-NH$_2$
Compound No. 285: [D-Tyr1,Pya(2)3,AzaGly7,Arg(Me)9]MS10
D-Tyr-Asn-Pya(2)-Asn-Ser-Phe-AzaGly-Leu-Arg(Me)-Phe-NH$_2$
Compound No. 286: [D-Tyr1,Pya(4)3,AzaGly7,Arg(Me)9]MS10
D-Tyr-Asn-Pya(4)-Asn-Ser-Phe-AzaGly-Leu-Arg(Me)-Phe-NH$_2$
Compound No. 287: [D-Tyr1,D-Ser2,AzaGly7,Arg(Me)9]MS10
D-Tyr-D-Ser-Trp-Asn-Ser-Phe-AzaGly-Leu-Arg(Me)-Phe-NH$_2$
Compound No. 288: [D-Tyr1,D-His2,AzaGly7,Arg(Me)9]MS10
D-Tyr-D-His-Trp-Asn-Ser-Phe-AzaGly-Leu-Arg(Me)-Phe-NH$_2$
Compound No. 289: des(1)-[D-Pya(3)2,AzaGly7,Arg(Me)9]MS10
D-Pya(3)-Trp-Asn-Ser-Phe-AzaGly-Leu-Arg(Me)-Phe-NH$_2$
Compound No. 290: [D-Pya(3)1,D-Asn2,Cha3,AzaGly7, Arg(Me)9]MS10
D-Pya(3)-D-Asn-Cha-Asn-Ser-Phe-AzaGly-Leu-Arg(Me)-Phe-NH$_2$
Compound No. 291: [D-Pya(3)1,D-Tyr2,Cha3,AzaGly7,Arg(Me)9]MS10
D-Pya(3)-D-Tyr-Cha-Asn-Ser-Phe-AzaGly-Leu-Arg(Me)-Phe-NH$_2$
Compound No. 293: [4Ψ5,CH$_2$NH]MS10
Tyr-Asn-Trp-AsnΨ(CH$_2$NH)Ser-Phe-Gly-Leu-Arg-Phe-NH$_2$
Compound No. 294: [1Ψ2,CH$_2$NH]MS10
TyrΨ(CH$_2$NH)Asn-Trp-Asn-Ser-Phe-Gly-Leu-Arg-Phe-NH$_2$ (SEQ ID NO: 190)
Compound No. 295: [2Ψ3,CH$_2$NH]MS10
Tyr-AsnΨ(CH$_2$NH)Trp-Asn-Ser-Phe-Gly-Leu-Arg-Phe-NH$_2$ (SEQ ID NO: 191)
Compound No. 296: [6Ψ7,CSNH,D-Tyr1,Arg(Me)9]MS10
D-Tyr-Asn-Trp-Asn-Ser-PheΨ(CSNH)Gly-Leu-Arg(Me)-Phe-NH$_2$ (SEQ ID NO: 192)
Compound No. 297: [D-Tyr1,Thr5,AzaGly7,Arg(Me)9]MS10
D-Tyr-Asn-Trp-Asn-Thr-Phe-AzaGly-Leu-Arg(Me)-Phe-NH$_2$
Compound No. 298: [D-Tyr1,D-Asn2,Thr5,AzaGly7,Arg(Me)9]MS10
D-Tyr-D-Asn-Trp-Asn-Thr-Phe-AzaGly-Leu-Arg(Me)-Phe-NH$_2$
Compound No. 299: [1Ψ2,CH$_2$NH,AzaGly7,Arg(Me)9]-MS10
TyrΨ(CH$_2$NH)Asn-Trp-Asn-Ser-Phe-AzaGly-Leu-Arg(Me)-Phe-NH$_2$ (SEQ ID NO: 193)
Compound No. 300: [1Ψ2,CH$_2$NH,D-Trp3,AzaGly7,Arg(Me)9]-MS10
TyrΨ(CH$_2$NH)Asn-D-Trp-Asn-Ser-Phe-AzaGly-Leu-Arg(Me)-Phe-NH$_2$
Compound No. 301: [D-Tyr1,Ala(2-Qui)3,AzaGly7,Arg(Me)9]MS10
D-Tyr-Asn-Ala(2-Qui)-Asn-Ser-Phe-AzaGly-Leu-Arg(Me)-Phe-NH$_2$
Compound No. 302: [D-Tyr1,D-Pya(4)3,AzaGly7,Arg(Me)9]MS10
D-Tyr-Asn-D-Pya(4)-Asn-Ser-Phe-AzaGly-Leu-Arg(Me)-Phe-NH$_2$ Compound No. 303: [D-Tyr1,D-Asn2,Pya(4)3,AzaGly7,Arg(Me)9]MS10
D-Tyr-D-Asn-Pya(4)-Asn-Ser-Phe-AzaGly-Leu-Arg(Me)-Phe-NH$_2$
Compound No. 304: [D-Asn2,Pya(4)3,AzaGly7,Arg(Me)9]MS10
Tyr-D-Asn-Pya(4)-Asn-Ser-Phe-AzaGly-Leu-Arg(Me)-Phe-NH$_2$
Compound No. 305: des(1)-[D-Tyr2,D-Pya(4)3,AzaGly7,Arg(Me)9]MS10
D-Tyr-D-Pya(4)-Asn-Ser-Phe-AzaGly-Leu-Arg(Me)-Phe-NH$_2$
Compound No. 306: [D-Pya(4)1,D-Asn2,Cha3,AzaGly7,Arg(Me)9]MS10
D-Pya(4)-D-Asn-Cha-Asn-Ser-Phe-AzaGly-Leu-Arg(Me)-Phe-NH$_2$
Compound No. 307: [7Ψ8,CH$_2$NH,D-Tyr1,Arg(Me)9]MS10
D-Tyr-Asn-Trp-Asn-Ser-Phe-GlyΨ(CH$_2$NH)Leu-Arg(Me)-Phe-NH$_2$
Compound No. 308: [6Ψ7,CH$_2$NH,D-Tyr1,Arg(Me)9]MS10
D-Tyr-Asn-Trp-Asn-Ser-PheΨ(CH$_2$NH)Gly-Leu-Arg(Me)-Phe-NH$_2$
Compound No. 310: [Nar9]MS10
Tyr-Asn-Trp-Asn-Ser-Phe-Gly-Leu-Nar-Phe-NH$_2$ (SEQ ID NO: 194)
Compound No. 311: [Nar(Me)9]MS10
Tyr-Asn-Trp-Asn-Ser-Phe-Gly-Leu-Nar(Me)-Phe-NH$_2$ (SEQ ID NO: 195)
Compound No. 312: [Har(Me)9]MS10
Tyr-Asn-Trp-Asn-Ser-Phe-Gly-Leu-Har(Me)-Phe-NH$_2$ (SEQ ID NO: 196)
Compound No. 313: [Dab9]MS10
Tyr-Asn-Trp-Asn-Ser-Phe-Gly-Leu-Dab-Phe-NH$_2$ (SEQ ID NO: 197)
Compound No. 314: [Orn9]MS10
Tyr-Asn-Trp-Asn-Ser-Phe-Gly-Leu-Orn-Phe-NH$_2$ (SEQ ID NO: 198)
Compound No. 315: des(1)-[D-Asn2,Cha3,AzaGly7,Arg(Me)9]MS10
D-Asn-Cha-Asn-Ser-Phe-AzaGly-Leu-Arg(Me)-Phe-NH$_2$
Compound No. 316: [D-Tyr1,D-Asn2,Thr3,AzaGly7,Arg(Me)9,Phe(4F)10]MS10
D-Tyr-D-Asn-Thr-Asn-Ser-Phe-AzaGly-Leu-Arg(Me)-Phe(4F)-NH$_2$
Compound No. 317: [D-Tyr1,D-Asn2,Pya(4)3,AzaGly7,Arg(Me)9,Phe(4F)10]MS10
D-Tyr-D-Asn-Pya(4)-Asn-Ser-Phe-AzaGly-Leu-Arg(Me)-Phe(4F)-NH$_2$
Compound No. 318: [D-Tyr1,AzaGly7,Arg(Me)9,Phe(4F)10]MS10
D-Tyr-Asn-Trp-Asn-Ser-Phe-AzaGly-Leu-Arg(Me)-Phe(4F)-NH$_2$
Compound No. 319: [6Ψ7,NHCO,D-Tyr1,Arg(Me)9]MS10
D-Tyr-Asn-Trp-Asn-Ser-PheΨ(NHCO)Gly-Leu-Arg(Me)-Phe-NH$_2$
Compound No. 322: des(1-3)-3-Pyridylpropionyl-[AzaGly7,Arg(Me)9]MS10
3-Pyridylpropionyl-Asn-Ser-Phe-AzaGly-Leu-Arg(Me)-Phe-NH$_2$ (SEQ ID NO: 199)
Compound No. 323: des(1-3)-4-Imidazoleacetyl-[AzaGly7,Arg(Me)9]MS10
4-Imidazoleacetyl-Asn-Ser-Phe-AzaGly-Leu-Arg(Me)-Phe-NH$_2$ (SEQ ID NO: 200)
Compound No. 324: des(1-3)-4-Piperidinecarbonyl-[AzaGly7,Arg(Me)9]MS10
Piperidinecarbonyl-Asn-Ser-Phe-AzaGly-Leu-Arg(Me)-Phe-NH$_2$ (SEQ ID NO: 201)
Compound No. 325: des(1-3)-1-Piperidineacetyl-[AzaGly7,Arg(Me)9]MS10
Piperidineacetyl-Asn-Ser-Phe-AzaGly-Leu-Arg(Me)-Phe-NH$_2$ (SEQ ID NO: 202)
Compound No. 326: des(1-3)-1-Methylpiperidinio-1-acetyl-[AzaGly7,Arg(Me)9]MS10
Methylpiperidino-1-acetyl-Asn-Ser-Phe-AzaGly-Leu-Arg(Me)-Phe-NH$_2$ (SEQ ID NO: 203)
Compound No. 327: des(1-3)-1-Pyridinioacetyl-[AzaGly7,Arg(Me)9]MS10
1-Pyridinoacetyl-Asn-Ser-Phe-AzaGly-Leu-Arg(Me)-Phe-NH$_2$ (SEQ ID NO: 204)
Compound No. 328: des(1-3)-D-Glucronyl-[AzaGly7,Arg(Me)9]MS10
D-Glucronyl-Asn-Ser-Phe-AzaGly-Leu-Arg(Me)-Phe-NH$_2$
Compound No. 375:2-Aminoethyl-Gly[D-Tyr1,Arg(Me)9]MS10
2-Aminoethyl-Gly-D-Tyr-Asn-Trp-Asn-Ser-Phe-Gly-Leu-Arg(Me)-Phe-NH$_2$
Compound No. 385: des(1)-[D-Tyr2,D-Pya(4)3,AzaGly7,Arg(Me)9,Trp10]MS10
D-Tyr-D-Pya(4)-Asn-Ser-Phe-AzaGly-Leu-Arg(Me)-Trp-NH$_2$
Compound No. 386: des(1-3)-3-Pyridylpropionyl-[AzaGly7,Arg(Me)9,Trp10]MS10
3-Pyridylpropionyl-Asn-Ser-Phe-AzaGly-Leu-Arg(Me)-Trp-NH$_2$ (SEQ ID NO: 205)
Compound No. 387:Dap-[D-Tyr1,Arg(Me)9]MS10
Dap-D-Tyr-Asn-Trp-Asn-Ser-Phe-Gly-Leu-Arg(Me)-Phe-NH$_2$
Compound No. 397:Methylthiocarbamoyl-Sar-[D-Tyr1,Arg(Me)9]MS10
Methylthiocarbamoyl-Sar-D-Tyr-Asn-Trp-Asn-Ser-Phe-Gly-Leu-Arg(Me)-Phe-NH$_2$
Compound No. 400: (S)-1-(Quinolin-8-yl-carbamoyl)-4-thiapentylcarbamoyl-[D-Tyr1,Arg(Me)9]MS10
(S)-1-(Quinolin-8-yl-carbamoyl)-4-thiapentylcarbamoyl-D-Tyr-Asn-Trp-Asn-Ser-Phe-Gly-Leu-Arg(Me)-Phe-NH$_2$;

Compounds described in WO 2006/001499 (the metastin derivatives (ii) represented by, e.g., the formula below, or salts thereof:

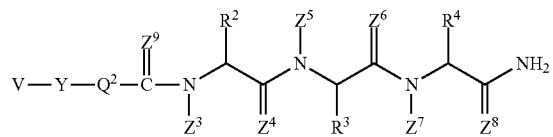

[wherein;
V represents a group represented by formula:

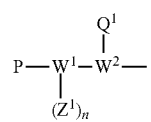

or a group represented by formula:

n represents 0 or 1;

$W^1$ represents N, CH or O (provided that when $W^1$ is N or CH, n represents 1 and when $W^1$ is O, n represents 0);

$W^2$ represents N or CH;

$Z^1$, $Z^3$, $Z^5$ and $Z^7$ each represents hydrogen atom or a $C_{1-3}$ alkyl group;

$Z^4$, $Z^6$ and $Z^8$ each represents hydrogen atom, O or S;

$R^2$ represents (1) hydrogen atom or (2) a cyclic or linear $C_{1-10}$ alkyl group, (3) a $C_{1-10}$ alkyl group consisting of a cyclic alkyl group and a linear alkyl group, or (4) a $C_{1-8}$ alkyl group optionally substituted with a substituent selected from the group consisting of an optionally substituted carbamoyl group, an optionally substituted hydroxyl group and an optionally substituted aromatic cyclic group;

$R^3$ represents (1) a $C_{1-8}$ alkyl group having an optionally substituted basic group and optionally having an additional substituent, (2) an aralkyl group having an optionally substituted basic group and optionally having an additional substituent, (3) a $C_{1-4}$ alkyl group having a non-aromatic cyclic hydrocarbon group of carbon atoms not greater than 7 having an optionally substituted basic group, and optionally having an additional substituent, or (4) a $C_{1-4}$ alkyl group having a non-aromatic heterocyclic group of carbon atoms not greater than 7 having an optionally substituted basic group, and optionally having an additional substituent;

$R^4$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and (6) an optionally substituted non-aromatic heterocyclic group having carbon atoms not greater than 7;

$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and (6) an optionally substituted non-aromatic heterocyclic group having carbon atoms not greater than 7;

$Q^2$ represents (1) $CH_2$, which may optionally be substituted with an optionally substituted $C_{1-4}$ alkyl group with a substituent selected from the group consisting of carbamoyl group and hydroxyl group, (2) NH, which may optionally be substituted with an optionally substituted $C_{1-4}$ alkyl group with a substituent selected from the group consisting of carbamoyl group and hydroxyl group, or (3) O;

Y represents a group represented by formula: —CONH—, —CSNH—, —$CH_2$NH—, —NHCO—, —$CH_2$O—, —$CH_2$S—, —COO—, —CSO— or —$CH_2CH_2$—, which may optionally be substituted with a $C_{1-6}$ alkyl group; and, $Z^9$ represents hydrogen atom, O or S; and, P and P', which may be the same or different, each may form a ring by combining P and P' or P and $Q^1$ together and represents:

(1) hydrogen atom;

(2) an optional amino acid residue continuously or discontinuously bound from the C terminus of the 1-48 amino acid sequence in the amino acid sequence represented by SEQ ID NO: 1;

(3) a group represented by formula:

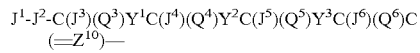

(wherein:

$J^1$ represents (a) hydrogen atom or (b) (i) a $C_{1-15}$ acyl group, (ii) a $C_{1-15}$ alkyl group, (iii) a $C_{6-14}$ aryl group, (iv) carbamoyl group, (v) carboxyl group, (vi) sulfino group, (vii) amidino group, (viii) glyoxyloyl group or (ix) amino group, which groups may optionally be substituted with a substituent containing an optionally substituted cyclic group;

$J^2$ represents (1) NH optionally substituted with a $C_{1-6}$ alkyl group, (2) $CH_2$ optionally substituted with a $C_{1-6}$ alkyl group, (3) O or (4) S;

$J^3$ through $J^6$ each represents hydrogen atom or a $C_{1-3}$ alkyl group;

$Q^3$ through $Q^6$ each represents a $C_{1-4}$ alkyl group, which may optionally have a substituent selected from the group consisting of:

(1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, (6) an optionally substituted non-aromatic cyclic hydrocarbon group having carbon atoms not greater than 7, (7) an optionally substituted amino group, (8) an optionally substituted guanidino group, (9) an optionally substituted hydroxyl group,

(10) an optionally substituted carboxyl group,

(11) an optionally substituted carbamoyl group, and

(12) an optionally substituted sulfhydryl group, or hydrogen atom;

$J^3$ and $Q^3$, $J^4$ and $Q^4$, $J^5$ and $Q^5$ or $J^6$ and $Q^6$ may be combined together, or, $J^2$ and $Q^3$, $Y^1$ and $Q^4$, $Y^2$ and $Q^5$, or $Y^3$ and $Q^6$ may be combined together, to form a ring;

$Y^1$ through $Y^3$ each represents a group represented by formula:

—CON($J^{13}$)—, —CSN($J^{13}$)—, —C($J^{14}$)N($J^{13}$)— or —N($J^{13}$)CO— (wherein $J^{13}$ and $J^{14}$ each represents hydrogen atom or a $C_{1-3}$ alkyl group); and, $Z^{10}$ represents hydrogen atom, O or S);

(4) a group represented by formula:

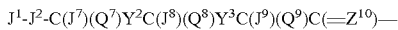

(wherein:
J¹ and J², each has the same significance as defined above;
J⁷ through J⁹ have the same significance as for J³;
Q⁷ through Q⁹ have the same significance as for Q³;
Y² and Y³ each has the same significance as defined above;
Z¹⁰ has the same significance as defined above;
J⁷ and Q⁷, J⁸ and Q⁸ or J⁹ and Q⁹ may be combined together, or, J² and Q⁷, Y² and Q⁸ or Y³ and Q⁹ may be combined together, to form a ring);

(5) a group represented by formula:

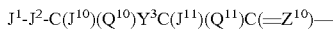

(wherein:
J¹ and J² have the same significance as defined above represents;
J¹⁰ and J¹¹ have the same significance as for J³;
Q¹⁰ and Q¹¹ have the same significance as for Q³;
Y³ has the same significance as defined above;
Z¹⁰ has the same significance as defined above; and,
J¹⁰ and Q¹⁰ or J¹¹ and Q¹¹ may be combined together, or J² and Q¹⁰ or Y³ and Q¹¹ may be combined together, to form a ring);

(6) a group represented by formula:

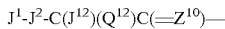

(wherein;
J¹ and J² have the same significance as defined above;
J¹² has the same significance as for J³;
Q¹² has the same significance as for Q³;
Z¹⁰ has the same significance as defined above; and,
J¹² and Q¹² may be combined together, or J² and Q¹² may be combined together, to form a ring); or, (7) a group represented by formula:

(wherein:
J¹ has the same significance as defined above)], preferably the following compounds:
D-Tyr-D-Pya(4)-Asn-Ser-Phe-AzaGly-Leu-Arg(Me)-Phe-NH₂ (Compound No. 305),
D-Tyr-D-Pya(4)-Asn-Ser-Phe-AzaGly-Leu-Arg(Me)-Trp-NH₂ (Compound No. 385),
D-Tyr-D-Pya(4)-Asn-Thr-Phe-AzaGly-Leu-Arg(Me)-Trp-NH₂ (Compound No. 501),
Benzoyl-Asn-Sr-Phe-AzaGly-Leu-Arg(Me)-Trp-NH₂ (Compound No. 509), (SEQ ID NO: 206),
D-Tyr-D-Trp-Asn-Thr-Phe-AzaGly-Leu-Arg(Me)-Trp-NH₂ (Compound No. 512),
Ac-D-Tyr-D-Pya(4)-Asn-Ser-Phe-AzaGly-Leu-Arg(Me)-Phe-NH₂ (Compound No. 516),
D-Tyr-D-Trp-Asn-Ser-Phe-AzaGly-Leu-Arg(Me)-Trp-NH₂ (Compound No. 540),
D-Arg-Acp-D-Tyr-D-Trp-Asn-Thr-Phe-AzaGly-Leu-Arg(Me)-Trp-NH₂ (Compound No. 541),
Benzoyl-Asn-Ser-Phe(4F)-AzaGly-Leu-Arg(Me)-Trp-NH₂ (Compound No. 545) (SEQ ID NO: 207),
D-Tyr-D-Pya(4)-Asn-Ser-Phe-AzaGly-Leu-Arg(Me)-PheΨ(CSNH)NH2(Compound No. 548)
Ac-D-Tyr-D-Trp-Asn-Thr-Phe-AzaGly-Leu-Arg(Me)-Trp-NH₂ (Compound No. 550),
Ac-D-Arg-Acp-D-Tyr-D-Trp-Asn-Thr-Phe-AzaGly-Leu-Arg(Me)-Trp-NH₂ (Compound No. 551),
D-Dap-Acp-D-Tyr-D-Trp-Asn-Thr-Phe-AzaGly-Leu-Arg(Me)-Trp-NH₂ (Compound No. 552),
D-Nle-Acp-D-Tyr-D-Trp-Asn-Thr-Phe-AzaGly-Leu-Arg(Me)-Trp-NH₂ (Compound No. 553),
D-Arg-γ-Abu-D-Tyr-D-Trp-Asn-Thr-Phe-AzaGly-Leu-Arg(Me)-Trp-NH₂ (Compound No. 555),
Ac-D-Tyr-D-Trp-Asn-Ser-Phe-AzaGly-Leu-Arg(Me)-Trp-NH₂ (Compound No. 558),
3-(4-Hydroxyphenyl)propionyl-D-Trp-Asn-Thr-Phe-AzaGly-Leu-Arg(Me)-Trp-NH₂ (Compound No. 559),
Ac-D-Tyr-D-Pya(4)-Asn-Thr-Phe-AzaGly-Leu-Arg(Me)-Trp-NH₂ (Compound No. 562),
Ac-D-Tyr-D-Trp-Asn-Val-Phe-AzaGly-Leu-Arg(Me)-Trp-NH₂ (Compound No. 564),
Cyclopropanecarbonyl-D-Tyr-D-Trp-Asn-Thr-Phe-AzaGly-Leu-Arg(Me)-Trp-NH₂ (Compound No. 566),
Butyryl-D-Tyr-D-Trp-Asn-Thr-Phe-AzaGly-Leu-Arg(Me)-Trp-NH₂ (Compound No. 567),
Ac-D-Tyr-D-Trp-Asn-Thr-Phe-AzaGly-Leu-Arg(Me)-Phe-NH₂ (Compound No. 571),
Ac-D-Tyr-D-Trp-Alb-Ser-Phe-AzaGly-Leu-Arg(Me)-Trp-NH₂ (Compound No. 579),
Ac-D-Tyr-D-Trp-Asn-Ser(Me)-Phe-AzaGly-Leu-Arg(Me)-Trp-NH₂ (Compound No. 580),
Ac-D-Tyr-D-Trp-Dap(Ac)-Ser-Phe-AzaGly-Leu-Arg(Me)-Trp-NH₂ (Compound No. 584),
Ac-D-Tyr-D-Trp-Dap(For)-Ser-Phe-AzaGly-Leu-Arg(Me)-Trp-NH₂ (Compound No. 585),
Ac-D-Tyr-D-Trp-Asn-Thr-Phe-AzaGly-Leu-Arg(Me)-Nal(2)-NH₂ (Compound No. 589),
Ac-D-Tyr-D-Trp-Asn-Thr-Phe-AzaGly-Leu-Arg(Me)-Thi-NH₂ (Compound No. 590),
Ac-D-Tyr-D-Trp-Asn-Thr-Phe-AzaGly-Leu-Arg(Me)-Tyr-NH₂ (Compound No. 591),
Ac-D-Tyr-D-Trp-Asn-Thr-Phe-AzaGly-Leu-Arg(Me)-Phe(4F)—NH₂ (Compound No. 592),
Ac-D-Tyr-D-Trp-Asn-Thr-Phe-AzaGly-Leu-Orn-Trp-NH₂ (Compound No. 599),
Ac-D-Tyr-D-Trp-Asn-Thr-Phe-AzaGly-Leu-Arg-Trp-NH₂ (Compound No. 600),
Ac-D-NMeTyr-D-Trp-Asn-Thr-Phe-AzaGly-Leu-Arg(Me)-Trp-NH₂ (Compound No. 602),
Ac-D-Tyr-D-Trp-Asn-Thr-Phe-AzaGly-Leu-Arg(symMe₂)-Trp-NH₂ (Compound No. 608),
For-D-Tyr-D-Trp-Asn-Thr-Phe-AzaGly-Leu-Arg(Me)-Trp-NH₂ (Compound No. 612),
Propionyl-D-Tyr-D-Trp-Asn-Thr-Phe-AzaGly-Leu-Arg(Me)-Trp-NH₂ (Compound No. 613),
Ac-Tyr-D-Trp-Asn-Thr-Phe-AzaGly-Leu-Arg(Me)-Trp-NH₂ (Compound No. 615),
Ac-D-Ala-D-Trp-Asn-Thr-Phe-AzaGly-Leu-Arg(Me)-Trp-NH₂ (Compound No. 616),
Ac-D-Leu-D-Trp-Asn-Thr-Phe-AzaGly-Leu-Arg(Me)-Trp-NH₂ (Compound No. 617),
Ac-D-Phe-D-Trp-Asn-Thr-Phe-AzaGly-Leu-Arg(Me)-Trp-NH₂ (Compound No. 618),
Ac-D-Lys-D-Trp-Asn-Thr-Phe-AzaGly-Leu-Arg(Me)-Trp-NH₂ (Compound No. 621),
Ac-D-Tyr-Trp-Asn-Thr-Phe-AzaGly-Leu-Arg(Me)-Trp-NH₂ (Compound No. 623),
Ac-D-Tyr-D-Ala-Asn-Thr-Phe-AzaGly-Leu-Arg(Me)-Trp-NH₂ (Compound No. 625),
Ac-D-Tyr-D-Leu-Asn-Thr-Phe-AzaGly-Leu-Arg(Me)-Trp-NH₂ (Compound No. 626),
Ac-D-Tyr-D-Phe-Asn-Thr-Phe-AzaGly-Leu-Arg(Me)-Trp-NH₂ (Compound No. 627),
Ac-D-Tyr-D-Lys-Asn-Thr-Phe-AzaGly-Leu-Arg(Me)-Trp-NH₂ (Compound No. 629), Ac-D-Tyr-D-Glu-Asn-Thr-Phe-AzaGly-Leu-Arg(Me)-Trp-NH$_2$ (Compound No. 630),
Ac-D-Tyr-D-Trp-Asn-Thr-Pya(4)-AzaGly-Leu-Arg(Me)-Trp-NH$_2$ (Compound No. 635),
Ac-D-Tyr-D-Trp-Asn-Thr-Phe(4F)-AzaGly-Leu-Arg(Me)-Trp-NH$_2$ (Compound No. 637),
Ac-D-Tyr-D-Pya(4)-Asn-Thr-Phe(4F)-AzaGly-Leu-Arg(Me)-Trp-NH$_2$ (Compound No. 638),
Ac-D-Tyr-D-Trp-Asn-Thr-Phe-AzaGly-Val-Arg(Me)-Trp-NH$_2$ (Compound No. 642),
Gly-D-Tyr-D-Trp-Asn-Thr-Phe-AzaGly-Leu-Arg(Me)-Trp-NH$_2$ (Compound No. 648),
Ac-Gly-D-Tyr-D-Trp-Asn-Thr-Phe-AzaGly-Leu-Arg(Me)-Trp-NH$_2$ (Compound No. 649),
D-Tyr-D-Tyr-D-Trp-Asn-Thr-Phe-AzaGly-Leu-Arg(Me)-Trp-NH$_2$ (Compound No. 650),
Ac-D-Tyr-D-Tyr-D-Trp-Asn-Thr-Phe-AzaGly-Leu-Arg(Me)-Trp-NH$_2$ (Compound No. 651),
pGlu-D-Tyr-D-Trp-Asn-Thr-Phe-AzaGly-Leu-Arg(Me)-Trp-NH$_2$ (Compound No. 652),
Ac-D-Tyr-Pro-Asn-Thr-Phe-AzaGly-Leu-Arg(Me)-Trp-NH$_2$ (Compound No. 657),
Ac-D-Tyr-D-Pya(2)-Asn-Thr-Phe-AzaGly-Leu-Arg(Me)-Trp-NH$_2$ (Compound No. 658),
Ac-D-Tyr-D-Pya(3)-Asn-Thr-Phe-AzaGly-Leu-Arg(Me)-Trp-NH$_2$ (Compound No. 660),
Ac-D-Tyr-Tic-Asn-Thr-Phe-AzaGly-Leu-Arg(Me)-Trp-NH$_2$ (Compound No. 662),
Ac-D-Trp-D-Trp-Asn-Thr-Phe-AzaGly-Leu-Arg(Me)-Trp-NH$_2$ (Compound No. 663),
Ac-D-Trp-Asn-Thr-Phe-AzaGly-Leu-Arg(Me)-Trp-NH$_2$ (Compound No. 666),
Hexanoyl-D-Trp-Asn-Thr-Phe-AzaGly-Leu-Arg(Me)-Trp-NH$_2$ (Compound No. 667),
3-Pyridinepropionyl-D-Trp-Asn-Thr-Phe-AzaGly-Leu-Arg(Me)-Trp-NH$_2$ (Compound No. 670),
Adipoyl-D-Trp-Asn-Thr-Phe-AzaGly-Leu-Arg(Me)-Trp-NH$_2$ (Compound No. 671),
Ac-D-Tyr-NMeTrp-Asn-Thr-Phe-AzaGly-Leu-Arg(Me)-Trp-NH$_2$ (Compound No. 672),
6-Aminocaproyl-D-Trp-Asn-Thr-Phe-AzaGly-Leu-Arg(Me)-Trp-NH$_2$ (Compound No. 674), or salts thereof; and Compounds described in WO 2007/072997 (the metastin derivatives represented by, e.g., the formula below, or salts thereof:

A metastin derivative represented by formula:

XX0-XX2-XX3-XX4-XX5-XX6-AzaGly-XX8-XX9-XX10-NH$_2$ (wherein:

XX0 represents formyl, C$_{1-20}$ alkanoyl, cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl, 6-aminocaproyl;

XX2 represents Tyr, D-Tyr, D-Ala, D-Leu, D-Phe, D-Lys, D-Trp or a chemical bond;

XX3 represents: D-Asp,D-Dap,D-Ser,D-Gln,D-His,D-NMeAla,D-NMePhe,Aze(2),Pic(2),Pic(3),Hyp,Thz, NMeAla,Gly,Aib,Abz(2),Abz(3),Sar,Leu,Lys,Glu, β-alanine, Pzc(2), Orn,His(3Me), Tyr(PO$_3$H$_2$), Pro(4NH$_2$) or Hyp (Bzl);

XX4 represents Asn, 2-amino-3-ureidopropionic acid, N$^β$-formyl-β-diaminopropionic acid, N$^β$-acetyl-β-diaminopropionic acid, N$^ω$-pentylasparagine, N$^ω$-cyclopropylasparagine, N$^ω$-benzylasparagine, 2,4-diaminobutanoic acid, His, Gln, Cit or a chemical bond;

XX5 represents Ser, Thr, Val, NMeSer, Gly, Ala, Hyp, D-Ala, D-Thr, D-Pro or a chemical bond;

XX6 represents Phe, Tyr, Trp, Tyr(Me), Thi, Nal(2), Cha, Pya(4), threo-Ser(3Phenyl), erythro-Ser(3Phenyl), or optionally substituted phenylalanine;

AzaGly represents azaglycine;

XX8 represents Leu, Nva or Val;

XX9 represents Arg, Orn, Arg(Me) or Arg(asymMe$_2$); and,

XX10 represents Phe, Trp, 2-naphthylalanine, 2-thienylalanine, tyrosine or 4-fluorophenylalanine); or a salt thereof preferably, the compounds below or salts thereof:

Ac-D-Tyr-D-Trp-Asn-Thr-Phe-AzaGly-Leu-D-Arg-Trp-NH$_2$ (Compound No. 708),
Ac-Asn-Thr-Phe-AzaGly-Leu-Arg(Me)-Trp-NH$_2$ (Compound No. 709) (SEQ ID NO: 208),
Decanoyl-Asn-Thr-Phe-AzaGly-Leu-Arg(Me)-Trp-NH$_2$ (Compound No. 710) (SEQ ID NO: 209),
Acp-Asn-Thr-Phe-AzaGly-Leu-Arg(Me)-Trp-NH$_2$ (Compound No. 712) (SEQ ID NO: 210),
Ac-Acp-Asn-Thr-Phe-AzaGly-Leu-Arg(Me)-Trp-NH$_2$ (Compound No. 713) (SEQ ID NO: 211),
Ac-D-Tyr-D-Trp-Asp(NHPen)-Thr-Phe-AzaGly-Leu-Arg(Me)-Trp-NH$_2$ (Compound No. 714),
Ac-D-Tyr-D-Trp-Asp(NHcPr)-Thr-Phe-AzaGly-Leu-Arg(Me)-Trp-NH$_2$ (Compound No. 715),
Ac-D-Tyr-D-Trp-Asp(NHBzl)-Thr-Phe-AzaGly-Leu-Arg(Me)-Trp-NH$_2$ (Compound No. 716),
Ac-D-Tyr-D-Trp-Alb-Thr-Phe-AzaGly-Leu-Arg(Me)-Trp-NH$_2$ (Compound No. 717),
Ac-D-Tyr-D-Pya(4)-Alb-Thr-Phe-AzaGly-Leu-Arg(Me)-Trp-NH$_2$ (Compound No. 718),
Ac-D-Tyr-D-Trp-Asn-D-Pro-Phe-AzaGly-Leu-Arg(Me)-Trp-NH$_2$ (Compound No. 719),
Ac-D-Tyr-Aze(2)-Asn-Thr-Phe-AzaGly-Leu-Arg(Me)-Trp-NH$_2$ (Compound No. 720),
Ac-D-Tyr-Pic(2)-Asn-Thr-Phe-AzaGly-Leu-Arg(Me)-Trp-NH$_2$ (Compound No. 721),
Ac-D-Tyr-Pic(3)-Asn-Thr-Phe-AzaGly-Leu-Arg(Me)-Trp-NH$_2$ (Compound No. 722)
Ac-D-Tyr-Hyp-Asn-Thr-Phe-AzaGly-Leu-Arg(Me)-Trp-NH$_2$ (Compound No. 723),
Ac-D-Tyr-Thz-Asn-Thr-Phe-AzaGly-Leu-Arg(Me)-Trp-NH$_2$ (Compound No. 724),
Ac-D-Tyr-NMeAla-Asn-Thr-Phe-AzaGly-Leu-Arg(Me)-Trp-NH$_2$ (Compound No. 725)
Ac-D-Tyr-Gly-Asn-Thr-Phe-AzaGly-Leu-Arg(Me)-Trp-NH$_2$ (Compound No. 726)
Ac-D-Tyr-Aib-Asn-Thr-Phe-AzaGly-Leu-Arg(Me)-Trp-NH$_2$ (Compound No. 727),
Ac-D-Tyr-Abz(2)-Asn-Thr-Phe-AzaGly-Leu-Arg(Me)-Trp-NH$_2$ (Compound No. 728)
Ac-D-Tyr-Aze(3)-Asn-Thr-Phe-AzaGly-Leu-Arg(Me)-Trp-NH$_2$ (Compound No. 730)
Ac-D-Tyr-Sar-Asn-Thr-Phe-AzaGly-Leu-Arg(Me)-Trp-NH$_2$ (Compound No. 731)
Ac-D-Tyr-D-NMeAla-Asn-Thr-Phe-AzaGly-Leu-Arg(Me)-Trp-NH$_2$ (Compound No. 732),
Ac-D-Tyr-Izc-Asn-Thr-Phe-AzaGly-Leu-Arg(Me)-Trp-NH$_2$ (Compound No. 734),
Ac-D-Tyr-D-Asp-Asn-Thr-Phe-AzaGly-Leu-Arg(Me)-Trp-NH$_2$ (Compound No. 735),
Ac-D-Tyr-D-Dap-Asn-Thr-Phe-AzaGly-Leu-Arg(Me)-Trp-NH$_2$ (Compound No. 736), Ac-D-Tyr-D-Ser-Asn-Thr-Phe-AzaGly-Leu-Arg(Me)-Trp-NH$_2$ (Compound No. 737),
Ac-D-Tyr-D-Gln-Asn-Thr-Phe-AzaGly-Leu-Arg(Me)-Trp-NH$_2$ (Compound No. 738),
Ac-D-Tyr-D-His-Asn-Thr-Phe-AzaGly-Leu-Arg(Me)-Trp-NH$_2$ (Compound No. 739),
Ac-D-Tyr-D-Trp-Dab-Thr-Phe-AzaGly-Leu-Arg(Me)-Trp-NH$_2$ (Compound No. 740),
Ac-D-Tyr-Ala-Asn-Thr-Phe-AzaGly-Leu-Arg(Me)-Trp-NH$_2$ (Compound No. 742),
Ac-D-Tyr-Leu-Asn-Thr-Phe-AzaGly-Leu-Arg(Me)-Trp-NH$_2$ (Compound No. 743),
Ac-D-Tyr-Ser-Asn-Thr-Phe-AzaGly-Leu-Arg(Me)-Trp-NH$_2$ (Compound No. 744),
Ac-D-Tyr-Lys-Asn-Thr-Phe-AzaGly-Leu-Arg(Me)-Trp-NH$_2$ (Compound No. 745),
Ac-D-Tyr-Glu-Asn-Thr-Phe-AzaGly-Leu-Arg(Me)-Trp-NH$_2$ (Compound No. 746),
Ac-D-Tyr-β-Ala-Asn-Thr-Phe-AzaGly-Leu-Arg(Me)-Trp-NH$_2$ (Compound No. 747),
Ac-D-Tyr-D-Trp-Asn-Thr-Phe(4Cl)-AzaGly-Leu-Arg(Me)-Trp-NH$_2$ (Compound No. 748),
Ac-D-Tyr-D-Trp-Asn-Thr-Phe(2F)-AzaGly-Leu-Arg(Me)-Trp-NH$_2$ (Compound No. 749),
Ac-D-Tyr-D-Trp-Asn-Thr-Phe(3F)-AzaGly-Leu-Arg(Me)-Trp-NH$_2$ (Compound No. 750),
Ac-D-Tyr-Lys-Asn-Thr-Phe(2F)-AzaGly-Leu-Arg(Me)-Trp-NH$_2$ (Compound No. 754),
Ac-D-Tyr-Glu-Asn-Thr-Phe(2F)-AzaGly-Leu-Arg(Me)-Trp-NH$_2$ (Compound No. 755),
Ac-D-Tyr-Lys-Asn-Thr-Phe(3F)-AzaGly-Leu-Arg(Me)-Trp-NH$_2$ (Compound No. 756),
Ac-D-Tyr-Glu-Asn-Thr-Phe(3F)-AzaGly-Leu-Arg(Me)-Trp-NH$_2$ (Compound No. 757),
Ac-D-Tyr-Lys-Asn-Thr-Phe(4Cl)-AzaGly-Leu-Arg(Me)-Trp-NH$_2$ (Compound No. 758),
Ac-D-Tyr-Glu-Asn-Thr-Phe(4Cl)-AzaGly-Leu-Arg(Me)-Trp-NH$_2$ (Compound No. 759),
Ac-D-Tyr-Pzc(2)-Asn-Thr-Phe-AzaGly-Leu-Arg(Me)-Trp-NH$_2$ (Compound No. 760),
Ac-D-Tyr-Hyp-Asn-Thr-Phe(2F)-AzaGly-Leu-Arg(Me)-Trp-NH$_2$ (Compound No. 763),
Ac-D-Tyr-Trp-Asn-Thr-Phe(2F)-AzaGly-Leu-Arg(Me)-Trp-NH$_2$ (Compound No. 764),
Ac-D-Tyr-Hyp-Asn-Thr-Phe(3F)-AzaGly-Leu-Arg(Me)-Trp-NH$_2$ (Compound No. 765),
Ac-D-Tyr-Trp-Asn-Thr-Phe(3F)-AzaGly-Leu-Arg(Me)-Trp-NH$_2$ (Compound No. 766),
Ac-D-Tyr-Hyp-Asn-Thr-Phe(4Cl)-AzaGly-Leu-Arg(Me)-Trp-NH$_2$ (Compound No. 767),
Ac-D-Tyr-Trp-Asn-Thr-Phe(4Cl)-AzaGly-Leu-Arg(Me)-Trp-NH$_2$ (Compound No. 768),
Ac-D-Tyr-Gly-Asn-Thr-Phe(4Cl)-AzaGly-Leu-Arg(Me)-Trp-NH$_2$ (Compound No. 769),
Ac-D-Tyr-Aib-Asn-Thr-Phe(4Cl)-AzaGly-Leu-Arg(Me)-Trp-NH$_2$ (Compound No. 770),
Ac-D-Tyr-Orn-Asn-Thr-Phe-AzaGly-Leu-Arg(Me)-Trp-NH$_2$ (Compound No. 771),
Ac-D-Tyr-Thr-Asn-Thr-Phe-AzaGly-Leu-Arg(Me)-Trp-NH$_2$ (Compound No. 772),
Ac-D-Tyr-His(3Me)-Asn-Thr-Phe-AzaGly-Leu-Arg(Me)-Trp-NH$_2$ (Compound No. 773),
Ac-D-Tyr-DL-Ala(Pip)-Asn-Thr-Phe-AzaGly-Leu-Arg(Me)-Trp-NH$_2$ (Compound No. 774),
Ac-D-Tyr-Tyr(PO$_3$H$_2$)-Asn-Thr-Phe-AzaGly-Leu-Arg(Me)-Trp-NH$_2$ (Compound No. 775),
Glycoloyl-D-Tyr-Hyp-Asn-Thr-Phe-AzaGly-Leu-Arg(Me)-Trp-NH$_2$ (Compound No. 776)
Ac-D-Tyr-Asn-Thr-Phe-AzaGly-Leu-Arg(Me)-Trp-NH$_2$ (Compound No. 777),
Ac-D-Tyr-Pro(4NH$_2$)-Asn-Thr-Phe-AzaGly-Leu-Arg(Me)-Trp-NH$_2$ (Compound No. 780),
Ac-D-Tyr-Hyp(Bzl)-Asn-Thr-Phe-AzaGly-Leu-Arg(Me)-Trp-NH$_2$ (Compound No. 781),
Ac-D-Tyr-D-NMePhe-Asn-Thr-Phe-AzaGly-Leu-Arg(Me)-Trp-NH$_2$ (Compound No. 782),
Ac-D-Tyr-Gly-Asn-Thr-Phe(2F)-AzaGly-Leu-Arg(Me)-Trp-NH$_2$ (Compound No. 783),
Ac-D-Tyr-Aib-Asn-Thr-Phe(2F)-AzaGly-Leu-Arg(Me)-Trp-NH$_2$ (Compound No. 784),
Ac-D-Tyr-Gly-Asn-Thr-Phe(3F)-AzaGly-Leu-Arg(Me)-Trp-NH$_2$ (Compound No. 785),
Ac-D-Tyr-Aib-Asn-Thr-Phe(3F)-AzaGly-Leu-Arg(Me)-Trp-NH$_2$ (Compound No. 786),
Ac-D-Tyr-Hyp-Asn-Thr-Phe(4F)-AzaGly-Leu-Arg(Me)-Trp-NH$_2$ (Compound No. 787),
Ac-D-Tyr-Glu-Asn-Thr-Phe(4F)-AzaGly-Leu-Arg(Me)-Trp-NH$_2$ (Compound No. 788),
Ac-D-Tyr-Lys-Asn-Thr-Phe(4F)-AzaGly-Leu-Arg(Me)-Trp-NH$_2$ (Compound No. 789),
Ac-D-Tyr-Gly-Asn-Thr-Phe(4F)-AzaGly-Leu-Arg(Me)-Trp-NH$_2$ (Compound No. 790),
Ac-D-Tyr-Aib-Asn-Thr-Phe(4F)-AzaGly-Leu-Arg(Me)-Trp-NH$_2$ (Compound No. 791),
Ac-D-Tyr-Hyp-Asn-Thr-D-Phe-AzaGly-Leu-Arg(Me)-Trp-NH$_2$ (Compound No. 794),
Ac-D-Tyr-Hyp-Asn-Thr-Phe-AzaGly-Leu-Arg-Trp-NH$_2$ (Compound No. 797),
Ac-D-Tyr-Hyp-Alb-Thr-Phe-AzaGly-Leu-Arg(Me)-Trp-NH$_2$ (Compound No. 800),
4-[Bis-(2-Pyridylmethyl)aminomethyl]benzoyl-Phe-AzaGly-Leu-Arg(Me)-Trp-NH$_2$ (Compound No. 801) (SEQ ID NO: 212),
Ac-D-Tyr-Hyp-Asn-NMeSer-Phe-AzaGly-Leu-Arg(Me)-Trp-NH$_2$ (Compound No. 809),
Ac-D-Tyr-Hyp-Asn-Hyp-Phe-AzaGly-Leu-Arg(Me)-Trp-NH$_2$ (Compound No. 810),
Ac-D-Tyr-Hyp-Asn-Gly-Phe-AzaGly-Leu-Arg(Me)-Trp-NH$_2$ (Compound No. 813),
Ac-D-Tyr-Hyp-Asn-Ala-Phe-AzaGly-Leu-Arg(Me)-Trp-NH$_2$ (Compound No. 814),
Ac-D-Tyr-Hyp-Asn-D-Ala-Phe-AzaGly-Leu-Arg(Me)-Trp-NH$_2$ (Compound No. 815),
Ac-D-Tyr-Hyp-His-Thr-Phe-AzaGly-Leu-Arg(Me)-Trp-NH$_2$ (Compound No. 816),
Ac-D-Tyr-Hyp-Gln-Thr-Phe-AzaGly-Leu-Arg(Me)-Trp-NH$_2$ (Compound No. 843),
Ac-D-Tyr-Hyp-D-Asn-Thr-Phe-AzaGly-Leu-Arg(Me)-Trp-NH$_2$ (Compound No. 844),
Ac-D-Tyr-Hyp-Cit-Thr-Phe-AzaGly-Leu-Arg(Me)-Trp-NH$_2$ (Compound No. 845),
Ac-D-Tyr-Hyp-Asn-D-Thr-Phe-AzaGly-Leu-Arg(Me)-Trp-NH$_2$ (Compound No. 846),
Ac-D-Tyr-Hyp-Asn-Thr-Phe-AzaGly-Ala(cPr)-Arg(Me)-Trp-NH$_2$ (Compound No. 856),
4-Ureidobenzoyl-Phe-AzaGly-Leu-Arg(Me)-Trp-NH$_2$ (Compound No. 860) (SEQ ID NO: 213),
Ac-D-Tyr-Hyp-Arg-Thr-Phe-AzaGly-Leu-Arg(Me)-Trp-NH$_2$ (Compound No. 861),
Ac-D-Tyr-Hyp-Gly-Thr-Phe-AzaGly-Leu-Arg(Me)-Trp-NH$_2$ (Compound No. 862),
Ac-D-Tyr-Hyp-Dap-Thr-Phe-AzaGly-Leu-Arg(Me)-Trp-NH$_2$ (Compound No. 863), Ac-D-Tyr-Hyp-Dab-Thr-Phe-AzaGly-Leu-Arg(Me)-Trp-NH₂ (Compound No. 864),
Ac-D-Tyr-Hyp-Asn-Thr-αMePhe-AzaGly-Leu-Arg(Me)-Trp-NH₂ (Compound No. 868),
Ac-D-Tyr-Hyp-Asn-Thr-Phe(2Me)-AzaGly-Leu-Arg(Me)-Trp-NH₂ (Compound No. 870),
Ac-D-Tyr-Hyp-Asn-Thr-Phe(3Me)-AzaGly-Leu-Arg(Me)-Trp-NH₂ (Compound No. 872),
Ac-D-Tyr-Hyp-Asn-Thr-Phe(4Me)-AzaGly-Leu-Arg(Me)-Trp-NH₂ (Compound No. 874),
Ac-D-Tyr-Hyp-Asn-Thr-threo-Ser(3Phenyl)-AzaGly-Leu-Arg(Me)-Trp-NH₂ (Compound No. 877),
Ac-D-Tyr-Hyp-Asn-Thr-erythro-Ser(3Phenyl)-AzaGly-Leu-Arg(Me)-Trp-NH₂ (Compound No. 882),
Ac-D-Tyr-Hyp-Nva-Thr-Phe-AzaGly-Leu-Arg(Me)-Trp-NH₂ (Compound No. 886),
Ac-Hyp-Asn-Thr-Phe-AzaGly-Leu-Arg(Me)-Trp-NH₂ (Compound No. 887) (SEQ ID NO: 214),
3-(p-Hydroxyphenyl)propionyl-Hyp-Asn-Thr-Phe-AzaGly-Leu-Arg(Me)-Trp-NH₂ (Compound No. 888) (SEQ ID NO: 215),
pGlu-Asn-Thr-Phe-AzaGly-Leu-Arg(Me)-Trp-NH₂ (Compound No. 889) (SEQ ID NO: 216),
Ac-D-Tyr-cisHyp-Asn-Thr-Phe-AzaGly-Leu-Arg(Me)-Trp-NH₂ (Compound No. 896),
Ac-D-Tyr-Pro(4F)-Asn-Thr-Phe-AzaGly-Leu-Arg(Me)-Trp-NH₂ (Compound No. 897),
Ac-Tyr-Hyp-Asn-Thr-Phe-AzaGly-Leu-Arg(Me)-Trp-NH₂ (Compound No. 899) (SEQ ID NO: 217)
are also useful as agents for preventing/treating rheumatic diseases (e.g., rheumatoid arthritis, osteoarthritis, gout, etc.) or the like. Tests can be performed by the publicly known procedures described above to determine that these compounds are useful for rheumatic diseases.

These compounds are also useful as an agent for preventing/treating autism, immunomodulation (regeneration of thymus, repopulation of thymus, enhanced T cell growth), diabetic neuropathy, diabetic nephropathy, diabetic retinopathy, arteriosclerosis, thrombotic disorders or lipotoxicity; an agent for preventing/treating hyperlipemia, type II diabetes mellitus, hypertension, diabetic neuropathy, diabetic nephropathy or diabetic retinopathy; an antianxiety agent; an anti-stress agent; an anti-insomnia agent; an antimanic-depressive agent; an agent for preventing/treating hypertension (e.g., essential hypertension, renal hypertension, salt sensitive hypertension, etc.), angina pectoris (e.g., stable angina, unstable angina, etc.), myocardial infarction, cerebrovascular disorders (e.g., asymptomatic cerebrovascular disorder, transient ischemic attack, apoplexy, cerebrovascular dementia, hypertensive encephalopathy, cerebral infarction, etc.), venous insufficiency, obliterative peripheral circulatory disturbances, Raynaud's disease, arteriosclerosis including atherosclerosis (e.g., aneurysm, coronary arteriosclerosis, cerebral arteriosclerosis, peripheral arteriosclerosis, etc.), vascular thickening or occlusion and organ impairments after intervention (e.g., percutaneous coronary intervention, stent placement, coronary thrombolytic therapy, etc.), portal hypertension, respiratory disorders (e.g., asthma, pulmonary hypertension, etc.); an agent for preventing/treating impaired glucose tolerance (IGT); an insulin secretagogue, an inhibitor for transition from IGT to diabetes;

an agent for preventing/treating diabetic complications [e.g., neuropathy, nephropathy, retinopathy, cataract, macroangiopathy, osteopenia, hyperosmolar diabetic coma, infectious diseases (e.g., respiratory infection, urinary tract infection, digestive tract infection, skin soft-tissue infection, lower leg infection), diabetic gangrene, xerostomia, hypacusis, cerebrovascular disorder, peripheral circulatory disturbance], osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, polycystic ovary syndrome, renal diseases (e.g., diabetic nephropathy, glomerulonephritis, glomerulosclerosis, nephrotic syndrome, hypertensive nephrosclerosis, end stage kidney disease), muscular dystrophy, cardiac infarction, angina pectoris, cerebrovascular disorders (e.g., cerebral infarction, apoplexy), Alzheimer's disease, Parkinson's disease, dementia, insulin resistance syndrome, Syndrome X, metabolic syndrome, hyperinsulinemia, hyperinsulinemia-induced sensory disorders, tumors (e.g., leukemia, skin cancer), irritable bowel syndrome, acute or chronic diarrhea, inflammatory diseases (e.g., deforming spondylitis, arthritis deformans, lumbago, gout, postoperative or posttraumatic inflammation, swelling, neuralgia, pharyngolaryngitis, cystitis, hepatitis (including nonalcoholic steatohepatitis), pneumonia, enteritis, inflammatory bowel disorder (including inflammatory bowel diseases), ulcerative colitis, gastric mucosa damage (including gastric mucosa damage induced by aspirin)), damages of small intestinal mucosa, malabsorption, testicular function disorder, visceral obesity syndrome, etc.; and, for reduction of visceral adiposity, inhibition of visceral fat accumulation, improvement of glucose metabolism, improvement of lipid metabolism, suppression of oxidized LDL production, improvement of lipoprotein metabolism, improvement of coronary artery metabolism, prevention or treatment of cardiovascular complication, prevention or treatment of heart failure complications, decrease in blood remnant, prevention or treatment of anovulation, prevention or treatment of hirsutism or prevention or treatment of hyperandrogenemia; as an agent for improving pancreas (β cells) function, a regenerative agent for pancreas (β cells), an agent for stimulating pancreatic (β cell) regeneration, an appetite regulator, etc.

These compounds can be used in combination with drugs other than the said compounds.

As drugs, which can be used in combination with these compounds (hereinafter sometimes simply referred to as concomitant drugs), the medicaments described as drugs which can be used in combination with the compounds of the present invention can be used in a similar manner.

The compounds of the present invention can be used in combination with drugs, e.g., chemotherapeutic agents for treating cancer, hormonal therapeutic agents, immunotherapeutic agents, drugs for inhibiting the actions of cell growth factors and their receptors, etc. (hereinafter simply referred to as concomitant agents). Examples of the "chemotherapeutic agents" include alkylating agents, antimetabolites, anticancer antibiotics, anticancer agents derived from plants, etc. Specifically, the drugs described later can be used.

Furthermore, the compound of the present invention has excellent blood stability, solubility and solution stability, as compared to native metastin such as metastin 54 (1-54) or metastin 10 (45-54).

The metastin derivative of the present invention or its salt or prodrug, metastin per se, or DNA encoding metastin, etc. is useful as an agent for suppressing gonadotropic hormone (e.g., FSH, LH) secretion or sex hormone [e.g., androgen (e.g., testosterone, androstenedione), estrogen (e.g., estradiol, estrone), progesterone] secretion; etc.; in particular, it is useful for suppressing gonadotropic hormone secretion or sex hormone secretion via down-regulation of gonadotropic hormone or sex hormone (wherein, the down-regulation of gonadotropic hormone or sex hormone may be pulse loss of LHRH or depletion of LHRH) or down-regulation of human OT7T175 (metastin receptor) protein consisting of the amino acid sequence represented by SEQ ID NO: 9; particularly useful as an agent for preventing or treating hormone-dependent cancers (e.g., prostate cancer, breast cancer, etc.; especially a prostate cancer, hormone-sensitive prostate cancer, etc.); an agent for preventing or treating endometriosis; an agent for inhibiting ovarian follicular maturation; a menstrual cycle-suspending agent; an agent for treating myoma of the uterus; an agent for treating early puberty; or as a contraceptive, etc. Where the metastin derivative of the present invention or its salt or prodrug, metastin per se, or DNA encoding metastin, etc. has normal agonist activity, an effective dose of the metastin derivative sufficient to suppress the secretion of gonadotropic hormone or sex hormone is administered at the site or tissue where the therapeutic effects are to be exerted, so that the metastin derivative is present in a dose more than required (i.e., the metastin derivative is administered in an excess over the normal effective dose, at which the metastin derivative exerts the effects of suppressing cancer metastasis, suppressing cancer growth, etc.; or the effect of promoting gonadotropic hormone secretion, the effect of promoting sex hormone secretion, etc.) to exhibit the effects of suppressing gonadotropic hormone secretion or sex hormone secretion. Specific examples include sustained or continuous administration of the normal effective dose (including an administration technique to gradually release the pharmaceutical ingredients by bolus administration); and the like. Further when the metastin derivative of the present invention or its salt or the prodrug thereof, etc. has a sufficient agonist activity more than required (a super-agonist activity), it becomes possible to sustain the activities more than exhibited by the necessary dose at the site or tissue where the therapeutic effect are to be exhibited. It is therefore sufficient even by normal effective dose administration to suppress the secretion of gonadotropic hormone or sex hormone, whereby the effect of suppressing gonadotropic hormone secretion or sex hormone secretion is exhibited.

In other words, an effective dose of the metastin derivative of the present invention or its salt or prodrug, metastin per se, or DNA encoding metastin, etc. sufficient to suppress the secretion of gonadotropic hormone or sex hormone is administered so that the metastin derivative is present in a dose more than required at the site or tissue where the therapeutic effects are to be exerted, or its activities can be sustained more than required, which enables to exhibit the effects of suppressing gonadotropic hormone secretion or suppressing sex hormone secretion.

The medicament comprising the compound of the present invention is low toxic. Therefore, the compound of the present invention can be safely administered either directly as it is or as a mixture with pharmacologically acceptable carriers, orally or parenterally (e.g., topically, rectally, intravenously, etc.), in the form of pharmaceutical preparations such as tablets (including dragees and film-coated tablets), powdery dosage forms, granules, capsules (including soft capsules), liquid dosage forms, injections, suppositories, sustained release dosage forms, etc., in accordance with publicly known means generally used in process for producing pharmaceutical preparations.

The compound of the present invention is contained in the pharmaceutical preparation of the present invention in about 0.01 to about 100 wt %, based on the total weight of the preparation.

A dose of the compound of the present invention may vary depending upon subject to be administered, target organ, conditions, route of administration, etc., and in oral administration, the compound is generally administered to the patient (as 60 kg body weight) with cancer in a daily dose of about 0.01 to about 100 mg, preferably about 0.1 to about 50 mg and more preferably about 0.1 to about 20 mg. In parenteral administration, a single dose of the compound may vary depending upon subject to be administered, target organ, conditions, route of administration, etc., and in the form of an injectable dosage form, it is advantageous to administer the compound to the patient (as 60 kg body weight) with cancer generally in a daily dose of about 0.001 to about 30 mg, preferably about 0.01 to about 20 mg, and more preferably about 0.01 to about 10 mg. For other animal species, the corresponding dose as converted per 60 kg weight can be administered.

Pharmacologically acceptable carriers, which may be used in manufacturing the pharmaceutical preparation of the present invention, include various organic or inorganic carrier substances conventionally used as materials for pharmaceutical preparations. These substances include, e.g., an excipient, a lubricant, a binder and a disintegrating agent in a solid dosage form, and a solvent, a dissolution aid, a suspending agent, an isotonizing agent, a buffer, a soothing agent, etc. in a liquid dosage form. In addition, conventional additives such as a preservative, an antioxidant, a colorant, a sweetener, an adsorbent, a wetting agent, etc. can be appropriately used in suitable amounts, if necessary. Examples of excipients include lactose, saccharose, D-mannitol, starch, cornstarch, crystalline cellulose, light anhydrous silicic acid, etc. Examples of lubricants include magnesium stearate, calcium stearate, talc, colloidal silica, etc.

Examples of binders include crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose, etc.

Examples of disintegrating agents include starch, carboxymethylcellulose, carboxymethylcellulose calcium, sodium carboxymethyl starch, L-hydroxypropylcellulose, etc.

Examples of solvents include water for injection, alcohol, propylene glycol, Macrogol, sesame oil, corn oil, olive oil, etc.

Examples of dissolution aids include polyethylene glycol, propylene glycol, D-mannitol, benzyl benzoate, ethanol, trisaminomethane, cholesterol, triethanolamine, sodium carbonate, sodium citrate, etc.

Examples of suspending agents include surfactants such as stearyl triethanolamine, sodium lauryl sulfate, lauryl aminopropionate, lecithin, benzalkonium chloride, benzethonium chloride, glycerin monostearate, etc.; hydrophilic polymers such as polyvinyl alcohol, polyvinyl pyrrolidone, sodium carboxymethylcellulose, methylcellulose, hydroxymethylcellulose, hydroxyethylcellulose, hydroxypropylcellulose, etc.

Examples of isotonizing agents include glucose, D-sorbitol, sodium chloride, glycerin, D-mannitol, etc.

Examples of buffers include buffering solutions of a phosphate, acetate, carbonate, citrate, etc.

Examples of soothing agents include benzyl alcohol, etc.

Examples of preservatives include p-hydroxybenzoates, chlorobutanol, benzyl alcohol, phenethyl alcohol, dehydroacetic acid, sorbic acid, etc.

Examples of antioxidants include a sulfite, ascorbic acid, α-tocopherol, etc.

Furthermore, the compound of the present invention can be used in combination with drugs other than the compound of the present invention.

Examples of the drugs, which can be used in combination with the compound of the present invention (hereinafter sometimes simply referred to as concomitant drugs), include chemotherapeutic agents for treating cancer, hormonal therapeutic agents, immunotherapeutic agents, drugs for inhibiting the actions of cell growth factors and their receptors, etc. (hereinafter simply referred to as concomitant agents).

Examples of "chemotherapeutic agents" include alkylating agents, antimetabolites, anticancer antibiotics, anticancer agents derived from plants, etc.

Examples of "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, rnelphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin, etc.

Examples of "antimetabolites" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, etc.), aminopterin, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, etc.

Examples of "anticancer antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, etc.

Examples of "anticancer agents derived from plants" include etoposide, etoposide phosphate, vinblastine sulfate, vincristine sulfate, vindesine sulfate, teniposide, paclitaxel, docetaxel, vinorelbine, etc.

Examples of "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, etc.), pill dosage forms, mepitiostane, testrolactone, aminoglutethimide, LH-RH agonists (e.g., goserelin acetate, buserelin, leuprorelin, etc.), droloxifene, epitiostanol, ethinylestradiol sulfonate, aromatase inhibitors (e.g., fadrozole hydrochloride, anastrozole, retrozole, exemestane, vorozole, formestane, etc.), anti-androgens (e.g., flutamide, bicartamide, nilutamide, etc.), 5α-reductase inhibitors (e.g., finasteride, episteride, etc.), adrenocorticohormone drugs (e.g., dexamethasone, prednisolone, betamethasone, triamcinolone, etc.), androgen synthesis inhibitors (e.g., abiraterone, etc.), retinoid and drugs that retard retinoid metabolism (e.g., liarozole, etc.), and among others, LH-RH agonists (e.g., goserelin acetate, buserelin, leuprorelin, etc.) are preferable.

Examples of "immunotherapeutic agents (BRM)" include picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, etc.

The "cell growth factors" in the "drugs for inhibiting the actions of cell growth factors and their receptors" can be any substance so long as it is a material for stimulating the cell growth and, normally, peptides which have a molecular weight of 20,000 or less and bind to their receptors to exhibit the actions in a lower level can be used as the factors. Specific examples are (1) EGF (epidermal growth factor) or substances having substantially the same activity as EGF [e.g., EGF, hereglin, etc.], (2) insulin or substances having substantially the same activity as insulin [e.g., insulin, IGF (insulin-like growth factor)-1, IGF-2, etc.], (3) FGF (fibroblast growth factor) or substances having substantially the same activity as FGF [e.g., acidic FGF, basic FGF, KGF (keratinocyte growth factor), FGF-10, etc.], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), etc.] and the like.

The "receptors of the cell growth factors" can be any receptor as long as it is capable of binding to the cell growth factors described above, and specific examples are EGF receptor, hereglin receptor (HER2), insulin receptor, IGF receptor, FGF receptor-1 or FGF receptor-2, etc.

As the "agent inhibiting the effect of cell growth factor" includes HER2 antibody (trastuzumab (Herceptin (trademark)), etc.), imatinib mesylate, ZD1839 or EGFR antibody (cetuximab (Erbitux (trademark)), etc.), antibody against VEGF (e.g., Bevacizumab (Avastin (trademark))), VEGFR antibody, VEGFR inhibitor, EGFR inhibitor (erlotinib (Tarceva (trademark)), gefitinib (Iressa (trademark)), etc.)

In addition to the aforesaid agents, there are also used L-asparginase, aceglatone, procarbazine hydrochloride, protoporphyrin-cobalt complex, mercury-hematoporphyrin sodium, topoisomerase I inhibitor (e.g., Irinotecan, Topotecan, etc.), topoisomerase II inhibitor (e.g., Sobzoxan, etc.), differentiation-inducing agent (e.g., retinoid, vitamin D group, etc.), angiogenesis inhibitor (e.g., thalidomide, SU11248, etc.), α-blocker (e.g., tamsulosin hydrochloride, naftopidil, urapidil, alfuzosin, terazosin, prazosin, silodosin, etc.), serine-threonine kinase inhibitor, endothelin receptor antagonist (e.g., atrasentan, etc.), proteasome inhibitor (e.g., bortezomib, etc.), Hsp90 inhibitor (e.g., 17-AAG, etc.), spironolactone, minoxidil, 11α-hydroxyprogesterone, bone resorption inhibitor/bone metastasis suppressor (e.g., zoledronic acid, alendronic acid, pamidronic acid, etidronic acid, ibandronic acid, clodronic acid), etc.

The combined use of the compound of the present invention and a concomitant drug exhibits the following excellent effects.

(1) The dose can be reduced as compared to the dose when the compound of the present invention or a concomitant drug is administered alone.

(2) A drug concomitantly administered with the compound of the present invention can be chosen depending on the condition (mild, severe, etc.) of a patient.

(3) A concomitant drug, whose functional mechanism is different from that of the compound of the present invention, can be chosen so that a treatment period can be set longer.

(4) A concomitant drug, whose functional mechanism is different from that of the compound of the present invention, can be chosen so that sustained therapeutic effects can be achieved.

(5) A synergistic effect can be obtained by the concomitant use of the compound of the present invention and a concomitant drug.

In addition, the compound of the present invention can reduce values of testosterone to emasculate level immediately after medication. Thus when the concomitant drug such as LH-RH agonist (e.g., goserelin acetate, buserelin, leuprorelin, etc.; preferably leuprorelin) is used in combination with the compound of the present invention, the values of testosterone can be reduced to emasculate level immediately after medication of the compound of the present invention. Further, since the combined use of the concomitant drug such as LH-RH agonist (e.g., goserelin acetate, buserelin, leuprorelin, etc.; preferably leuprorelin) and the compound of the present invention results in prolonged preservation of hormone-dependent period, it can advantageously be used.

Hereinafter, the combined use of the compound of the present invention and the concomitant drug is referred to as "the combined preparation of the present invention."

When the combined preparation of the present invention is used, a dosing period of the compound of the present invention and the concomitant drug is not restricted; the compound of the present invention or its pharmaceutical composition and the concomitant drug or its pharmaceutical composition may be administered to the subject to be administered either simultaneously or at certain time intervals. The dose of the concomitant drug may be modified according to the dose used clinically and may be appropriately chosen depending upon subject to be administered, route for administration, disease, combination, etc.

A mode for administration of the combined preparation of the present invention is not particularly limited, but it is sufficient that the compound of the present invention is used in combination with the concomitant drug at the time of administration. For such mode of administration, there are, for example, (1) administration of a single dosage form obtained by mixing the compound of the present invention and the concomitant drug together at the same time, (2) simultaneous administration of two dosage forms prepared separately from the compound of the present invention and the concomitant drug through the same route for administration, (3) administration of two dosage forms prepared separately from the compound of the present invention and the concomitant drug at certain time intervals through the same route for administration, (4) simultaneous administration of two dosage forms prepared separately from the compound of the present invention and the concomitant drug through different routes for administration, (5) administration of two dosage forms prepared separately from the compound of the present invention and the concomitant drug at certain time intervals (e.g., administration of the compound of the present invention and the concomitant drug in this order, or administration in a reversed order) through different routes for administration, etc.

The combined preparation of the present invention is low toxic and thus can be safely administered orally or parenterally (e.g., topically, rectally, intravenously, etc.) in the form of pharmaceutical preparations such as tablets (including dragees and film-coated tablets), powdery dosage forms, granules, capsules (including soft capsules), liquid dosage forms, injections, suppositories, sustained release dosage forms, etc., which are obtained by mixing the compound of the present invention or (and) the concomitant drug described above with pharmacologically acceptable carriers by publicly known methods. Injectable dosage forms can be administered intravenously, intramuscularly or subcutaneously, into the organ, or directly at the focus.

Pharmacologically acceptable carriers, which may be used to manufacture the combined preparation of the present invention, include various organic or inorganic carrier substances conventionally used as materials for pharmaceutical preparations. These substances include, e.g., an excipient, a lubricant, a binder and a disintegrating agent in a solid dosage form, and a solvent, a dissolution aid, a suspending agent, an isotonizing agent, a buffer, a soothing agent, etc. in a liquid dosage form. In addition, conventional additives such as a preservative, an antioxidant, a colorant, a sweetener, an adsorbent, a wetting agent, etc. can be appropriately used in suitable amounts, if necessary.

Examples of excipients include lactose, saccharose, D-mannitol, starch, cornstarch, crystalline cellulose, light anhydrous silicic acid, etc.

Examples of lubricants include magnesium stearate, calcium stearate, talc, colloidal silica, etc.

Examples of binders include crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose, etc.

Examples of disintegrating agents include starch, carboxymethylcellulose, carboxymethylcellulose calcium, sodium carboxymethyl starch, L-hydroxypropylcellulose, etc.

Examples of solvents include water for injection, alcohol, propylene glycol, Macrogol, sesame oil, corn oil, olive oil, etc.

Examples of dissolution aids include polyethylene glycol, propylene glycol, D-mannitol, benzyl benzoate, ethanol, trisaminomethane, cholesterol, triethanolamine, sodium carbonate, sodium citrate, etc.

Examples of suspending agents include surfactants such as stearyltriethanolamine, sodium lauryl sulfate, lauryl aminopropionate, lecithin, benzalkonium chloride, benzethonium chloride, glycerin monostearate, etc.; hydrophilic polymers such as polyvinyl alcohol, polyvinyl pyrrolidone, sodium carboxymethylcellulose, methylcellulose, hydroxymethylcellulose, hydroxyethylcellulose, hydroxypropylcellulose, etc.

Examples of isotonizing agents include glucose, D-sorbitol, sodium chloride, glycerin, D-mannitol, etc.

Examples of buffers include buffering solutions of a phosphate, acetate, carbonate, citrate, etc.

Examples of soothing agents include benzyl alcohol, etc.

Examples of preservatives include p-hydroxybenzoates, chlorobutanol, benzyl alcohol, phenethyl alcohol, dehydroacetic acid, sorbic acid, etc.

Examples of antioxidants include a sulfite, ascorbic acid, α-tocopherol, etc.

In the combined preparation of the present invention, a ratio of the compound of the present invention to the concomitant drug can be appropriately chosen depending upon subject to be administered, route for administration, disease, etc.

For example, the amount of the compound of the present invention contained in the combined preparation of the present invention varies depending on the dosage form of the preparation, but is usually about 0.01 to 100% by weight, preferably about 0.1 to 50% by weight, and more preferably about 0.5 to 20% by weight, based on the total weight of the preparation.

The amount of the concomitant drug contained in the combined preparation of the present invention varies depending on the dosage form of the preparation, but is usually about 0.01 to 100% by weight, preferably about 0.1 to 50% by weight, and more preferably about 0.5 to 20% by weight, based on the total weight of the preparation.

The amount of additives such as a carrier, etc. contained in the combined preparation of the present invention varies depending on the dosage form of the preparation, and is usually about 1 to 99.99% by weight, preferably about 10 to 90% by weight, based on the total weight of the preparation.

These amounts may be the same, also when the compound of the present invention and the concomitant drug are separately prepared, respectively.

These preparations can be manufactured by per se publicly known methods conventionally used in general.

For example, the compound of the present invention or the concomitant drug can be prepared into an injectable dosage form by formulating with a dispersing agent (e.g., Tween 80 (manufactured by Atlas Powder Company, USA), HCO 60 (manufactured by Nikko Chemicals Co., Ltd.), polyethylene glycol, carboxymethyl cellulose, sodium alginate, hydroxypropylmethyl cellulose, dextrin, etc.), a stabilizer (e.g., ascorbic acid, sodium pyrosulfite), a surfactant (e.g., polysorbate 80, macrogol, etc.), a solubilizing agent (e.g., glycerin, ethanol, etc.), a buffering agent (e.g., phosphoric acid or its alkali metal salt, citric acid or its alkali metal salt, etc.), an isotonizing agent (e.g., sodium chloride, potassium chloride, mannitol, sorbitol, glucose, etc.), a pH adjusting agent (e.g., hydrochloric acid, sodium hydroxide, etc.), a preservative (e.g., ethyl p-oxybenzoate, benzoic acid, methylparabene, propylparabene, benzyl alcohol, etc.), a solubilizer (e.g., concentrated glycerin, meglumine, etc.), a dissolution aid (e.g., propylene glycol, saccharose, etc.), a soothing agent (e.g., glucose, benzyl alcohol, etc.), to prepare into aqueous injection; or by dissolving, suspending, or emulsifying with a vegetable oil such as olive oil, sesame oil, cottonseed oil, corn oil, etc., a dissolution aid such as propylene glycol or the like to prepare into an oily injection.

An oral dosage form can be produced in a conventional manner by adding to the compound of the present invention or the concomitant drug, for example, an excipient (e.g., lactose, saccharose, starch, etc.), a disintegrating agent (e.g., starch, calcium carbonate, etc.), a binder (e.g., starch, gum arabic, carboxymethyl cellulose, polyvinylpyrrolidone, hydroxypropyl cellulose, etc.), a lubricant (e.g., talc, magnesium stearate, polyethylene glycol 6000, etc.) and other additives, compressing the resulting mixture and, if necessary, coating the compressed product for the purpose of taste masking, enteric degradation or sustained release by techniques per se publicly known. Coating agents for this purpose include, for example, hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (manufactured by Rohm Company, Germany, methacrylic acid/acrylic acid copolymer) and dyes (e.g., iron oxide, titanium dioxide). The oral dosage form may be either an immediate release dosage form or a sustained release dosage form.

For example, in a suppository, the compound of the present invention or the concomitant drug is prepared into an oily or aqueous solid, semi-solid or liquid composition by techniques per se publicly known. Oily bases used for the composition described above include glycerides of higher fatty acids [e.g., cacao butter, uitepsols (manufactured by Dynamite Nobel Company, Germany), etc.], moderate fatty acids [e.g., miglyols (manufactured by Dynamite Nobel Company, Germany), etc.], vegetable oils (e.g., sesame oil, soybean oil, cottonseed oil, etc.), and the like. Aqueous bases include, for example, polyethylene glycols and propylene glycol. Bases for aqueous gels include, for example, natural rubbers, cellulose derivatives, vinyl polymers, acrylic polymers, etc.

Examples of the sustained release dosage form above include sustained release microcapsules, and the like.

Sustained release microcapsules can be obtained by per se publicly known methods, and are preferably prepared in the form of, e.g., a sustained release dosage form by the method [2] shown below and administered.

Preferably, the compound of the present invention is prepared into a dosage form for oral administration such as a solid dosage form (e.g., powdery dosage form, granules, tablets, capsules) or into a dosage form for rectal administration such as a suppository, etc. A dosage form for oral administration is particularly preferred.

The concomitant drug can be prepared into the dosage form described above, depending on the kind of drug.

Hereinafter, [1] an injectable preparation of the compound of the present invention or the concomitant drug and its production, [2] a sustained release or immediate release preparation of the compound of the present invention or the concomitant drug and its production and [3] a sublingual, buccal or rapid oral disintegrating preparations of the compound of the present invention or the concomitant drug and its production will be specifically described.

[1] Injectable Preparation and its Production

An injectable preparation obtained by dissolving the compound of the present invention or the concomitant drug in water is preferred. The injectable preparation may contain a benzoate and/or a salicylate.

The injectable preparation is obtained by dissolving the compound of the present invention or the concomitant drug and optionally a benzoate and/or a salicylate in water.

Examples of the benzoate and/or salicylate described above include an alkali metal salt such as sodium and potassium salts, etc., an alkaline earth metal salt such as calcium and magnesium salts, etc., an ammonium salt, a meglumine salt, a salt of an organic acid such as trometamol, and the like.

The concentration of the compound of the present invention or the concomitant drug in the injectable preparation is about 0.05 to 50 w/v %, preferably about 0.3 to 20 w/v %. The concentration of the benzoate and/or salicylate is 0.5 to 50 w/v %, preferably 3 to 20 w/v %.

Furthermore, additives generally used in an injectable preparation such as a stabilizer (ascorbic acid, sodium pyrosulfite, etc.), a surfactant (polysorbate 80, macrogol, etc.), a solubilizing agent (glycerin, ethanol, etc.), a buffering agent (phosphoric acid and its alkali metal salt, citric acid and its alkali metal salt, etc.), an isotonizing agent (sodium chloride, potassium chloride, etc.), a dispersing agent (hydroxypropylmethyl cellulose, dextrin), a pH adjusting agent (hydrochloric acid, sodium hydroxide, etc.), a preservative (ethyl p-oxybenzoate, benzoic acid, etc.), a solubilizer (concentrated glycerin, meglumine, etc.), a dissolution aid (propylene glycol, saccharose, etc.), a soothing agent (glucose, benzyl alcohol, etc.) are appropriately added to the preparation. Any of these additives is added in an amount generally used in an injectable preparation.

The injectable preparation is adjusted to pH of 2 to 12, preferably 2.5 to 8.0 by adding a pH adjusting agent.

The injectable preparation is obtained by dissolving both the compound of the present invention or the concomitant drug and optionally a benzoate and/or salicylate, and, if necessary, the above additives in water. These components may be dissolved in any order according to the same manner as in a conventional injectable preparation.

An aqueous solution for injection is preferably warmed, and used as an injectable preparation after sterilization by filtration or autoclaved as in a conventional injectable preparation to provide for an injectable preparation.

An aqueous injectable preparation is preferably autoclaved, e.g., at 100 to 121° C. for 5 to 30 minutes.

Moreover, the preparation may be in a solution form to which antibacterial activity is imparted to be usable as a multiple dosage form in divided dosing.

[2] Sustained Release or Immediate Release Preparation and its Production

A preferred sustained release preparation comprises a core comprising the compound of the present invention or the concomitant drug, which is optionally coated with a water-insoluble material or a swelling polymer. For example, a sustained release preparation for oral administration of a once-daily dosage form is preferred.

Examples of the water-insoluble material used for the coating agent include cellulose ethers such as ethyl cellulose, butyl cellulose, etc., cellulose esters such as cellulose acetate, cellulose propionate, etc., polyvinyl esters such as polyvinyl acetate, polyvinyl butyrate, etc., acrylic acid polymers such as an acrylic acid/methacrylic acid copolymer, a methyl methacrylate copolymer, an ethoxyethyl methacrylate/cinnamoethyl methacrylate/aminoalkyl methacrylate copolymer, a polyacrylic acid, a polymethacrylic acid, a methacrylic acid alkylamide copolymer, a poly(methyl methacrylate), a polymethacrylate, an aminoalkyl methacrylate copolymer, a poly(methacrylic anhydride), a glycidyl methacrylate copolymer, in particular, a series of Eudragits (Rohm & Pharma) such as Eudragit RS-100, RL-100, RS-30D, RL-30D, RL-PO and RS-PO (ethyl acrylate/methyl methacrylate/chlorotrimethyl methacrylate/ethyl ammonium copolymer) and Eudragit NE-30D (methyl methacrylate/ethyl acrylate copolymer), etc., hydrogenated oils such as hydrogenated castor oil (e.g., LUBRI WAX (Freund Industrial Co., Ltd.), etc.), waxes such as carnauba wax, a fatty acid glycerin ester, paraffin, etc., polyglycerin fatty acid esters, etc.

The swelling polymer is preferably a polymer having an acidic removable group and exhibiting pH-dependent swelling, and a polymer having an acidic removable group, which undergoes a less swelling at an acidic pH such as in the stomach but is swollen extensively at a neutral pH such as in the small and large intestines, is preferred.

Examples of such a polymer having an acidic removable group and exhibiting pH-dependent swelling include a crosslinked polyacrylic acid polymer such as Carbomers 934P, 940, 941, 974P, 980, 1342, etc., polycarbophil and calcium polycarbophil (all manufactured by BF Goodrich Chemicals), Hivis Wakos 103, 104, 105 and 304 (all manufactured by Wako Pure Chemical Industries, Ltd.), etc.

The coating agent used in the sustained release preparation may further contain a hydrophilic material.

Examples of the hydrophilic material include a polysaccharide which may have a sulfate group, such as pullulan, dextrin, alkali metal alginates, etc., a polysaccharide having a hydroxyalkyl group or a carboxyalkyl group such as hydroxypropyl cellulose, hydroxypropylmethyl cellulose, sodium carboxymethylcellulose, etc., methyl cellulose, polyvinyl pyrrolidone, polyvinyl alcohol, polyethylene glycol, etc.

The amount of the water-insoluble material contained in the coating agent of the sustained release preparation is about 30 to about 90% (w/w), preferably about 35 to about 80% (w/w), more preferably about 40 to about 75% (w/w), and the swelling polymer content is about 3 to about 30% (w/w), preferably about 3 to about 15% (w/w). The coating agent may further contain a hydrophilic material, and the amount of the hydrophilic material contained in the coating agent is about 50% (w/w) or less, preferably about 5 to about 40% (w/w), more preferably about 5 to about 35% (w/w). As used herein, the % (w/w) above is used to mean a % by weight based on the coating agent composition, which is the remainder of the coating agent solution after removing any solvent (e.g., water, a lower alcohol such as methanol, ethanol, etc.).

The sustained release preparation is manufactured by preparing a core containing a drug as illustrated below, followed by coating the resulting core with a coating agent solution obtained by heat-melting a water-insoluble material or a swelling polymer or by dissolving or dispersing such a material in a solvent.

I. Production of Drug-Containing Core

The shape of a core containing a drug to be coated with a coating agent (hereinafter sometimes simply referred to as a core) is not specifically limited but preferably prepared into a particulate shape such as granules, fine granules, or the like.

When the core is granules or fine granules, they have a mean particle size of preferably about 150 to about 2,000 µm, more preferably about 500 to about 1,400 µm.

The core can be prepared in a conventional manner. For example, a drug is mixed with a suitable excipient, binder, disintegrating agent, lubricant, stabilizer, etc., and then subjected to wet extrusion granulation, fluidized bed granulation, or the like.

The drug content in the core is about 0.5 to about 95% (w/w), preferably about 5.0 to about 80% (w/w), more preferably about 30 to about 70% (w/w).

Examples of the excipient contained in the core include a saccharide such as saccharose, lactose, mannitol, glucose, etc., starch, crystalline cellulose, calcium phosphate, cornstarch, etc. Among others, crystalline cellulose and cornstarch are preferred.

Examples of the binder used include polyvinyl alcohol, hydroxypropyl cellulose, polyethylene glycol, polyvinyl pyrrolidone, Pluronic F68, gum arabic, gelatin, starch, etc. Examples of the disintegrating agent include calcium carboxymethyl cellulose (ECG505), sodium croscarmellose (Ac-Di-Sol), crosslinked polyvinyl pyrrolidone (crospovidone), low substituted hydroxypropyl cellulose (L-HPC), etc. Among others, hydroxypropyl cellulose, polyvinyl pyrrolidone and low substituted hydroxypropyl cellulose are preferred. Examples of the lubricant and the anticoagulant include talc, magnesium stearate and its inorganic salts, and examples of the lubricant include polyethylene glycol, etc. Examples of the stabilizer include an acid such as tartaric acid, citric acid, succinic acid, fumaric acid, maleic acid, etc.

In addition to the technique described above, the core can be prepared by using other techniques such as an tumbling granulation technique, a pan coating technique, a fluidized bed coating technique and a melt granulation technique, wherein a drug or a mixture of the drug with an excipient, a lubricant, etc. is portionwise added to inert carrier particles as seeds for the core with spraying a binder dissolved in a suitable solvent such as water, a lower alcohol (e.g., methanol, ethanol, etc.) or the like. Examples of the inert carrier particles include those prepared from saccharose, lactose, starch, crystalline cellulose and waxes, and, preferably, these carriers have a mean particle size of about 100 µm to about 1,500 µm.

In order to separate the drug contained in the core from a coating agent, the surface of the core may be covered with a protective material. Examples of the protective material include the hydrophilic material described above and water-insoluble material. The preferred protective material is polyethylene glycol or a polysaccharide having a hydroxyalkyl group or a carboxyalkyl group, more preferably, hydroxypropylmethyl cellulose and hydroxypropyl cellulose. The protective material may contain, as a stabilizer, an acid such as tartaric acid, citric acid, succinic acid, fumaric acid, maleic acid, etc., and a lubricant such as talc. When the protective material is used, the amount thereof to be coated is about 1 to about 15% (w/w), preferably about 1 to about 10% (w/w), more preferably about 2 to about 8% (w/w) based on the core.

The protective material can be coated by a conventional coating method and specifically, the core is spray-coated with the protective material by a fluidized bed coating technique, a pan coating technique, etc.

II. Coating of Core with Coating Agent

The core obtained in I above is coated with a coating agent solution prepared by melt-heating the water-insoluble material and pH-dependent swelling polymer described above and a hydrophilic material or by dissolving or dispersing them in a solvent to obtain a sustained release preparation.

As a coating method of the core with the coating agent solution, there are, for example, spray-coating, etc.

The composition ratio of the water-insoluble material, swelling polymer and hydrophilic material in the coating agent solution can be appropriately chosen to be within the amounts of the respective components contained in the coating.

The amount of the coating agent is about 1 to about 90% (w/w), preferably about 5 to about 50% (w/w), more preferably about 5 to about 35% (w/w) based on the core (excluding the protective material coating).

As the solvent for the coating agent solution, water and an organic solvent can be used singly or as a mixture thereof. When a mixture is used, the ratio of water and the organic solvent (water/organic solvent: a weight ratio) may vary with the range of 1 to 100%, and is preferably 1 to about 30%. The organic solvent is not particularly limited so far as it can dissolve the water-insoluble material, and examples of the solvent include a lower alcohol such as methyl alcohol, ethyl alcohol, isopropyl alcohol, n-butyl alcohol, etc., a lower alkanone such as acetone, acetonitrile, chloroform, methylene chloride, etc. In particular, a lower alcohol is preferred, with ethyl alcohol and isopropyl alcohol being more preferred. Water and a mixture of water and an organic solvent are used preferably as solvents for the coating agent solution. In this case, an acid such as tartaric acid, citric acid, succinic acid, fumaric acid, maleic acid, etc. may be added to the coating agent solution, if necessary, for the purpose of stabilizing the coating agent solution.

To carry out the coating through spray coating, the coating can be made using a conventional coating method. Specifically, the core is sprayed with a coating agent solution by a fluidized bed coating technique, a pan coating technique, or the like. At this time, a lubricant such as talc, titanium oxide, magnesium stearate, calcium stearate, light silicic anhydride, etc., and a plasticizer such as glycerin fatty ester, hardened castor oil, triethyl citrate, cetyl alcohol, stearyl alcohol, etc. may also be added.

After coating with a coating agent, an antistatic agent such as talc may also be admixed, if necessary.

The immediate release preparation may be a liquid (solution, suspension, emulsion, etc.) or a solid (particles, pills, tablets, etc.). An oral preparation and a parenteral preparation such as an injectable preparation may be used, and an oral preparation is preferred.

The immediate release preparation may usually contain a carrier, additives and an excipient (hereinafter sometimes abbreviated as excipients) which are conventionally used in the pharmaceutical field, in addition to a drug which is an active ingredient. The pharmaceutical excipients are not specifically limited so long as they are excipients conventionally used in the pharmaceutical field. Examples of the excipient for an oral solid preparation include lactose, starch, corn starch, crystalline cellulose (Avicel PH101, manufactured by Asahi Kasei Corporation, etc.), powdered sugar, granulated sugar, mannitol, light silicic anhydride, magnesium carbonate, calcium carbonate, L-cysteine, etc., with corn starch and mannitol being preferred. Any of these excipients may be employed alone or in combination with each other. The amounts of the excipients are, for example, about 4.5 to about 99.4 w/w %, preferably about 20 to about 98.5 w/w %, more preferably about 30 to about 97 w/w %, based on the total weight of the immediate release preparation. The content of drug in the immediate release preparation may appropriately be selected from the range of about 0.5% to about 95%, preferably about 1% to about 60% to the whole amount of the immediate release preparation.

When the immediate release preparation is an oral solid preparation, the preparation contains a disintegrating agent in addition to the components described above. Examples of the disintegrating agent include calcium carboxymethylcellulose (ECG505 manufactured by GOTOKU CHEMICAL Co., Ltd.), sodium croscarmellose (for example, Ac-Di-Sol manufactured by Asahi Kasei Corporation), crospovidone (for example, COLIDON CL manufactured by BASF), low-substituted hydroxypropyl cellulose (Shin-Etsu chemical Co., Ltd.), carboxymethyl starch (MATSUTANI CHEMICAL INDUSTRY Co., Ltd.), sodium carboxymethyl starch (EX-ORITAB manufactured by KIMURA SANGYO), partial α starch (PCS manufactured by Asahi Kasei Corporation), etc. For example, the disintegrating agent that disintegrates granules by water absorption or swelling upon contact with water, or forming a channel between the active component comprising the core and an excipient can be used. Any of these disintegrating agents can be used alone or in combination with each other. The amount of the disintegrating agent used may be appropriately chosen depending upon the type and the amount of the drug used or a particular preparation design for the intended release performance. For example, the amount is about 0.05 to about 30 w/w %, preferably about 0.5 to about 15 w/w % based on the total weight of the immediate release preparation.

When the immediate release preparation is an oral solid preparation, the oral solid preparation may optionally contain additives conventionally used in a solid preparation, in addition to the components described above. Examples of the additives include binders (for example, sucrose, gelatin, powdery gum arabic, methyl cellulose, hydroxypropyl cellulose, hydroxypropylmethyl cellulose, carboxymethylcellulose, polyvinyl pyrrolidone, pullran, dextrin, etc.), lubricants (polyethylene glycol, magnesium stearate, talc, light silicic anhydride (for example, aerosil (NIPPON AEROSIL)), surfactants (for example, anionic surfactants such as sodium alkyl sulfate, nonionic surfactants such as polyoxyethylene fatty ester, polyoxyethylene sorbitan fatty ester, polyoxyethylene castor oil derivatives, etc.), colorants (for example, tar colorants, caramel, colcothar, titanium oxide, riboflavins), if necessary, corrigents (for example, sweeteners, flavors, etc.), adsorbents, preservatives, wetting agents, antistatic agents, etc. Furthermore, an organic acid such as tartaric acid, citric acid, succinic acid, fumaric acid or the like can also be added as a stabilizer.

As the binder above, hydroxypropyl cellulose, polyethylene glycol and polyvinyl pyrrolidone, etc. are preferably used.

The immediate release preparation can be prepared by mixing the components described above and kneading the mixture, if necessary, and then molding according to a conventional technique for making pharmaceutical preparations. The mixing above can be carried out in a conventional manner, e.g., by mixing, kneading, etc. Specifically, where the immediate release preparation is in the form of particles, the preparation can be prepared by mixing components with a vertical granulator, a multi-purpose kneader (manufactured by HATA IRON WORKS CO., LTD), a fluidized bed granulator FD-5S (manufactured by POWREX CORPORATION) or thee like, and then granulating the resulting by wet extrusion granulation or fluidized bed granulation by a technique similar to that for preparing the core of the sustained release preparation described above.

The immediate release preparation and the sustained release preparation thus obtained can be compounded, as they are, or, together with appropriate pharmaceutical excipients, in pharmaceutical preparations separately in a conventional manner to prepare respective preparations for administering in combination with each other simultaneously or at certain time intervals. Alternatively, both preparations may be compounded in a single dosage form for oral administration (e.g., granules, fine granules, tablets, capsules) as they are, or, together with appropriate pharmaceutical excipients. Both preparations in the form of granules or fine granules may also be filled in a single capsule for oral administration.

[3] Sublingual, Buccal or Rapid Oral Disintegrating Preparation and its Production A sublingual, buccal or rapid oral disintegrating preparation may be in the form of a solid preparation such as a tablet, or may be in the form of an oral mucosal patch (film) or oral disintegrating film.

The sublingual, buccal or rapid oral disintegrating preparation is preferably a preparation containing the compound of the present invention or the concomitant drug and an excipient. The preparation may also contain auxiliary agents such as a lubricant, an isotonizing agent, a hydrophilic carrier, a water-dispersible polymer, a stabilizer, etc. Further for the purpose of promoting the absorption and enhancing the bioavailability, the preparation may also contain β-cyclodextrin or β-cyclodextrin derivatives (e.g., hydroxypropyl-β-cyclodextrin, etc.), and the like.

Examples of the above excipient include lactose, saccharose, D-mannitol, starch, crystalline cellulose, light silicic anhydride, etc. Examples of the lubricant include magnesium stearate, calcium stearate, talc, colloidal silica, etc., with magnesium stearate and colloidal silica being preferred. Examples of the isotonizing agent include sodium chloride, glucose, fructose, mannitol, sorbitol, lactose, saccharose, glycerin and urea, with mannitol being particularly preferred. As the hydrophilic carrier, there are, for example, a swelling hydrophilic carrier such as crystalline cellulose, ethyl cellulose, crosslinked polyvinyl pyrrolidone, light silicic anhydride, silicic acid, dicalcium phosphate, calcium carbonate, etc., with crystalline cellulose (e.g., microcrystalline cellulose, etc.) being preferred. As the water-dispersible polymer, there are, for example, a gum (e.g., tragacanth gum, acacia gum, guar gum), alginate (e.g., sodium alginate), cellulose derivatives (e.g., methyl cellulose, carboxymethylcellulose, hydroxymethyl cellulose, hydroxypropyl cellulose, hydroxypropylmethyl cellulose), gelatin, water-soluble starch, polyacrylic acid (e.g., carbomer), polymethacrylic acid, polyvinyl alcohol, polyethylene glycol, polyvinyl pyrrolidone, polycarbophil, ascorbate palmitate salt, etc., with hydroxypropylmethyl cellulose, polyacrylic acid, alginate, gelatin, carboxymethylcellulose, polyvinyl pyrrolidone and polyethylene glycol being preferred. Hydroxypropylmethyl cellulose is particularly preferred. As the stabilizer, there are, for example, cysteine, thiosorbitol, tartatic acid, citric acid, sodium carbonate, ascrobic acid, glycine, sodium sulfite, etc., with citric acid and ascorbic acid being particularly preferred.

The sublingual, buccal or rapid oral disintegrating preparation can be prepared by mixing the compound of the present invention or the concomitant drug and an excipient by a method per se known. Furthermore, if desired, the auxiliary agents described above, such as the lubricant, isotonizing agent, hydrophilic carrier, water-dispersible polymer, stabilizer, colorant, sweetener, preservative, etc. may also be admixed. After mixing the components described above simultaneously or at certain time intervals, the mixture is compressed into tablets to obtain the sublingual, buccal or rapid oral disintegration tablet. In order to obtain a suitable hardness, a solvent such as water, an alcohol, etc. can be used to moisturize or wet the components before or after tabletting, followed by drying.

In preparing the oral mucosal patch (film), the compound of the present invention or the concomitant drug and the water-dispersible polymer (preferably, hydroxypropyl cellulose, hydroxypropylmethyl cellulose), excipient, etc. described above are dissolved in a solvent such as water, etc. and then the resulting solution is cast into a film. In addition, additives such as a plasticizer, a stabilizer, an antioxidant, a preservative, a colorant, a buffering agent, a sweeteners, etc. may be added to the preparation. A glycol such as polyethylene glycol, propylene glycol, etc. may be added to impart an appropriate elasticity to a film, and a bioadhesive polymer (e.g., polycarbophile, carbopol) may also be added to enhance the adhesion of the film to the oral mucosal lining. The casting can be carried out by pouring a solution onto a non-adhesive surface, spreading the solution using a coater such as a doctor blade in a uniform thickness (preferably, approximately 10 to 1000 microns), and then drying the solution to form a film. The film thus formed is dried at room temperature or while warming, and then cut into pieces each having a desired surface area.

A preferred rapid oral disintegrating preparation is, for example, a rapid diffusion preparation in a solid network form, which comprises the compound of the present invention or the concomitant drug and a water-soluble or water-diffusible carrier inert to the compound of the present invention or the concomitant drug. The network is formed by sublimating a solvent from the solid composition comprising a solution of the compound of the present invention or the concomitant drug in a suitable solvent.

In addition to the compound of the present invention or the concomitant drug, the composition of the rapid oral disintegrating preparation may preferably contain a matrix-forming agent and secondary components.

Examples of the matrix-forming agent include gelatins, dextrins and animal or vegetable proteins from soybean, wheat, psyllium seed, etc.; gummy materials such as gum arabic, guar gum, agar, xanthane gum, etc.; polysaccharides; alginates; carboxymethylcelluloses; carrageenans; dextrans; pectins; synthetic polymers such as polyvinyl pyrrolidones; materials derived from gelatin-gum arabic complexes, etc. The matrix-forming agent further includes saccharides such as mannitol, dextrose, lactose, galactose, trehalose, etc.; cyclic saccharides such as cyclodextrins, etc.; inorganic salts such as sodium phosphate, sodium chloride, aluminum silicate, etc.; amino acids having 2 to 12 carbon atoms such as glycine, L-alanine, L-aspartic acid, L-glutamic acid, L-hydroxyproline, L-isoleucine, L-leucine, L-phenylalanine, etc.

One or more matrix-forming agents can be incorporated into a solution or suspension before solidification. The matrix-forming agents may be present in addition to a surfactant, or may be present in the absence of a surfactant. The matrix-forming agents serve not only to form a matrix itself, but also assist to maintain diffusion of the compound of the present invention or the concomitant drug in the solution or suspension.

The composition may contain a secondary component such as a preservative, an antioxidant, a surfactant, a thickening agent, a colorant, pH adjusting agent, a flavor, a sweetener, a taste masking agent, etc. As the suitable colorant, there are, for example, iron oxide red, black and yellow, FD & C dyes available from EMS & EVERALD such as FD & C Blue No. 2 and FD & C Red No. 40, etc. Examples of the suitable flavor include mint, raspberry, licorice, orange, lemon, grape fruit, caramel, vanilla, cherry, grape flavor and a combination thereof. Examples of the suitable pH adjusting agent include citric acid, tartaric acid, phosphoric acid, hydrochloric acid and maleic acid. Examples of the suitable sweetener include aspartame, acesulfame K and thaumatine. Examples of the suitable taste masking agent include sodium bicarbonate, ion exchange resins, cyclodextrin inclusion compounds, adsorbents and microencapsulated apomorphine.

The preparation generally contains the compound of the present invention or the concomitant drug in an amount of about 0.1 to about 50% by weight, preferably about 0.1 to about 30% by weight and, preferably, the preparation (the sublingual tablet, buccal, etc. described above) allows 90% or more of the compound of the present invention or the concomitant drug to be dissolved (in water) within a time period of about 1 to about 60 minutes, preferably about 1 minute to about 15 minutes, more preferably about 2 minutes to about 5 minutes, or is a rapid oral disintegrating preparation which disintegrates within about 1 to about 60 seconds, preferably about 1 to about 30 seconds, more preferably about 1 to about 10 seconds, after being placed in the oral cavity.

The amount of the above excipient is about 10 to about 99% by weight, preferably about 30 to about 90% by weight based on the total weight of the preparation. The amount of β-cyclodextrin or β-cyclodextrin derivative is about 0 to about 30% by weight based on the total weight of the preparation. The amount of the lubricant is about 0.01 to about 10% by weight, preferably about 1 to about 5% by weight based on the total weight of the preparation. The amount of the isotonizing agent is about 0.1 to about 90% by weight, preferably about 10 to about 70% by weight based on the total weight of the preparation. The amount of the hydrophilic carrier is about 0.1 to about 50% by weight, preferably about 10 to about 30% by weight based on the total weight of the preparation. The amount of the water-dispersible polymer is about 0.1 to about 30% by weight, preferably about 10 to about 25% by weight based on the total weight of the preparation. The amount of the stabilizer is about 0.1 to about 10% by weight, preferably about 1 to about 5% by weight based on the total weight of the preparation. If necessary, the preparation described above may further contain additives such as a colorant, a sweetener, a preservative, etc.

A dose of the combined preparations of the present invention varies depending upon kind of the compound of the present invention, age, body weight, conditions, dosage form, route for administration, dosing period, etc.

A dose of the compound of the present invention may vary depending upon subject to be administered, target organ, conditions, route of administration, etc., and in oral administration, the compound is generally administered to the patient (as 60 kg body weight) with cancer in a daily dose of about 0.01 to about 100 mg, preferably about 0.1 to about 50 mg and more preferably about 0.1 to about 20 mg. In parenteral administration, a single dose of the compound may vary depending upon subject to be administered, target organ, conditions, route of administration, etc., and in the form of an injectable dosage form, it is advantageous to intravenously administer the compound to the patient (as 60 kg body weight) with cancer generally in a daily dose of about 0.001 to about 30 mg, preferably about 0.01 to about 20 mg, and more preferably about 0.01 to about 10 mg. For other animal species, the corresponding dose as converted per 60 kg weight can be administered. Of course, the dose may vary depending on individual conditions as described above; in such a case, a dose less than the dose given above may be sufficient, or a dose higher than the range above may be used.

It is possible to set any range of a dose for the concomitant drug, so long as it causes no adverse side effects. A daily dose of the concomitant drug may vary depending on the severity of disease, the age, sex, body weight and susceptibility of the subject, dosing period and intervals, characteristics, formulation, type and active components of the pharmaceutical preparation, etc. and is not particularly limited. For example, in oral administration, the dose is about 0.001 to 2000 mg, preferably about 0.01 to 500 mg, and more preferably about 0.1 to 100 mg per kg body weight of mammals in terms of a drug; usually, this dose is administered by dividing 1 to 4 times per day.

When the pharmaceutical preparations of the present invention are administered, they may be administered concomitantly. Alternatively, the concomitant drug is first administered and then the compound of the present invention is administered, or the compound of the present invention is first administered and then the concomitant drug is administered. When they are administered at certain time intervals, the intervals vary depending on the active component to be administered, dosage form and route of administration; for example, when the concomitant drug is first administered, the compound of the present invention may be administered within 1 minute to 3 days, preferably 10 minutes to 1 day, more preferably 15 minutes to 1 hour after the administration of the concomitant drug. When the compound of the present invention is first administered, the concomitant drug may be administered within 1 minute to 1 day, preferably 10 minutes to 6 hours, more preferably 15 minutes to 1 hour after the administration of the compound of the present invention.

As a preferred method of administration, for example, about 0.001 to 200 mg/kg of the concomitant drug in the form of an oral dosage preparation is administered orally and, after about 15 minutes, about 0.005 to 0.5 mg/kg of the compound of the present invention in the form of a parenteral preparation is administered parenterally as a daily dose.

As the metastins, there are used, for example, human metastin described in WO 00/24890, mouse or rat metastin described in WO 01/75104, etc.

Specific examples of human metastin include a peptide comprising the N-terminal 47th-54th amino acid sequence in the amino acid sequence represented by SEQ ID NO: 1 and consisting of 8 to 54 amino acid residues, and the like.

The "peptide comprising the N-terminal 47th-54th amino acid sequence in the amino acid sequence represented by SEQ ID NO: 1 and consisting of 8 to 54 amino acid residues" may be any peptide, as far as it is a peptide comprising the N-terminal 47th-54th amino acid sequence in the amino acid sequence represented by SEQ ID NO: 1 and consisting of 8 to 54 amino acid residues, but means that these peptides have substantially the same physiological activity (e.g., a receptor binding activity, a signal transduction action, a sugar level elevating action, a pancreatic glucagon secretion stimulating action, a urine formation promoting action, etc.). Specifically, there are used (i) a peptide having the amino acid sequence represented by SEQ ID NO: 1, (ii) a peptide comprising the N-terminal 47th-54th amino acid sequence at the C terminus in the amino acid sequence represented by SEQ ID NO: 1 and consisting of 8 to 15 amino acid residues, etc.

More specifically, human metastin used includes (i) a peptide consisting of the amino acid sequence represented by SEQ ID NO: 1 (human metastin 54 (1-54)), (ii) a peptide consisting of the N-terminal 40th-54th amino acid sequence in the amino acid sequence represented by SEQ ID NO: 1 (human metastin 15 (40-54); SEQ ID NO: 15), (iii) a peptide consisting of the N-terminal 45th-54th amino acid sequence in the amino acid sequence represented by SEQ ID NO: 1 (human metastin 10 (45-54); SEQ ID NO: 16), (iv) a peptide consisting of the N-terminal 46th-54th amino acid sequence in the amino acid sequence represented by SEQ ID NO: 1 (human metastin 9 (46-54); SEQ ID NO: 17), (v) a peptide consisting of the N-terminal 47th-54th amino acid sequence in the amino acid sequence represented by SEQ ID NO: 1 (human metastin 8 (47-54); SEQ ID NO: 18), etc.

As mouse metastin (A), there are used, for example, (i) a peptide comprising the N-terminal 134th-141st amino acid sequence in the amino acid sequence represented by SEQ ID NO: 3 and consisting of 8 to 52 amino acid residues. Specific examples of mouse metastin (A) used include (i) a peptide consisting of the N-terminal 90th-141st amino acid sequence in the amino acid sequence represented by SEQ ID NO: 3, (ii) a peptide consisting of the N-terminal 132nd-141st amino acid sequence in the amino acid sequence represented by SEQ ID NO: 3, (iii) a peptide consisting of the N-terminal 127th-141st amino acid sequence in the amino acid sequence represented by SEQ ID NO: 3, and the like.

As mouse metastin (B), there are used, for example, (i) a peptide comprising the N-terminal 138th-145th amino acid sequence in the amino acid sequence represented by SEQ ID NO: 5 and consisting of 8 to 52 amino acid residues. Specific examples of mouse metastin (B) used include a peptide consisting of the N-terminal 94th-145th amino acid sequence in the amino acid sequence represented by SEQ ID NO: 5, and the like. As rat metastin, there are used, for example, (i) a peptide comprising the N-terminal 112th-119th amino acid sequence in the amino acid sequence represented by SEQ ID NO: 7 and consisting of 8 to 52 amino acid residues. Specific examples of rat metastin used include (i) a peptide consisting of the N-terminal 68th-119th amino acid sequence in the amino acid sequence represented by SEQ ID NO: 7, (ii) a peptide consisting of the N-terminal 110th-119th amino acid sequence in the amino acid sequence represented by SEQ ID NO: 7, (iii) a peptide consisting of the N-terminal 105th-119th amino acid sequence in the amino acid sequence represented by SEQ ID NO: 7, and the like.

Throughout the specification, the metastins are represented in accordance with the conventional way of describing peptides, that is, the N-terminus (amino terminus) at the left hand and the C-terminus (carboxyl terminus) at the right hand. In the peptide represented by SEQ ID NO: 1, the C-terminus may be in any form of a carboxyl group (—COOH), a carboxylate (—COO$^-$), an amide (—CONH$_2$) and an ester (—COOR). Herein, examples of R of the ester group or alkyl amide include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, benzhydryl, etc., or an α-naphthyl-$C_{1-2}$ alkyl group such as α-naphthylmethyl, etc.; pivaloyloxymethyl group, which are widely used as an ester for oral use, and the like.

Furthermore, the metastins include peptides, wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated peptides such as glycopeptides bound to sugar chains.

For salts of the metastin of the present invention, preferred are salts with physiologically acceptable bases (e.g., alkali metal salts) or acids (e.g., organic acids or inorganic acids), etc., especially preferred are physiologically acceptable acid addition salts. Examples of such salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

As the DNAs encoding metastins, there are used, for example, DNAs encoding human metastin described in WO 00/24890, DNAs encoding mouse or rat metastin described in WO 01/75104, etc.

The DNAs encoding the metastins may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

The DNA encoding human metastin, mouse metastin precursor (A), mouse metastin precursor (B) or rat metastin precursor may be any DNA, so long as each is a DNA containing a base sequence represented by SEQ ID NO: 2, SEQ ID NO: 4, SEQ ID NO: 6 or SEQ ID NO: 8, or a DNA having a base sequence hybridizable to the base sequence represented by any base sequence represented by SEQ ID NO: 2, SEQ ID NO: 4, SEQ ID NO: 6 or SEQ ID NO: 8 under highly stringent conditions and encoding the human metastin, mouse metastin (A), mouse metastin (B) or rat metastin described above.

Specific examples of the DNA hybridizable to the base sequence represented by any of SEQ ID NO: 2, SEQ ID NO: 4, SEQ ID NO: 6 or SEQ ID NO: 8 include DNAs containing a base sequence having at least about 70% homology, preferably at least about 80% homology, more preferably at least about 90% homology and the most preferably at least about 95% homology, to the base sequence represented by any of SEQ ID NO: 2, SEQ ID NO: 4, SEQ ID NO: 6 or SEQ ID NO: 8.

Homology in the base sequence can be measured using the homology scoring algorithm NCBI BLAST (National Center for Biotechnology Information Basic Local Alignment Search Tool) under the following conditions (an expectation value=10; gaps are allowed; filtering=ON; match score=1; mismatch score=−3).

The hybridization can be carried out by per se publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

Specifically, as the DNA encoding the human metastin consisting of the amino acid sequence represented by SEQ ID NO: 1, the DNA consisting of the base sequence represented by SEQ ID NO: 2 is used. Accordingly, for the base sequence encoding the human metastin consisting of the various amino acid sequences described above, a base sequence corresponding to each of the partial amino acid sequences in the amino acid sequence represented by SEQ ID NO: 1 may be chosen from the base sequence represented by SEQ ID NO: 2.

As the DNA encoding the mouse metastin precursor (A) comprising the amino acid sequence represented by SEQ ID NO: 3, there are employed a DNA consisting of the base sequence represented by SEQ ID NO: 4, and the like. Accordingly, for the base sequence encoding the mouse metastin precursor (A) consisting of the various amino acid sequences described above, a base sequence corresponding to each of the partial amino acid sequences in the amino acid sequence represented by SEQ ID NO: 3 may be chosen from the base sequence represented by SEQ ID NO: 4.

As the DNA encoding the mouse metastin precursor (B) comprising the amino acid sequence represented by SEQ ID NO: 5, there are employed a DNA consisting of the base sequence represented by SEQ ID NO: 6, and the like. Accordingly, for the base sequence encoding the mouse metastin precursor (B) comprising of the various amino acid sequences described above, a base sequence corresponding to each of the partial amino acid sequences in the amino acid sequence represented by SEQ ID NO: 5 may be chosen from the base sequence represented by SEQ ID NO: 6.

As the DNA encoding the rat metastin comprising the amino acid sequence represented by SEQ ID NO: 7, there are employed a DNA consisting of the base sequence represented by SEQ ID NO: 8, and the like. Accordingly, for the base sequence encoding the rat metastin consisting of the various amino acid sequences described above, a base sequence corresponding to each of the partial amino acid sequences in the amino acid sequence represented by SEQ 1D NO: 7 may be chosen from the base sequence represented by SEQ ID NO: 8.

More specifically, for the peptide consisting of the amino acid sequence represented by SEQ ID NO: 1 (human metastin 54 (1-54)), a DNA containing the base sequence represented by SEQ ID NO: 2, etc. is used.

For the peptide consisting of the N-terminal 40th-54th amino acid sequence in the amino acid sequence represented by SEQ ID NO: 1 (human metastin 15 (40-54); SEQ ID NO: 15), a DNA containing the base sequence represented by SEQ ID NO: 19, etc. is used.

For the peptide consisting of the N-terminal 45th-54th amino acid sequence in the amino acid sequence represented by SEQ ID NO: 1 (human metastin 10 (45-54); represented by SEQ ID NO: 16), a DNA containing the base sequence represented by SEQ ID NO: 20, etc. is used.

For the peptide consisting of the N-terminal 46th-54th amino acid sequence in the amino acid sequence represented by SEQ ID NO: 1 (human metastin 9 (46-54); represented by SEQ ID NO: 17), a DNA containing the base sequence represented by SEQ ID NO: 21, etc. is used.

For the peptide consisting of the N-terminal 47th-54th amino acid sequence in the amino acid sequence represented by SEQ ID NO: 1 (human metastin 8 (47-54); represented by SEQ ID NO: 18), a DNA containing the base sequence represented by SEQ ID NO: 22, etc. is used.

As the metastin receptor, its partial peptides or salts thereof, there are used, for example, a human metastin receptor, its partial peptides or salts thereof described in WO 00/24890, a mouse or rat human metastin receptor, its partial peptides or salts thereof described in WO 01/75104, etc.

Specifically, a protein comprising the same or substantially the same amino acid sequence as the amino acid sequence represented by SEQ ID NO: 9, SEQ ID NO: 11 or SEQ ID NO: 13, etc. is used as the metastin receptor.

The amino acid sequence which is substantially the same amino acid sequence as the amino acid sequence represented by SEQ ID NO: 9, SEQ ID NO: 11 or SEQ ID NO: 13 includes, for example, an amino acid sequence having at least about 70% homology, preferably at least about 80% homology, more preferably at least about 90% homology, and most preferably at least about 95% homology, to the amino acid sequence represented by SEQ ID NO: 9, SEQ ID NO: 11 or SEQ ID NO: 13.

Homology of the amino acid sequences can be determined using the homology scoring algorithm NCBI BLAST (National Center for Biotechnology Information Basic Local Alignment Search Tool) under the following conditions (an expectation value=10; gaps are allowed; matrix=BLOSUM62; filtering=OFF).

As the protein comprising substantially the same amino acid sequence as the amino acid sequence represented by SEQ ID NO: 9, SEQ ID NO: 11 or SEQ ID NO: 13, preferred is a protein having substantially the same amino acid sequence as the amino acid sequence represented by SEQ ID NO: 9, SEQ ID NO: 11 or SEQ ID NO: 13 and having the activity of the same nature as that of a protein having the amino acid sequence represented by SEQ ID NO: 9, SEQ ID NO: 11 or SEQ ID NO: 13, etc.

As the activity of substantially the same nature, there are, for example, a ligand binding activity, a signal transduction activity, and the like. The "substantially the same nature" is used to mean that the nature of these activities is equivalent in terms of quality. Thus, the activities such as a ligand binding activity, a signal transduction activity, etc. are preferably equivalent (e.g., about 0.01 to 100 times, preferably about 0.5 to 10 times, more preferably 0.5 to 2 times), but differences in quantitative factors such as a level of these activities, or such as a molecular weight of the protein may be present and allowable.

The activities such as a ligand binding activity, a signal transduction activity, etc. can be assayed by per se publicly known method with modifications and may be determined according to methods of determining a ligand or screening methods described in, e.g., WO 00/24890 or WO 01/75104.

Examples of the metastin receptor used include proteins comprising (i) the amino acid sequence represented by SEQ ID NO: 9, SEQ ID NO: 11 or SEQ ID NO: 13, of which at least 1 or 2 (preferably about 1 to about 30, more preferably about 1 to about 10 and most preferably several (1 or 2)) amino acids are deleted; (ii) the amino acid sequence represented by SEQ ID NO: 9, SEQ ID NO: 11 or SEQ ID NO: 13, to which at least 1 or 2 (preferably about 1 to about 30, more preferably about 1 to about 10 and most preferably several (1 or 2)) amino acids are added; (iii) the amino acid sequence represented by SEQ ID NO: 9, SEQ ID NO: 11 or SEQ ID NO: 13, in which at least 1 or 2 (preferably about 1 to about 30, more preferably about 1 to about 10 and most preferably several (1 or 2)) amino acids are substituted by other amino acids; or (iv) a combination of these amino acid sequences; and the like.

Throughout the specification, the metastin receptors are represented in accordance with the conventional way of describing peptides, that is, the N-terminus (amino terminus) at the left hand and the C-terminus (carboxyl terminus) at the right hand. In the metastin receptors including the metastin receptor represented by SEQ ID NO: 9, SEQ ID NO: 11 or SEQ ID NO: 13, the C-terminus may be in any form of a carboxyl group (—COOH), a carboxylate (—COO—), an amide (—CONH$_2$) and an ester (—COOR). Herein, examples of R of the ester group include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc., or an α-naphthyl-$C_{1-2}$ alkyl group such as α-naphthylmethyl, etc.; and pivaloyloxymethyl group, which are widely used as an ester for oral use, and the like.

Where the metastin receptors contain a carboxyl group (or a carboxylate) at a position other than the C-terminus, the carboxyl group may be amidated or esterified and such amides or esters are also included within the receptor protein of the present invention. In this case, the ester group used may be the same group as the C-terminal esters described above.

Furthermore, the metastin receptors include those wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

Specific examples of the metastin receptors include human metastin receptor consisting of the amino acid sequence represented by SEQ ID NO: 9, rat metastin receptor consisting of the amino acid sequence represented by SEQ ID NO: 11, mouse metastin receptor consisting of the amino acid sequence represented by SEQ ID NO: 13, etc.

The partial peptides of the metastin receptor (hereinafter sometimes simply referred to as the partial peptide) may be any peptide, so long as they are partial peptides of the metastin receptor described above; there are used those such as protein molecules of the metastin receptor, which are the sites exposed outside the cell membrane, and having a ligand binding activity.

Specifically, the partial peptide of the metastin receptor consisting of the amino acid sequence represented by SEQ ID NO: 9, SEQ ID NO: 11 or SEQ ID NO: 13 is a peptide containing the parts analyzed to be extracellular domains (hydrophilic domains) in the hydrophobic plotting analysis. A peptide containing a hydrophobic domain in part can be used as well. In addition, the peptide may contain each domain separately or a plurality of domains together.

In the metastin receptor, preferred partial peptides are those having the number of amino acids of at least 20, preferably at least 50, and more preferably at least 100, in the amino acid sequence described above, which constitutes the metastin receptor.

The partial peptide may be a peptide having the amino acid sequence described above, of which at least 1 or 2 (preferably about 1 to about 10 and more preferably several (1 or 2)) amino acids are deleted; to which at least 1 or 2 (preferably about 1 to about 10 and more preferably several (1 or 2)) amino acids are added; or, in which at least 1 or 2 (preferably about 1 to about 10 and more preferably several (1 or 2)) amino acids are substituted by other amino acids. In the partial peptide, the C terminus may be any form of a carboxyl group (—COOH), a carboxylate (—COO⁻), an amide (—CONH$_2$) and an ester (—COOR), as in the metastin receptor described above.

Furthermore, the partial peptides include peptides, wherein the amino group at the N-terminal methionine residue is protected with a protecting group; those wherein the N-terminal region is cleaved in vivo and the glutamyl group thus formed is pyroglutaminated; those wherein a substituent on the side chain of an amino acid in the molecule is protected with a suitable protecting group, or conjugated peptides such as glycopeptides bound to sugar chains, as in the metastin receptors described above.

For salts of the metastin receptor or the partial peptide, preferred are salts with physiologically acceptable acids, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

As the DNA encoding the metastin receptor or its partial peptides, there are used, for example, a DNA encoding the human metastin receptor or its partial peptides described in WO 00/24890, a DNA encoding the mouse or rat metastin receptor or its partial peptides described in WO 01/75104, etc.

The DNAs encoding the metastin receptor or its partial peptides may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding human metastin receptor, mouse metastin receptor or rat metastin receptor may be any DNA, so long as it is a DNA comprising each base sequence represented by SEQ ID NO: 10, SEQ ID NO: 12 or SEQ ID NO: 14, or a DNA comprising a base sequence hybridizable to the base sequence represented by SEQ ID NO: 10, SEQ ID NO: 12 or SEQ ID NO: 14 under highly stringent conditions and encoding a receptor having the activity of substantially the same nature (e.g., a ligand binding activity, a signal transduction activity, etc.) as that of the human metastin receptor, mouse metastin receptor or rat metastin receptor consisting of the amino acid sequence represented by SEQ ID NO: 10, SEQ ID NO: 12 or SEQ ID NO: 14.

Examples of the DNA hybridizable to the base sequence represented by any of SEQ ID NO: 10, SEQ ID NO: 12 or SEQ ID NO: 14 include DNAs comprising a base sequence having at least about 70% homology, preferably at least about 80% homology, more preferably at least about 90% homology and the most preferably at least about 95% homology, to the base sequence represented by any of SEQ ID NO: 10, SEQ ID NO: 12 or SEQ ID NO: 14.

Homology in the base sequence can be measured using the homology scoring algorithm NCBI BLAST (National Center for Biotechnology Information Basic Local Alignment Search Tool) under the following conditions (an expectation value=10; gaps are allowed; filtering=ON; match score=1; mismatch score=−3).

The hybridization can be carried out by per se publicly known methods or by modifications of these methods, for example, according to the method described in Molecular Cloning, 2nd (J. Sambrook et al., Cold Spring Harbor Lab. Press, 1989), etc. A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, as the DNA encoding the human metastin receptor consisting of the amino acid sequence represented by SEQ ID NO: 9, the DNA consisting of the base sequence represented by SEQ ID NO: 10 is used.

As the DNA encoding the rat metastin receptor consisting of the amino acid sequence represented by SEQ ID NO: 11, the DNA consisting of the base sequence represented by SEQ ID NO: 12 is used.

As the DNA encoding the mouse metastin receptor consisting of the amino acid sequence represented by SEQ ID NO: 13, the DNA consisting of the base sequence represented by SEQ ID NO: 14 is used.

The metastin receptors, their partial peptides or salts thereof and the DNAs encoding the metastin receptors or their partial peptides can be obtained or produced by the methods described in WO 00/24890 or WO 01/75104.

The present invention will be described in detail by referring to EXAMPLES, FORMULATION EXAMPLES AND TEST EXAMPLES, but is not deemed to be limited thereto, and any modification may be made without departing from the scope of the present invention.

In the following EXAMPLES, the term "room temperature" normally means a temperature of about 10° C. to about 35° C. In percentages, the yield is shown by mol/mol % and the solvent used in chromatography by vol%, and the remaining by wt %. In proton NMR spectra, data on OH, NH protons, etc. that are broad and unidentified are not shown.

The other abbreviations used in the specification mean as follows.

| Abbreviation | Description |
|---|---|
| 10Ψ, CSNH | The C-terminal-$CONH_2$ at the 10-position is substituted with —$CSNH_2$. |
| 1Ψ2, $CH_2NH$ | The —CONH— bond between the 1- and 2-positions is substituted with the —$CH_2NH$-bond. |
| 2Ψ3, $CH_2NH$ | The —CONH— bond between the 2- and 3-positions is substituted with the —$CH_2NH$-bond. |
| 3Ψ4, $CH_2NH$ | The —CONH— bond between the 3- and 4-positions is substituted with the —$CH_2NH$— bond. |
| 4Ψ5, $CH_2NH$ | The —CONH— bond between the 4- and 5-positions is substituted with the —$CH_2NH$— bond. |
| 6Ψ7, CSNH | The —CONH— bond between the 6- and 7-positions is substituted with the —CSNH— bond. |
| 6Ψ7, NHCO | The —CONH— bond between the 6- and 7-positions is substituted with the —NHCO— bond. |
| 6Ψ7, $CH_2NH$ | The —CONH— bond between the 6- and 7-positions is substituted with the —$CH_2NH$— bond. |
| 6Ψ7, $CH_2O$ | The —CONH— bond between the 6- and 7-positions is substituted with the —$CH_2O$— bond. |
| 7Ψ8, $CH_2NH$ | The —CONH— bond between the 7- and 8-positions is substituted with the —$CH_2NH$— bond. |
| 8Ψ9, $CH_2NH$ | The —CONH— bond between the 8- and 9-positions is substituted with the —$CH_2NH$— bond. |
| 9Ψ10, $CH_2NH$ | The —CONH— bond between the 9- and 10-positions is substituted with the —$CH_2NH$— bond. |
| Aad | 2-aminoadipic acid |
| Abu | 2-aminobutanoic acid |
| Abz(2) | 2-aminobenzoic acid |
| Abz(3) | 3-aminobenzoic acid |
| Ac | acetyl |
| AcONB | N-acetoxy-5-norbornene-2,3-dicarboximide |
| Acp | 6-aminocaproic acid |
| AcOEt | ethyl acetate |
| AcOH | acetic acid |
| Aib | α-aminoisobutanoic acid |
| Ala(2-Qui) | 2-quinolylalanine |
| Ala(3-Bzt) | 3-benzothienylalanine |
| Ala(cBu) | cyclobutylalanine |
| Ala(cPr) | cyclopropylalanine |
| Ala(Pip) | (4-piperidin-1-yl)alanine |
| Alb | Albizziin 2-amino-3-ureidopropionic acid |
| Ambz(4) | 4-aminomethylbenzoyl |
| Arg(Ac) | $N^{\omega}$-acetylarginine |
| Arg($Boc_2$, Me) | $N^{\omega,\omega'}$-bis-tert-butoxycarbonyl-$N^{\omega}$-methylarginine |
| Arg(Et) | $N^{\omega}$-ethylarginine |
| Arg(Me) | $N^{\omega}$-methylarginine |

-continued

| Abbreviation | Description |
|---|---|
| Arg(asyMe$_2$) or Arg(Me$_2$)asym | asymmetric-N$^{\omega,\omega}$-dimethylarginine |
| Arg(symMe$_2$) or Arg(Me$_2$)sym | symmetric-N$^{\omega,\omega'}$-dimethylarginine |
| Arg(NO$_2$) | N$^{\omega}$-nitroarginine |
| Arg(Pbf) | N$^{\omega}$-2,2,4,6,7-pentamethyldihydrobenzofuransulfonylarginine |
| Arg(n-Pr) | N$^{\omega}$-propylarginine |
| Arg(Tos) | N$^{\omega}$-tosylarginine |
| Asp(NHMe) | N$^{\omega}$-methylasparagine |
| Asp(NMe$_2$) | N$^{\omega,\omega}$-dimethylasparagine |
| Asp(NHPen) | N$^{\omega}$-pentylasparagine |
| Asp(NHcPr) | N$^{\omega}$-cyclopropylasparagine |
| Asp(NHBzl) | N$^{\omega}$-benzylasparagine |
| AzaGly | azaglycine |
| AzaPhe | azaphenylalanine |
| Aze(2) | azetidine-2-carboxylic acid |
| β-Ala | β-alanine |
| Boc | tert-butoxycarbonyl |
| Boc$_2$O | di-tert-butyl dicarbonate |
| Br-Z | 2-bromobenzyloxycarbonyl |
| Bu$^t$ | tert-butyl |
| Bzl | benzyl |
| CDI | 1,1'-carbonyldiimidazole |
| Cha | cyclohexylalanine |
| CIP | 2-chloro-1,3-dimethylimidazolium tetrafluoroborate |
| Cit | citrulline |
| Clt resin | 2-chlorotrytyl resin |
| Cl-Z | 2-chlorobenzyloxycarbonyl |
| Dab | 2,4-diaminobutanoic acid |
| Dap | 2,3-diaminopropionic acid |
| Dap(Ac) | N$^β$-acetyl-β-diaminopropionic acid |
| Dap(For) | N$^β$-formyl-β-diaminopropionic acid |
| Dap(Gly) | N$^β$-glycyl-β-diaminopropionic acid |
| Dap(GnGly) | N$^β$-(N-guanidinoglycyl)-β-diaminopropionic acid |
| DCM | dichloromethane |
| DEA | diethylamine |
| DIEA | N,N-diisopropylethylamine |
| DIPCDI | 1,3-diisopropylcarbodiimide |
| DMAP | 4-dimethylaminopyridine |
| DMF | N,N-dimethylformamide |
| EDC | 1-ethyl-3-(3-dimethylaminopropyl)carbodiimide |
| EDT | 1,2-ethanedithiol |
| Fmoc | 9-fluorenylmethoxycarbonyl |
| For | formyl |
| γ-Abu | 4-aminobutanoic acid |
| γ-MeLeu, Leu(Me) | γ-methylleucine |
| GlyΨ((E)CH═CH)Leu | The —CONH— between Gly and Leu is substituted with (E) type alkene. |
| GlyΨ(CH$_2$CH$_2$)Leu | The —CONH— between Gly and Leu is substituted with the —CH$_2$CH$_2$— bond. |
| GlyΨ(CH$_2$S)Leu | The —CONH— between Gly and Leu is substituted with the —CH$_2$S— bond. |
| Gn | guanidino |
| GuAmb | 4-guanidinomethylbenzoyl |
| Har | homoarginine |
| Har(Me) | N$^{\omega}$-methylhomoarginine |
| His(3Me) | 3-methylhistidine π-methylhistidine |
| HOAt | 1-hydroxy-7-azabenzotriazole |
| HOBt | 1-hydroxybenzotriazole |
| HOOBt | 3,4-dihydro-3-hydroxy-4-oxo-1,2,3-benzotriazine |
| HONB | N-hydroxy-5-norbornene-2,3-dicarboximide |
| Hph | homophenylalanine |
| Hyp | trans-4-hydroxyproline |
| Hyp(Bzl) | O-benzyl-trans-4-hydroxyproline |
| IndPr | 3-(indole-3-yl)propionyl |
| Izc | imidazolidine-2-carboxylic acid |
| Lys(Me$_2$) | N$^{\epsilon,\epsilon}$-dimethyllysine |
| MBHA | p-methylbenzhydrylamine |
| MeOH | methanol |
| Mtt | 4-methyltrytyl |
| N((CH$_2$)$_3$Gn)Gly | N-(3-guanidinopropyl)glycine |
| Nal(1) | 1-naphthylalanine |
| Nal(2) | 2-naphthylalanine |
| Nar | norarginine |
| Nar(Me) | N$^{\omega}$-methylnorarginine |
| Nle | norleucine |
| NMeAla | N$^{\alpha}$-methylalanine |
| NMeArg | N$^{\alpha}$-methylarginine |
| NMeAsn | N$^{\alpha}$-methylasparagine |

| Abbreviation | Description |
| --- | --- |
| NMeLeu | $N^{\alpha}$-methylleucine |
| NMePhe | $N^{\alpha}$-methylphenylalanine |
| NMeSer | $N^{\alpha}$-methylserine |
| NMeTrp | $N^{\alpha}$-methyltryptophan |
| NMeTyr | $N^{\alpha}$-methyltyrosine |
| Nva | norvaline |
| OBu$^t$ | tert-butoxy |
| Orn | ornithine |
| Orn(Mtt) | $N^{\delta}$-(4-methyltrytyl)ornithine |
| PAL | 5-(4-(9-fluorenylmethoxycarbonyl)aminomethyl-3,5-dimethoxyphenoxy)valeric acid |
| Pbf | 2,2,4,6,7-pentamethyldihydrobenzofuran-5-sulfonyl |
| pGlu | pyroglutamic acid |
| Phe(2Cl) | 2-chlorophenylalanine |
| Phe(2F) | 2-fluorophenylalanine |
| Phe(3,4Cl$_2$) | 3,4-dichlorophenylalanine |
| Phe(3,4F$_2$) | 3,4-difluorophenylalanine |
| Phe(3CF$_3$) | 3-trifluoromethylphenylalanine |
| Phe(3Cl) | 3-chlorophenylalanine |
| Phe(3F) | 3-fluorophenylalanine |
| Phe(4Cl) | 4-chlorophenylalanine |
| Phe(4CN) | 4-cyanophenylalanine |
| Phe(4F) | 4-fluorophenylalanine |
| Phe(4Gn) | 4-guanidinophenylalanine |
| Phe(4NH$_2$) | 4-aminophenylalanine |
| Phe(4NO$_2$) | 4-nitrophenylalanine |
| Phe(4CN) | 4-cyanophenylalanine |
| Phe(F$_5$) | pentafluorophenylalanine |
| Phe(2Me) | 2-methylphenylalanine |
| Phe(3Me) | 3-methylphenylalanine |
| Phe(4Me) | 4-methylphenylalanine |
| PheΨ(CH$_2$CH$_2$)AzaGly | The —CONH— between Phe and AzaGly is substituted with the —CH$_2$CH$_2$— bond. |
| PheΨ((E)CH=CH)Gly | The —CONH— bond between Phe and Gly is substituted with the (E) type alkene. |
| PheΨ(CH$_2$CH2)Gly | The —CONH— bond between Phe and Gly is substituted with the —CH$_2$CH$_2$— bond. |
| PheΨ(CH$_2$S)Gly | The —CONH— bond between Phe and Gly is substituted with the —CH$_2$S— bond. |
| PheΨ((R)CH(OH)—(E)CH=)Gly | The —CONH— bond between Phe and Gly is substituted with the —CH(OH)—CH— bond, the —CH(OH)— moiety takes (R) configuration, and the moiety between the carbon atom in the —CH— moiety and α carbon atom of the Gly is (E) type alkene. |
| PheΨ((S)CH(OH)—(E)CH=)Gly | The —CONH— bond between Phe and Gly is substituted with the —CH(OH)—CH— bond, the —CH(OH)— moiety takes (S) configuration, and the moiety between the carbon atom in the —CH— moiety and α carbon atom of the Gly is (E) type alkene. |
| PheΨ((R)CH(OH)—CH$_2$)Gly | The —CONH— bond between Phe and Gly and is substituted with the —CH(OH)—CH$_2$— bond, and the —CH(OH)—moiety takes (R) configuration. |
| PheΨ((S)CH(OH)—CH$_2$)Gly | The —CONH— bond between Phe and Gly is substituted with the —CH(OH)—CH$_2$— bond and the —CH(OH)— moiety takes (S) configuration. |
| PheΨ(CH$_2$O)Gly | The —CONH— bond between Phe and Gly is substituted with the —CH$_2$O— bond. |
| PheΨ(COCH$_2$)Gly | The —CONH— bond between Phe and Gly is substituted with the —COCH$_2$— bond. |
| PheΨ(CSNH) —NH$_2$ | The C-terminal phenylalanylamide is substituted with phenylalanylthioamide. |
| Phg | phenylglycine |
| PhOH | phenol |
| PhSMe | thioanisole |
| Pic(2) | pipecolinic acid |
| Pic(3) | 3-piperidinecarboxylic acid |
| Pip | pipecolinic acid |
| Pro | proline |
| Pro(4F) | trans-4-fluoroproline |
| Pro(4NH$_2$) | cis-4-aminoproline |
| Pya(2) | 2-pyridylalanine |
| Pya(3) | 3-pyridylalanine |
| Pya(4) | 4-pyridylalanine |
| PyAOP | (7-azabenzotriazole-1-yloxy)-tris(pyrrolidino)phosphonium hexafluorophosphate |
| PyBOP | (benzotriazol-1-yloxy)-tris(pyrrolidino)phosphonium hexafluorophosphate |

| Abbreviation | Description |
|---|---|
| PyBrop | bromo-tris(pyrrolidino)phosphonium hexafluorophosphate |
| Pzc(2) | piperazine-2-carboxylic acid |
| Sar | N-methylglycine |
| Ser(Ac) | O-acetylserine |
| Ser(Me) | O-methylserine |
| Thi | 2-thienylalanine |
| Thz | thioproline |
| Tic | 1,2,3,4-tetrahydroisoquinoline-2-carboxylic acid |
| TIS | triisopropylsilane |
| Tle | tert-leucine |
| Tos | tosyl |
| Trp(For) | $N^{in}$-formyltryptophan |
| Trt | trytyl |
| Tyr(Me) | O-methyltyrosine |
| Tyr(PO$_3$H$_2$) | O-phosphotyrosine |
| TyrΨ(CH$_2$NH)Asn | The —CONH— between Tyr and Asn is substituted with the —CH$_2$NH— bond. |
| TFA | trifluoroacetic acid |
| TFE | trifluoroethanol |
| Z | benzyloxycarbonyl |

In the specification and drawings, where the codes of bases and amino acids are denoted by abbreviations, they are based on the abbreviations in accordance with the IUPAC-IUB Commission on Biochemical Nomenclature or the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| Y | thymine or cytosine |
| N | thymine, cytosine, adenine or guanine |
| R | adenine or guanine |
| M | cytosine or adenine |
| W | thymine or adenine |
| S | cytosine or guanine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate. |
| TFA | trifluoroacetic acid |
| EIA | enzyme immunoassay |
| Gly or G | glycine |
| Ala or A | alanine |
| Val or V | valine |
| Leu or L | leucine |
| Ile or I | isoleucine |
| Ser or S | serine |
| Thr or T | threonine |
| Cys or C | cysteine |
| Met or M | methionine |
| Glu or E | glutamic acid |
| Asp or D | aspartic acid |
| Lys or K | lysine |
| Arg or R | arginine |
| His or H | histidine |
| Phe or F | phenylalanine |
| Tyr or Y | tyrosine |
| Trp or W | tryptophan |
| Pro or P | proline |
| Asn or N | asparagine |
| Gln or Q | glutamine |
| pGlu | pyroglutamic acid |

The sequence identification numbers in the sequence listing of the specification indicates the following sequence, respectively.

[SEQ ID NO: 1]
This shows the amino acid sequence of human-derived metastin (Metastin).

[SEQ ID NO: 2]
This shows the base sequence of DNA encoding human metastin.

[SEQ ID NO: 3]
This shows the amino acid sequence of mouse metastin precursor (A).

[SEQ ID NO: 4]
This shows the base sequence of DNA encoding mouse metastin precursor (A), which is the base sequence in plasmid pCMV-mKiSS-1 harbored on transformant Escherichia coli OB/pCMV-mKiSS-1.

[SEQ ID NO: 5]
This shows the amino acid sequence of mouse metastin precursor (B).

[SEQ ID NO: 6]
This shows the base sequence of DNA encoding mouse metastin precursor (B), which is the base sequence in plasmid pCR2.1-mKiSS-1.4A harbored on transformant Escherichia coli DH5α/pCR2.1-mKiSS-1.4A.

[SEQ ID NO: 7]
This shows the amino acid sequence of rat-derived metastin precursor.

[SEQ ID NO: 8]
This shows the base sequence of DNA encoding rat metastin precursor.

[SEQ ID NO: 9]
This shows the amino acid sequence of human OT7T175 (metastin receptor).

[SEQ ID NO: 10]
This shows the base sequence of DNA encoding human OT7T175 (metastin receptor).

[SEQ ID NO: 11]

This shows the amino acid sequence of rat OT7T175 (metastin receptor).

[SEQ ID NO: 12]

This shows the base sequence of DNA encoding rat OT7T175 (metastin receptor).

[SEQ ID NO: 13]

This shows the amino acid sequence of mouse OT7T175 (metastin receptor).

[SEQ ID NO: 14]

This shows the base sequence of DNA encoding mouse OT7T175 (metastin receptor).

[SEQ ID NO: 15]

This shows the amino acid sequence of human metastin 15 (40-54).

[SEQ ID NO: 16]

This shows the amino acid sequence of human metastin 10 (45-54) (MS10).

[SEQ ID NO: 17]

This shows the amino acid sequence of human metastin 9 (46-54).

[SEQ ID NO: 18]

This shows the amino acid sequence of human metastin 8 (47-54).

[SEQ ID NO: 19]

This shows the base sequence of DNA encoding human metastin 15 (40-54).

[SEQ ID NO: 20]

This shows the base sequence of DNA encoding human metastin 10 (45-54).

[SEQ ID NO: 21]

This shows the base sequence of DNA encoding human metastin 9 (46-54).

[SEQ ID NO: 22]

This shows the base sequence of DNA encoding human metastin 8 (47-54)

The transformant *Escherichia coli* DH10B/pCMV-mKiSS-1 has been on deposit since Jan. 24, 2000 with International Patent Organisms Depository, National Institute of Advanced Industrial Science and Technology (the former Ministry of International Trade and Industry, Agency of Industrial Science and Technology, National Institute of Bioscience and Human Technology (NIBH)), located at Central 6, 1-1-1 Higashi, Tsukuba, Ibaraki (postal code 305-8566), Japan, as the Accession Number FERM BP-7003 and since Dec. 16, 1999 with Institute for Fermentation (IFO), located at 2-17-85, Juso-Honmachi, Yodogawa-ku, Osaka-shi, Osaka, Japan, as the Accession Number TO 16348.

The transformant *Escherichia coli* DH5α/pCR2.1-mKiSS-1.4A has been on deposit since Mar. 6, 2000 with International Patent Organisms Depository, National Institute of Advanced Industrial Science and Technology (the former Ministry of International Trade and Industry, Agency of Industrial Science and Technology, National Institute of Bioscience and Human Technology (NIBH)), located at Central 6, 1-1-1 Higashi, Tsukuba, Ibaraki (postal code 305-8566), Japan, as the Accession Number FERM BP-7073 and since Feb. 16, 2000 with Institute for Fermentation (IFO), located at 2-17-85 Juso-Honmachi, Yodogawa-ku, Osaka-shi, Osaka, Japan, as the Accession Number IFO 16360.

REFERENCE EXAMPLE 1

Production of
N-methyl-N,N'-Bis-Boc-1-guanylpyrazole

In a nitrogen atmosphere, 720 mg of 60% NaH in oil was dissolved in 20 mL of dry DMF and 20 mL of dry DMF solution of 5.59 g of N,N'-Bis-Boc-1-guanylpyrazole commercially available was added to the solution at 0° C., followed by stirring for 10 minutes. After 1.68 mL of methyl iodide was added thereto, the mixture was stirred at room temperature for 24 hours. After the solvent was removed by distillation, the residue was dissolved in AcOEt and the solution was washed with 1N HCl aq. solution, satd. NaHCO$_3$ aq. solution and then satd. NaCl aq. solution. After drying over Na$_2$SO$_4$, the solvent was concentrated and the concentrate was purified by flash column chromatography (ethyl acetate/n-hexane=1/4) using silica gel 60 (200 mL) to give 5.35 g (yield 91.6%) of N-methyl-N,N'-bis-Boc-1-guanylpyrazole.

$^1$H NMR (300 MHz, CDCl$_3$): δ 8.00 (br s, 1H), 7.69 (br s, 1H), 6.42 (dd, 1H, J=2.7, 1.5 Hz), 3.25 (s, 3H), 1.53 (s, 9H), 1.30 (s, 9H)

Elemental analysis as $C_{15}H_{24}N_4O_4$

Calcd.: C, 55.54; H, 7.46; N, 17.27

Found: C, 55.36; H, 7.48; N, 17.06

Rf1: 0.64, Rf2: 0.79

Developing solvent for TLC:

Rf1 (ethyl acetate/n-hexane=1/2), Rf2 (methanol/chloroform=2/98)

Elution time on HPLC: 26.7 mins.

Elution Conditions:

Column: Wakosil-II 5C18 HG (4.6×100 mm)

Eluant: Linear density gradient elution with eluants A/B=100/0-20/80, using eluant A: 0.1% TFA-water and eluant B: 0.1% TFA-containing acetonitrile (40 mins.)

Flow rate: 1.0 mL/min.

REFERENCE EXAMPLE 2

Production of
N-methyl-N,N'-Bis-Z-1-guanylpyrazole

In an argon atmosphere, 40 mg of 60% NaH in oil was dissolved in 5 mL of dry DMF and 5 mL of dry DMF solution of 380 mg of N,N'-Bis-Z-1-guanylpyrazole commercially available was added to the solution at 0° C., followed by stirring for 10 minutes. After 125 μL of methyl iodide was added thereto, the mixture was stirred at room temperature for 15 hours. After the solvent was distilled off, the residue was dissolved in AcOEt and the solution was washed with 1N HCl aq. solution, satd. NaHCO$_3$ aq. solution and then satd. NaCl aq. solution. After drying over Na$_2$SO$_4$, the solvent was concentrated to give 393 mg of the crude product. From the crude product, 170 mg was purified by flash column chromatography (ethyl acetate/n-hexane=1/4) using silica gel 60 (75 mL) to give 152 mg (yield 89.5%) of N-methyl-N,N'-bis-Z-1-guanylpyrazole.

$^1$H NMR (300 MHz, CDCl$_3$): δ 7.97 (br s, 1H), 7.61 (d, 1H, J=1.0 Hz), 7.37-7.32 (m, 4H), 7.29-7.26 (m, 4H), 7.16-7.13 (m, 2H), 6.36 (dd, 1H, J=2.8, 1.6 Hz), 5.18 (s, 2H), 5.04 (s, 2H), 3.22 (s, 3H)

Elemental analysis as $C_{21}H_{20}N_4O_4$

Calcd.: C, 64.28; H, 5.14; N, 14.28

Found: C, 64.09; H, 5.24; N, 14.43

Rf1: 0.50, Rf2: 0.86

Developing solvent for TLC:

Rf1 (ethyl acetate/n-hexane=1/2)

Rf2 (methanol/chloroform=2/98)

Elution time on HPLC: 28.9 mins.
Elution Conditions:
   Column: Wakosil-II 5C18 HG (4.6×100 mm)
   Eluant: Linear density gradient elution with eluants A/B=100/0-20/80, using eluant A: 0.1% TFA-water and eluant B: 0.1% TFA-containing acetonitrile (40 mins.)
   Flow rate: 1.0 mL/min.

EXAMPLE 1

(Synthesis A): Production of des(1)-Ac-[D-Tyr2, Hyp3,Thr5,Arg(Me)9,Trp10]MS10 (Compound No. 796)

After 5 g (0.4 mmol/g) of Rink Amide MBHA resin commercially available was swollen in DMF, the resin was treated with 50 mL of 20% piperidine/DMF solution for 20 minutes to remove the Fmoc group. The resulting resin was washed with DMF and treated with 4.213 g (8 mmol) of Fmoc-Trp (Boc)-OH, 1.272 mL (8 mmol) of DIPCDI and 16 mL (8 mmol) of 0.5M HOAt/DMF solution at room temperature for 90 minutes, whereby Trp(Boc) was introduced to give the Fmoc-Trp(Boc)-Rink Amide MBHA resin. In a similar manner, Orn(Mtt) was introduced to give 2 mmol of the Fmoc-Orn(Mtt)-Trp(Boc)-Rink Amide MBHA resin. After the resin obtained was washed and swollen in DCM, 50 mL of TFA/TIS/DCM (1/5/94) was added thereto, followed by shaking for 10 minutes and removing the solution through filtration. This procedure was repeated until yellow color caused by free Mtt group in a TFA/TIS/DCM (1/5/94) solution disappeared when the solution was added; thus the Mtt group was removed. The resulting Fmoc-Orn-Trp(Boc)-Rink Amide MBHA resin was neutralized with 5%-DIEA/DCM solution. After washing with DCM, 25 mL of DCM-TFE (4:1) and 1.946 g (6 mmol) of N-methyl-N,N'-bis-Boc-1-guanylpyrazole obtained in REFERENCE EXAMPLE 1 were added to the resin. DIEA was added to the mixture to adjust pH of the resulting solution to 10. The solution was shaken for 15 hours to give 6.195 g of Fmoc-Arg(Boc$_2$,Me)-Trp(Boc)-Rink Amide MBHA resin. Fmoc-Leu was introduced into the obtained resin as in the manner described above. In the Fmoc-Leu-Arg(Boc$_2$,Me)-Trp(Boc)-Rink Amide MBHA resin obtained, 859 mg (0.25 mmol) of the resin was used as a starting material, which was reacted on an ABI 433A (Fmoc/DCC/HOBt 0.25 mmol protocol) to introduce Gly, Phe, Thr (Bu$^t$), Asn(Trt), Hyp(Bu$^t$) and D-Tyr(Bu$^t$) in this order. Thus, H-D-Tyr(Bu$^t$)-Hyp(Bu$^t$)-Asn(Trt)-Thr(Bu$^t$)-Phe-Gly-Leu-Arg(Boc$_2$,Me)-Trp(Boc)-Rink Amide MBHA resin was obtained. Subsequently, the resin was treated for 20 minutes in DMF with 94.4 µl (1 mmol) of Ac$_2$O and 174.2 µl (1 mmol) of DIEA for N-terminal acetylation to give Ac-D-Tyr(Bu$^t$)-Hyp(Bu$^t$)-Asn(Trt)-Thr(Bu$^t$)-Phe-Gly-Leu-Arg(Boc$_2$,Me)-Trp(Boc)-Rink Amide MBHA resin. To the resin obtained, 6 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was then removed. This procedure was repeated twice. After washing, the residue was extracted with an aqueous acetic acid solution and the resin was removed by filtration. Then, linear density gradient elution (60 minutes) to A/B: 74/26-64/36 was performed at a flow rate of 15 mL/min using: eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 114.6 mg, were dissolved in 100 mL of water and 390 µL of ion exchange resin BioRAD AG1×8 AcO$^-$ form was added to the solution, followed by stirring for an hour. The resin was removed by cotton plug filtration through silica wool, the same amount of the resin was again added and the mixture was stirred for an hour. The solution was filtered through a membrane filter to remove the resin and lyophilized to give 93.4 mg of white powders as the acetate.
Mass spectrum (M+H)$^+$1224.6 (calcd. 1224.6)
Elution time on HPLC: 11.8 mins.
Elution Conditions:
   Column: YMC ODS-AM301 (4.6×100 mm)
   Eluant: Linear density gradient elution with eluants A/B=80/20-30/70, using eluant A: 0.1% TFA-water and eluant B: 0.1% TFA-containing acetonitrile (25 mins.)
   Flow rate: 1.0 mL/min.
   Amino acid analysis (20% hydrochloric acid containing 4% thioglycolic acid, 110° C., hydrolysis for 24 hours; figures in parentheses show theoretical values.): Asp 0.98 (1); Thr 0.95 (1); Gly 0.99 (1); Leu 0.99 (1); Tyr 0.98 (1); Phe 1.00 (1)

EXAMPLE 2

(Synthesis B): Production of des(1)-Ac-[D-Tyr2, Hyp3,Thr5,Phe6Ψ(CH$_2$O)Gly7,Arg(Me)9,Trp10] MS10 (Compound No. 834)

After 1.80 g of Z-Phe was dissolved in 20 mL of MeOH, 73 mg of DMAP, 1.38 g of WSCD HCl were added at 0° C., followed by stirring at 4° C. for 12 hours. The solvent was concentrated and the concentrate was dissolved in AcOEt, followed by washing with 1N HCl aq., satd. NaHCO$_3$ aq., and satd. NaCl aq. After drying over Na$_2$SO$_4$, the solvent was concentrated to give Z-Phe-OMe as oil. After dissolving in 20 mL of dry THF, 196 mg of LiBH$_4$ was added thereto and the mixture was stirred at room temperature for 15 hours. The solvent was concentrated and the concentrate was dissolved in AcOEt and the residue was washed with 1N HCl aq., satd. NaHCO$_3$ aq., and satd. NaCl aq. After drying over Na$_2$SO$_4$, the solvent was concentrated and ether-petroleum ether was added to give 1.45 g (yield 85%) of Z-Phe-ol as precipitates. After 60 mg of 60% NaH was suspended in 10 mL of dry THF, 285 mg of Z-Phe-ol, 264 mg of 18-crown-6 and 1.48 mL of tert-butyl bromoacetate were added at 0° C. While returning to room temperature, the mixture was stirred for 15 hours.
After the solvent was removed by distillation under reduced pressure, the residue was dissolved in AcOEt and then washed with 1N HCl aq., satd. NaHCO$_3$ aq. and satd. NaCl aq. After drying over Na$_2$SO$_4$, the solvent was concentrated and the concentrate was purified by flash column chromatography to give 217 mg (yield 54%) of Z-PheΨ(CH$_2$O)Gly-OBu$^t$ as oil. After 160 mg of Z-PheΨ(CH$_2$O)Gly-OBu$^t$ was dissolved in 20 mL of MeOH, 10% Pd—C was added, followed by catalytic hydrogenation for 3 hours in a hydrogen flow. The catalyst was removed by filtration and the solvent was concentrated to dryness. The residue was dissolved in 15 mL, of DCM and 114 mg of Fmoc-Cl and 139 µL of DIEA were added. The mixture was stirred for 12 hours. After the solvent was removed by distillation, the residue was dissolved in AcOEt and the solution was washed with 1N HCl aq., satd. NaHCO$_3$ aq. and satd. NaCl aq. After drying over Na$_2$SO$_4$, the solvent was concentrated and the concentrate was purified by flash column chromatography. Diethyl ether-petroleum ether was added to give 150 mg (yield 77%) of Fmoc-PheΨ(CH$_2$O)Gly-OBu$^t$ as precipitates. Fmoc-Leu-Arg(Me, Boc$_2$)-Trp(Boc)-Rink Amide MBHA resin, 86 mg (25 µmol), obtained in EXAMPLE 1, 32 mg of Fmoc-PheΨ(CH$_2$O)Gly-OH (prepared by treating Fmoc-PheΨ(CH$_2$O)

Gly-OBu$^t$ with 50% TFA/DCM for an hour), 200 μL of 0.5M HOAt/DMF, 52 mg of PyBrop and 53 μL of DMA were added and the mixture was shaken for 24 hours. The resin was washed and 5 mL of 20% piperidine/DMF was added thereto, followed by shaking room temperature for 30 minutes. After the resin was washed, Thr(Bu$^t$), Asn(Trt), Hyp(Bu$^t$) and D-Tyr(Bu$^t$) were sequentially introduced in this order on an ABI 433A (Fmoc/DCC/HOBt 0.25 mmol protocol) sequentially to give H-D-Tyr(Bu$^t$)-Hyp(Bu$^t$)-Asn(Trt)-Thr(Bu$^t$)-PheΨ(CH$_2$O)Gly-Leu-Arg(Boc$_2$,Me)-Trp(Boc)-Rink Amide MBHA resin. Subsequently, the resin was treated in DMF with 9.4 μl (0.1 mmol) of Ac$_2$O and 17.4 μl (0.1 mmol) of DIEA for 20 minutes for N-terminal acetylation to give Ac-D-Tyr(Bu$^t$)-Hyp(Bu$^t$)-Asn(Trt)-Thr(Bu$^t$)-PheΨ(CH$_2$O)Gly-Leu-Arg(Boc$_2$,Me)-Trp(Boc)-Rink Amide MBHA resin. To the resin obtained, 1 mL of TFA/PhSMe/m-cresol/H$_2$O/TIS/EDT (80/5/5/5/2.5/2.5) was added and the mixture was stirred for 90 minutes. Diethyl ether was added to the reaction solution to give the precipitates. The procedure of centrifugation followed by removing the supernatant was repeated twice for washing. The residue was extracted with an aqueous acetic acid solution. After the resin was removed by filtration, linear density gradient elution (60 minutes) to A/B: 75/25-65/35 was performed at a flow rate of 15 mL/min using: eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 2.5 mg, were dissolved in 100 mL of water and 10 μL of ion exchange resin BioRAD AG1×8 AcO- form was added thereto. The mixture was stirred for an hour. The solution was filtered through a membrane filter to remove the resin and lyophilized to give 2.0 mg of white powders as the acetate.

Mass spectrum (M+H)$^+$1211.3 (calcd. 1211.6)
Elution time on HPLC: 19.4 mins.
Elution Conditions:
  Column: Wakosil-II 5C18 HG (4.6×100 mm)
  Eluant: Linear density gradient elution with eluants A/B=100/0-0/50, using eluant A: 0.1% TFA-water and eluant B: 0.1% TFA-containing acetonitrile (25 mins.)
  Flow rate: 1.0 mL/min.

EXAMPLE 3

(Synthesis C): Production of des(1)-Ac-[D-Tyr2, Hyp3,Thr5,Phe6T(CH$_2$CH$_2$)Gly7,Arg(Me)9,Trp10] MS10 (Compound No. 850)

After 4.44 g (0.45 mmol/g) of Rink Amide MBHA resin commercially available was swollen in DMF, the resin was treated with 50 mL of 20% piperidine/DMF solution for 20 minutes to remove the Fmoc group. The resulting resin was washed with DMF and treated in DMF with 4.21 g (8 mmol) of Fmoc-Trp(Boc)-OH, 1.27 mL (8 mmol) of DIPCDI and 1.31 g (8 mmol) of HOOBt at room temperature for 90 minutes, whereby Trp(Boc) was introduced to give the Fmoc-Trp(Boc)-Rink Amide MBHA resin. In a similar manner, Orn(Mtt) was introduced to give 2 mmol of the Fmoc-Orn(Mtt)-Trp(Boc)-Rink Amide MBHA resin. After the resin obtained was washed and swollen in toluene, 30 mL of TFA/TIS/TFE/toluene (1/5/47/47) was added, followed by shaking for 30 minutes and removing the solution by filtration. This procedure was repeated until yellow color caused by free Mtt group in a TFA/TIS/TFE/toluene (1/5/47/47) solution disappeared when the solution was added; thus the Mtt group was removed. The resulting Fmoc-Orn-Trp(Boc)-Rink Amide MBHA resin was neutralized with 5%-DIEA/toluene solution. After washing with toluene, 15 mL of toluene-TFE (4:1) and 1.95 g (6 mmol) of N-methyl-N,N'-bis-Boc-1-guanylpyrazole obtained in REFERENCE EXAMPLE 1 were added to the resin. DIEA was added to the mixture to adjust pH of the solution to 10. The solution was shaken for 15 hours to give Fmoc-Arg(Boc$_2$,Me)-Trp(Boc)-Rink Amide MBHA resin (2 mmol). After the resin obtained was dried in MeOH, 0.03 mmol was weighed and reswollen in DMF. Leu was introduced in the same manner as described above to give 0.03 mmol of Fmoc-Leu-Arg(Boc$_2$,Me)-Trp(Boc)-Rink Amide MBHA resin. After Fmoc deprotection in 20% piperidine/DMF solution, the resin was treated in DMF with 51.5 mg (0.12 mmol) of Fmoc-Phe-Ψ(CH$_2$CH$_2$)-Gly-OH obtained in REFERENCE EXAMPLE 3, 19.1 μl (0.12 mmol) of DIPCDI and 240 μl of 0.5 M HOAt/DMF solution at room temperature for 150 minutes. The resin was washed with DMF and then treated with 10.9 μl of (0.12 mmol) of Ac$_2$O and 20.9 μl (0.12 mmol) of DIEA for capping of residual amino groups. Subsequently, the resin was shaken overnight in 2 mL of DMF solution of Ac-D-Tyr-Hyp-Asn-Thr-OH (0.06 mmol) synthesized in a conventional manner of the liquid-phase process, 31.2 mg (0.06 mmol) of PyAOP, 120 μl (0.06 mmol) of 0.5 M HOAt/DMF solution and 10.5 μl (0.06 mmol) of DMA to give Ac-D-Tyr-Hyp-Asn-Thr-Phe-Ψ(CH$_2$CH$_2$)-Gly-Leu-Arg(Boc$_2$,Me)-Trp(Boc)-Rink Amide MBHA resin. After drying, 1.5 mL of TFA/PhSMe/m-cresol/H$_2$O/TIS/EDT (80/5/5/5/2.5/2.5) was added to the resin and stirred for 90 minutes.

Diethyl ether was added to each reaction solution to give the precipitate and after centrifugation, the supernatant was removed; this procedure was repeated twice for washing. The residue was extracted with an aqueous acetic acid solution and the extract was filtered to remove the resin. Thereafter, linear density gradient elution (60 minutes) to A/B: 71.5/28.5-61.5/38.5 was performed at a flow rate of 15 mL/min using eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized to give 5.5 mg of white powders.

Mass spectrum (M+H)$^+$1209.7 (calcd. 1209.6)
Elution time on HPLC: 12.2 mins.
Elution Conditions:
  Column: SHISEIDO CAPCELL PAK C18 MGII (4.6×100 mm)
  Eluant: Linear density gradient elution with eluants A/B=80/20-30/70, using eluant A: 0.1% TFA-water and eluant B: 0.1% TFA-containing acetonitrile (25 mins.)
  Flow rate: 1.0 mL/min.

REFERENCE EXAMPLE 3

Synthesis of Fmoc-Phe-Ψ(CH$_2$CH$_2$)-Gly-OH

After 97.4 mg (0.269 mmol) of Boc-Phe-Ψ[(E)CH=CH]-Gly-OBu$^t$, which is a compound known by the literature, was dissolved in 10 mL of AcOEt, 10 mg of 10% Pd/C was added and the mixture was stirred in a hydrogen gas flow at room temperature for 4 hours. The Pd catalyst was removed by filtration through celite, and the filtrate was concentrated under reduced pressure. Subsequently, the residue was dissolved in 4 mL of TFA and the solution was stirred at room temperature for 2 hours. TFA was distilled off under reduced pressure and the residue was dissolved in 2.25 mL of acetonitrile: H$_2$O (2:1). Under ice cooling, acetonitrile (3 mL) solution of 236 μL (1.69 mmol) of TEA and 95.1 mg (0.282 mmol) of Fmoc-OSu was dropwise added sequentially and the mixture was stirred at the same temperature for 2 hours. After 20 mL of 0.1N HCl aq. was added, the whole was extracted with AcOEt. The organic layer was washed twice with 0.1 N HCl aq. and then dried over anhydrous $MgSO_4$. After concentrating under reduced pressure, the product was purified by flash column chromatography (ethyl acetate/n-hexane=3/2) using Wakosil C-300 to give 118 mg (quantitative) of Fmoc-Phe-Ψ($CH_2CH_2$)-Gly-OH.

EXAMPLE 4

(Synthesis D): Production of des(1)-Ac-[D-Tyr2, Hyp3,Thr5,Phe6Ψ(COCH$_2$)Gly7,Arg(Me)9,Trp10] MS10 (Compound No. 851)

Using as a starting material Boc-Phe-Ψ(COCH$_2$)-Gly-OBu$^t$ which is a compound known by the literature, Fmoc-Phe-Ψ(COCH$_2$)-Gly-OH synthesized according to REFERENCE EXAMPLE 3 as a raw material was treated in a manner similar to REFERENCE EXAMPLE 3 to give Ac-D-Tyr-Hyp-Asn-Thr-Phe-Ψ(COCH$_2$)-Gly-Leu-Arg(Boc$_2$, Me)-Trp(Boc)-Rink Amide MBHA resin. After drying the resin, 1.5 mL of TFA/PhSMe/m-cresol/H$_2$O/TIS (80/5/5/5/5) was added and the mixture was stirred for 90 minutes. Diethyl ether was added to each reaction solution to give the precipitate and after centrifugation, the supernatant was removed; this procedure was repeated twice for washing. The residue was extracted with an aqueous acetic acid solution and the extract was filtered to remove the resin. Then, linear density gradient elution (60 minutes) to A/B: 72.5/27.5-62.5/37.5 was performed at a flow rate of 15 mL/min using eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized to give 4.0 mg of white powders.
Mass spectrum (M+H)$^+$1224.2 (calcd. 1223.6)
Elution time on HPLC: 11.8 mins.
Elution Conditions:
Column: SHISEIDO CAPCELL PAK C18 MGII (4.6×100 mm)
Eluant: Linear density gradient elution with eluants A/B=80/20-30/70, using eluant A: 0.1% TFA-water and eluant B: 0.1% TFA-containing acetonitrile (25 mins.)
Flow rate: 1.0 mL/min.

EXAMPLE 5

(Synthesis E): Production of des(1)-Ac-[D-Tyr2, Hyp3,Thr5,Gly7W(CH$_2$NH)Leu8,Arg(Me)9,Trp10] MS10 (Compound No. 854)

Fmoc-Gly-OH, 1 g (3.36 mmol), 361.0 mg (3.70 mmol) of CH$_3$ONHCH$_3$ and 447.3 mg (3.53 mmol) of HOBt were dissolved in DMF. Under ice cooling, 677 mg (3.53 mmol) of WSCI.HCl and 1.94 mL (11.1 mmol) of DIEA were added to the solution, followed by stirring overnight. After the reaction solution was concentrated, 10% aqueous citric acid solution was added and the precipitated solid was extracted with AcOEt. The organic layer was washed with 10% aqueous citric acid solution, 5% NaHCO$_3$ aqueous solution and satd. sodium chloride aqueous solution, and dried over anhydrous Na$_2$SO$_4$. The oily Fmoc-Gly-N(CH$_3$)OCH$_3$ product obtained by concentrating the solvent was dissolved in THF. Under ice cooling, 332 mg (0.726 mmol) of LiAlH$_4$ was added by small portions to the solution over 15 minutes. After stirring at 0° C. for 30 minutes, 150 mL of diethyl ether and 150 mL of 20% citric acid aqueous solution were sequentially added to the reaction solution, which was then vigorously stirred for an hour. The organic layers were collected and the aqueous layer was again extracted with 150 mL of diethyl ether. The pooled organic layer was washed sequentially with 5% NaHCO$_3$ aqueous solution, water, 10% citric acid aqueous solution, water and then satd. sodium chloride aqueous solution, and dried over anhydrous Na$_2$SO$_4$. The organic layer obtained was concentrated to give Fmoc-Gly-al as an oily substance.

After removal of the N-terminal Fmoc group in (0.291 mmol/g) 171.8 mg (0.05 mmol) of Fmoc-Leu-Arg(Boc$_2$, Me)-Trp(Boc)-Rink Amide MBHA resin, 56.2 mg (0.2 mmol) of Fmoc-Gly-al dissolved in DMF and 50 µl of AcOH were added and the mixture was stirred for 10 minutes. Subsequently, 12.3 mg (0.2 mmol) of NaBH$_3$CN was added and the mixture was stirred overnight. The reaction process was monitored by Kaiser test and found not to be sufficient. The coupling was performed again. After completion of the reaction, capping of the unreacted amino groups and protection of the reducing amino moieties were effected by treating with 107.7 mg (0.5 mmol) of Boc-OSu and 87.1 µl (0.5 mmol) of DIEA. Phe, Thr(Bu$^t$), Asn(Trt), Hyp(Bu$^t$) and D-Tyr(Bu$^t$) were introduced on the resin obtained using an ABI peptide synthesizer. Subsequently, the N-terminal amino group was treated with 9.5 µl (0.1 mmol) of Ac$_2$O and 17.4 µl (0.1 mmol) of DIEA in DMF for 20 minutes for acetylation. The resin was then washed and dried to give 162.3 mg of Ac-D-Tyr-Hyp-Asn-Thr-Phe-GlyΨ(CH$_2$NH)Leu-Arg(Boc$_2$,Me)-Trp(Boc)-Rink Amide MBHA resin. After the resin was dried, 1 mL of TFA/PhSMe/m-cresol/H$_2$O/TIS/EDT (80/5/5/5/2.5/2.5) was added and the mixture was stirred for 90 minutes. Diethyl ether was added to each reaction solution to give the precipitate and after centrifugation, the supernatant was removed; this procedure was repeated twice for washing. The residue was extracted with an aqueous acetic acid solution and the extract was filtered to remove the resin. Thereafter, linear density gradient elution (60 minutes) to A/B: 77/23-67/33 was performed at a flow rate of 15 mL/min using eluant A: 0.1% TFA-water and eluant B: 0.1% TFA-containing acetonitrile on preparative HPLC using Daisopak-SP100-5-ODS-P 2×25 cm, 120A column (20×250 mm). The fractions containing the product were collected and lyophilized to give 0.6 mg of white powders.
Mass spectrum (M+H)$^+$1210.6 (calcd. 1210.6)
Elution time on HPLC: 10.9 mins.
Elution Conditions:
Column: SHISEIDO CAPCELL PAK C18 MGII (4.6×100 mm)
Eluant: Linear density gradient elution with eluants A/B=80/20-30/70, using eluant A: 0.1% TFA-water and eluant B: 0.1% TFA-containing acetonitrile (25 mins.)
Flow rate: 1.0 mL/min.

EXAMPLE 6

(Synthesis F): Production of des(1)-Ac-[D-Tyr2, Hyp3,Thr5,Phe6Ψ[(S)CHOH—CH$_2$]Gly7,Arg(Me) 9,Trp10]MS10 (Compound No. 857)

10% Pd/C (3 mg) was added to a MeOH (3 mL) solution of Compound 858 (1.02 mg) synthesized as in EXAMPLE 3. After stirring in a hydrogen gas flow for 6 hours, the mixture was settled overnight in a hydrogen atmosphere. After Pd/C was removed by filtration, linear density gradient elution (60 minutes) to A/B: 72/28-62/38 was performed at a flow rate of 15 mL/min using eluant A: 0.1% TFA-water and eluant B:

0.1% TFA-containing acetonitrile on preparative HPLC using YMC Pack R&D-ODS-5-B S-5, 120A column (30×250 mm). The fractions containing the product were collected and lyophilized to give 0.3 mg of white powders.
Mass spectrum (M+H)$^+$1226.2 (calcd. 1225.6)
Elution time on HPLC: 11.9 mins.
Elution Conditions:
　Column: SHISEIDO CAPCELL PAK C18 MGII (4.6×100 mm)
　Eluant: Linear density gradient elution with eluants A/B=80/20-30/70, using eluant A: 0.1% TFA-water and eluant B: 0.1% TFA-containing acetonitrile (25 mins.)
　Flow rate: 1.0 mL/min.

EXAMPLE 7

(Synthesis G): Production of des(1)-Ac-[D-Tyr2, Hyp3,Thr5,Gly7Ψ[(E)CH=CH)Leu8,Arg(Me)9, Trp10]MS10 (Compound No. 892)

HCl.H-Ser-OMe, 3.5 g (22.6 mmol), was suspended in (40 mL) of chloroform. Under ice cooling, DIEA (8.7 mL, 49.7 mmol) and Pbf-Cl (5.86 g, 20.3 mmol) were sequentially added and stirred overnight while gradually elevating to room temperature. After the reaction was stopped by adding satd. citric acid aqueous solution, chloroform was distilled off under reduced pressure and the whole was extracted with AcOEt. The organic layer was washed sequentially with satd. citric acid aqueous solution, satd. sodium bicarbonate aqueous solution and satd. sodium chloride aqueous solution, and then dried over anhydrous MgSO$_4$. After concentration under reduced pressure, flash chromatography was performed using AcOEt: n-hexane=1:1 to give Pbf-Ser-OMe (6.94 g, 82.7%).

In an argon atmosphere under ice cooling, 923 μl (2.03 mmol) of a toluene solution of 2.2 M diethyl azodicarboxylate was added to a solution of 500 mg (1.35 mmol) of Pbf-Ser-OMe, 522 mg (2.03 mmol) of PPh$_3$ in THF (20 mL). The mixture was stirred overnight at room temperature and then THF was distilled off under reduced pressure. Flash chromatography was performed using AcOEt: n-hexane=1:1 to give 481 mg of aziridine methyl ester (quantitative).

In an argon atmosphere, 429 μl (0.644 mmol) of a toluene solution of 1.5 M DIBAL-H was dropwise added to a toluene (10 mL) solution of aziridine methyl ester (198 mg, 0.56 mmol) at −78° C. After stirring for 20 minutes at the same temperature, the reaction was stopped with 0.1 N HCl aqueous solution. The whole was extracted with diethyl ether and the organic layer was washed sequentially with 0.1 N HCl aqueous solution and satd. sodium chloride aqueous solution. After drying over anhydrous MgSO$_4$, the reaction mixture was concentrated under reduced pressure to give the aldehyde as an oily substance. On the other hand, 146 μL (0.84 mmol) of DIEA and 197 μL (0.84 mmol) of (EtO)$_2$P(O)CH$_2$CO$_2$Bu$^t$ were sequentially added under ice cooling, to a suspension of 35.6 mg (0.84 mmol) of anhydrous LiCl in acetonitrile (2 mL). The mixture was stirred at the same temperature for 20 minutes and then an acetonitrile (4 mL) solution of the aldehyde obtained above was dropwise added thereto, followed by stirring at 0° C. for 3 hours. After the whole was extracted with AcOEt, the organic layer was washed sequentially with satd. citric acid aqueous solution, satd. sodium bicarbonate aqueous solution and satd. sodium chloride aqueous solution, and then dried over anhydrous MgSO$_4$. The mixture was concentrated under reduced pressure and the concentrate was recrystallized from diethyl ether/n-hexane to give 86.5 mg of the objective aziridine enoate. The mother liquor was concentrated under reduced pressure and subjected to flash chromatography using AcOEt: n-hexane=1:19 to give additional 82.4 mg of the objective aziridine enoate (total yield: 71.5%).

In an argon atmosphere, 1.59 mL (3.17 mmol) of a 2.0 M THF solution of i-BuMgCl was dropwise added at −78° C. to an anhydrous THF (6 mL) solution of 284 mg (3.17 mmol) of CuCN and 269 mg (6.34 mmol) of anhydrous LiCl. The temperature was elevated to 0° C. and the mixture was stirred for 10 minutes. The mixture was again cooled to −78° C., and 402 μL (3.17 mmol) of BF$_3$.Et$_2$O and an anhydrous THF (6 mL) solution of 334 mg (0.792 mmol) of aziridine enoate were dropwise added sequentially. The mixture was stirred at the same temperature for 20 minutes. After quenching with satd. Ammonium chloride aqueous solution: 28% ammonia aqueous solution (1:1), the mixture was stirred at room temperature until the reaction solution turned blue. The whole was extracted with diethyl ether. The organic layer was washed with water and dried over anhydrous MgSO$_4$. After concentration under reduced pressure, the residue was dissolved in 95% TFA aqueous solution (10 mL) and stirred at room temperature for 3 hours. TFA was removed by distillation under reduced pressure and azeotropically distilled off twice with diethyl ether. The residue was recrystallized from diethyl ether/n-hexane to give 254 mg of Pbf-GlyΨ[(E)-CH=CH]Leu-OH as white powders (75.7%).

After 180 mg (0.425 mmol) of Pbf-GlyΨ[(E)-CH=CH]Leu-OH and 352 μL (3 mmol) of thioanisole were dissolved in TFA (2.65 mL), the solution was stirred at room temperature for 24 hours. TFA was distilled off under reduced pressure and the resulting residue was dissolved in acetonitrile: H$_2$O (2:1, 9 mL). Under ice cooling, triethylamine was added until the solution became basis and 168 mg (0.446 mmol) of Fmoc-OSu was further added thereto. While elevating to room temperature, the mixture was stirred for 4 hours and the whole was extracted with AcOEt. The organic layer was washed sequentially with 0.1 N HCl aqueous solution and satd. Sodium chloride aqueous solution, and dried over anhydrous MgSO$_4$. Following concentration under reduced pressure, flash chromatography using AcOEt: n-hexane=3.5:6.5 was performed to give 145 mg of Fmoc-GlyΨ[(E)-CH=CH]Leu-OH (89%).

After 287 mg (0.1 mmol) of Fmoc-Arg(Boc$_2$,Me)-Trp(Boc)-Rink Amide MBHA resin (0.349 mmol/g) was swollen in DMF, the mixture was treated with 20% piperidine/DMF solution to cleave the Fmoc group. Subsequently, the resin was treated in DMF with 133 mg (0.338 mmol) of Fmoc-GlyΨ[(E)-CH=CH]Leu-OH, 58.9 μl (0.338 mmol) of DIEA, 676 μl (0.338 mmol) of 0.5 M HOAt/DMF solution and 176 mg (0.338 mmol) of PyAOP at room temperature for 12 hours. After the resin was washed with DMF, the N-terminal peptide was extended by the Fmoc solid-phase synthesis to give Ac-D-Tyr(Bu$^t$)-Hyp(OBu$^t$)-Asn(Trt)-Thr(Bu$^t$)-Phe-GlyΨ[(E)CH=CH]Leu-Arg(Boc$_2$,M e)-Trp(Boc)-Rink Amide MBHA resin. After the resin was dried, 4 mL of TFA/PhSMe/m-cresol/H$_2$O/TIS/EDT (80/5/5/5/2.5/2.5) was added thereto and the mixture was stirred for 180 minutes. Diethyl ether was added to each reaction solution to give the precipitate and after centrifugation, the supernatant was removed; this procedure was repeated twice for washing. The residue was extracted with an aqueous acetic acid solution and the extract was filtered to remove the resin. Thereafter, linear density gradient elution (60 minutes) to A/B: 71.5/28.5-61.5/38.5 was performed at a flow rate of 15 mL/min using eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized to give 19.6 mg of white powders.

Mass spectrum (M+H)⁺1207.5 (calcd. 1207.6)
Elution time on HPLC: 14.6 mins.
Elution Conditions:
  Column: SHISEIDO CAPCELL PAK C18 MGII (4.6×100 mm)
  Eluant: Linear density gradient elution with eluants A/B=80/20-30/70, using eluant A: 0.1% TFA-water and eluant B: 0.1% TFA-containing acetonitrile (25 mins.)
  Flow rate: 1.0 mL/min.

EXAMPLE 8

(Synthesis H): Production of des(1)-Ac-[D-Tyr2, Hyp3,Thr5,Gly7Ψ(CH$_2$CH$_2$)Leu8,Arg(Me)9,Trp10] MS10 (Compound No. 893)

After 9.9 mg of des(1)-Ac-[D-Tyr2,Hyp3,Thr5,Gly7Ψ((E) CH=CH)Leu8,Arg(Me)9,Trp10]MS10 (Compound No. 892) was dissolved in 4 mL of MeOH, 20 mg of 10% Pd/C was added to the solution and suspended therein. In a hydrogen atmosphere, the mixture was stirred for 9 hours and then the Pd catalyst was removed by filtration. MeOH was distilled off under reduced pressure. After the residue was dissolved in 1.5 mL of 50% AcOH aqueous solution, linear density gradient elution (60 minutes) to A/B: 72/28-62/38 was performed at a flow rate of 15 mL/min using eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized to give 4.1 mg of white powders.
Mass spectrum (M+H)⁺1209.1 (calcd. 1209.6)
Elution time on HPLC: 19.0 mins.
Elution Conditions:
  Column: SHISEIDO CAPCELL PAK C18 MGII (4.6×100 mm)
  Eluant: Linear density gradient elution with eluants A/B=195/5-45/55, using eluant A: 0.1% TFA-water and eluant B: 0.1% TFA-containing acetonitrile (25 mins.)
  Flow rate: 1.0 mL/min.

EXAMPLE 9

Production of des(1)-Ac-[D-Tyr2,Hyp3,Thr5,Cha6, Ala(cPr)8,Arg(Me)9,Trp10]MS10 (Compound No. 894)

Fmoc-Arg(Me, Boc$_2$)-Trp(Boc)-Rink Amide MBHA resin, 2.744 g (0.952 mmol), was weighed and charged in a reaction vessel, washed with DMF and then stirred in DMF for 20 minutes to swell the resin. Following deprotection of the N-terminal Fmoc group by treating with 20% piperidine/DMF, the resin was treated with 669.1 mg (1.904 mmol) of Fmoc-Ala(cPr)-OH, 7.616 mL (3.808 mmol) of 0.5M HOAt/DMF solution and 0.454 mL (2.856 mmol) of DIPCDI for 150 minutes. After the resin was washed with DMF, the reaction process was monitored by the ninhydrin test and found not to be sufficient. Thus, the resin was again treated in DMF with 233.0 mg (0.663 mmol) of Fmoc-Ala(cPr)-OH, 1.989 mL (0.995 mmol) of 0.5M HOAt/DMF solution, 518.6 mg (0.995 mmol) of PyAOP and 0.578 mL (3.315 mmol) of DIEA for 60 hours to complete the reaction. Gly, Cha, Thr(Bu$^t$), Asn(Trt), Hyp(Bu$^t$) and D-Tyr(Bu$^t$) were introduced in this order into the obtained resin, by the Fmoc solid-phase synthesis using 4 mmol each of Fmoc-amino acid/DIPCDI/HOOBt. The N-terminal Fmoc group of Fmoc-D-Tyr(Bu$^t$)-Hyp(Bu$^t$)-Asn-Thr (Bu$^t$)-Cha-Gly-Ala(cPr)-Arg(Me, Boc$_2$)-Trp(Boc)-Rink Amide MBHA resin obtained was deprotected by 20% piperidine/DMF treatment to remove the N-terminal Fmoc group of the resin obtained. Then, the resin was suspended in about 10 mL of DMF, and 377 µl (4 mmol) of Ac$_2$O and 697 µl (4 mmol) of DIEA were added to the suspension. The mixture was stirred for 20 minutes. The resin was washed with DMF. After it was confirmed that the reaction proceeded, the resin was washed in MeOH and dried.

To 3.5004 g of the resulting resin, 35 mL of TFA: thioanisole: m-cresol: H$_2$O: EDT: TIS (80:5:5:5:2.5:2.5) was added and the mixture was stirred for 90 minutes at room temperature. While removing the resin by passing through a glass filter, the reaction solution was dropwise added to chilled ether with stirring to make the crude peptide white powders. The resin was thoroughly washed with a deprotection solution and then returned to the reaction solution. The resin was treated again with the same volume of the deprotection solution at room temperature for 20 hours and ether was likewise added dropwise to make the product white powders.

The mixture of white powders and ether was separated by centrifugation, respectively. The ether was removed by decantation and this procedure was repeated twice to remove the acid and scavenger. The residue was dried and extracted with acetic acid aqueous solution. The extract was passed through a 0.45 µm disk filter to remove fine particles, followed by concentration with an evaporator. The residue was diluted in acetonitrile-aqueous solution and lyophilized to give total 1.118 g of white to brown powders.

The crude peptide obtained was purified separately six times on preparative HPLC using SHISEIDO CAPCELL PAK MGII column (50×250 mm). Linear density gradient elution (60 minutes) to A/B: 72/28-62/38 was performed at a flow rate of 45 mL/min using eluant A: 0.1% TFA-water and eluant B: 0.1% TFA-containing acetonitrile on preparative HPLC. The product eluted out was fractionated in test tubes by about 14 mL each. By monitoring each fraction on HPLC, the fractions containing the product only were identified. The fractions were pooled and lyophilized to give 389.3 mg of white powders.

In AcCN-water, 389.3 mg (316.9 µmol) of the purified sample obtained was dissolved and 1.320 mL (1.585 mmol equivalent) of AG 1×8 AcO-resin was added to the solution. While occasionally stirring manually, the solution was settled for an hour, and filtered through a PTFE membrane filter having a 3 µm pore diameter. The filtrate was transferred to a recovery flask and the solvent was distilled off. Then, 3 mL of acetic acid was added to the residue. After the mixture was sonicated for 5 minutes with an ultrasonicator, 12 mL of water was added to the solution. While cooling on a dry ice bath, the resulting 20% acetic acid solution was lyophilized to give 368.6 mg of white powders.

Mass spectrum (M+H)⁺1228.9 (calcd. 1228.6)

Elution time on HPLC: 12.9 mins.

Elution Conditions:
  Column: YMC ODS-AM301 (4.6×100 mm)
  Eluant: Linear density gradient elution with eluants A/B=80/20-30/70, using eluant A: 0.1% TFA-water and eluant B: 0.1% TFA-containing acetonitrile (25 mins.)
  Flow rate: 1.0 mL/min.
  Amino acid analysis (20% hydrochloric acid containing 4% thioglycolic acid, 110° C., hydrolysis for 24 hours; figures in parentheses show theoretical values.): Asp 0.92 (1); Thr 0.89 (1); Gly 0.92 (1); Tyr 0.99 (1); Cha 1.00 (1)

EXAMPLE 10

Production of des(1)-Ac-[D-Tyr2,Hyp3,Alb4,Thr5, Cha6,Gly7Ψ((E)CH=CH)Leu8,Arg(Me)9,Trp10]MS10 (Compound No. 903)

After 4.32 g (1.5 mmol) of Fmoc-Arg(Boc$_2$,Me)-Trp (Boc)-Rink Amide MBHA resin (0.347 mmol/g) was eqally divided into three and swollen in DMF, the mixture was treated with 20% piperidine/DMF solution to cleave the Fmoc group. Subsequently, each resin was treated in DMF with 590 mg (1.5 mmol) of Fmoc-GlyΨ[(E)-CH=CH]Leu-OH, 26 μl (1.5 mmol) of DIEA, 3.0 ml (1.5 mmol) of 0.5 M HOAt/DMF solution and 782 mg (1.5 mmol) of PyAOP at room temperature for 12 hours. After the resin was washed with DMF and combined, Cha, Thr(Bu$^t$), Mb, Hyp(Bu$^t$) and D-Tyr(Bu$^t$) were introduced in this order into the obtained resin, by the Fmoc solid-phase synthesis using Fmoc-amino acid/DIPCDI/HOAt to give Fmoc-D-Tyr(Bu$^t$)-Hyp(OBu$^t$)-Asn(Trt)-Thr(Bu$^t$)-Cha-GlylΨ[(E)CH=CH]Leu-Arg(Boc$_2$,Me)-Trp(Boc)-Rink Amide MBHA resin. The resin thus obtained was deprotected by 20% piperidine/DMF treatment, and washed. The resin was then suspended in DMF, and 548 μl (6.0 mmol) of Ac$_2$O and 1.04 ml (6.0 mmol) of DIEA were added, respectively, followed by stirring for 20 minutes. The resin was washed with DME After it was confirmed that the reaction proceeded, the resin was washed in MeOH and dried to give Ac-D-Tyr(Bu$^t$)-Hyp(Bu$^t$)-Alb-Thr(Bu$^t$)-Cha-GlyΨ[(E)CH=CH]Leu-Arg(Boc$_2$,Me)-Trp (Boc)-Rink Amide MBHA resin. The resulting resin was divided into 1 g, 2 g and 2.2 g, to which 25 mL, 50 mL and 50 mL of TFA: thioanisole: m-cresol: H$_2$O: EDT: TIS (80:5:5:5:2.5:2.5) were added, respectively. After stirring for 180 minutes at room temperature, the reaction solution was dropwise added onto chilled ether while removing the resin by passing through a glass filter, thereby to make the crude peptide white powders. The crude peptide obtained was purified separately 10 times on preparative HPLC using SHISEIDO CAPCELL PAK MGII column (50×250 mm). Linear density gradient elution (60 minutes) to A/B: 68/32-58/42 was performed at a flow rate of 45 mL/min using eluant A: 0.1% TFA-water and eluant B: 0.1% TFA-containing acetonitrile on preparative HPLC. The product eluted out was fractionated in test tubes by about 14 mL each. By monitoring each fraction on HPLC, the fractions containing the product only were identified. The fractions were pooled and lyophilized to give 352.2 mg of white powders.

In AcCN-water, 352.2 mg (286.7 μmol) of the purified sample obtained was dissolved and 1.195 mL (1.433 mmol equivalent) of AG 1×8 AcO$^-$ resin was added to the solution. While occasionally stirring manually, the solution was settled for an hour, and filtered through a PTFE membrane filter having a 3 μm pore diameter. The filtrate was transferred to a recovery flask and the solvent was distilled off. Then, 3 mL of acetic acid was added to the residue. After the mixture was sonicated for 5 minutes with an ultrasonicator, 12 mL of water was added to the solution. While cooling on a dry ice bath, the resulting 20% acetic acid solution was lyophilized to give 321.8 mg of white powders.

Mass spectrum (M+H)$^+$1228.4 (calcd. 1228.7)
Elution time on HPLC: 20.2 mins.
Elution Conditions:
  Column: SHISEIDO CAPCELL PAK C18 MGII (4.6×100 mm)
  Eluant: Linear density gradient elution with eluants A/B=95/5-45/55, using eluant A: 0.1% TFA-water and eluant B: 0.1% TFA-containing acetonitrile (25 mins.)
  Flow rate: 1.0 mL/min.
Amino acid analysis (20% hydrochloric acid containing 4% thioglycolic acid, 110° C., hydrolysis for 24 hours; figures in parentheses show theoretical values.): Thr 0.95 (1); Tyr 0.95 (1); Cha 1.00 (1)

EXAMPLE 11

Production of des(1)-Ac-[D-Tyr2,Hyp3,Thr5,Cha6, Gly7Ψ((E)CH=CH)Leu8,Trp10]MS10 (Compound No. 926)

Using as a starting material 3.33 g (1.5 mmol) of Fmoc-Rink Amide MBHA resin (0.45 mmol/g), the Fmoc solid-phase synthesis was carried out to give Fmoc-Arg(Pbf)-Trp (Boc)-Rink Amide MBHA resin. After Fmoc-Arg(Pbf)-Trp (Boc)-Rink Amide MBHA resin was swollen in DMF, the mixture was treated with 20% piperidine/DMF solution to cleave the Fmoc group. Subsequently, the resin was treated in DMF with 1.57 g (4.0 mmol) of Fmoc-GlyΨ[(E)—CH=CH]Leu-OH, 1.39 ml (8.0 mmol) of DIEA, 8.0 ml (4.0 mmol) of 0.5 M HOAt/DMF solution and 2.09 g (4.0 mmol) of PyAOP at room temperature for 24 hours. After the resin was washed with DMF, the N-terminal peptide was extended by the Fmoc solid-phase synthesis to give Fmoc-Cha-GlyΨ[(E)CH=CH]Leu-Arg(Pbf)-Trp(Boc)-Rink Amide MBHA resin (SEQ ID NO: 218). After deprotection of the N-terminal Fmoc group by 20% piperidine/DMF treatment, the resin was treated in DMF with Ac-D-Tyr-Hyp-Asn-Thr-OH 2.48 g (4.5 mmol), 734 mg (4.5 mmol) of HOOBt and 716 mL (4.5 mmol) of DIPCDI for 60 hours. The resulting Ac-D-Tyr-Hyp-Asn-Thr-Cha-GlyΨ[(E)CH=CH]Leu-Arg(Pbf)-Trp(Boc)-Rink Amide MBHA resin was washed in MeOH and dried. To the whole of the resulting resin, 60 mL of TFA: thioanisole: m-cresol: H$_2$O: EDT: TIS (80:5:5:5:2.5:2.5) was added. After stirring for 90 minutes at room temperature, the reaction solution was dropwise added onto chilled ether while removing the resin by passing through a glass filter, thereby to make the crude peptide white powders.

The crude peptide obtained was purified separately five times on preparative HPLC using SHISEIDO CAPCELL PAK MGII column (50×250 mm). Linear density gradient elution (60 minutes) to AB: 69/31-59/41 or 68/32-58/42 was performed at a flow rate of 45 mL/min using eluant A: 0.1% TFA-water and eluant B: 0.1% TFA-containing acetonitrile on preparative HPLC. The product eluted out was fractionated in test tubes by about 14 mL each. By monitoring each fraction on HPLC, the fractions containing the product only were identified. The fractions were pooled and lyophilized to give white powders.

The whole was dissolved in acetonitrile-water and 0.824 mL (1.005 mmol equivalent) of AG 1×8 AcO$^-$ resin was added to the solution. While occasionally stirring manually, the solution was settled for an hour, and filtered through a PTFE membrane filter having a 3 μm pore diameter. The filtrate was transferred to a recovery flask and the solvent was distilled off. Then, 2 mL of acetic acid was added to the residue. After the mixture was sonicated for 5 minutes with an ultrasonicator, 8 mL of water was added to the solution. While cooling on a dry ice bath, the resulting 20% acetic acid solution was lyophilized to give 304.7 mg of white powders.
Mass spectrum (M+H)$^+$1199.6 (calcd. 1199.7)
Elution time on HPLC: 20.2 mins.
Elution Conditions:
  Column: SHISEIDO CAPCELL PAK C18 MGII (4.6×100 mm)
  Eluant: Linear density gradient elution with eluants A/B=95/5-45/55, using eluant A: 0.1% TFA-water and eluant B: 0.1% TFA-containing acetonitrile (25 mins.)
  Flow rate: 1.0 mL/min.
Amino acid analysis (20% hydrochloric acid containing 4% thioglycolic acid, 110° C., hydrolysis for 24 hours; figures in parentheses show theoretical values.): Asp:0.93 (1); Thr 0.89 (1); Tyr 0.96 (1); Cha 1.00 (1); Arg 0.98 (1)

EXAMPLE 12

Production of des(1)-Ac-[D-Tyr2,Hyp3,Alb4,Thr5, Cha6,Gly7Ψ((E)CH=CH)Leu8,Trp10]MS10 (Compound No. 927)

After 3.66 g (0.55 mmol) of Fmoc-Rink Amide MBHA resin was swollen in DMF, the peptide chain was extended by the Fmoc solid-phase synthesis. The N-terminal Fmoc group of Fmoc-D-Tyr(Bu$^t$)-Hyp(Bu$^t$)-Alb-Thr(Bu$^t$)-Cha-GlyΨ[(E)-CH=CH]Leu-Arg(Pbf)-Trp(Boc)-Rink Amide MBHA resin thus obtained was deprotected by 20% piperidine/DMF treatment, and washed. The resin was then suspended in about 10 mL of DMF, and 208 μl (2.2 mmol) of Ac$_2$O and 383 μl (2.2 mmol) of DIEA were added, respectively, followed by stirring for 20 minutes. The resin was washed with DMF. After it was confirmed that the reaction proceeded, the resin was washed in MeOH and dried.

To 5.9695 g of the resulting resin, 50 mL of TFA: thioanisole: m-cresol: H$_2$O: EDT: TIS (80:5:5:5:2.5:2.5) was added and the mixture was stirred for 90 minutes at room temperature. While removing the resin by passing through a glass filter, the reaction solution was dropwise added to chilled ether with stirring to make the crude peptide white powders. The resin was thoroughly washed with a deprotection solution and then returned to the reaction solution. The resin was treated again with the same volume of the deprotection solution at room temperature for 20 hours and ether was likewise added dropwise to make the product white powders.

The mixture of white powders and ether was separated by centrifugation, respectively. The ether was removed by decantation and this procedure was repeated twice to remove the acid and scavenger. The residue was dried and extracted with acetic acid aqueous solution. The extract was passed through a 0.45 μm disk filter to remove fine particles, followed by concentration with an evaporator. The residue was diluted in acetonitrile-aqueous solution and lyophilized to give total 1.646 g of white to brown powders.

The crude peptide obtained was purified separately six times on preparative HPLC using SHISEIDO CAPCELL PAK MGII column (50×250 mm). Linear density gradient elution (60 minutes) to A/B: 68/32-58/42 was performed at a flow rate of 45 mL/min using eluant A: 0.1% TFA-water and eluant B: 0.1% TFA-containing acetonitrile on preparative HPLC. The product eluted out was fractionated in test tubes by about 14 mL each. By monitoring each fraction on HPLC, the fractions containing the product only were identified. The fractions were pooled and lyophilized to give 436.9 mg of white powders.

In AcCN-water, 416.9 mg (343.3 μmol) of the purified sample obtained, and 1.430 mL (1.717 mmol equivalent) of AG 1×8 AcO$^-$ resin was added to the solution. While occasionally stirring manually, the solution was settled for an hour, and filtered through a PTFE membrane filter having a 3 μm pore diameter. The filtrate was transferred to a recovery flask and the solvent was distilled off. Then, 4 mL of acetic acid was added to the residue. After the mixture was sonicated for 5 minutes with an ultrasonicator, 16 mL of water was added to the solution. While cooling on a dry ice bath, the resulting 20% acetic acid solution was lyophilized to give 368.4 mg of white powders.
Mass spectrum (M+H)$^+$1214.6 (calcd. 1214.7)
Elution time on HPLC: 20.1 mins.
Elution Conditions:
  Column: SHISEIDO CAPCELL PAK C18 MGII (4.6×100 mm)
  Eluant: Linear density gradient elution with eluants A/B=95/5-45/55, using eluant A: 0.1% TFA-water and eluant B: 0.1% TFA-containing acetonitrile (25 mins.)
  Flow rate: 1.0 mL/min.
Amino acid analysis (20% hydrochloric acid containing 4% thioglycolic acid, 110° C., hydrolysis for 24 hours; figures in parentheses show theoretical values.): Thr 0.95 (1); Tyr 0.97 (1); Cha 1.00 (1); Arg 0.99 (1)

EXAMPLE 13

(Synthesis I): Production of des(1)-Ac-[D-Tyr2, Hyp3,Thr5,Gly7Ψ(CH$_2$S)Leu8,Arg(Me)9,Trp10] MS10 (Compound No. 929)

To a DCM (5 mL) solution of 289 mg (1.30 mmol) of benzyl L-leucinate, 2.1 mL (26 mmol) of pyridine and 1 mL (13 mmol) of methanesulfonylchloride were sequentially added at 0° C. After the mixture was stirred at the same temperature for 3 hours, satd. citric acid aqueous solution was added to stop the reaction. After the whole was extracted with AcOEt, the organic layer was washed sequentially with satd. citric acid aqueous solution, satd. sodium bicarbonate aqueous solution and satd. sodium chloride aqueous solution, and then dried over anhydrous MgSO$_4$. After concentration under reduced pressure, flash chromatography using AcOEt: n-hexane=1:3 was applied to give 636 mg of the mesyloxy compound. The whole of the mesyloxy compound was dissolved in DMF (10 mL) and 535 mg (5.2 mmol) of NaBr was added. The mixture was heated for an hour while heating at 130° C. on an oil bath. After cooling, the whole was extracted with AcOEt and the organic layer was washed with satd. sodium chloride aqueous solution and dried over anhydrous MgSO$_4$. Following concentration under reduced pressure, flash chromatography was performed using AcOEt: n-hexane=1:15 to give 266 mg of the bromo compound (71.7%). To a DMF (2 mL) solution of 61 mg (0.214 mmol) of the bromo compound, 177 mg (1.28 mmol) of K$_2$CO$_3$ and 108 μL (0.642 mmol) of BocNHCH$_2$CH$_2$SH were added and the mixture was stirred overnight at room temperature. The whole was extracted with AcOEt. The organic layer was washed with satd. sodium chloride aqueous solution and dried over anhydrous MgSO$_4$. After concentration under reduced pressure, flash chromatography was performed using AcOEt: n-hexane=1:7 to give 75.1 mg of Boc-GlyΨ(CH$_2$S)Leu-OBzl as an oily substance (91.9%). In MeOH 75.1 mg (0.197 mmol) of Boc-GlyΨ(CH$_2$S)Leu-OBn was dissolved. It was attempted to remove the benzyl ester by treating the solution with HCONH$_4$ in the presence of Pd/C. Since the reaction proceeded only slightly, Pd/C was removed by filtration and the filtrate was extracted with AcOEt. The resulting residue was treated in MeOH (1 mL) with 394 μL (0.394 mmol) of 1M NaOH aqueous solution at room temperature for 2 days. The whole was extracted with AcOEt and the organic layer was washed and dried over anhydrous MgSO$_4$. The residue obtained after concentration under reduced pressure was dissolved in 3 mL of TFA, and the solution was stirred at room temperature for 2 hours. TFA was removed by distillation under reduced pressure and azeotropically distilled twice with toluene. The residue obtained was dissolved in acetonitrile: H$_2$O (2:1, 3 mL). Under ice cooling, Et$_3$N was added to the solution until the solution became basic, and 66.5 mg (0.446 mmol) of Fmoc-OSu was further added thereto. While elevating to room temperature, the mixture was stirred for 3 hours and then the whole was extracted with AcOEt. The organic layer was washed sequentially with 0.1 N HCl aqueous solution and satd. sodium chloride aqueous solution, and then dried over anhydrous MgSO$_4$. The residue, 72 mg, obtained after concentration under reduced pressure was used as Fmoc-GlyΨ(CH$_2$S)Leu-OH for the following step.

After 57.3 mg (0.02 mmol) of Fmoc-Arg(Boc$_2$,Me)-Trp (Boc)-Rink Amide MBHA resin (0.349 mmol/g) was swollen in DMF, the mixture was treated with 20% piperidine/DMF solution to cleave the Fmoc group. Subsequently, the resin was treated in DMF with 36 mg (0.0871 mmol) of Fmoc-GlyΨ(CH$_2$S)Leu-OH, 15.2 µl (0.0871 mmol) of DIEA, 174 µl (0.0871 mmol) of 0.5 M HOAt/DMF solution and 45.4 mg (0.0871 mmol) of PyAOP at room temperature for 12 hours. After the resin was washed with DMF, the peptide chain was extended by conducting condensation using 0.08 mmol each of Fmoc-Phe-OH, 0.5 M HOAt/DMF solution and DIPCDI and then 0.08 mmol each of Ac-D-Tyr-Hyp-Asn-Thr, PyAOP, 0.5 M HOAt/DMF solution and DIEA to give Ac-D-Tyr-Hyp-Asn-Thr-Phe-GlyΨ(CH$_2$S)Leu-Arg(Boc$_2$,Me)-Trp(Boc)-Rink Amide MBHA resin. After the resin was dried, 1.2 mL of TFA/PhSMe/m-cresol/H$_2$O/TIS/EDT (80/5/5/5/2.5/2.5) was added, followed by stirring for 180 minutes. Diethyl ether was added to each reaction solution to give the precipitate and after centrifugation, the supernatant was removed; this procedure was repeated twicefor washing. The residue was extracted with an aqueous acetic acid solution and the extract was filtered to remove the resin. Thereafter, linear density gradient elution (60 minutes) to AB: 72.5/27.5-62.5/37.5 was performed at a flow rate of 15 mL/min using eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized to give 2.7 mg of white powders.

Mass spectrum (M+H)$^+$1227.0 (calcd. 1227.6)
Elution time on HPLC: 19.5 mins.
Elution Conditions:
Column: SHISEIDO CAPCELL PAK C18 MGII (4.6×100 mm)
Eluant: Linear density gradient elution with eluants A/B=95/5-45/55, using eluant A: 0.1% TFA-water and eluant B: 0.1% TFA-containing acetonitrile (25 mins.)
Flow rate: 1.0 mL/min.

EXAMPLE 14

(Synthesis J): Production of des(1)-Ac-[D-Tyr2, Hyp3,Thr5,Phe6Ψ(CH$_2$S)Gly7,Arg(Me)9,Trp10] MS10 (Compound No. 944)

After 157 mg (0.597 mmol) of PPh$_3$ was added to a DCM (1.5 mL) solution of 100 mg (0.398 mmol) of Boc-Phe-ol and 165 mg (0.498 mmol) of CBr$_4$ at 0° C., the mixture was stirred at the same temperature for 2 hours. The solvent was distilled off under reduced pressure and the residue was purified by flash chromatography using AcOEt: n-hexane=1:10 to give 67 mg of the bromo compound as an oily substance (53.6%). To a DMF (1 mL) solution of 64 mg (0.204 mmol) of the bromo compound, 67.7 mg (0.49 mmol) of K$_2$CO$_3$ and 21.9 µL (0.245 mmol) of HSCH$_2$CO$_2$Me were added, followed by stirring at room temperature for 3 hours. The whole was extracted with AcOEt the organic layer was washed with satd. sodium chloride aqueous solution, and dried over anhydrous MgSO$_4$. After concentration under reduced pressure, flash chromatography was conducted using AcOEt: n-hexane=1:5 to give 51.5 mg of Boc-PheΨ(CH$_2$S)Gly-OMe as an oily substance (74.4%). In 1.2 mL of THF:MeOH (3:1), 51.5 mg (0.152 mmol) of Boc-PheΨ(CH$_2$S)Gly-OMe was dissolved and 600 µL of 1M NaOH aqueous solution was added, followed by stirring at room temperature for an hour. After 1M HCl aqueous solution was added to stop the reaction, the whole was extracted with AcOEt and the organic layer was washed with 1M HCl aqueous solution, dried over anhydrous MgSO$_4$ and concentrated under reduced pressure. The residue was dissolved in 1.2 mL of TFA, and the solution was stirred at room temperature for 2 hours. TFA was removed by distillation under reduced pressure and azeotropically distilled twice with toluene. The residue obtained was dissolved in acetonitrile: H$_2$O (2:1, 2.25 mL). Under ice cooling, Et$_3$N was added to the solution until the solution became basic, and 46.7 mg (0.152 mmol) of Fmoc-OSu was further added thereto. While elevating to room temperature, the mixture was stirred overnight and the whole was then extracted with AcOEt. The organic layer was washed sequentially with 0.1 N HCl aqueous solution and satd. sodium chloride aqueous solution, and then dried over anhydrous MgSO$_4$. The residue, 62.5 mg, obtained after concentration under reduced pressure was used as Fmoc-PheΨ(CH$_2$S)Gly-OH for the next step.

After 133 mg (0.045 mmol) of Fmoc-Arg(Boc$_2$,Me)-Trp (Boc)-Rink Amide MBHA resin (0.349 mmol/g) was swollen in DMF, the mixture was treated with 20% piperidine/DMF solution to cleave the Fmoc group. The resin was treated in DMF with 63.6 mg (0.18 mmol) of Fmoc-Leu-OH, 360 µl (0.18 mmol) of 0.5 M HOAt/DMF solution and 716 µL (0.18 mmol) of DIPCDI at room temperature for 1.5 hours. Subsequently, the resin was treated with 20% piperidine/DMF solution to cleave the Fmoc group. The resin was then treated in DMF with 62.5 mg (0.139 mmol) of Fmoc-PheΨ(CH$_2$S)Gly-OH, 24.2 µl (0.139 mmol) of DIEA, 278 µl (0.139 mmol) of 0.5 M HOAt/DMF solution and 72.5 mg (0.139 mmol) of PyAOP at room temperature for 12 hours. The resin was further treated with 20% piperidine/DMF solution to cleave the Fmoc group. The resin was then treated in DMF with 99.3 mg (0.18 mmol) of Ac-D-Tyr-Hyp-Asn-Thr-OH, 31.4 µl (0.18 mmol) of DIEA, 360 µl (0.18 mmol) of 0.5 M HOAt/DMF solution and 93.9 mg (0.18 mmol) of PyAOP at room temperature for 12 hours to give Ac-D-Tyr-Hyp-Asn-Thr-PheΨ(CH$_2$S)Gly-Leu-Arg(Boc$_2$,Me)-Trp(Boc)-Rink Amide MBHA resin. After the resin was dried, 1.5 mL of TFA/PhSMe/m-cresol/H$_2$O/TIS/EDT (80/5/5/5/2.5/2.5) was added, followed by stirring for 120 minutes. Diethyl ether was added to each reaction solution to give the precipitate and after centrifugation, the supernatant was removed; this procedure was repeated twice for washing. The residue was extracted with an aqueous acetic acid solution and the extract was filtered to remove the resin. Thereafter, linear density gradient elution (60 minutes) to A/B: 74/26-64/36 was performed at a flow rate of 15 mL/min using eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized to give 5.0 mg of white powders.
Mass spectrum (M+H)$^+$1227.6 (calcd. 1227.6)
Elution time on HPLC: 19.0 mins.
Elution Conditions:
Column: SHISEIDO CAPCELL PAK C18 MGII (4.6×100 mm)
Eluent: Linear density gradient elution with eluants A/B=95/5-45/55, using eluant A: 0.1% TFA-water and eluant B: 0.1% TFA-containing acetonitrile (25 mins.)
Flow rate: 1.0 mL/min.

EXAMPLE 15

(Synthesis K): Production of des(1)-Ac-[D-Tyr2, Hyp3,Alb4,Thr5,Cha6,Gly7Ψ(CH$_2$CH$_2$)Leu8, Trp10]MS10 (Compound No. 952)

After 15.7 mg of des(1)-Ac-[D-Tyr2,Hyp3,Alb4,Thr5, Cha6,Gly7Ψ((E)CH=CH)Leu8,Trp10]MS10 (Compound No. 927) was dissolved in 3 mL of MeOH, 6.7 mg of 10% Pd/C was added to the solution and suspended therein. In a hydrogen atmosphere, the mixture was stirred overnight and then the Pd catalyst was removed by filtration. MeOH was distilled off under reduced pressure. After the residue was dissolved in 1.5 mL of 50% AcOH aqueous solution, linear density gradient elution (60 minutes) to A/B: 72.5/27.5-63.5/26.5 was performed at a flow rate of 15 mL/min using eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized to give 7.2 mg of white powders.
Mass spectrum (M+H)$^+$1216.4 (calcd. 1216.7)
Elution time on HPLC: 20.2 mins.
Elution Conditions:
Column: SHISEIDO CAPCELL PAK C18 MGII (4.6×100 mm)
Eluent: Linear density gradient elution with eluants A/B=95/5-45/55, using eluant A: 0.1% TFA-water and eluant B: 0.1% TFA-containing acetonitrile (25 mins.)
Flow rate: 1.0 mL/min.

EXAMPLE 16

(Synthesis L): Production of des(1)-Ac-[D-Tyr2, Hyp3,Thr5,Phe6Ψ(CH$_2$CH$_2$)AzaGly7,Arg(Me)9, Trp10]MS10 (Compound No. 968)

In a nitrogen atmosphere, 21.9 mL (32.8 mmol) of a toluene solution of 1.5 M DIBAL-H was dropwise added to a toluene (150 mL) solution of 5.63 g (16.4 mmol) of Z-Phe-NMe(OMe) at −78° C. After stirring for 20 minutes at the same temperature, the reaction was stopped with 0.1 N HCl aqueous solution. The whole was extracted with diethyl ether and the organic layer was washed sequentially with 1 M HCl aqueous solution and satd. sodium chloride aqueous solution. After drying over anhydrous MgSO$_4$, the mixture was concentrated under reduced pressure to give the aldehyde as an oily substance. On the other hand, 3.57 mL (20.5 mmol) of DIEA and 4.81 mL (20.5 mmol) of (EtO)$_2$P(O)CH$_2$CO$_2$Bu$^t$ were sequentially added under ice cooling to a suspension of 869 mg (20.5 mmol) of anhydrous LiCl in acetonitrile (40 mL). The mixture was stirred at the same temperature for 20 minutes and then a solution of the aldehyde obtained above in acetonitrile (4 mL) was dropwise added. While elevating to room temperature, the mixture was stirred overnight. The whole was extracted with AcOEt and the organic layer was washed sequentially with satd. citric acid aqueous solution, satd. sodium bicarbonate aqueous solution and satd. sodium chloride aqueous solution, and then dried over anhydrous MgSO$_4$. After concentration under reduced pressure, flash chromatography was performed using AcOEt: n-hexane=1:8 to give 5.0 g of the α,β-unsaturated ester as white powders (79.9%). After 1.29 g (3.38 mmol) of the α,β-unsaturated ester was dissolved in 10 mL of TFA, the solution was stirred at room temperature for 1.5 hours. TFA was removed by distillation under reduced pressure and then azeotropically distilled off twice with toluene. The residue was dissolved in 15 mL of DMF, and 771 mg (5.07 mmol) of HOBt.NH$_3$ and 972 mg (5.07 mmol) of EDC.HCl were added, followed by stirring at room temperature overnight. The organic layer was washed sequentially with satd. citric acid aqueous solution, satd. sodium bicarbonate aqueous solution and satd. sodium chloride aqueous solution, and then dried over anhydrous MgSO$_4$. After concentration under reduced pressure, the residue was dissolved in 60 mL of MeOH and 10% Pd/C was added thereto, followed by stirring overnight in a hydrogen atmosphere. The Pd/C was removed by filtration through celite and the filtrate was concentrated under reduced pressure. The residue was dissolved in 6 mL of chloroform, and 589 μL (3.38mmol) of DIEA and 738 mg (3.38mmol) of Boc$_2$O were added thereto, followed by stirring at room temperature for 12 hours. The whole was extracted with AcOEt and the organic layer was washed sequentially with satd. citric acid aqueous solution, satd. sodium bicarbonate aqueous solution and satd. sodium chloride aqueous solution, and then dried over anhydrous MgSO$_4$. After concentration under reduced pressure, the obtained powders were recrystallized from AcOEt/n-hexane/diethyl ether to give 611 mg of the carboxylic acid amide as white powders (61.8%). After 200 mg (0.684 mmol) of the carboxylic acid amide was dissolved in THF, 111 μL (1.37 mmol) of pyridine and 589 mg of C$_6$H$_5$I(OCOCF$_3$)$_2$ were added to the solution. The mixture was then stirred at room temperature for 3 hours, and 477 μL (2.74 mmol) of DIEA and 307 mg (1.37 mmol) of HCl.H-Leu-OBu$^t$ were sequentially added. The mixture was further stirred at room temperature overnight. The whole was extracted with AcOEt and the organic layer was washed sequentially with satd. citric acid aqueous solution, satd. sodium bicarbonate aqueous solution and satd. sodium chloride aqueous solution, and then dried over anhydrous MgSO$_4$. After concentration under reduced pressure, flash chromatography was performed using AcOEt: n-hexane=1:2 to give 200 mg of Boc-PheΨ(CH$_2$CH$_2$)AzGly-Leu-OBu$^t$ as oily substance (61.1%). Then, 200 mg (0.419 mmol) of Boc-PheΨ(CH$_2$CH$_2$)AzGly-Leu-OBu$^t$ was dissolved in 4 mL of TFA and the solution was stirred at room temperature for 1.5 hours. TFA was distilled off under reduced pressure and then distilled azeotropically twice. The residue obtained was dissolved in acetonitrile: H$_2$O (2:1, 4.5 mL). Under ice cooling, Et$_3$N was added until the solution became basic and 158 mg (0.419 mmol) of Fmoc-OSu was further added thereto. While elevating to room temperature, the mixture was stirred overnight. The whole was then extracted with AcOEt. H$_2$O was added to form the precipitate and the precipitate was taken up by filtration, washed sequentially with H$_2$O and n-hexane and dried under reduced pressure to give 250 mg of Fmoc-PheΨ(CH$_2$CH$_2$)AzGly-Leu-OH.
After 86.5 mg (0.03 mmol) of Fmoc-Arg(Boc$_2$,Me)-Trp(Boc)-Rink Amide MBHA resin (0.347 mmol/g) was swollen in DMF, the mixture was treated with 20% piperidine/DMF solution to cleave the Fmoc group. Subsequently, the resin was treated in DMF with 65.2 mg (0.12 mmol) of Fmoc-PheΨ(CH₂CH₂)AzaGly-Leu-OH, 20.9 μl (0.12 mmol) of DIEA, 240 μl (0.12 mmol) of 0.5 M HOAt/DMF solution and 62.5 mg (0.12 mmol) of PyAOP at room temperature for 12 hours. After washing with DMF, the resin was treated with 20% piperidine/DMF solution to cleave the Fmoc group. Subsequently, the resin was treated in DMF with 66.2 mg (0.12 mmol) of Ac-D-Tyr-Hyp-Asn-Thr-OH, 20.9 μl (0.12 mmol) of DIEA, 240 μl (0.12 mmol) of 0.5 M HOAt/DMF solution and 62.5 mg (0.12 mmol) of PyAOP at room temperature for 7 hours to give Ac-D-Tyr-Hyp-Asn-Thr-PheΨ(CH₂CH₂)AzaGly-Leu-Arg(Boc₂,Me)-Trp(Boc)-Rink Amide MBHA resin. After the resin was washed with MeOH and dried, 1.5 mL of TFA/PhSMe/m-cresol/H₂O/TIS/EDT (80/5/5/5/2.5/2.5) was added and the mixture was stirred for 90 minutes. Diethyl ether was added to each reaction solution to give the precipitate and after centrifugation, the supernatant was removed; this procedure was repeated twice for washing. The residue was extracted with an aqueous acetic acid solution and the extract was filtered to remove the resin. Then, linear density gradient elution (60 minutes) to AB: 73.5/26.5-63.5/36.5 was performed at a flow rate of 15 mL/min using eluant A: 0.1% TFA-water and eluant B: 0.1% TFA-containing acetonitrile on preparative HPLC using YMC Pack R&D-ODS-5-B S-5, 120A column (30×250 mm). The fractions containing the product were collected and lyophilized to give 3.6 mg of white powders.

Mass spectrum $(M+H)^+$ 1210.3 (calcd. 1210.6)
Elution time on HPLC: 18.3 mins.
Elution Conditions:
  Column: SHISEIDO CAPCELL PAK C18 MGII (4.6×100 mm)
  Eluant: Linear density gradient elution with eluants A/B=95/5-45/55, using eluant A: 0.1% TFA-water and eluant B: 0.1% TFA-containing acetonitrile (25 mins.)
  Flow rate: 1.0 mL/min.

The compounds synthesized in EXAMPLES 1 to 16 and the compounds synthesized by the procedures similar to EXAMPLES 1 to 16 are shown in TABLE 2 below, in terms of their structures, physicochemical properties, etc.

The description "Synthesis" in the table indicates that:
  the compounds described in EXAMPLES 1-16 were synthesized by Synthesis A through G described at the column "Synthesis" of the respective compounds or the compounds described in EXAMPLES 1-16 can be synthesized by Synthesis A through G described at the column "Synthesis" of the respective compounds; and,
  the compounds not described in EXAMPLES 1-16 were synthesized by a modification of the synthesis described in "Synthesis" for the respective compounds.

The description "HPLC condition" in the table indicates that:
  the compounds described in EXAMPLES 1-16 can be eluted under the conditions by a, b, c or d described at the column "HPLC Conditions" for the respective compounds; and,
  the compounds not described in EXAMPLES 1-16 were eluted under the conditions by a, b, c or d described at the column "HPLC Conditions" for the respective compounds.

TABLE 2

| Compound number | Structure | M + H⁺ (obs.) | M + H⁺ (cal.) | HPLC (min.) | HPLC condition | Synthesis method |
|---|---|---|---|---|---|---|
| 796 | des(1)-Ac-[D-Tyr2,Hyp3,Thr5,Arg(Me)9,Trp10]MS10 | 1224.6 | 1224.6 | 11.8 | a | A |
| 803 | des(1)-Ac-[D-Tyr2,Hyp3,Thr5,Ala7,Arg(Me)9,Trp10]MS10 | 1238.5 | 1238.6 | 12.0 | a | A |
| 804 | des(1)-Ac-[D-Tyr2,Hyp3,Thr5,Ser7,Arg(Me)9,Trp10]MS10 | 1254.4 | 1254.6 | 11.7 | a | A |
| 811 | des(1)-Ac-[D-Tyr2,Hyp3,Thr5,Aib7,Arg(Me)9,Trp10]MS10 | 1252.8 | 1252.6 | 12.2 | a | A |
| 818 | des(1)-Ac-[D-Tyr2,Hyp3,Thr5,Abu7,Arg(Me)9,Trp10]MS10 | 1252.7 | 1252.6 | 12.5 | a | A |
| 822 | des(1)-Ac-[D-Tyr2,Hyp3,Thr5,Cha6,Arg(Me)9,Trp10]MS10 | 1231.0 | 1230.7 | 13.4 | a | A |
| 823 | des(1)-Ac-[D-Tyr2,Hyp3,Thr5,Cha6,Ala7,Arg(Me)9,Trp10]MS10 | 1245.0 | 1244.7 | 13.3 | a | A |
| 827 | des(1)-Ac-[D-Tyr2,Hyp3,Thr5,Dap7,Arg(Me)9,Trp10]MS10 | 1254.0 | 1253.6 | 11.5 | a | A |
| 828 | des(1)-Ac-[D-Tyr2,Hyp3,Thr5,Ser(Me)7,Arg(Me)9,Trp10]MS10 | 1269.0 | 1268.6 | 12.3 | a | A |
| 834 | des(1)-Ac-[D-Tyr2,Hyp3,Thr5,Phe6Ψ(CH₂O)Gly7,Arg(Me)9,Trp10]MS10 | 1211.3 | 1211.6 | 19.4 | b | B |
| 839 | des(1)-Ac-[D-Tyr2,Hyp3,Thr5,Pya(2)6,Arg(Me)9,Trp10]MS10 | 1225.4 | 1225.6 | 7.6 | a | A |
| 847 | des(1)-Ac-[D-Tyr2,Hyp3,Thr5,Val7,Arg(Me)9,Trp10]MS10 | 1266.8 | 1266.7 | 19.2 | b | A |
| 848 | des(1)-Ac-[D-Tyr2,Hyp3,Thr5,Pya(3)6,Arg(Me)9,Trp10]MS10 | 1225.9 | 1225.6 | 7.5 | a | A |
| 849 | des(1)-Ac-[D-Tyr2,Hyp3,Thr5,Pya(4)6,Arg(Me)9,Trp10]MS10 | 1226.0 | 1225.6 | 7.3 | a | A |
| 850 | des(1)-Ac-[D-Tyr2,Hyp3,Thr5,Phe6Ψ(CH₂CH₂)Gly7,Arg(Me)9,Trp10]MS10 | 1209.7 | 1209.6 | 12.2 | c | C |
| 851 | des(1)-Ac-[D-Tyr2,Hyp3,Thr5,Phe6Ψ(COCH₂)Gly7,Arg(Me)9,Trp10]MS10 | 1224.2 | 1223.6 | 11.8 | c | D |
| 852 | des(1)-Ac-[D-Tyr2,Glu3,Thr5,Arg(Me)9,Trp10]MS10 | 1241.0 | 1240.6 | 12.1 | a | A |
| 853 | des(1)-Ac-[D-Tyr2,Glu3,Thr5,Cha6,Arg(Me)9,Trp10]MS10 | 1247.3 | 1246.7 | 13.4 | a | A |
| 854 | des(1)-Ac-[D-Tyr2,Hyp3,Thr5,Gly7Ψ(CH₂NH)Leu8,Arg(Me)9,Trp10]MS10 | 1210.6 | 1210.6 | 10.9 | a | E |
| 855 | des(1)-Ac-[D-Tyr2,Hyp3,Thr5,Ala(cPr)6,Arg(Me)9,Trp10]MS10 | 1188.8 | 1188.6 | 10.6 | a | A |
| 857 | des(1)-Ac-[D-Tyr2,Hyp3,Thr5,Phe6Ψ((S)CHOH—CH₂)Gly7,Arg(Me)9,Trp10]MS10 | 1226.2 | 1225.6 | 11.9 | c | F |
| 858 | des(1)-Ac-[D-Tyr2,Hyp3,Thr5,Phe6Ψ((S)CHOH—(E)OH=)Gly7,Arg(Me)9,Trp10]MS10 | 1224.2 | 1223.6 | 11.7 | c | C |
| 859 | des(1)-Ac-[D-Tyr2,Hyp3,Thr5,Phe6Ψ((E)CH=CH)Gly7,Arg(Me)9,Trp10]MS10 | 1208.1. | 1207.6 | 12.3 | c | C |
| 866 | des(1)-Ac-[D-Tyr2,Hyp3,Thr5,Phe6Ψ((R)CHOH—(E)CH=)Gly7,Arg(Me)9,Trp10]MS10 | 1224.2 | 1223.6 | 11.5 | c | C |
| 867 | des(1)-Ac-[D-Tyr2,Hyp3,Thr5,Phe6Ψ((R)CHOH—CH₂)Gly7,Arg(Me)9,Trp10]MS10 | 1226.3 | 1225.6 | 11.5 | c | F |
| 869 | des(1)-Ac-[D-Tyr2,Hyp3,Thr5,αMaPhe6,Arg(Me)9,Trp10]MS10 | 1239.0 | 1238.6 | 13.0 | a | A |
| 871 | des(1)-Ac-[D-Tyr2,Hyp3,Thr5,Phe(2Me)6,Arg(Me)9,Trp10]MS10 | 1238.6 | 1238.6 | 12.9 | a | A |
| 873 | des(1)-Ac-[D-Tyr2,Hyp3,Thr5,Phe(3Me)6,Arg(Me)9,Trp10]MS10 | 1238.7 | 1238.6 | 13.0 | a | A |
| 875 | des(1)-Ac-[D-Tyr2,Hyp3,Thr5,Phe(4Me)6,Arg(Me)9,Trp10]MS10 | 1238.5 | 1238.6 | 12.9 | a | A |
| 885 | des(1)-Ac-[D-Tyr2,Hyp3,Alb4,Thr5,Arg(Me)9,Trp10]MS10 | 1239.7 | 1239.6 | 12.2 | a | A |
| 892 | des(1)-Ac-[D-Tyr2,Hyp3,Thr5,Gly7Ψ((E)CH=CH)Leu8,Arg(Me)9,Trp10]MS10 | 1207.5 | 1207.6 | 14.6 | c | G |
| 893 | des(1)-Ac-[D-Tyr2,Hyp3,Thr5,Gly7Ψ((E)CH₂CH₂)Leu8,Arg(Me)9,Trp10]MS10 | 1209.1 | 1209.6 | 19.0 | d | H |
| 894 | des(1)-Ac-[D-Tyr2,Hyp3,Thr5,Cha6,Ala(cPr)8,Arg(Me)9,Trp10]MS10 | 1228.9 | 1228.6 | 12.9 | a | A |
| 895 | des(1)-Ac-[D-Tyr2,Glu3,Thr5,Cha6,Ala(cPr)8,Arg(Me)9,Trp10]MS10 | 1244.8 | 1244.6 | 12.6 | a | A |
| 902 | des(1)-Ac-[D-Tyr2,Hyp3,Thr5,Cha6,Gly7Ψ((E)CH=CH)Leu8,Arg(Me)9,Trp10]MS10 | 1213.5 | 1213.7 | 20.2 | d | G |
| 903 | des(1)-Ac-[D-Tyr2,Hyp3,Alb4,Thr5,Cha6,Gly7Ψ((E)CH=CH)Leu8,Arg(Me)9,Trp10]MS10 | 1228.4 | 1228.7 | 20.2 | d | G |
| 904 | des(1)-Ac-[D-Tyr2,Glu3,Thr5,Cha6,Gly7Ψ((E)CH=CH)Leu8,Arg(Me)9,Trp10]MS10 | 1229.2 | 1229.7 | 20.5 | d | G |

TABLE 2-continued

| Compound number | Structure | M + H+ (obs.) | M + H+ (cal.) | HPLC (min.) | HPLC condition | Synthesis method |
|---|---|---|---|---|---|---|
| 905 | des(1)-Ac-[D-Tyr2,Glu3,Alb4,Thr5,Cha6,Gly7Ψ((E)CH=OH)Leu8,Arg(Me)9,Trp10]MS10 | 1244.3 | 1244.7 | 20.3 | d | G |
| 906 | des(1)-Ac-[D-Tyr2,Hyp3,Alb4,Thr5,Gly7Ψ((E)CH=CH)Leu8,Arg(Me)9,Trp10]MS10 | 1222.6 | 1222.6 | 19.1 | d | G |
| 907 | des(1)-Ac-[D-Tyr2,Glu3,Thr5,Gly7Ψ((E)CH=CH)Leu8,Arg(Me)9,Trp10]MS10 | 1223.6 | 1223.6 | 19.1 | d | G |
| 908 | des(1)-Ac-[D-Tyr2,Glu3,Alb4,Thr5,Gly7Ψ((E)CH=CH)Leu8,Arg(Me)9,Trp10]MS10 | 1238.7 | 1238.6 | 19.3 | d | G |
| 909 | des(1)-Ac-[D-Tyr2,Asp3,Thr5,Cha6,Ala(cPr)8,Arg(Me)9,Trp10]MS10 | 1230.7 | 1230.6 | 12.0 | a | A |
| 910 | des(1)-Ac-[D-Tyr2,Aad3,Thr5,Cha6,Ala(cPr)8,Arg(Me)9,Trp10]MS10 | 1258.6 | 1258.7 | 12.4 | a | A |
| 911 | des(1)-Ac-[D-Tyr2,Lys3,Thr5,Cha6,Ala(cPr)8,Arg(Me)9,Trp10]MS10 | 1243.6 | 1243.7 | 10.9 | a | A |
| 912 | des(1)-Ac-[D-Tyr2,Aib3,Thr5,Cha6,Ala(cPr)8,Arg(Me)9,Trp10]MS10 | 1200.6 | 1200.7 | 13.9 | a | A |
| 913 | des(1)-Ac-[D-Tyr2,Hyp3,Gln4,Thr5,Cha6,Gly7Ψ((E)CH=CH)Leu8,Arg(Me)9,Trp10]MS10 | 1227.5 | 1227.7 | 20.2 | d | G |
| 914 | des(1)-Ac-[D-Tyr2,Hyp3,Cit4,Thr5,Cha6,Gly7Ψ((E)CH=CH)Leu8,Arg(Me)9,Trp10]MS10 | 1256.2 | 1256.7 | 19.9 | d | G |
| 915 | des(1)-Ac-[D-Tyr2,Hyp3,Glu4,Thr5,Cha6,Gly7Ψ((E)CH=CH)Leu8,Arg(Me)9,Trp10]MS10 | 1228.4 | 1228.7 | 20.7 | d | G |
| 916 | des(1)-Ac-[D-Tyr2,Hyp3,Thr5,Ala(cPr)8,Arg(Me)9,Trp10]MS10 | 1222.5 | 1222.6 | 10.8 | a | A |
| 917 | des(1)-Ac-[D-Tyr2,Hyp3,Ser(Me)8,Arg(Me)9,Trp10]MS10 | 1212.4 | 1212.6 | 9.3 | a | A |
| 918 | des(1)-Ac-[D-Tyr2,Hyp3,Thr5,Nva8,Arg(Me)9,Trp10]MS10 | 1210.1 | 1210.6 | 10.6 | a | A |
| 919 | des(1)-Ac-[D-Tyr2,Hyp3,Thr5,Nal(2)6,Arg(Me)9,Trp10]MS10 | 1274.1 | 1274.6 | 13.6 | a | A |
| 920 | des(1)-Ac-[D-Tyr2,Hyp3,Thr5,Cha6,Ser(Me)a,Arg(Me)9,Trp10]MS10 | 1218.3 | 1218.6 | 10.8 | a | A |
| 921 | des(1)-Ac-[D-Tyr2,Hyp3,Thr5,Cha6,Nva8,Arg(Me)9,Trp10]MS10 | 1216.5 | 1216.6 | 12.0 | a | A |
| 923 | des(1)-Ac-[D-Tyr2,Glu3,Thr5,Cha6,Ser(Me)8,Arg(Me)9,Trp10]MS10 | 1234.6 | 1234.6 | 10.4 | a | A |
| 924 | des(1)-Ac-[D-Tyr2,Glu3,Thr5,Cha6,Nva8,Arg(Me)9,Trp10]MS10 | 1232.6 | 1232.6 | 12.0 | a | A |
| 925 | des(1)-Ac-[D-Tyr2,Hyp3,Thr5,Gly7Ψ((E)CH=CH)Leu8,Trp10]MS10 | 1193.6 | 1193.6 | 19.0 | d | G |
| 926 | des(1)-Ac-[D-Tyr2,Hyp3,Thr5,Cha6,Gly7Ψ((E)CH=CH)Leu8,Trp10]MS10 | 1199.6 | 1199.7 | 20.2 | d | G |
| 927 | des(1)-Ac-[D-Tyr2,Hyp3,Alb4,Thr5,Cha6,Gly7Ψ((E)CH=CH)Leu8,Trp10]MS10 | 1214.6 | 1214.7 | 20.1 | d | G |
| 929 | des(1)-Ac-[D-Tyr2,Hyp3,Thr5,Gly7Ψ(CH2S)Leu8,Arg(Me)9,Trp10]MS10 | 1227.0 | 1227.6 | 19.5 | d | I |
| 931 | des(1)-Ac-[D-Tyr2,Hyp3,Thr5,Cha6,Gly7Ψ(CH2S)Leu8,Arg(Me)9,Trp10]MS10 | 1233.4 | 1233.6 | 20.7 | d | I |
| 932 | des(1)-Ac-[D-Tyr2,Hyp3,Thr5,Cha6,Nle8,Arg(Me)9,Trp10]MS10 | 1230.6 | 1230.7 | 12.9 | a | A |
| 933 | des(1)-Ac-[D-Tyr2,Hyp3,Thr5,Cha6,Leu(Me)8,Arg(Me)9,Trp10]MS10 | 1244.6 | 1244.7 | 13.3 | a | A |
| 934 | des(1)-Ac-[D-Tyr2,Hyp3,Thr5,Cha6,8,Arg(Me)9,Trp10]MS10 | 1270.5 | 1270.7 | 14.8 | a | A |
| 940 | des(1)-Ac-[D-Tyr2,Hyp3,Thr5,Cha6,Ala(cPr)8,Trp10]MS10 | 1214.1 | 1214.6 | 12.2 | a | A |
| 942 | des(1)-Ac-[D-Tyr2,Glu3,Thr5,Cha6,Ala(cPr)8,Trp10]MS10 | 1230.4 | 1230.6 | 12.4 | a | A |
| 944 | des(1)-Ac-[D-Tyr2,Hyp3,Thr5,Phe6Ψ(CH2S)Gly7,Arg(Me)9,Trp10]MS10 | 1227.6 | 1227.6 | 19.0 | d | J |
| 945 | des(1)-Ac-[D-Tyr2,Hyp3,Thr5,Ala(cBu)6,Ala(cPr)8,Arg(Me)9,Trp10]MS10 | 1200.7 | 1200.6 | 10.5 | a | A |
| 946 | des(1)-Ac-[D-Tyr2,Hyp3,Thr5,Cha6,Ala(cBu)8,Arg(Me)9,Trp10]MS10 | 1242.8 | 1242.7 | 13.2 | a | A |
| 947 | des(1)-Ac-[D-Tyr2,Hyp3,Alb4,Ala5,Cha6,Ala(cPr)8,Arg(Me)9,Trp10]MS10 | 1213.7 | 1213.7 | 12.7 | a | A |
| 948 | des(1)-Ac-[D-Tyr2,Hyp3,Alb4,Ser5,Cha6,Ala(cPr)8,Arg(Me)9,Trp10]MS10 | 1229.7 | 1229.6 | 12.1 | a | A |
| 949 | des(1)-Ac-[D-Tyr2,Hyp3,Alb4,Gly5,Cha6,Ala(cPr)8,Arg(Me)9,Trp10]MS10 | 1199.8 | 1199.6 | 12.1 | a | A |
| 951 | des(1)-Ac-[D-Tyr2,Hyp3,Alb4,Dap5,Cha6,Ala(cPr)8,Arg(Me)9,Trp10]MS10 | 1228.8 | 1228.7 | 10.6 | a | A |
| 952 | des(1)-Ac-[D-Tyr2,Hyp3,Alb4,Thr5,Cha6,Gly7Ψ(CH2CH2)Leu8,Trp10]MS10 | 1216.4 | 1216.7 | 20.2 | d | K |
| 953 | des(1)-Ac-[D-Tyr2,Hyp3,Alb4,Thr5,Cha6,Ala(cPr)8,Arg(Me)9,Trp10]MS10 | 1243.8 | 1243.7 | 10.6 | a | A |
| 956 | des(1)-Ac-[D-Tyr2,Hyp3,Thr5,Cha6,Gly7Ψ(CH2CH2)Leu8,Trp10]MS10 | 1201.6 | 1201.7 | 20.2 | d | K |
| 957 | des(1)-Ac-[D-Tyr2,Hyp3,Alb4,Thr5,Cha6,Gly7Ψ(CH2CH2)Leu8,Arg(Me)9,Trp10]MS10 | 1230.7 | 1230.7 | 20.3 | d | K |
| 959 | des(1)-Ac-[D-Tyr2,Pro(4F)3,Thr5,Cha6,Ala(cPr)8,Arg(Me)9,Trp10]MS10 | 1230.7 | 1230.6 | 11.8 | a | A |
| 968 | des(1)-Ac-[D-Tyr2,Hyp3,Thr5,Phe6Ψ(CH2CH2)AzaGly7,Arg(Me)9,Trp10]MS10 | 1210.3 | 1210.6 | 18.3 | d | L | a: 20-70% AcCN/25 min, flow 1 ml/min, YMC ODS AM-301 (4.6 × 100 mm)
b: 0-50% AcCN/25 min, flow 1 ml/min, Wakosil-II 5C18 HG (4.6 × 100 mm)
c: 20-70% AcCN/25 min flow 1 ml/min SHISEIDO CAPCELL PAK C18 MGII (4.6 × 100 mm)
d: 5-55% AcCN/25 min flow 1 ml/min SHISEIDO CAPCELL PAK C18 MGII (4.6 × 100 mm)

TEST EXAMPLE 1

Measurement of Agonist Activity by Assaying Changes in Intracellular Calcium Ion Level
1) Preparation of Human Metastin and Rat Metastin Stable Expression cell lines Human metastin and rat metastin stable expression cell lines were obtained by transfecting the expression plasmid for animal cells into CHO/dhfr− cells using CellPhect Transfection Kit (manufactured by GE Healthcare). First, 240 μL of Buffer A (attached to CellPhect Transfection Kit) was added to 9.6 μg of plasmid DNA dissolved in 240 μL of distilled water followed by stirring. After the mixture was settled for 10 minutes, 480 μL of Buffer B (attached to CellPhect Transfection Kit) was added to the mixture, which was vigorously stirred to form liposomes containing the DNA. Then, 4×10$^5$ CHO/dhfr− cells (obtained from ATCC) were inoculated on a 60 mm Petri dish. After culturing the cells in Ham's F-12 medium (manufactured by Nissui Seiyaku Co., Ltd.) supplemented with 10% fetal bovine serum (manufactured by BIO WHITTAKER, Inc.) at 37° C. for 2 days in 5% carbon dioxide gas, 480 mL of the liposomes were dropwise added to the cells on the Petri dish. After culturing the cells in a $CO_2$ incubator (5% $CO_2$, 37° C.) for 6 hours, the cells were washed twice with serum-free Ham's F-12 medium and 3 mL of 15% glycerol was added to the cells on the Petri dish followed by treatment for 2 minutes. The cells were again washed twice with serum-free Ham's F-12 medium followed by incubation in Ham's F-12 medium supplemented with 10% fetal bovine serum in a $CO_2$ incubator (5% $CO_2$, 37° C.) for 15 hours. The cells were dispersed by trypsin treatment to recover from the Petri dish. The recovered cells were inoculated on a 6-well plate in 1.25×10$^4$ cells each/well and incubation was initiated in a $CO_2$ incubator (5% $CO_2$, 37° C.) in Dulbecco's modified Eagle medium (DMEM, manufactured by Nissui Seiyaku) containing 10% dialyzed fetal bovine serum (manufactured by JRH BIOSCIENCES, Inc.). The plasmid-transfected CHO transformants grew in the medium but the non-transfected cells gradually died, accordingly the medium was exchanged on Days 1 and 2 after the initiation of incubation to remove the dead cells. Approximately 20 colonies of the CHO transformants that kept growing on Days 8 to 10 after the incubation were isolated. From the cells in these colonies, cells showing high reactivity with the ligand peptide metastin (hereinafter merely referred to as h175KB19 and h175KB29 strains) were selected to provide for the following experiment.

2) Cell Seeding

Human metastin expression CHO cell line (h175KB19 strain is described in a separate section) and rat metastin expression CHO cell line (h175KB29 strain is described in a separate section) were seeded in a 96-well plate (type 3904, manufactured by Corning) at $3 \times 10^4$ cells/well, followed by incubation in a $CO_2$ incubator (5% $CO_2$, 37° C.) for 24 hours. For the medium, MEMα medium (nucleic acid-free, manufactured by Nikken Bio Medical Laboratory) supplemented with dialyzed 10% fetal bovine serum (manufactured by Thermo, MultiSer) was used.

3) Loading with Fluo-4 NW in Cells

As an assay buffer, 1×Hanks' balanced salt solution (HBSS, manufactured by GIBCO) supplemented with 0.1% BSA, 20 mM HEPES (pH 7.4, manufactured by GIBCO) and 1 mM Probenecid (manufactured by Molecular Probes) was prepared. The medium in the wells of the cell-seeded plate was removed and 100 μL each of the assay buffer (kept warm at 37° C.) was added to each well. After 10 mL of the assay buffer (the volume for assaying two plates) was charged in one Fluo-4NW dye mix (Component A, Fluo-4 NW calcium assay kit (starter pack), manufactured by Molecular Probes) bottle, the mixture was gently stirred to prepare the Fluo-4 NW loading solution. This loading solution was charged in each well by 50 μl each and reacted in a $CO_2$ incubator (5% $CO_2$, 37° C.) for 30 minutes for loading with Fluo-4 NW into the cells. Subsequently, the cells were settled at room temperature (25° C.) for 15 minutes and then used for assay.

4) Measurement of Agonist Activity

To monitor the agonist activity of a test compound, the test compound diluted in the assay buffer described above was dispensed into a 96-well plate (type 3363, manufactured by Corning) by 80 μl each/well to prepare the compound plate. Fluo-4 NW-loaded cell plate and compound plate were set on a Fluorometric Imaging Plate Reader (FLIPR, manufactured by Molecular Devices) and 50 μl each was dispensed in each well through an automated pipettor in the FLIPR. The agonist response when stimulated with the compound was monitored via CCD camera in the FLIPR in terms of changes in intracellular calcium ion levels (changes in fluorescence of Fluo-4 NW).

Human Metastin (45-54)* specific agonist activity refers to the value obtained by subtracting the fluorescence change in the control group without any additive from the fluorescence change induced by Metastin (45-54). The specific agonist activity of a test compound refers to the value obtained by subtracting the fluorescence change observed in the control group in the absence of any test compound from the fluorescence change observed when added with the test compound. The compound level showing the 50% agonist response activity ($EC_{50}$ value) was calculated from the dose-response curve. When the maximum response of human Metastin (45-54) specific agonist activity was made 100%, the $EC_{50}$ was calculated on a test compound showing 70% or more of the maximum activity as compared to the maximum response.

* Peptide used and synthesized from the 45th to 54th in the amino acid sequence for human metastin [human Metastin (45-54)] is the synthetic product from Peptide Institute, Inc.

The agonist activity of each test compound [expressed by the specific activity of the $EC_{50}$ of a test compound based on the $EC_{50}$ of Metastin (45-54)] is shown in TABLE 3. The data reveal that the compounds of the present invention have excellent agonist activities on the metastin receptors.

TABLE 3

| Compound No. | Specific Activity |
| --- | --- |
| 796 | 1.2 |
| 803 | 0.5 |
| 804 | 0.6 |
| 811 | 1.5 |
| 818 | 1.0 |
| 822 | 0.3 |
| 823 | 0.5 |
| 827 | 1.3 |
| 828 | 1.2 |
| 834 | 0.5 |
| 839 | 1.2 |
| 847 | 1.7 |
| 848 | 0.9 |
| 849 | 0.9 |
| 850 | 1.3 |
| 851 | 1.1 |
| 852 | 0.5 |
| 853 | 0.6 |
| 854 | 2.9 |
| 855 | 1.9 |
| 857 | 1.2 |
| 858 | 1.7 |
| 859 | 0.7 |
| 866 | 1.4 |
| 867 | 0.8 |
| 869 | 3.8 |
| 871 | 0.7 |
| 873 | 0.8 |
| 875 | 0.9 |
| 885 | 0.5 |
| 892 | 0.6 |
| 893 | 0.8 |
| 894 | 0.5 |
| 895 | 0.4 |
| 902 | 0.6 |
| 903 | 0.4 |
| 904 | 0.5 |
| 905 | 0.5 |
| 906 | 0.6 |
| 907 | 0.6 |
| 908 | 0.5 |
| 909 | 2.5 |
| 910 | 1.1 |
| 911 | 0.7 |
| 912 | 0.6 |
| 913 | 1.4 |
| 914 | 0.9 |
| 915 | 4.6 |
| 916 | 0.8 |
| 917 | 0.8 |
| 918 | 0.7 |
| 919 | 1.0 |
| 920 | 0.5 |
| 921 | 0.5 |
| 923 | 0.5 |
| 924 | 0.4 |
| 925 | 0.4 |
| 926 | 0.6 |
| 927 | 0.5 |
| 929 | 1.2 |
| 931 | 1.7 |
| 932 | 0.6 |
| 933 | 1.4 |
| 934 | 3.5 |
| 940 | 0.5 |
| 942 | 0.4 |
| 944 | 0.7 |
| 945 | 0.7 |
| 946 | 0.5 |
| 947 | 0.5 |
| 948 | 0.5 |
| 949 | 0.7 |
| 951 | 0.7 |
| 952 | 1.3 |
| 953 | 0.5 |
| 956 | 1.1 |
| 957 | 1.1 |

TABLE 3-continued

| Compound No. | Specific Activity |
|---|---|
| 959 | 0.4 |
| 968 | 0.6 |

TEST EXAMPLE 2

Evaluation of Blood Testosterone Level Reducing Effect of Metastin Peptide Derivatives Using Mature Male Rats In the metastin peptide derivatives listed in TABLES 1 and 2, the blood testosterone level reducing effects were evaluated on the compounds except for compound Nos. 828, 847, 854, 857, 866, 869, 915, 917 and 934.

A metastin peptide derivative (hereinafter referred to as peptide) was dissolved in 50% DMSO aqueous solution (DMSO: Sigma-Aldrich, distilled water for injection: Otsuka Pharmaceutical) to prepare a peptide solution with the concentration of 0.1, 0.03 or 0.01 mM. This peptide solution was filled in five ALZET osmotic pumps (Model 2001, 0.2 mL in volume, release rate: 0.001 mL/hr, DURECT Corporation). The ALZET pump filled with the peptide solution was implanted subcutaneously in 5 CD(SD)IGS male rats of 9 weeks old after birth (Charles River Japan, Inc.) on the back under ethereal anesthesia by one pump/animal. For negative control, 50% DMSO aqueous solution was filled in 5 ALZET osmotic pumps, which were similarly implanted in 5 male CD(SD)IGS rats (Charles River Japan, Inc.), respectively. These rats were fed for 6 days under normal feeding conditions. After weighing, the animal was decapitated to collect blood. After 0.03 mL/mL blood of aprotinin (Trasylol, Bayer) solution containing 0.1 g/mL EDTA.2Na was added to blood, the plasma was separated and recovered by centrifugation at 1,800×g for 30 minutes. From the plasma obtained, 0.05 mL was applied to radioimmunoassay (DPC.Total Testosterone Kit, Diagnostic Products Corporation) to measure the plasma testosterone level in each rat. The peptides are listed in TABLE 4, when the number of rats showing the testosterone level below the measurement limit (0.04 ng/mL of plasma level) in radioimmunoassay was 3 or more in the 5 rats receiving the peptides.

TABLE 4

| Compound No. |
|---|
| 822 |
| 853 |
| 892 |
| 894 |
| 895 |
| 902 |
| 903 |
| 904 |
| 905 |
| 907 |
| 910 |
| 912 |
| 924 |
| 925 |
| 926 |
| 927 |
| 931 |
| 956 |
| 957 |
| 959 |

INDUSTRIAL APPLICABILITY

According to the present invention, there are provided stable metastin derivatives having excellent biological activities (a cancer metastasis suppressing activity, a cancer growth suppressing activity, a gonadotropic hormone secretion stimulating activity, sex hormone secretion stimulating activity, a gonadotropic hormone secretion suppressing activity, sex hormone secretion suppressing activity, etc.).

The invention claimed is:

1. A compound represented by the formula below, or a salt thereof,

XX0-XX2-XX3-XX4-XX5-T-XX9-XX10-NH$_2$ wherein:

XX0 represents $C_{1-12}$ alkanoyl;

XX2 represents D-Tyr;

XX3 represents Hyp or Pro(4F);

XX4 represents Asn or 2-amino-3-ureidopropionic acid;

XX5 represents Thr;

T represents a group represented by formula II:

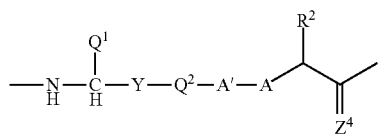

(II)

$Z^4$ represents O, $R^2$ represents a linear $C_{1-10}$ alkyl group, which may optionally be substituted with a $C_{3-8}$ cycloalkyl group;

$Q^1$ represents a $C_{1-4}$ alkyl group, which may optionally be substituted with an optionally substituted non-aromatic cyclic hydrocarbon group having carbon atoms not greater than 7;

A represents a carbon atom substituted with hydrogen atom;

A' represents a carbon atom substituted with hydrogen atom or O;

$Q^2$ represents $CH_2$;

Y represents —CONH—;

XX9 represents Arg or Arg(Me); and,

XX10 represents Trp.

2. The compound according to claim 1, wherein the non-aromatic cyclic hydrocarbon group having carbon atoms not greater than 7 is a $C_{3-7}$ cycloalkyl group.

3. The compound according to claim 1, wherein the A' represents a carbon atom substituted with hydrogen atom.

4. A medicament comprising the compound according to claim 1, or a salt thereof and pharmacologically acceptable carrier.

\* \* \* \* \*